United States Patent
Beconi et al.

(10) Patent No.: US 10,364,263 B2
(45) Date of Patent: Jul. 30, 2019

(54) CYCLIC PHOSPHATES AND CYCLIC PHOSPHORAMIDATES FOR THE TREATMENT OF NEUROLOGIC DISORDERS

(71) Applicant: Retrophin, Inc., San Diego, CA (US)

(72) Inventors: Maria Beconi, Bedford, MA (US); Daniel Elbaum, Newton, MA (US); Steven Harper, Rome (IT); Savina Malancona, Rome (IT)

(73) Assignee: Retrophin, Inc., San Diego, CA (US)

( * ) Notice: Subject to any disclaimer, the term of this patent is extended or adjusted under 35 U.S.C. 154(b) by 0 days.

(21) Appl. No.: 16/060,347

(22) PCT Filed: Dec. 8, 2016

(86) PCT No.: PCT/US2016/000128
§ 371 (c)(1),
(2) Date: Jun. 7, 2018

(87) PCT Pub. No.: WO2017/099822
PCT Pub. Date: Jun. 15, 2017

(65) Prior Publication Data
US 2018/0362564 A1 Dec. 20, 2018

Related U.S. Application Data

(60) Provisional application No. 62/264,735, filed on Dec. 8, 2015.

(51) Int. Cl.
| | | |
|---|---|---|
| *A61K 31/66* | (2006.01) | |
| *C07F 9/6574* | (2006.01) | |
| *C07F 9/655* | (2006.01) | |
| *A61P 25/28* | (2006.01) | |
| *A61P 25/08* | (2006.01) | |
| *A61P 25/16* | (2006.01) | |

(52) U.S. Cl.
CPC .......... *C07F 9/65742* (2013.01); *A61K 31/66* (2013.01); *A61P 25/08* (2018.01); *A61P 25/16* (2018.01); *A61P 25/28* (2018.01); *C07F 9/6552* (2013.01)

(58) Field of Classification Search
None
See application file for complete search history.

(56) References Cited

U.S. PATENT DOCUMENTS

2014/0212382 A1* 7/2014 Schinazi ................ C07H 19/20
424/85.4

FOREIGN PATENT DOCUMENTS

| AU | 2013251345 B2 | 8/2017 |
|---|---|---|
| CN | 104520307 B | 12/2016 |
| JP | 2009-504704 A | 2/2009 |
| RU | 2002110463 A | 2/2004 |
| WO | 01/21772 A2 | 3/2001 |
| WO | 03/008626 A2 | 1/2003 |
| WO | 2007/020193 A2 | 2/2007 |
| WO | 2012/158811 A2 | 11/2012 |
| WO | 2013/163576 A1 | 10/2013 |
| WO | 2015/061792 A1 | 4/2015 |
| WO | 2016/178876 A2 | 11/2016 |

OTHER PUBLICATIONS

Balibar et al., "Pantethine Rescues Phosphopantothenoylcysteine Synthetase and Phosphopantothenoylcysteine Decarboxylase Deficiency in *Escherichia coli* but not Pseudomonas aeruginosa," *Journal of Bacteriology* 193(13):3304-3312, 2011.
Derudas et al., "The Application of Phosphoramidate Protide Technology to Acyclovir Confers Anti-HIV Inhibition," *J. Med. Chem.* 52:5520-5530, 2009.
Garcia et al., "Germline Deletion of Pantothenate Kinases 1 and 2 Reveals the Key Roles for CoA in Postnatal Metabolism," *PLoS One* 7(7):e40871, Jul. 2012, 13 pages.
Gregory et al., "Pantothenate Kinase-Associated Neurodegeneration," NCBI Bookshelf, 22 pages, accessed on Jun. 30, 2014.
Hanna et al., "Hallervorden-Spatz Disease" [online], updated on Feb. 28, 2012, URL=http://emedicine.medscape.com/article/1150519-overview, 9 pages.
Hanna et al., "Pantothenate Kinase-Associated Neurodegeneration (PKAN)," Dec. 7, 2016, URL=https://emedicine.medscape.com/article/1150519-overview, download date Feb. 24, 2017, 8 pages.
Hayflick, "Unraveling the Hallervorden-Spatz syndrome: pantothenate kinase-associated neurodegeneration is the name . . . ," *Curr. Opin. Pediatr.* 15:572-577, 2003.
Hecker et al., "Prodrugs of Phosphates and Phosphonates," *J. Med. Chem.* 51:2328-2345, 2008.
Hwang et al., "Enzymatic and Cellular Study of a Serotonin N-acetyltransferase Phosphopantetheine-based Prodrug," *Bioorganic & Medicinal Chemistry* 15:2147-2155, 2007.
International Search Report and Written Opinion, dated Mar. 1, 2017, for International Application No. PCT/US2016/000128, 9 pages.

(Continued)

*Primary Examiner* — Heidi Reese
(74) *Attorney, Agent, or Firm* — Seed Intellectual Property Law Group LLP

(57) ABSTRACT

Compounds having the following formula (I): and pharmaceutically acceptable salts thereof, wherein A, B, D, E and $R_1$ are as defined herein, are provided. Methods comprising the use of such compounds for the treatment of neurological disorders, such as pantothenate kinase-associated neurodegeneration, and pharmaceutical compositions containing such compounds, and their use in the treatment of neurological disorders, also are provided.

Formula I

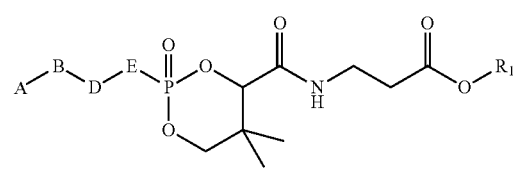

22 Claims, No Drawings

(56) References Cited

OTHER PUBLICATIONS

International Search Report and Written Opinion, dated Jan. 29, 2015, for International Application No. PCT/US2014/062451, 11 pages.
International Search Report, dated Jul. 4, 2013, for International Application No. PCT/US2013/038458, 4 pages.
Jackowski et al., "Metabolism of 4'-Phosphopantetheine in *Escherichia coli*," *Journal of Bacteriology* 158(1):115-120, 1984.
Madela et al., "Progress in the development of anti-hepatitis C virus nucleoside and nucleotide prodrugs," *Future Med. Chem.* 4(5):625-650, 2012.
McGuigan et al., "Aryl Phosphoramidate Derivatives of d4T Have Improved Anti HIV Efficacy in Tissue Culture and May Act by the Generation of a Novel Intracellular Metabolite," *J. Med. Chem.* 39:1748-1753, 1996.
Pellecchia et al., "The diverse phenotype and genotype of pantothenate kinase-associated neurodegeneration," *Neurology* 64:1810-1812, 2005.
Gregory et al., "Neurodegeneration With Brain Iron Accumulation," *Orphanet Encyclopedia*, Sep. 2004, 9 pages.
Leonardi et al., "Coenzyme A: Back in Action," *Progress in Lipid Research* 44:125-153, 2005.

\* cited by examiner

CYCLIC PHOSPHATES AND CYCLIC PHOSPHORAMIDATES FOR THE TREATMENT OF NEUROLOGIC DISORDERS

BACKGROUND

Technical Field

The present disclosure relates to cyclic phosphates and cyclic phosphoramidates, pharmaceutical compositions containing such compounds, and their use in the treatment of neurologic disorders (such as pantothenate kinase-associated neurodegeneration).

Description of the Related Art

Pantothenate kinase-associated neurodegeneration (PKAN) is a form of neurodegeneration with brain iron accumulation (NBIA) that causes extrapyramidal dysfunction (e.g., dystonia, rigidity, choreoathetosis) (A. M. Gregory and S. J. Hayflick, "Neurodegeneration With Brain Iron Accumulation," *Orphanet Encyclopedia*, September 2004). PKAN is thought to be a genetic disorder resulting from lack of the enzyme pantothenate kinase, which is responsible for the conversion of pantothenic acid (vitamin B5) to 4'-phosphopantothenic acid. 4'-Phosphopantothenic acid is subsequently converted into Coenzyme A (CoA) (as shown below) (R. Leonardi, Y.-M. Zhang, C. O. Rock, and S. Jackowski, "Coenzyme A: Back In Action," *Progress in Lipid Research*, 2005, 44, 125-153).

In particular, pantothenic acid is converted to 4'-phosphopantothenic acid via the enzyme pantothenate kinase (PANK), which is converted to 4'-phosphopantothenoylcysteine via the enzyme 4'-phosphopantothenoylcysteine synthase (PPCS), and subsequently decarboxylated to 4'-phosphopantetheine via 4'-phosphopantothenoylcysteine decarboxylase (PPCDC). 4'-phosphopantetheine is then appended to adenosine by the action of phosphopantethine adenyltransferase (PPAT) to afford dephospho CoA, which is finally converted to coenzyme A (CoA) via dephospho-CoA kinase (DPCK).

Classic PKAN usually presents in a child's first ten to fifteen years, though there is also an atypical form that can occur up to age 40. PKAN is a progressively degenerative disease that leads to loss of musculoskeletal function with a devastating effect on quality of life.

One approach to treating PKAN could be to administer 4'-phosphopantothenic acid. This approach has been mentioned in the literature, but it has been recognized that the highly charged molecule would not be able to permeate the lipophilic cell membrane (C. J. Balibar, M. F. Hollis-Symynkywicz, and J. Tao, "Pantethine Rescues Phosphopantothenoylcysteine Synthetase And Phosphopantothenoylcysteine Decarboxylase Deficiency In *Escherichia Coli* But Not In *Pseudomonas aeruginosa*," *J. Bacteriol.*, 2011, 193, 3304-3312).

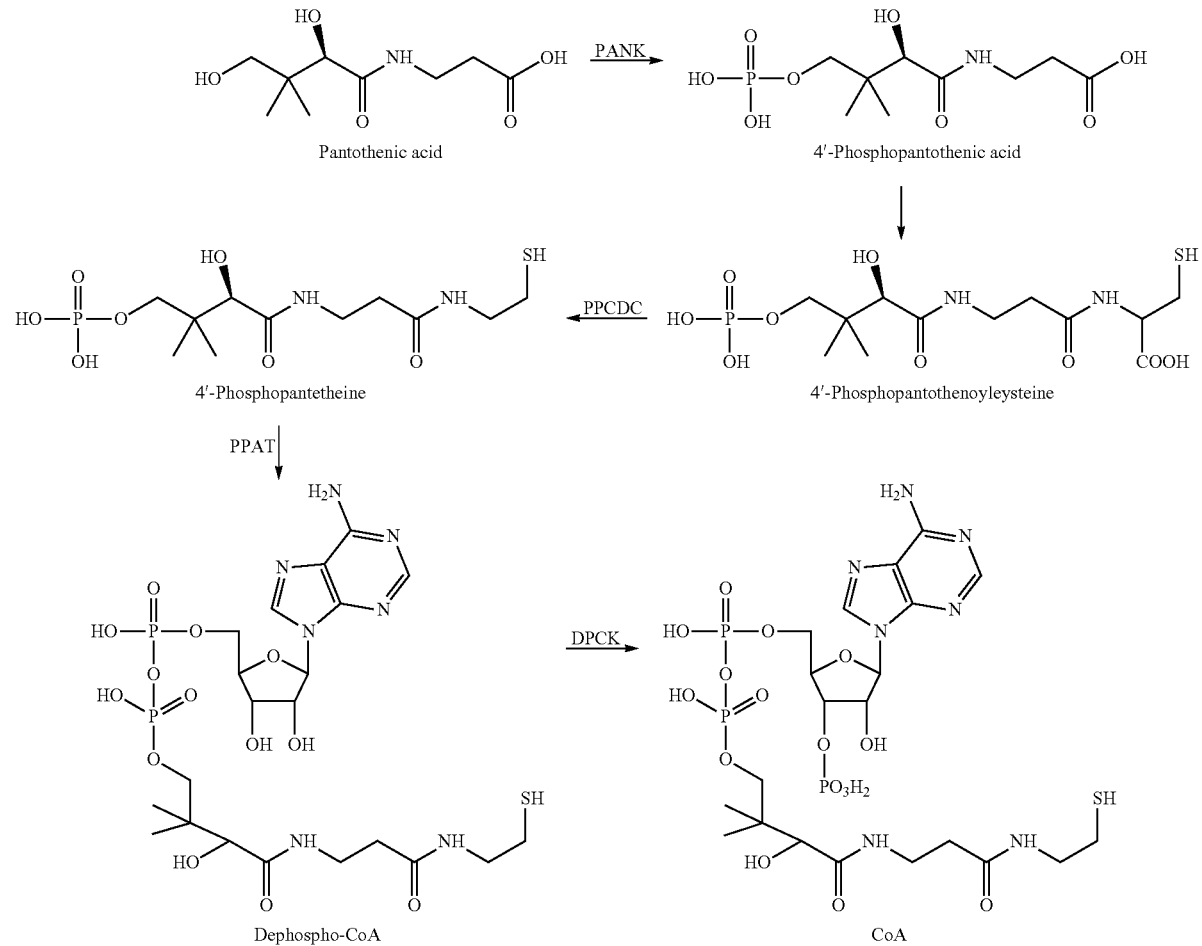

BRIEF SUMMARY

In certain aspects, the present invention is directed to compounds having the following structure (I):

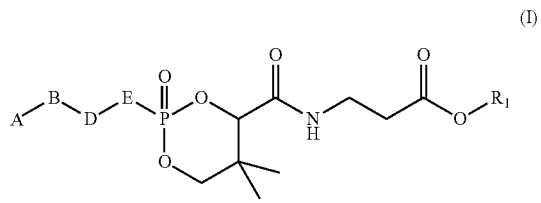

and pharmaceutically acceptable salts thereof, wherein A, B, D, E and $R_1$ are as defined herein.

The present invention also is directed to pharmaceutical compositions comprising a compound of Formula I, or a pharmaceutically acceptable salt thereof, and a pharmaceutically acceptable carrier, diluent or excipient.

The present invention also provides a method of increasing Coenzyme A levels in a subject in need thereof, the method comprising administering to the subject an effective amount of a compound of Formula I, or a pharmaceutically acceptable salt thereof.

The present invention also provides a method of treating a subject having a disorder associated with pantothenate kinase enzyme deficiency, the method comprising administering to a subject in need thereof an effective amount of a compound of Formula I, or a pharmaceutically acceptable salt thereof. In some embodiments, the disorder is pantothenate kinase associated neurodegeneration.

These and other aspects of the present invention will become apparent upon reference to the following detailed description. All references disclosed herein are hereby incorporated by reference in their entirety as if each was incorporated individually.

DETAILED DESCRIPTION

The instant invention provides cyclic phosphates and cyclic phosphoramidates. In some embodiments, compounds, pharmaceutical compositions, and methods of use are provided.

In the following description, certain specific details are set forth in order to provide a thorough understanding of various embodiments of the invention. However, one skilled in the art will understand that the invention may be practiced without these details.

Unless defined otherwise, all technical and scientific terms used herein have the same meaning as is commonly understood by one of skill in the art to which this invention belongs. As used herein, certain items may have the following defined meanings.

Unless the context requires otherwise, throughout the present specification and claims, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and claims, the singular for "a," "an," and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

As used herein, "about" and "approximately" generally refer to an acceptable degree of error for the quantity measured, given the nature or precision of the measurements. Typical, exemplary degrees of error may be within 20%, 10%, or 5% of a given value or range of values. Alternatively, and particularly in biological systems, the terms "about" and "approximately" may mean values that are within an order of magnitude, potentially within 5-fold or 2-fold of a given value. When not explicitly stated, the terms "about" and "approximately" mean equal to a value, or within 20% of that value.

As used herein, numerical quantities are precise to the degree reflected in the number of significant figures reported. For example, a value of 0.1 is understood to mean from 0.05 to 0.14. As another example, the interval of values 0.1 to 0.2 includes the range from 0.05 to 0.24.

The term "alkyl" refers to a straight or branched hydrocarbon chain radical consisting solely of carbon and hydrogen atoms, containing no unsaturation. Unless otherwise specified, the term "alkyl" refers to a group having from one to eight carbon atoms (for example, one to six carbon atoms (i.e., $C_1$-$C_6$), or one to four carbon atoms (i.e., $C_1$-$C_4$)), and which is attached to the rest of the molecule by a single bond. Examples of alkyl groups include, but are not limited to, methyl, ethyl, n-propyl, i-propyl, n-butyl, t-butyl, s-hntyl, n-pentyl, nenpentyl and s-pentyl.

The term "alkenyl" refers to an aliphatic hydrocarbon group containing at least one carbon-carbon double bond and which may be a straight or branched chain. Unless otherwise specified, the term "alkenyl" refers to a group having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond. Unless otherwise specified, the term "alkynyl" refers to a group having in the range of 2 up to about 12 carbon atoms (for instance, 2 to 10 carbon atoms), e.g., ethynyl, propynyl, and butynyl.

The term "cycloalkyl" denotes a non-aromatic mono or multicyclic ring system of about 3 to 12 carbon atoms such as cyclopropyl, cyclobutyl, cyclopentyl, and cyclohexyl.

The term "cycloalkylalkyl" refers to a cyclic ring-containing group containing in the range of about 3 up to 8 carbon atoms directly attached to an alkylene group which is then attached to the main structure at any carbon in the alkyl group that results in the creation of a stable structure such as cyclopropylmethyl, cyclobutylethyl, and cyclopentylethyl.

The term "cycloalkenyl" refers to a non-aromatic mono or multicyclic ring system of about 3 to 12 carbon atoms and comprising at least one carbon-carbon double bond within the ring system. Examples of cycloalkenyls include, but are not limited to, cyclopropenyl, cyclobutenyl, cyclopentenyl, cyclohexenyl, and the like.

The term "cycloalkenylalkyl" refers to a radical of the form —$R_aR_b$, wherein $R_a$ is an alkylene group as defined herein and $R_b$ is a cycloalkenyl group as defined herein. Examples of cycloalkenylalkyls include, but are not limited to, cyclopropenylmethyl, cyclobutenylmethyl, cyclopentenymethyl, or cyclohexenylmethyl, and the like.

The term "aryl" refers to a mono- or multi-cyclic aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkylene group as defined herein, e.g., —$CH_2C_6H_5$, and —$C_2H_4C_6H_5$.

The term "heteroatoms" as used herein refers to non-carbon and non-hydrogen atoms, capable of forming covalent bonds with carbon, and is not otherwise limited. Typical heteroatoms are N, O, P, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When phrases such as "heteroatoms selected from the group consisting of O, NH, NR' and S," or "[variable] is O, S . . . " are used, they are understood to encompass all of the sulfide, sulfoxide, and sulfone oxidation states of sulfur.

The term "heterocyclyl" refers to a non-aromatic 3- to 15-member ring radical, which consists of carbon atoms and at least one heteroatom of nitrogen, phosphorus, oxygen, or sulfur. The heterocyclic ring radical may be a mono-, bi-, tri-, or tetracyclic ring system, which may include fused, bridged or spiro ring systems, and the nitrogen, phosphorus, carbon, oxygen, or sulfur atoms in the heterocyclic ring radical may be optionally oxidized to various oxidation states. In addition, the nitrogen atom may be optionally quaternized.

The term "heterocyclylalkyl" refers to a radical of the formula —$R_aR_c$ where $R_a$ is an alkylene group as defined above and $R_c$ is a heterocyclyl group as defined above, e.g., —$CH_2$-heterocyclyl, and —$C_2H_4$-heterocyclyl.

The term "heteroaryl" refers to an optionally substituted 5- to 14-member aromatic ring having one or more heteroatoms of N, O, or S as ring atoms. The heteroaryl may be a mono-, bi- or tricyclic ring system. Examples of such heteroaryl ring radicals include, but are not limited to, oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl, and isoquinolyl.

The term "heteroarylalkyl" refers to a radical of the formula —$R_aR_d$ where $R_a$ is an alkylene group as defined herein and $R_d$ is a heteroaryl group as defined above, e.g., —$CH_2$-heteroaryl, and —$C_2H_4$-heteroaryl.

When two R groups are said to be joined together to form a ring, it is meant that together with the carbon atom or a non-carbon atom (e.g., nitrogen atom), to which they are bonded, they may furthermore form a ring system. In general, they are bonded to one another to form a 3- to 7-membered ring, or a 5- to 7-membered ring. Non-limiting specific examples are cyclopentyl, cyclohexyl, cycloheptyl, piperidinyl, piperazinyl, pyrolidinyl, pyrrolyl, and pyridinyl.

The term "pantothenic acid" as used herein refers to both the protonated form and the deprotonated form (i.e., pantothenate) of pantothenic acid. Likewise, the term "4'-phosphopantothenic acid" as used herein refers to both the protonated form and the deprotonated form (i.e., 4'-phosphopantothenate) of 4'-phosphopantothenic acid.

By a "ring system" as the term is used herein is meant a moiety comprising one, two, three, or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

The term "spiro-substituted cycloalkyl" refers to a cycloalkyl ring in which two ring atoms are bound to the same atom of the substituted group. Examples of spiro-substituted cycloalkyl groups include the following: 1,1-dimethylcyclopropanyl, 1-methylcyclopentanyl-1-carboxylic acid, and 1-aminocyclopropanyl-1-carboxamide.

The term "heterocyclic ring" refers to a ring system as defined above consisting of carbon atoms and at least one heteroatom of nitrogen, phosphorus, oxygen, or sulfur. The heterocyclic ring radical may be a mono-, bi-, tri-, or tetracyclic ring system, which may include fused, bridged or spiro ring systems, and the nitrogen, phosphorus, carbon, oxygen, or sulfur atoms in the heterocyclic ring radical may be optionally oxidized to various oxidation states. In addition, the nitrogen atom may be optionally quaternized.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain.

"Cycloalkylene" refers to a divalent cycloalkyl radical.

"Alkylcarbonyl" refers to a radical of the formula —C(=O)$R_e$, where $R_e$ is an alkyl group as defined herein.

The term "alkoxy" refers to a radical of the formula —O$R_e$ where $R_e$ is an alkyl group as defined above containing one to twelve carbon atoms. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The term "carbonyl," refers to a —C(=O)— group.

As used herein, the term "halogen" refers to a fluorine, chlorine, bromine, or iodine atom. As used herein, the term "halo" refers to a fluoro, chloro, bromo, or iodo radical.

"Hydroxy" or "hydroxyl" refers to the —OH radical.

The term "oxo" refers to the =O substituent.

The term "amino" refers to the —$NH_2$ radical.

"Hydrazone" refers to the —N $NH_2$ substituent.

"Imino" refers to the =NH substituent.

"Nitro" refers to the —$NO_2$ radical.

"Cyano" refers to the —CN radical.

"Thioxo" refers to the =S substituent.

"Aminoalkyl" refers to a radical of the formula —$R_a$—$NR_fR_f$ where $R_a$ is an alkylene group as defined herein, and each $R_f$ is independently a hydrogen, an alkyl group, an aryl group, or a heteroaryl group.

"Alkylamino" and "dialkylamino" refer to radicals of the formula —NHR$_e$ or —NR$_e$R$_e$ where each R$_e$ is, independently, an alkyl group as defined above containing one to twelve carbon atoms. Examples include, but are not limited to, methylamino, ethylamino, dimethylamino, diethylamino, and the like.

"Alkylaminoalkyl" refers to an alkyl group having one alkylamino substituent. The alkylamino substituent can be on a tertiary, secondary or primary carbon. "Dialkylaminoalkyl" refers to an alkyl group having at dialkylamino substituent.

"Aminocarbonyl" refers to a radical of the formula —C(=O)NH$_2$.

"Alkylaminocarbonyl" refers to a radical of the formula —C(=O)NR$_e$R$_e$, where each R$_e$ is independently an alkyl group as defined herein. Unless stated otherwise specifically in the specification, an alkylaminocarbonyl group may be optionally substituted as described below.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Unless stated otherwise specifically in the specification, all of the above groups may be unsubstituted or substituted.

The term "substituted," unless otherwise specified, refers to substitution with any one or any combination of the following substituents: hydrogen, hydroxy, halogen, carboxyl, cyano, nitro, oxo (=O), thio (=S), alkyl, alkoxy, alkenyl, alkynyl, aryl, arylalkyl, cycloalkyl, cycloalkenyl, aryl, heterocyclyl, heteroaryl, —COOR$^x$, —C(O)R$^x$, —C(S) R$^x$, —C(O)NR$^x$R$^y$, —C(O)ONR$^x$R$^y$, —NR$^y$R$^z$, —NR$^x$-CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$ NR$^x$R$^y$—, —OR$^x$, —OR$^x$C(O)NR$^y$R$^z$, —OR$^x$C(O)OR$^y$—, —OC(O) R$^x$, —OC(O)NR$^x$R$^y$, —R$^x$NR$^y$C(O)R$^z$, —R$^x$OR$^y$, —R$^x$C(O) OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$, and R$^z$ in each of the above groups can be independently hydrogen atom, alkyl, alkoxy, alkenyl, alkynyl, aryl, arylalkyl, cycloalkyl, cycloalkenyl, amino, aryl, heteroaryl, heterocyclyl, or any two of R$^x$, R$^y$, and R$^z$ may be joined to form a saturated or unsaturated 3- to 10-member ring, which may optionally include heteroatoms which may be same or different and are O, N, P, or S.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

The term "subject" refers to a mammal, such as a domestic pet (for example, a dog or cat), or human. Preferably, the subject is a human.

The phrase "effective amount" refers to the amount which, when administered to a subject or patient for treating a disease, is sufficient to effect such treatment for the disease.

The term "dosage unit form" is the form of a pharmaceutical product, including, but not limited to, the form in which the pharmaceutical product is marketed for use. Examples include, but are not limited to, pills, tablets, capsules, and liquid solutions and suspensions.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, "deficiency" of an enzyme refers to the absence of or reduced levels or activity of the enzyme, or the presence of a defective enzyme having decreased activity or function.

As used herein, "deficiency" of a metabolic product refers to the absence of or reduced levels of a metabolic product.

As used herein, "overexpression" of an enzyme refers to an excess in production or activity of the enzyme.

As used herein, "downstream product" of an enzyme refers to substance for which the referenced enzyme is a synthetic precursor. For example, acetyl coenzyme A ("Acetyl-CoA") is a downstream product of Coenzyme A.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, caffeine, and meglumine.

The invention disclosed herein is also meant to encompass all pharmaceutically acceptable compounds of the structures disclosed herein being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{33}P$, $^{35}S$, $^{18}F$, $^{36}Cl$, $^{123}I$, and $^{125}I$, respectively. Certain isotopically-labeled compounds of structures disclosed herein, for example, those incorporating a radioactive isotope, are useful in drug and/or substrate tissue distribution studies. These radiolabeled compounds could be useful to help determine or measure the effectiveness of the compounds, by characterizing, for example, the site or mode of action, or binding affinity to a pharmacologically important site of action. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples. "Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents, or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention, or their pharmaceutically acceptable salts, may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention includes all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. For example, the carbon and phosphorous atoms marked with an "*" in the following structure are stereocenters. All stereoisomers of the compounds disclosed herein are also included in the scope of the invention.

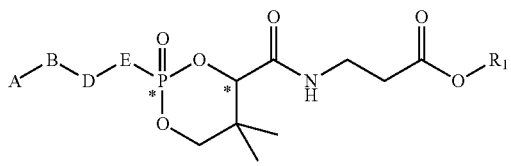

The various substituents (e.g., $R_1$, D, B, A) also include stereocenters in some embodiments and all such stereocenters and stereoisomeric mixtures are included in the scope of the present invention.

The present invention includes tautomers of any of the disclosed compounds.

Additional definitions are set forth throughout this disclosure.

Compounds

In certain aspects, the present invention provides compounds having the formula (I):

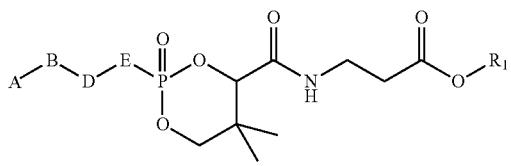

Formula I or a pharmaceutically acceptable salt thereof, wherein
E is O or $NR_2$;
D is absent, aryl, $C_1$-$C_3$ alkylene, $C_1$-$C_3$ alkylene substituted with $R_3$, C(O)O(alkylene) or C(O)O(alkylene) substituted with $R_3$;
B is absent, $C_1$-$C_3$ alkylene, $C_3$-$C_6$ cycloalkylene, ($C_1$-$C_3$ alkylene)$NR_2$, C(O)$NR_2$(alkylene), aryl, heteroaryl or heterocyclyl, wherein each of said $C_1$-$C_3$ alkylene, $C_3$-$C_6$ cycloalkylene, ($C_1$-$C_3$ alkylene)$NR_2$, C(O)$NR_2$(alkylene), aryl, heteroaryl and heterocyclyl is unsubstituted or substituted with $R_6$ or $R_5$;
A is absent, H, $OR_5$, $R_5$C(O), $R_5$OC(O), $R_5$OC(O)O, $R_5$C(O)O, $R_5$C(O)S, $NR_2R_5$C(O), $R_5$C(O)$NR_2$, $R_5$S(O)$NR_2$, $R_5$SO$_2NR_2$, $NR_2R_5$, CN, $C_1$-$C_6$ alkyl, $C_3$-$C_6$ cycloalkyl, heterocyclyl, aryl or heteroaryl, wherein each of said $C_1$-$C_6$ alkyl, $C_3$-$C_6$ cycloalkyl, heterocyclyl, aryl and heteroaryl is unsubstituted or substituted with $R_6$;
$R_1$ is H, $C_1$-$C_6$ alkyl, aryl, arylalkyl, heteroaryl, heteroarylalkyl, heterocyclyl, heterocyclylalkyl, $C_3$-$C_6$ cycloalkyl, or cycloalkylalkyl, wherein each of said $C_1$-$C_6$ alkyl, aryl, arylalkyl, heteroaryl, heteroarylalkyl, heterocyclyl, heterocyclylalkyl, $C_3$-$C_6$ cycloalkyl, and cycloalkylalkyl is unsubstituted or substituted with $R_6$;
$R_2$ is H or $C_1$-$C_6$ alkyl;
$R_3$ is H, $C_1$-$C_6$ alkyl, hydroxy, amino, arylalkyl, heteroarylalkyl or $C_3$-$C_6$ cycloalkyl, wherein each of said $C_1$-$C_6$ alkyl, arylalkyl, heteroarylalkyl and $C_3$-$C_6$ cycloalkyl is unsubstituted or substituted with $R_4$;
$R_4$ is $C_1$-$C_6$ alkyl, $C_1$-$C_6$ alkoxy, hydroxy or amino;
$R_5$ is H, $C_1$-$C_6$ alkyl, $C_1$-$C_6$ alkoxy, aryl, arylalkyl, heteroaryl, heteroarylalkyl, heterocyclyl, heterocyclylalkyl, $C_3$-$C_6$ cycloalkyl, cycloalkylalkyl, amino, alkylamino, dialkylamino, aminoalkyl, alkylaminoalkyl or dialkylaminoalkyl, wherein each of said $C_1$-$C_6$ alkyl, $C_1$-$C_6$ alkoxy, aryl, arylalkyl, heteroaryl, heteroarylalkyl, heterocyclyl, heterocyclylalkyl, amino, alkylamino, dialkylamino, aminoalkyl, alkylaminoalkyl and dialkylaminoalkyl is unsubstituted or substituted with $R_6$ or $R_8$;
$R_6$ is $C_1$-$C_6$ alkyl, $C_1$-$C_6$ alkoxy, hydroxyl, amino, halo, oxo, CN, $NO_2$, $SF_5$, heterocyclyl, heterocyclylalkyl, aryl, arylalkyl, $C_3$-$C_6$ cycloalkyl, $C_3$-$C_4$ spiro-substituted cycloalkyl, cycloalkylalkyl, $SO_2R_7$, $R_7$C(O)S, $R_7$C(O), $R_7$C(O)$NR_2$, $R_7$OC(O) or $R_7$OC(O)$NR_2$, wherein each of said $C_1$-$C_6$ alkyl, $C_1$-$C_6$ alkoxy, heterocyclyl, heterocyclylalkyl, aryl, arylalkyl, $C_3$-$C_6$ cycloalkyl, $C_3$-$C_4$ spiro-substituted cycloalkyl and cycloalkylalkyl is unsubstituted or substituted with $R_7$;
$R_7$ is H, $C_1$-$C_6$ alkyl, $C_1$-$C_6$ alkoxy, hydroxyl, halo, oxo, CN, $NO_2$, $SF_5$, arylakyl, heteroarylalkyl, amino, alkylamino or dialkylamino; and
$R_8$ is $R_6$OC(O) or $R_6$OC(O)$NR_2$;
or
D is absent, and A, B, and E together form a 6-membered heterocyclic or heteroaryl ring, wherein said heterocyclic or heteroaryl ring is unsubstituted or substituted with $R_6$, In some embodiments, compounds of Formula I of the present invention have (R)-absolute stereochemistry at the carbon atom marked with an "*" in the following structure:

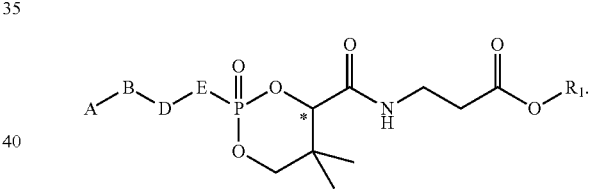

In certain embodiments, a compound having Formula I wherein E is $NR_2$ is provided. In some embodiments of the compound of Formula I, E is $NR_2$ and $R_2$ is hydrogen.

In some embodiments of the compound of Formula I, E is $NR_2$ and $R_1$ is methyl.

Still another embodiment of the invention is a compound of Formula I wherein E is $NR_2$ and D is $C_1$-$C_3$ alkylene or $C_1$-$C_3$ alkylene substituted with $R_3$. In further embodiments, E is $NR_2$ and D is methylene substituted with $R_3$. In still other embodiments, E is $NR_2$ and D is $C_1$-$C_3$ alkylene or $C_1$-$C_3$ alkylene substituted with $R_3$, wherein $R_3$ is $C_1$-$C_6$ alkyl, $C_3$-$C_6$ cycloalkyl, arylalkyl, arylalkyl substituted with $R_4$, or heteroarylalkyl. In still other embodiments, E is $NR_2$ and D is $C_1$-$C_3$ alkylene or $C_1$-$C_3$ alkylene substituted with $R_3$, wherein $R_3$ is $C_1$-$C_6$ alkyl or heteroarylalkyl.

Yet another embodiment of the invention is a compound of Formula I, wherein E is $NR_2$ and B is absent, heterocyclyl, or heterocyclyl substituted with $R_6$. In specific embodiments, E is $NR_2$ and B is absent. In certain other embodiments, E is $NR_2$ and B is heterocyclyl or heterocyclyl substituted with $R_6$.

Still other embodiments provide a compound of Formula I wherein E is $NR_2$ and A is $C_1$-$C_6$ alkyl, $C_3$-$C_6$ cycloalkyl, heterocyclyl, aryl or heteroaryl, wherein each of said $C_1$-$C_6$ alkyl, $C_3$-$C_6$ cycloalkyl, heterocyclyl, aryl and heteroaryl is substituted with $R_6$.

In yet other embodiments, the invention provides a compound of Formula I wherein E is $NR_2$ and A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl.

In still other embodiments, a compound of Formula I is provided wherein E is $NR_2$ and A is $OR_5$, $R_5C(O)$, $R_5OC(O)$, $R_5OC(O)O$, $R_5C(O)O$, $NR_2R_5C(O)$, $R_5C(O)NR_2$, $R_5S(O)NR_2$ or $R_5SO_2NR_2$.

In still other particular embodiments, the invention provides a compound of Formula I wherein E is $NR_2$ and A is $OR_5$, $R_5C(O)$, $R_5OC(O)$ or $R_5C(O)O$.

In further embodiments, a compound of Formula I wherein E is $NR_2$ and A is $R_5OC(O)$ or $R_5C(O)O$ is provided. Compounds of Formula I wherein E is $NR_2$ and A is $R_5OC(O)$ are also within the scope of the invention.

Still another embodiment of the invention is a compound of Formula I wherein E is $NR_2$ and A is $NR_2R_5C(O)$ or $R_5C(O)NR_2$.

Still another embodiment of the invention is a compound of Formula I wherein E is $NR_2$ and A is $R_5S(O)NR_2$ or $R_5SO_2NR_2$.

Still another embodiment of the invention is a compound of Formula I wherein E is $NR_2$ and A is heterocyclyl, aryl or heteroaryl.

Yet another embodiment of the invention is a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is H, $C_1$-$C_6$ alkyl, $C_1$-$C_6$ alkoxy, aryl, arylalkyl, heteroaryl, heteroarylalkyl, heterocyclyl, heterocyclylalkyl, $C_3$-$C_6$ cycloalkyl, cycloalkylalkyl, amino, alkylamino, dialkylamino, aminoalkyl, alkylaminoalkyl or dialkylaminoalkyl.

In some embodiments, the invention provides a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is $C_1$-$C_6$ alkyl, $C_1$-$C_6$ alkoxy, aryl, arylalkyl, heteroaryl, heteroarylalkyl, heterocyclyl, heterocyclylalkyl, $C_3$-$C_6$ cycloalkyl, cycloalkylalkyl, amino, alkylamino, dialkylamino, aminoalkyl, alkylaminoalkyl or dialkylaminoalkyl, wherein each of said $C_1$-$C_6$ alkyl, $C_1$-$C_6$ alkoxy, aryl, arylalkyl, heteroaryl, heteroarylalkyl, heterocyclyl, heterocyclylalkyl, amino, alkylamino, dialkylamino, aminoalkyl, alkylaminoalkyl and dialkylaminoalkyl is substituted with $R_6$.

In further embodiments, the invention provides a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is $C_1$-$C_6$ alkyl, aryl, arylalkyl, heteroaryl or heteroarylalkyl.

In still further embodiments, the invention provides a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is $C_1$-$C_6$ alkyl, arylalkyl or heteroarylalkyl.

Certain embodiments of the invention provide a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)$ $NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is $C_1$-$C_6$ alkyl or arylalkyl.

Still further embodiments of the invention provide a compound of Formula I wherein E is $NR_2$; A is $OR_5$, $R_5C(O)$, $R_5OC(O)$, $R_5C(O)O$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl; and $R_5$ is $C_1$-$C_6$ alkyl, arylalkyl substituted with $R_6$ or heteroarylalkyl substituted with $R_6$.

Embodiments of the invention also provide a compound of Formula I wherein $R_6$ is $C_1$-$C_6$ alkyl, halo, oxo or $R_7C(O)$. In some embodiments, $R_6$ is $C_1$-$C_6$ alkyl or oxo.

In some embodiments, a compound of Formula I wherein E is O is provided.

Another embodiment of the invention is a compound of Formula I wherein E is O and D is absent, aryl, $C_1$-$C_3$ alkylene, $C(O)O(alkylene)$ or $C_1$-$C_3$ alkylene substituted with $R_3$. Still other embodiments provide a compound of Formula I wherein E is O and D is $C_1$-$C_3$ alkylene or $C_1$-$C_3$ alkylene substituted with $R_3$. Certain embodiments provide a compound of Formula I wherein E is O and D is $C_1$-$C_3$ alkylene. Certain other embodiments provide a compound of Formula I wherein E is O and D is aryl or $C(O)O(alkylene)$.

Still another embodiment of the invention is a compound of Formula I wherein E is O and B is absent, $C_1$-$C_3$ alkylene, $C_3$-$C_6$ cycloalkylene, $C(O)NR_2(alkylene)$ or heterocyclyl.

Still another embodiment of the invention is a compound of Formula I wherein E is O and B is $C_1$-$C_3$ alkylene, $C_1$-$C_3$ alkylene substituted with $R_6$, ($C_1$-$C_3$ alkylene)$NR_2$ or ($C_1$-$C_3$ alkylene)$NR_2$ substituted with $R_8$. In a particular embodiment, $R_8$ is $R_6OC(O)$.

Still another embodiment of the invention is a compound of Formula I wherein E is O and A is H, $OR_5$, $R_5OC(O)$, $R_5OC(O)O$, $R_5C(O)O$, $R_5C(O)S$, $NR_2R_5C(O)$, $R_5C(O)NR_2$, $R_5S(O)NR_2$, $R_5SO_2NR_2$, $NR_2R_5$, $C_1$-$C_6$ alkyl, $C_3$-$C_6$ cycloalkyl, heterocyclyl, aryl or heteroaryl. Some embodiments provide a compound of Formula I wherein E is O and A is H, $R_5OC(O)$, $R_5OC(O)O$, $R_5C(O)O$, $R_5C(O)S$, aryl or heteroaryl. Certain embodiments provide a compound of Formula I wherein E is O and A is $R_5OC(O)$, $R_5C(O)O$, $R_5C(O)S$, or $R_5OC(O)O$. In some embodiments, a compound of Formula I wherein E is O and A is $R_5C(O)O$ or $R_5OC(O)$ is provided.

Still another embodiment of the invention is a compound of Formula I wherein E is O and $R_5$ is H, $C_1$-$C_6$ alkyl, aryl, arylalkyl, heteroaryl, heteroarylalkyl, heterocyclyl, heterocyclylalkyl, heterocyclylalkyl substituted with $R_6$ or heteroaryl substituted with $R_6$ or $R_8$. Some embodiments provide a compound of Formula I wherein E is O and $R_5$ is $C_1$-$C_6$ alkyl, $C_1$-$C_6$ alkyl substituted with $R_8$, aryl or heteroaryl. In certain embodiments, a compound of Formula I, wherein E is O and $R_5$ is $C_1$-$C_6$ alkyl or $C_1$-$C_6$ alkyl substituted with $R_8$, is provided.

In a still further embodiment, the present disclosure provides a compound of Formula I, wherein $R_5$ is $C_1$-$C_6$ alkyl, aryl, arylalkyl, heteroaryl, heteroarylalkyl, heterocyclyl, or heterocyclylalkyl, wherein each of said $C_1$-$C_6$ alkyl, aryl, arylalkyl, heteroaryl, heteroarylalkyl, heterocyclyl, or heterocyclylalkyl is substituted with $R_8$: and $R_8$ is $R_6OC(O)$ $NR_3$.

Still further embodiments of the invention provide a compound of Formula I wherein E is O; $R_5$ is H, $C_1$-$C_6$ alkyl, aryl, arylalkyl, heteroaryl, heteroarylalkyl, heterocyclyl, heterocyclylalkyl, heterocyclylalkyl substituted with $R_6$ or heteroaryl substituted with $R_6$, and $R_6$ is $C_1$-$C_6$ alkyl, oxo, CN, heterocyclylalkyl, arylalkyl, $C_3$-$C_4$ spiro-substituted cycloalkyl, $SO_2R_7$ or $R_7C(O)$. Still further embodiments of the invention provide a compound of Formula I wherein E is O; $R_5$ is H, $C_1$-$C_6$ alkyl, aryl, arylalkyl, heteroaryl, heteroarylalkyl, heterocyclyl, heterocyclylalkyl, heterocyclylalkyl substituted with $R_6$ or heteroaryl substituted with $R_6$; and $R_6$ is $C_1$-$C_6$ alkyl or oxo. Still further embodiments of the invention provide a compound of Formula I wherein E is O; $R_5$ is H, $C_1$-$C_6$ alkyl, aryl, arylalkyl, heteroaryl, heteroarylalkyl, heterocyclyl, heterocyclylalkyl, heterocyclylalkyl substituted with $R_6$ or heteroaryl substituted with $R_6$; and $R_6$ is alkyl or arylalkyl. Still further embodiments of the invention provide a compound of Formula I wherein E is O; $R_5$ is H, $C_1$-$C_6$ alkyl, aryl, arylalkyl, heteroaryl, heteroarylalkyl, heterocyclyl, heterocyclylalkyl, heterocyclylalkyl substituted with $R_6$ or heteroaryl substituted with $R_6$; and $R_6$ is $C_1$-$C_6$ alkyl.

In some embodiments, a compound of Formula I is provided wherein $R_1$ is H, $C_1$-$C_6$ alkyl, heteroarylalkyl or heterocyclyl, wherein each of said $C_1$-$C_6$ alkyl, heteroarylalkyl, and heterocyclyl is unsubstituted or substituted with $R_6$.

In one embodiment, a compound of Formula I is provided wherein: E is $NR_2$; D is $C_1$-$C_3$ alkylene or $C_1$-$C_3$ alkylene substituted with $R_3$; B is absent; A is $OR_5$, $R_5C(O)$, $R_5OC(O)$ or $R_5C(O)O$; $R_1$ is H or $C_1$-$C_6$ alkyl unsubstituted or substituted with $R_6$; $R_2$ is H; $R_3$ is $C_1$-$C_6$ alkyl or arylalkyl; and $R_5$ is $C_1$-$C_6$ alkyl, aryl, arylalkyl, heteroaryl, or heteroarylalkyl, wherein each of said aryl, arylalkyl, heteroaryl, or heteroarylalkyl is unsubstituted or substituted with $R_6$.

In yet another embodiment, a compound of Formula I is provided wherein: E is $NR_2$; D is $C_1$-$C_3$ alkylene substituted with $R_3$; B is absent; A is $R_5OC(O)$; $R_1$ is H or $C_1$-$C_6$ alkyl unsubstituted or substituted with $R_6$; $R_2$ is H; $R_3$ is $C_1$-$C_6$ alkyl; and $R_5$ is arylalkyl.

In yet another embodiment, a compound of Formula I is provided, wherein: E is O; D is $C_1$-$C_3$ alkylene or aryl; B is $C_1$-$C_3$ alkylene substituted with $R_6$ or ($C_1$-$C_3$ alkylene)$NR_2$; and A is $R_5OC(O)$, $R_5C(O)O$ or $R_5C(O)S$.

In yet another embodiment, a compound of Formula I is provided, wherein: E is O; D is $C_1$-$C_3$ alkylene or aryl; B is $C_1$-$C_3$ alkylene substituted with $R_6$ or ($C_1$-$C_3$ alkylene)$NR_2$; A is $R_5OC(O)$, $R_5C(O)O$ or $R_5C(O)S$; $R_5$ is $C_1$-$C_6$ alkyl or $C_1$-$C_6$ alkyl unsubstituted or substituted with $R_8$; $R_8$ is $R_6OC(O)NR_2$; and $R_6$ is arylalkyl.

In various different embodiments, the compound has one of the structures set forth in Tables 1-3 below.

TABLE 1

Exemplary amino-acid phosphoramidate compounds.

| No. | Compound | Chemical Name |
|---|---|---|
| 1 | | (2S)-methyl 2-(((4R)-4-((3-methoxy-3-oxopropyl)carbamoyl)-5,5-dimethyl-2-oxido-1,3,2-dioxaphosphinan-2-yl)amino)-3-methylbutanoate |
| 2 | | methyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 3 | | (2S)-3,5-dimethylbenzyl 2-(((4R)-4-((3-methoxy-3-oxopropyl)carbamoyl)-5,5-dimethyl-2-oxido-1,3,2-dioxaphosphinan-2-yl)amino)propanoate |
| 4 | | methyl 3-((2R)-4-((6,8-dimethyl-2-oxido-4H-benzo[d][1,3,2]dioxaphosphinin-2-yl)oxy)-2-hydroxy-3,3-dimethylbutanamido)propanoate |
| 5 | | methyl 3-((4R)-2-(((S)-1-methoxy-1-oxopropan-2-yl)amino)-5,5-dimethyl-2-oxido-1,3,2-dioxaphosphinane-4-carboxamido)propanoate |

TABLE 1-continued

Exemplary amino-acid phosphoramidate compounds.

| No. | Compound | Chemical Name |
|---|---|---|
| 6 | | ethyl (2S)-2-[[(4R)-4-[(3-methoxy-3-oxo-propyl)carbamoyl]-5,5-dimethyl-2-oxo-1,3,2-dioxaphosphinan-2-yl]amino]-4-phenyl-butanoate |
| 7 | | 2-ethylbutyl ((4R)-4-((3-methoxy-3-oxopropyl)carbamoyl)-5,5-dimethyl-2-oxido-1,3,2-dioxaphosphinan-2-yl)-L-alaninate |
| 8 | | ethyl ((4R)-4-((3-methoxy-3-oxopropyl)carbamoyl)-5,5-dimethyl-2-oxido-3,3-dioxaphosphinan-2-yl)-L-leucinate |
| 9 | | methyl ((4R)-4-((3-methoxy-3-oxopropyl)carbamoyl)-5,5-dimethyl-2-oxido-1,3,2-dioxaphosphinan-2-yl)-L-phenylalaninate |
| 10 | | benzyl ((4R)-4-((3-methoxy-3-oxopropyl)carbamoyl)-5,5-dimethyl-2-oxido-1,3,2-dioxaphosphinan-2-yl)-L-phenylalaninate |
| 11 | | benzyl ((4R)-4-((3-methoxy-3-oxopropyl)carbamoyl)-5,5-dimethyl-2-oxido-1,3,2-dioxaphosphinan-2-yl)-L-alaninate |
| 12 | | methyl 3-((4R)-2-(((S)-1-cyclohexyl-2-methoxy-2-oxoethyl)amino)-5,5-dimethyl-2-oxido-1,3,2-dioxaphosphinane-4-carboxamido)propanoate |

TABLE 1-continued

Exemplary amino-acid phosphoramidate compounds.

| No. | Compound | Chemical Name |
|---|---|---|
| 13 | | benzyl ((4R)-4-((3-methoxy-3-oxopropyl)carbamoyl)-5,5-dimethyl-2-oxido-1,3,2-dioxaphosphinan-2-yl)-L-valinate |
| 14 | | methyl 3-((4R)-2-(((S)-2-(tert-butoxy)-1-cyclohexyl-2-oxoethyl)amino)-5,5-dimethyl-2-oxido-1,3,2-dioxaphosphinane-4-carboxamido)propanoate |
| 15 | | tert-butyl (2S)-3-(4-(tert-butoxy)pheny))-2-(((4R)-4-((3-methoxy-3-oxopropyl)carbamoyl)-5,5-dimethyl-2-oxido-1,3,2-dioxaphosphinan-2-yl)amino)propanoate |
| 16 | | methyl 3-((4R)-2-(((R)-1-methoxy-1-oxopropan-2-yl)amino)-5,5-dimethyl-2-oxido-1,3,2-dioxaphosphinane-4-carboxamido)propanoate |
| 17 | | 2-ethylbutyl ((2S,4R)-4-((3-methoxy-3-oxopropyl)carbamoyl)-5,5-dimethyl-2-oxido-1,3,2-dioxaphosphinan-2-yl)-L-alaninate |
| 18 | | methyl ((2R,4R)-5,5-dimethyl-2-oxido-4-((3-oxo-3-(pyridin-4-ylmethoxy)propyl)carbamoyl)-1,3,2-dioxaphosphinan-2-yl)-L-alaninate or methyl ((2S,4R)-5,5-dimethyl-2-oxido-4-((3-oxo-3-(pyridin-4-ylmethoxy)propyl)carbamoyl)-1,3,2-dioxaphosphinan-2-yl)-L-alaninate |
| 19 | | methyl ((4R)-5,5-dimethyl-2-oxido-4-((3-oxo-3-(2-(pyrrolidin-1-yl)ethoxy)propyl)carbamoyl)-1,3,2-dioxaphosphinan-2-yl)-L-alaninate |
| 20 | | (2S)-methyl 2-(((4R)-5,5-dimethyl-2-oxido-4-((3-oxo-3-(pyridin-4-ylmethoxy)propyl)carbamoyl)-1,3,2-dioxaphosphinan-2-yl)amino)propanoate |

TABLE 1-continued

Exemplary amino-acid phosphoramidate compounds.

| No. | Compound | Chemical Name |
|---|---|---|
| 21 | | (2S)-methyl 2-(((4R)-5,5-dimethyl-4-((3-((5-methylisoxazol-3-yl)methoxy)-3-oxopropyl)carbamoyl)-2-oxido-1,3,2-dioxaphosphinan-2-yl)amino)propanoate |
| 22 | | methyl ((2R,4R)-5,5-dimethyl-4-((3-((1-methyl-1H-imidazol-4-yl)methoxy)-3-oxopropyl)carbamoyl)-2-oxido-1,3,2-dioxaphosphinan-2-yl)-L-alaninate |
| 22A | | methyl ((4R)-5,5-dimethyl-4-((3-((1-methyl-1H-imidazol-4-yl)methoxy)-3-oxopropyl)carbamoyl)-2-oxido-1,3,2-dioxaphosphinan-2-yl)-L-alaninate |
| 23 | | methyl 3-((4R)-5,5-dimethyl-2-oxido-2-(((S)-1-oxo-1-(((R)-5-oxopyrrolidin-2-yl)methoxy)propan-2-yl)amino)-1,3,2-dioxaphosphinane-4-carboxamido)propanoate |
| 24 | | methyl 3-((4R)-5,5-dimethyl-2-oxido-2-(((S)-1-oxo-1-(pyridin-3-ylmethoxy)propan-2-yl)amino)-1,3,2-dioxaphosphinane-4-carboxamido)propanoate |
| 25 | | (2S)-methyl 2-(((4R)-4-((3-methoxy-3-oxopropyl)carbamoyl)-5,5-dimethyl-2-oxido-1,3,2-dioxaphosphinan-2-yl)amino)-3-(pyridin-3-yl)propanoate |
| 26 | | methyl 3-((4R)-5,5-dimethyl-2-oxido-2-(((R)-1-oxo-1-phenethoxypropan-2-yl)amino)-1,3,2-dioxaphosphinane-4-carboxamido)propanoate |
| 27 | | methyl 3-((4R)-5,5-dimethyl-2-(((S)-1-(2-morpholinoethoxy)-1-oxopropan-2-yl)amino)-2-oxido-1,3,2-dioxaphosphinane-4-carboxamido)propanoate |

TABLE 1-continued

Exemplary amino-acid phosphoramidate compounds.

| No. | Compound | Chemical Name |
|---|---|---|
| 28 | | methyl 3-((4R)-5,5-dimethyl-2-oxido-2-(((R)-1-oxo-1-(pyridin-3-ylmethoxy)propan-2-yl)amino)-1,3,2-dioxaphosphinane-4-carboxamido)propanoate |
| 29 | | benzyl (2S)-2-(((4R)-4-((3-methoxy-3-oxopropyl)carbamoyl)-5,5-dimethyl-2-oxido-1,3,2-dioxaphosphinan-2-yl)amino)-3-(thiazol-5-yl)propanoate |
| 30 | | (2S)-benzyl 2-(((4R)-4-((3-methoxy-3-oxopropyl)carbamoyl)-5,5-dimethyl-2-oxido-1,3,2-dioxaphosphinan-2-yl)amino)-3-(pyridin-3-yl)propanoate |
| 31 | | methyl 3-((4R)-5,5-dimethyl-2-(((S)-1-(2-(4-methylthiazol-5-yl)ethoxy)-1-oxopropan-2-yl)amino)-2-oxido-1,3,2-dioxaphosphinane-4-carboxamido)propanoate |
| 32 | | methyl 3-((4R)-5,5-dimethyl-2-(((R)-1-(2-(4-methylthiazol-5-yl)ethoxy)-1-oxopropan-2-yl)amino)-2-oxido-1,3,2-dioxaphosphinane-4-carboxamido)propanoate |
| 33 | | tert-butyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 34 | | methyl 3-((4R)-5,5-dimethyl-2-oxido-2-(((2S)-1-oxo-1-((tetrahydrofuran-3-yl)oxy)propan-2-yl)amino)-1,3,2-dioxaphosphinane-4-carboxamido)propanoate |
| 35 | | methyl 3-((2R,4R)-5,5-dimethyl-2-oxido-2-(((S)-1-oxo-1-(2-(pyridin-2-yl)ethoxy)propan-2-yl)amino)-1,3,2-dioxaphosphinane-4-carboxamido)propanoate |

TABLE 1-continued

Exemplary amino-acid phosphoramidate compounds.

| No. | Compound | Chemical Name |
|---|---|---|
| 35A | | methyl 3-((4R)-5,5-dimethyl-2-oxido-2-(((S)-1-oxo-1-(2-(pyridin-2-yl)ethoxy)propan-2-yl)amino)-1,3,2-dioxaphosphinane-4-carboxamido)propanoate |
| 36 | | phenethyl (2S)-2-(((4R)-4-((3-methoxy-3-oxopropyl)carbamoyl)-5,5-dimethyl-2-oxido-1,3,2-dioxaphosphinan-2-yl)amino)-3-(pyridin-3-yl)propanoate |
| 37 | | cyclopropylmethyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 38 | | phenethyl ((4R)-5,5-dimethyl-2-oxido-4-((3-oxo-3-(pyridin-4-ylmethoxy)propyl)carbamoyl)-1,3,2-dioxaphosphinan-2-yl)-L-alaninate |
| 39 | | phenethyl ((4R)-5,5-dimethyl-2-oxido-4-((3-oxo-3-(pyrazin-2-ylmethoxy)propyl)carbamoyl)-1,3,2-dioxaphosphinan-2-yl)-L-alaninate |
| 40 | | (5-methylisoxazol-3-yl)methyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 41 | | 3-((4R)-5,5-dimethyl-2-oxido-2-(((S)-1-oxo-1-phenethoxypropan-2-yl)amino)-1,3,2-dioxaphosphinane-4-carboxamido)propanoic acid |
| 42 | | methyl 3-((2S,4R)-5,5-dimethyl-2-oxido-2-(((R)-1-oxo-1-(pyrazin-2-ylmethoxy)propan-2-yl)amino)-1,3,2-dioxaphosphinane-4-carboxamido)propanoate |

TABLE 1-continued

Exemplary amino-acid phosphoramidate compounds.

| No. | Compound | Chemical Name |
|---|---|---|
| 42A | | methyl 3-((4R)-5,5-dimethyl-2-oxido-2-(((R)-1-oxo-1-(pyrazin-2-ylmethoxy)propan-2-yl)amino)-1,3,2-dioxaphosphinane-4-carboxamido)propanoate |
| 43 | | 2,3-dihydio-1H-inden-2-yl ((2R,4R)-4-((3-methoxy-3-oxopropyl)carbamoyl)-5,5-dimethyl-2-oxido-1,3,2-dioxaphosphinan-2-yl)-L-alaninate |
| 43A | | 2,3-dihydro-1H-inden-2-yl ((4R)-4-((3-methoxy-3-oxopropyl)carbamoyl)-5,5-dimethyl-2-oxido-1,3,2-dioxaphosphinan-2-yl)-L-alaninate |
| 44 | | phenethyl ((4R)-5,5-dimethyl-2-oxido-4-((3-oxo-3-(2-(pyrrolidin-1-yl)ethoxy)propyl)carbamoyl)-1,3,2-dioxaphosphinan-2-yl)-L-alaninate |
| 45 | | phenethyl ((2S,4R)-4-((3-methoxy-3-oxopropyl)carbamoyl)-5,5-dimethyl-2-oxido-1,3,2-dioxaphosphinan-2-yl)-L-valinate |
| 45A | | phenethyl ((4R)-4-((3-methoxy-3-oxopropyl)carbamoyl)-5,5-dimethyl-2-oxido-1,3,2-dioxaphosphinan-2-yl)-L-valinate |
| 46 | | methyl 3-((2R,4R)-5,5-dimethyl-2-oxido-2-(((S)-1-oxo-1-(3-phenylpropoxy)propan-2-yl)amino)-1,3,2-dioxaphosphinane-4-carboxamido)propanoate |
| 46A | | methyl 3-((4R)-5,5-dimethyl-2-oxido-2-(((S)-1-oxo-1-(3-phenylpropoxy)propan-2-yl)amino)-1,3,2-dioxaphosphinane-4-carboxamido)propanoate |

TABLE 1-continued

Exemplary amino-acid phosphoramidate compounds.

| No. | Compound | Chemical Name |
|---|---|---|
| 47 | | ((R)-5-oxopyrrolidin-2-yl)methyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 48 | | methyl 3-((2R,4R)-5,5-dimethyl-2-oxido-2-(((S)-1-oxo-1-phenethoxypropan-2-yl)amino)-1,3,2-dioxaphosphinane-4-carboxamido)propanoate |
| 48A | | methyl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 49 | | phenethyl ((2S,4R)-4-((3-(tert-butoxy)-3-oxopropyl)carbamoyl)-5,5-dimethyl-2-oxido-1,3,2-dioxaphosphinan-2-yl)-L-valinate |
| 49A | | phenethyl ((4R)-4-((3-(tert-butoxy)-3-oxopropyl)carbamoyl)-5,5-dimethyl-2-oxido-1,3,2-dioxaphosphinan-2-yl)-L-valinate |
| 1-50 | | 2-ethylbutyl ((2R,4R)-4-((3-methoxy-3-oxopropyl)carbamoyl)-5,5-dimethyl-2-oxido-1,3,2-dioxaphosphinan-2-yl)-L-alaninate |
| 1-51 | | ((4R)-4-((3-methoxy-3-oxopropyl)carbamoyl)-5,5-dimethyl-2-oxido-1,3,2-dioxaphosphinan-2-yl)-L-alanine |
| 1-52 | | methyl 3-((2R,4R)-2-(((S)-1-methoxy-1-oxopropan-2-yl)amino)-5,5-dimethyl-2-oxido-3,3,2-dioxaphosphinane-4-carboxamido)propanoate |

TABLE 1-continued

Exemplary amino-acid phosphoramidate compounds.

| No. | Compound | Chemical Name |
|---|---|---|
| 1-53 | | methyl 3-((2S,4R)-2-(((S)-1-methoxy-1-oxopropan-2-yl)amino)-5,5-dimethyl-2-oxido-1,3,2-dioxaphosphinane-4-carboxamido)propanoate |
| 1-54 | | 2,3-dihydro-1H-inden-2-yl 3-((4R)-5,5-dimethyl-2-oxido-2-(((S)-1-oxo-1-phenethoxypropan-2-yl)amino)-1,3,2-dioxaphosphinane-4-carboxamido)propanoate |
| 1-55 | | phenethyl ((4R)-5,5-dimethyl-2-oxido-4-((3-oxo-3-(((R)-tetrahydrofuran-3-yl)oxy)propyl)carbamoyl)-1,3,2-dioxaphosphinan-2-yl)-L-alaninate |

TABLE 2

Exemplary simple phosphate compounds.

| No. | Compound | Chemical Name |
|---|---|---|
| 50 | | methyl 3-((2S,4R)-2-(isopentyloxy)-5,5-dimethyl-2-oxido-1,3,2-dioxaphosphinane-4-carboxamido)propanoate |
| 50A | | methyl 3-((4R)-2-(isopentyloxy)-5,5-dimethyl-2-oxido-1,3,2-dioxaphosphinane-4-carboxamido)propanoate |
| 51 | | benzyl 3-((4R)-2-hydroxy-5,5-dimethyl-2-oxido-1,3,2-dioxaphosphinane-4-carboxamido)propanoate |
| 52 | | methyl 3-((4R)-5,5-dimethyl-2-(3-morpholinopropoxy)-2-oxido-1,3,2-dioxaphosphinane-4-carboxamido)propanoate |

TABLE 2-continued

Exemplary simple phosphate compounds.

| No. | Compound | Chemical Name |
|---|---|---|
| 53 | | methyl 3-((4R)-2-(3-(benzyloxy)propoxy)-5,5-dimethyl-2-oxido-1,3,2-dioxaphosphinane-4-carboxamido)propanoate |
| 54 | | methyl 3-((2R,4R)-2-(benzyloxy)-5,5-dimethyl-2-oxido-1,3,2-dioxaphosphinane-4-carboxamido)propanoate |
| 55 | | methyl 3-((4R)-2-hydroxy-5,5-dimethyl-2-oxido-1,3,2-dioxaphosphinane-4-carboxamido)propanoate |
| 56 | | methyl 3-((2S,4R)-2-(benzyloxy)-5,5-dimethyl-2-oxido-1,3,2-dioxaphosphinane-4-carboxamido)propanoate |
| 57 | | methyl 3-(((2R,4R)-4-((3-methoxy-3-oxopropyl)carbamoyl)-5,5-dimethyl-2-oxido-1,3,2-dioxaphosphinan-2-yl)oxy)-2,2-dimethylpropanoate |
| 57A | | methyl 3-(((4R)-4-((3-methoxy-3-oxopropyl)carbamoyl)-5,5-dimethyl-2-oxido-1,3,2-dioxaphosphinan-2-yl)oxy)-2,2-dimethylpropanoate |
| 58 | | methyl 3-((2S,4R)-5,5-dimethyl-2-phenethoxy-1,3,2-dioxaphosphinane-4-carboxamido)propanoate |
| 58A | | methyl 3-((4R)-5,5-dimethyl-2-oxido-2-phenethoxy-1,3,2-dioxaphosphinane-4-carboxamido)propanoate |

TABLE 2-continued

Exemplary simple phosphate compounds.

| No. | Compound | Chemical Name |
|---|---|---|
| 59 | | methyl 3-((2R)-2-hydroxy-4-(((4R)-4-((3-methoxy-3-oxopropyl)carbamoyl)-5,5-dimethyl-2-oxido-1,3,2-dioxaphosphuian-2-yl)oxy)-3,3-dimethylbutanamido)propanoate |
| 60 | | methyl 3-((4R)-5,5-dimethyl-2-oxido-2-(2-(thiophen-2-yl)ethoxy)-1,3,2-dioxaphosphinane-4-carboxamido)propanoate |
| 61 | | methyl 3-((4R)-5,5-dimethyl-2-oxido-2-(2-(pyridin-3-yl)ethoxy)-1,3,2-dioxaphosphinane-4-carboxamido)propanoate |
| 62 | | methyl 3-((2S,4R)-5,5-dimethyl-2-oxido-2-(pyridin-3-ylmethoxy)-1,3,2-dioxaphosphinane-4-carboxamido)propanoate |
| 63 | | tert-butyl 3-((2R,4R)-2-(benzyloxy)-5,5-dimethyl-2-oxido-1,3,2-dioxaphosphinane-4-carboxamido)propanoate |
| 63A | | tert-butyl 3-((4R)-2-(benzyloxy)-5,5-dimethyl-2-oxido-1,3,2-dioxaphosphinane-4-carboxamido)propanoate |
| 64 | | (((4R)-4-((3-methoxy-3-oxopropyl)carbamoyl)-5,5-dimethyl-2-oxido-1,3,2-dioxaphosphinan-2-yl)oxy)methyl benzoate |
| 65 | | (((4R)-4-((3-methoxy-3-oxopropyl)carbamoyl)-5,5-dimethyl-2-oxido-1,3,2-dioxaphosphinan-2-yl)oxy)methyl pivalate |

TABLE 2-continued

Exemplary simple phosphate compounds.

| No. | Compound | Chemical Name |
|---|---|---|
| 66 | | (((4R)-4-((3-methoxy-3-oxopropyl)carbamoyl)-5,5-dimethyl-2-oxido-1,3,2-dioxaphosphinan-2-yl)oxy)methyl butyrate |
| 67 | | (((4R)-4-((3-methoxy-3-oxopropyl)carbamoyl)-5,5-dimethyl-2-oxido-1,3,2-dioxaphosphinan-2-yl)oxy)methyl 2-ethylbutanoate |
| 68 | | methyl 3-((4R)-2-(acetoxymethoxy)-5,5-dimethyl-2-oxido-1,3,2-dioxaphosphinane-4-carboxamido)propanoate |
| 69 | | methyl 3-((4R)-2-(((isopropoxycarbonyl)oxy)methoxy)-5,5-dimethyl-2-oxido-1,3,2-dioxaphosphinane-4-carboxamido)propanoate |
| 70 | | (((4R)-4-((3-methoxy-3-oxopropyl)carbamoyl)-5,5-dimethyl-2-oxido-1,3,2-dioxaphosphinan-2-yl)oxy)methyl thiazole-5-carboxylate |
| 71 | | (((2R,4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate |
| 72 | | (((4R)-4-((3-methoxy-3-oxopropyl)carbamoyl)-5,5-dimethyl-2-oxido-1,3,2-dioxaphosphinan-2-yl)oxy)methyl isonicotinate |
| 73 | | (((4R)-4-((3-methoxy-3-oxopropyl)carbamoyl)-5,5-dimethyl-2-oxido-1,3,2-dioxaphosphinan-2-yl)oxy)methyl acetyl-L-leucinate |

TABLE 2-continued

Exemplary simple phosphate compounds.

| No. | Compound | Chemical Name |
|---|---|---|
| 74 | | (((2S,4R)-5,5-dimethyl-4-((3-((5-methylisoxazol-3-yl)methoxy)-3-oxopropyl)carbamoyl)-2-oxido-1,3,2-dioxaphosphinan-2-yl)oxy)methyl pivalate |
| 74A | | (((4R)-5,5-dimethyl-4-((3-((5-methylisoxazol-3-yl)methoxy)-3-oxopropyl)carbamoyl)-2-oxido-1,3,2-dioxaphosphinan-2-yl)oxy)methyl pivalate |
| 75 | | (((4R)-4-((3-(tert-butoxy)-3-oxopropyl)carbamoyl)-5,5-dimethyl-2-oxido-1,3,2-dioxaphosphinan-2-yl)oxy)methyl pivalate |
| 76 | | (((4R)-4-((3-methoxy-3-oxopropyl)carbamoyl)-5,5-dimethyl-2-oxido-1,3,2-dioxaphosphinan-2-yl)oxy)methyl 4-(pyrrolidin-1-ylmethyl)benzoate |
| 77 | | (((2S,4R)-4-((3-(2-cyanoethoxy)-3-oxopropyl)carbamoyl)-5,5-dimethyl-2-oxido-1,3,2-dioxaphosphinan-2-yl)oxy)methyl pivalate |
| 77A | | (((4R)-4-((3-(2-cyanoethoxy)-3-oxopropyl)carbamoyl)-5,5-dimethyl-2-oxido-1,3,2-dioxaphosphinan-2-yl)oxy)methyl pivalate |
| 78 | | (((2S,4R)-5,5-dimethyl-4-((3-(2-(methylsulfonyl)ethoxy)-3-oxopropyl)carbamoyl)-2-oxido-1,3,2-dioxaphosphinan-2-yl)oxy)methyl pivalate |
| 78A | | (((4R)-5,5-dimethyl-4-((3-(2-(methylsulfonyl)ethoxy)-3-oxopropyl)carbamoyl)-2-oxido-1,3,2-dioxaphosphinan-2-yl)oxy)methyl pivalate |

TABLE 2-continued

Exemplary simple phosphate compounds.

| No. | Compound | Chemical Name |
|---|---|---|
| 79 | | (((2S,4R)-5,5-dimethyl-2-oxido-4-((3-oxo-3-(thiazol-5-ylmethoxy)propyl)carbamoyl)-1,3,2-dioxaphosphinan-2-yl)oxy)methyl pivalate |
| 79A | | (((4R)-5,5-dimethyl-2-oxido-4-((3-oxo-3-(thiazol-5-ylmethoxy)propyl)carbamoyl)-1,3,2-dioxaphosphinan-2-yl)oxy)methyl pivalate |
| 80 | | methyl 3-((4R)-2-((2-(4-acetylpiperazin-1-yl)acetoxy)methoxy)-5,5-dimethyl-2-oxido-1,3,2-dioxaphosphinane-4-carboxamido)propanoate |
| 81 | | (((2S,4R)-5,5-dimethyl-2-oxido-4-((3-oxo-3-((5-oxopyrrolidin-2-yl)methoxy)propyl)carbamoyl)-1,3,2-dioxaphosphinan-2-yl)oxy)methyl pivalate |
| 81A | | (((4R)-5,5-dimethyl-2-oxido-4-((3-oxo-3-((5-oxopyrrolidin-2-yl)methoxy)propyl)carbamoyl)-1,3,2-dioxaphosphinan-2-yl)oxy)methyl pivalate |
| 82 | | (((2S,4R)-5,5-dimethyl-2-oxido-4-((3-oxo-3-(2-(pyridin-2-yl)ethoxy)propyl)carbamoyl)-1,3,2-dioxaphosphinan-2-yl)oxy)methyl pivalate |
| 82A | | (((4R)-5,5-dimethyl-2-oxido-4-((3-oxo-3-(2-(pyridin-2-yl)ethoxy)propyl)carbamoyl)-1,3,2-dioxaphosphinan-2-yl)oxy)methyl pivalate |
| 83 | | (((4R)-4-((3-methoxy-3-oxopropyl)carbamoyl)-5,5-dimethyl-2-oxido-1,3,2-dioxaphosphinan-2-yl)oxy)methyl 1-carbamoylcyclopropane-1-carboxylate |

TABLE 2-continued

Exemplary simple phosphate compounds.

| No. | Compound | Chemical Name |
|---|---|---|
| 84 | | (((4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate |
| 85 | | 1-(tert-butyl) 3-((((4R)-4-((3-methoxy-3-oxopropyl)carbamoyl)-5,5-dimethyl-2-oxido-1,3,2-dioxaphosphinan-2-yl)oxy)methyl) 3-methylazetidine-1,3-dicarboxylate |
| 86 | | (((4R)-4-((3-methoxy-3-oxopropyl)carbamoyl)-5,5-dimethyl-2-oxido-1,3,2-dioxaphosphinan-2-yl)oxy)methyl pyrazine-2-carboxylate |
| 87 | | (((4R)-4-((3-methoxy-3-oxopropy))carbamoyl)-5,5-dimethyl-2-oxido-1,3,2-dioxaphosphinan-2-yl)oxy)methyl oxazole-5-carboxylate |
| 88 | | methyl 3-((4R)-2-(((tert-butoxycarbonyl)oxy)methoxy)-5,5-dimethyl-2-oxido-1,3,2-dioxaphosphinane-4-carboxamido)propanoate |
| 89 | | (((2R)4R)-4-((3-methoxy-3-oxopropyl)carbamoyl)-5,5-dimethyl-2-oxido-1,3,2-dioxaphosphinan-2-yl)oxy)methyl pivalate |
| 90 | | (((2S,4R)-4-((3-methoxy-3-oxopropyl)carbamoyl)-5,5-dimethyl-2-oxido-1,3,2-dioxaphosphinan-2-yl)oxy)methyl pivalate |
| 91 | | 3-((2S,4R)-5,5-dimethyl-2-oxido-2-((pivaloyloxy)methoxy)-1,3,2-dioxaphosphinane-4-carboxamido)propanoic acid |

TABLE 2-continued

Exemplary simple phosphate compounds.

| No. | Compound | Chemical Name |
|---|---|---|
| 91A | | 3-((4R)-5,5-dimethyl-2-oxido-2-((pivaloyloxy)methoxy)-1,3,2-dioxaphosphinane-4-carboxamido)propanoic acid |
| 92 | | (((2S,4R)-5,5-dimethyl-2-oxido-4-((3-oxo-3-(pyrrolidin-3-yloxy)propyl)carbamoyl)-1,3,2-dioxaphosphinan-2-yl)oxy)methyl pivalate |
| 92A | | (((4R)-5,5-dimethyl-2-oxido-4-((3-oxo-3-(pyrrolidin-3-yloxy)propyl)carbamoyl)-1,3,2-dioxaphosphinan-2-yl)oxy)methyl pivalate |
| 93 | | (((2S,4R)-4-((3-((1-benzylpyrrolidin-3-yl)oxy)-3-oxopropyl)carbamoyl)-5,5-dimethyl-2-oxido-1,3,2-dioxaphosphinan-2-yl)oxy)methyl pivalate |
| 93A | | (((4R)-4-((3-((1-benzylpyrrolidin-3-yl)oxy)-3-oxopropyl)carbamoyl)-5,5-dimethyl-2-oxido-1,3,2-dioxaphosphinan-2-yl)oxy)methyl pivalate |
| 94 | | (((4R)-5,5-dimethyl-2-oxido-4-((3-oxo-3-((tetrahydrofuran-3-yl)oxy)propyl)carbamoyl)-1,3,2-dioxaphosphinan-2-yl)oxy)methyl pivalate |
| 95 | | (((4R)-5,5-dimethyl-2-oxido-4-((3-oxo-3-(pyrimidin-2-ylmethoxy)propyl)carbamoyl)1,3,2-dioxaphosphinan-2-yl)oxy)methyl pivalate |
| 96 | | (((2S,4R)-4-((3-(3-ethoxypropoxy)-3-oxopropyl)carbamoyl)-5,5-dimethyl-2-oxido-1,3,2-dioxaphosphinan-2-yl)oxy)methyl pivalate |

TABLE 2-continued

Exemplary simple phosphate compounds.

| No. | Compound | Chemical Name |
|---|---|---|
| 96A | | (((4R)-4-((3-(3-ethoxypropoxy)-3-oxopropyl)carbamoyl)-5,5-dimethy)-2-oxido-1,3,2-dioxaphosphinan-2-yl)oxy)methyl pivalate |
| 97 | | methyl 3-((4R)-5,5-dimethyl-2-oxido-2-((((pyridin-3-ylmethoxy)carbonyl)oxy)methoxy)-1,3,2-dioxaphosphinane-4-carboxamido)propanoate |
| 98 | | 1-(((4R)-4-((3-methoxy-3-oxopropyl)carbamoyl)-5,5-dimethyl-2-oxido-1,3,2-dioxaphosphinan-2-yl)oxy)ethyl benzoate |
| 99 | | (((4R)-5,5-dimethyl-4-((3-((1-methylpiperidin-3-yl)oxy)-3-oxopropyl)carbamoyl)-2-oxido-1,3,2-dioxaphosphinan-2-yl)oxy)methyl pivalate |
| 100 | | 3-((4R)-5,5-dimethyl-2-oxido-2-((pivaloyloxy)methoxy)-1,3,2-dioxaphosphinane-4-carboxamido)propanoic acid |
| 101 | | (((4R)-5,5-dimethyl-2-oxido-4-((3-oxo-3-(pyrldin-4-ylmethoxy)propyl)carbamoyl)-1,3,2-dioxaphosphinan-2-yl)oxy)methyl pivalate |
| 102 | | 1-(((2R,4R)-4-((3-methoxy-3-oxopropyl)carbamoyl)-5,5-dimethyl-2-oxido-1,3,2-dioxaphosphinan-2-yl)oxy)ethyl pivalate |
| 102A | | 1-(((4R)-4-((3-methoxy-3-oxopropyl)carbamoyl)-5,5-dimethyl-2-oxido-1,3,2-dioxaphosphinan-2-yl)oxy)ethyl pivalate |

TABLE 2-continued

Exemplary simple phosphate compounds.

| No. | Compound | Chemical Name |
|---|---|---|
| 103 | | (((4R)-4-((3-methoxy-3-oxopropyl)carbamoyl)-5,5-dimethyl-2-oxido-1,3,2-dioxaphosphinan-2-yl)oxy)methyl isobutyrate |
| 104 | | 3-((4R)-2-(((isopropoxycarbonyl)oxy)methoxy)-5,5-dimethyl-2-oxido-1,3,2-dioxaphosphinane-4-carboxamido)propanoic acid |
| 105 | | tert-butyl 3-((2S,4R)-2-(((isopropoxycarbonyl)oxy)methoxy)-5,5-dimethyl-2-oxido-1,3,2-dioxaphosphinane-4-carboxamido)propanoate |
| 105A | | tert-butyl 3-((4R)-2-(((isopropoxycarbonyl)oxy)methoxy)-5,5-dimethyl-2-oxido-1,3,2-dioxaphosphinane-4-carboxainido)propanoate |
| 106 | | 1-(((2S,4R)-4-((3-methoxy-3-oxopropyl)carbamoyl)-5,5-dimethyl-2-oxido-1,3,2-dioxaphosphinan-2-yl)oxy)ethyl isobutyrate |
| 106A | | 1-(((4R)-4-((3-methoxy-3-oxopropyl)carbamoyl)-5,5-dimethyl-2-oxido-1,3,2-dioxaphosphinan-2-yl)oxy) ethyl isobutyrate |
| 107 | | (((2S,4R)-4-((3-ethoxy-3-oxopropyl)carbamoyl)-5,5-dimethyl-2-oxido-1,3,2-dioxaphosphinan-2-yl)oxy)methyl pivalate |
| 107A | | (((4R)-4-((3-ethoxy-3-oxopropyl)carbamoyl)-5,5-dimethyl-2-oxido-1,3,2-dioxaphosphinan-2-yl)oxy)methyl pivalate |

TABLE 2-continued

Exemplary simple phosphate compounds.

| No. | Compound | Chemical Name |
|---|---|---|
| 108 | | 3-((4R)-2-hydroxy-5,5-dimethyl-2-oxido-1,3,2-dioxaphosphinane-4-carboxamido)propanoic acid |
| 2-109 | | methyl 3-((4R)-5,5-dimethyl-2-oxido-2-phenoxy-1,3,2-dioxaphosphinane-4-carboxamido-15N)propanoate-1,2,3-13C3 |
| 2-110 | | isopropyl 3-((4R)-2-hydroxy-5,5-dimethyl-2-oxido-1,3,2-dioxaphosphinane-4-carboxamido)propanoate |
| 2-111 | | tert-butyl 3-[[(4R)-5,5-dimethyl-2-oxidanyl-2-oxidanylidene-1,3,2-dioxaphosphinan-4-yl]carbonylamino]propanoate |
| 2-112 | | benzyl 3-((4R)-2-(benzyloxy)-5,5-dimethyl-2-oxido-1,3,2-dioxaphosphinane-4-carboxamido-15N)propanoate-1,2,3-13C3 |
| 2-113 | | (((2S,4R)-5,5-dimethyl-2-oxido-4-((3-oxo-3-(((S)-5-oxopyrrolidin-2-yl)methoxy)propyl)carbamoyl)-1,3,2-dioxaphosphinan-2-yl)oxy)methyl pivalate |
| 2-114 | | methyl 3-((4R)-5,5-dimethyl-2-oxido-2-(2-(3-oxomorpholino)ethoxy)-1,3,2-dioxaphosphinane-4-carboxamido)propanoate |
| 2-115 | | methyl 3-((2R,4R)-2-(2-acetamidoethoxy)-5,5-dimethyl-2-oxido-1,3,2-dioxaphosphinane-4-carboxamido)propanoate |

TABLE 2-continued

Exemplary simple phosphate compounds.

| No. | Compound | Chemical Name |
|---|---|---|
| 2-116 | | methyl 3-((2S,4R)-2-(1-cyanophenoxy)-5,5-dimethyl-2-oxido-1,3,2-dioxaphosphinane-4-carboxamido)propanoate |
| 2-116A | | methyl 3-((4R)-2-(4-cyanophenoxy)-5,5-dimethyl-2-oxido-1,3,2-dioxaphosphinane-4-carboxamido)propanoate |
| 2-117 | | methyl 2-(((2S,4R)-4-((3-methoxy-3-oxopropyl)carbamoyl)-5,5-dimethyl-2-oxido-1,3,2-dioxaphosphinan-2-yl)oxy)benzoate |
| 2-117A | | methyl 2-(((4R)-4-((3-methoxy-3-oxopropyl)carbamoyl)-5,5-dimethyl-2-oxido-1,3,2-dioxaphosphinan-2-yl)oxy)benzoate |
| 2-118 | | methyl 3-((4R)-2-(4-fluorophenoxy)-5,5-dimethyl-2-oxido-1,3,2-dioxaphosphinane-4-carboxamido)propanoate |
| 2-119 | | methyl 3-((2S,4R)-5,5-dimethyl-2-oxido-2-(4-(trifluoromethyl)phenoxy)-1,3,2-dioxaphosphinane-4-carboxamido)propanoate |
| 2-119A | | methyl 3-((4R)-5,5-dimethyl-2-oxido-2-(4-(trifluoromethyl)phenoxy)-1,3,2-dioxaphosphinane-4-carboxamido)propanoate |

TABLE 2-continued

Exemplary simple phosphate compounds.

| No. | Compound | Chemical Name |
|---|---|---|
| 2-120 | | methyl 3-((2R,4R)-5,5-dimethyl-2-(4-nitrophenoxy)-2-oxido-1,3,2-dioxaphosphinane-4-carboxamido)propanoate |
| 2-121 | | methyl 3-((2S,4R)-5,5-dimethyl-2-(4-nitrophenoxy)-2-oxido-1,3,2-dioxaphosphinane-4-carboxamido)propanoate |
| 2-122 | | methyl 3-((4R)-5,5-dimethyl-2-oxido-2-((6-(trifluoromethyl)pyridin-3-yl)oxy)-1,3,2-dioxaphosphinane-4-carboxamido)propanoate |
| 2-123 | | methyl 3-((2S,4R)-5,5-dimethyl-2-oxido-2-(2,2,2-trifluoroethoxy)-1,3,2-dioxaphosphinane-4-carboxamido)propanoate |
| 2-124 | | methyl 3-((2S,4R)-5,5-dimethyl-2-oxido-2-(4-(pentafluoro-16-sulfanyl)phenoxy)-1,3,2-dioxaphosphinane-4-carboxamido)propanoate |
| 2-125 | | methyl 3-((2R,4R)-5,5-dimethyl-2-oxido-2-(4-(pentafluoro-16-sulfanyl)phenoxy)-1,3,2-dioxaphosphinane-4-carboxamido)propanoate |
| 2-126 | | methyl 3-((2S,4R)-2-((1,1-dioxido-3-oxobenzo[d]isothiazol-2(3H)-yl)methoxy)-5,5-dimethyl-2-oxido-1,3,2-dioxaphosphinane-4-carboxamido)propanoate |
| 2-126A | | methyl 3-((4R)-2-((1,1-dioxido-3-oxobenzo[d]isothiazol-2(3H)-yl)methoxy)-5,5-dimethyl-2-oxido-1,3,2-dioxaphosphinane-4-carboxamido)propanoate |

TABLE 2-continued

Exemplary simple phosphate compounds.

| No. | Compound | Chemical Name |
|---|---|---|
| 2-127 | | (((2S,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate |
| 2-127A | | (((4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate |
| 2-128 | | (((2S,4R)-4-((3-isopropoxy-3-oxopropyl)carbamoyl)-5,5-dimethyl-2-oxido-1,3,2-dioxaphosphinan-2-yl)oxy)methyl pivalate |
| 2-128A | | (((4R)-4-((3-isopropoxy-3-oxopropyl)carbamoyl)-5,5-dimethyl-2-oxido-1,3,2-dioxaphosphinan-2-yl)oxy)methyl pivalate |
| 2-129 | | (((2R,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate |
| 2-130 | | 3-((2S,4R)-2-(((isopropoxycarbonyl)oxy)methoxy)-5,5-dimethyl-2-oxido-1,3,2-dioxaphosphinane-4-carboxamido)propanoic acid |
| 2-131 | | (((2S,4R)-4-((3-methoxy-3-oxopropyl)carbamoyl)-5,5-dimethy)-2-oxido-1,3,2-dioxaphosphinan-2-yl)oxy)methyl 1-carbamoylcyclopropane-1-carboxylate |
| 2-132 | | methyl 3-((2S,4R)-2-((1H-imidazol-1-yl)methoxy)-5,5-dimethyl-2-oxido-1,3,2-dioxaphosphinane-4-carboxamido)propanoate |

TABLE 2-continued

Exemplary simple phosphate compounds.

| No. | Compound | Chemical Name |
|---|---|---|
| 2-133 | | methyl 3-((4R)-5,5-dimethyl-2-oxido-2-(2-(pivaloylthio)ethoxy)-1,3,2-dioxaphosphinane-4-carboxamido)propanoate |
| 2-134 | | methyl 3-((4R)-5,5-dimethyl-2-(4-nitrophenoxy)-2-oxido-1,3,2-dioxaphosphinane-4-carboxamido)propanoate |
| 2-135 | | methyl 3-((4R)-2-(((((S)-1-(diethylamino)-1-oxo-3-phenylpropan-2-yl)carbamoyl)oxy)methoxy)-5,5-dimethyl-2-oxido-1,3,2-dioxaphosphinane-4-carboxamido)propanoate |
| 2-136 | | methyl 3-((4R)-2-((((2-(acetylthio)ethyl)carbamoyl)oxy)methoxy)-5,5-dimethyl-2-oxido-1,3,2-dioxaphosphinane-4-carboxamido)propanoate |
| 2-137 | | ethyl (((((4R)-4-((3-methoxy-3-oxopropyl)carbamoyl)-5,5-dimethyl-2-oxido-1,3,2-dioxaphosphinan-2-yl)oxy)methoxy)carbonyl)-L-phenylalaninate |
| 2-138 | | methyl 3-((2R,4R)-5,5-dimethyl-2-oxido-2-(2,2,2-trifluoroethoxy)-1,3,2-dioxaphosphinane-4-carboxamido)propanoate |
| 2-139 | | (((4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate |
| 2-140 | | (((4R)-4-((3-methoxy-3-oxopropyl)carbamoyl)-5,5-dimethyl-2-oxido-1,3,2-dioxaphosphinan-2-yl)oxy)methyl isothiazole-5-carboxylate |

TABLE 2-continued

Exemplary simple phosphate compounds.

| No. | Compound | Chemical Name |
|---|---|---|
| 2-141 | | (((4R)-4-((3-methoxy-3-oxopropyl)carbamoyl)-5,5-dimethyl-2-oxido-1,3,2-dioxaphosphinan-2-yl)oxy)methyl isoxazole-5-carboxylate |
| 2-142 | | (((4R)-4-((3-methoxy-3-oxopropyl)carbamoyl)-5,5-dimethyl-2-oxido-1,3,2-dioxaphosphinan-2-yl)oxy)methyl 1-methyl-1H-pyrazole-5-carboxylate |
| 2-143 | | methyl 3-((4R)-5,5-dimethyl-2-oxido-2-((((2-(pivaloylthio)ethyl)carbamoyl)oxy)methoxy)-1,3,2-dioxaphosphinane-4-carboxamido)propanoate |
| 2-144 | | (((4R)-4-((3-methoxy-3-oxopropyl)carbamoyl)-5,5-dimethyl-2-oxido-1,3,2-dioxaphosphinan-2-yl)oxy)methyl 3-(tert-butyl)-1-methyl-1H-pyrazole-5-carboxylate |
| 2-145 | | (((4R)-4-((3-methoxy-3-oxopropyl)carbamoyl)-5,5-dimethyl-2-oxido-1,3,2-dioxaphosphinan-2-yl)oxy)methyl 1,3-dimethyl-1H-pyrazole-5-carboxylate |
| 2-146 | | (((4R)-4-((3-methoxy-3-oxopropyl)carbamoyl)-5,5-dimethyl-2-oxido-1,3,2-dioxaphosphinan-2-yl)oxy)methyl 3-(tert-butyl)-1H-pyrazole-5-carboxylate |
| 2-147 | | (((4R)-4-((3-methoxy-3-oxopropyl)carbamoyl)-5,5-dimethyl-2-oxido-1,3,2-dioxaphosphinan-2-yl)oxy)methyl 4-methyloxazole-5-carboxylate |
| 2-148 | | methyl N-(((((4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |

TABLE 2-continued

Exemplary simple phosphate compounds.

| No. | Compound | Chemical Name |
|---|---|---|
| 2-149 | | (((2S,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate |
| 2-150 | | (((2R,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate |
| 2-151 | | (((2S,4R)-4-((3-methoxy-3-oxopropyl)carbamoyl)-5,5-dimethyl-2-oxido-1,3,2-dioxaphosphinan-2-yl)oxy)methyl oxazole-5-carboxylate |
| 2-152 | | methyl 3-((4R)-2-((((1-acetoxy-2-methylpropan-2-yl)carbamoyl)oxy)methoxy)-5,5-dimethyl-2-oxido-1,3,2-dioxaphosphinane-4-carboxamido)propanoate |
| 2-153 | | N-(((((4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteine |
| 2-154 | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl pivalate |
| 2-155 | | methyl 3-((4R)-2-((((2-acetoxyethyl)carbamoyl)oxy)methoxy)-5,5-dimethyl-2-oxido-1,3,2-dioxaphosphinane-4-carboxamido)propanoate |
| 2-156 | | methyl 3-((4R)-2-((((1-acetoxy-2-methylpropan-2-yl)carbamoyl)oxy)methoxy)-5,5-dimethyl-2-oxido-1,3,2-dioxaphosphinane-4-carboxamido)propanoate |

TABLE 2-continued

Exemplary simple phosphate compounds.

| No. | Compound | Chemical Name |
|---|---|---|
| 2-157 | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl L-valinate |
| 2-158 | | 2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)-2-methylpropyl L-valinate |
| 2-158A | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)-2-methylpropyl L-valinate |
| 2-159 | | methyl 3-((4R)-2-((((2-((L-valyl)thio)ethyl)carbamoyl)oxy)methoxy)-5,5-dimethyl-2-oxido-1,3,2-dioxaphosphinane-4-carboxamido)propanoate |
| 2-160 | | 2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl((benzyloxy)carbonyl)-L-valinate |
| 2-161 | | 2-((((((2R,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl((benzyloxy)carbonyl)-L-valinate |

TABLE 2-continued

Exemplary simple phosphate compounds.

| No. | Compound | Chemical Name |
|---|---|---|
| 2-162 | | methyl (S)-2-amino-3-(4-((((2S,4R)-4-((3-methoxy-3-oxopropyl)carbamoyl)-5,5-dimethyl-2-oxido-1,3,2-dioxaphosphinan-2-yl)oxy)phenyl)propanoate |
| 2-163 | | methyl (S)-2-amino-3-(4-((((2R,4R)-4-((3-methoxy-3-oxopropyl)carbamoyl)-5,5-dimethyl-2-oxido-1,3,2-dioxaphosphinan-2-yl)oxy)phenyl)propanoate |
| 2-164 | | benzyl N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |
| 2-165 | | methyl 3-((2R,4R)-2-(4-cyanophenoxy)-5,5-dimethyl-2-oxido-1,3,2-dioxaphosphinane-4-carboxamido)propanoate |
| 2-166 | | methyl 2-(((2R,4R)-4-((3-methoxy-3-oxopropyl)carbamoyl)-5,5-dimethy)-2-oxido-1,3,2-dioxaphosphinan-2-yl)oxy)benzoate |
| 2-166A | | methyl 2-(((4R)-4-((3-methoxy-3-oxopropyl)carbamoyl)-5,5-dimethyl-2-oxido-1,3,2-dioxaphosphinan-2-yl)oxy)benzoate |
| 2-167 | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)-2-methylpropyl pivalate |

TABLE 2-continued

Exemplary simple phosphate compounds.

| No. | Compound | Chemical Name |
|---|---|---|
| 2-168 | | methyl 3-((4R)-2-((((2-acetoxyethyl)carbamoyl)oxy)methoxy)-5,5-dimethyl-2-oxido-1,3,2-dioxaphosphinane-4-carboxamido)propanoate |
| 2-169 | | (((2S,4R)-4-((3-methoxy-3-oxopropyl)carbamoyl)-5,5-dimethyl-2-oxido-1,3,2-dioxaphosphinan-2-yl)oxy)methyl 3-(tert-butyl)-1-methyl-1H-pyrazole-5-carboxylate |
| 2-170 | | (((2R,4R)-4-((3-methoxy-3-oxopropyl)carbamoyl)-5,5-dimethyl-2-oxido-1,3,2-dioxaphosphinan-2-yl)oxy)methyl 3-(tert-butyl)-1-methyl-1H-pyrazole-5-carboxylate |
| 2-172 | | 2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)-2-methylpropyl ((benzyloxy)carbonyl)-L-valinate |
| 2-172A | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)-2-methylpropyl ((benzyloxy)carbonyl)-L-valinate |
| 2-173 | | (((4R)-4-((3-methoxy-3-oxopropyl)carbamoyl)-5,5-dimethyl-2-oxido-1,3,2-dioxaphosphinan-2-yl)oxy)methyl 4-(tert-butyl)thiazole-5-carboxylate |
| 2-174 | | benzyl N-(((((4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |

TABLE 2-continued

Exemplary simple phosphate compounds.

| No. | Compound | Chemical Name |
|---|---|---|
| 2-175 | | methyl 3-((4R)-2-(((S)-9-isopropyl-3,8,11-trioxo-13-phenyl-2,12-dioxa-7-thia-4,10-diazatridecyl)oxy)-5,5-dimethyl-2-oxido-1,3,2-dioxaphosphinane-4-carboxamido)propanoate |
| 2-176 | | (((2S,4R)-4-((3-methoxy-3-oxopropyl)carbamoyl)-5,5-dimethyl-2-oxido-1,3,2-dioxaphosphinan-2-yl)oxy)methyl 4-methylisothiazole-5-carboxylate |
| 2-177 | | (((2R,4R)-4-((3-methoxy-3-oxopropyl)carbamoyl)-5,5-dimethyl-2-oxido-1,3,2-dioxaphosphinan-2-yl)oxy)methyl 4-methylisothiazole-5-carboxylate |
| 2-178 | | methyl 3-((2S,4R)-2-(4-fluorophenoxy)-5,5-dimethyl-2-oxido-1,3,2-dioxaphosphinane-4-carboxamido)propanoate |
| 2-179 | | methyl 3-((2R,4R)-2-(4-fluorophenoxy)-5,5-dimethyl-2-oxido-1,3,2-dioxaphosphinane-4-carboxamido)propanoate |
| 2-180 | | N-(((((4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteine |
| 2-181 | | 2-((((((4R)-4-((3-methoxy-3-oxopropyl)carbamoyl)-5,5-dimethyl-2-oxido-1,3,2-dioxaphosphuian-2-yl)oxy)methoxy)carbonyl)amino)ethyl((benzyloxy)carbonyl)-L-valinate |
| 2-182 | | (((2S,4R)-4-((3-methoxy-3-oxopropyl)carbamoyl)-5,5-dimethyl-2-oxido-1,3,2-dioxaphosphinan-2-yl)oxy)methyl 1,3-dimethyl-1H-pyrazole-5-carboxylate |

TABLE 2-continued

Exemplary simple phosphate compounds.

| No. | Compound | Chemical Name |
|---|---|---|
| 2-183 | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl pivalate |
| 2-184 | | (((2S,4R)-4-((3-methoxy-3-oxopropyl)carbamoyl)-5,5-dimethyl-2-oxido-1,3,2-dioxaphosphinan-2-yl)oxy)methyl 1-methyl-1H-pyrazole-5-carboxylate |
| 2-185 | | (((2R,4R)-4-((3-methoxy-3-oxopropyl)carbamoyl)-5,5-dimethyl-2-oxido-1,3,2-dioxaphosphinan-2-yl)oxy)methyl 1-methyl-1H-pyrazole-5-carboxylate |
| 2-186 | | (((2S,4R)-4-((3-methoxy-3-oxopropyl)carbamoyl)-5,5-dimethyl-2-oxido-1,3,2-dioxaphosphuian-2-yl)oxy)methyl 3-(tert-butyl)-1H-pyrazole-5-carboxylate |
| 2-187 | | (((2S,4R)-4-((3-methoxy-3-oxopropyl)carbamoyl)-5,5-dimethyl-2-oxido-1,3,2-dioxaphosphinan-2-yl)oxy)methyl 4-isopropylthiazole-5-carboxylate |
| 2-188 | | (((2R,4R)-4-((3-methoxy-3-oxopropyl)carbamoyl)-5,5-dimethyl-2-oxido-1,3,2-dioxaphosphinan-2-yl)oxy)methyl 4-isopropylthiazole-5-carboxylate |
| 2-189 | | 3-(tert-butyl) 4-(((((4R)-4-((3-methoxy-3-oxopropyl)carbamoyl)-5,5-dimethyl-2-oxido-1,3,2-dioxaphosphinan-2-yl)oxy)methyl) (4S)-2-oxooxazolidine-3,4-dicarboxylate |

TABLE 2-continued

Exemplary simple phosphate compounds.

| No. | Compound | Chemical Name |
|---|---|---|
| 2-190 | | (((2R,4R)-4-((3-methoxy-3-oxopropyl)carbamoyl)-5,5-dimethyl-2-oxido-1,3,2-dioxaphosphinan-2-yl)oxy)methyl 1,3-dimethyl-1H-pyrazole-5-carboxylate |
| 2-191 | | (((4R)-4-((3-methoxy-3-oxopropyl)carbamoyl)-5,5-dimethyl-2-oxido-1,3,2-dioxaphosphinan-2-yl)oxy)methyl (4S)-2-oxooxazolidine-4-carboxylate |
| 2-192 | | (((2S,4R)-4-((3-methoxy-3-oxopropyl)carbamoyl)-5,5-dimethyl-2-oxido-1,3,2-dioxaphosphinan-2-yl)oxy)methyl 4-(tert-butyl)thiazole-5-carboxylate |
| 2-193 | | methyl 3-((2R,4R)-2-((((2-((L-valyl)thio)ethyl)carbamoyl)oxy)methoxy)-5,5-dimethyl-2-oxido-1,3,2-dioxaphosphinane-4-carboxamido)propanoate |
| 2-194 | | methyl 3-((2S,4R)-2-((((2-((L-valyl)thio)ethyl)carbamoyl)oxy)methoxy)-5,5-dimethyl-2-oxido-1,3,2-dioxaphosphinane-4-carboxamido)propanoate |
| 2-195 | | 2-((((((4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl L-valinate |
| 2-196 | | 3-(tert-butyl) 4-((((4R)-4-((3-methoxy-3-oxopropyl)carbamoyl)-5,5-dimethyl-2-oxido-1,3,2-dioxaphosphinan-2-yl)oxy)methyl) (4R)-2-oxooxazolidine-3,4-dicarboxylate |
| 2-197 | | methyl 3-((2R,4R)-5,5-dimethyl-2-oxido-2-(4-(trifluoromethyl)phenoxy)-1,3,2-dioxaphosphinane-4-carboxamido)propanoate |

TABLE 2-continued

Exemplary simple phosphate compounds.

| No. | Compound | Chemical Name |
|---|---|---|
| 2-198 | | methyl 3-((2R,4R)-5,5-dimethyl-2-oxido-2-((6-(trifluoromethyl)pyridin-3-yl)oxy)-1,3,2-dioxaphosphinane-4-carboxamido)propanoate |
| 2-199 | | 2-oxo-2-phenylethyl N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |
| 2-200 | | N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteine |
| 2-201 | | N-(((((2R,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteine |
| 2-202 | | 2-oxo-2-phenylethyl N-(((((4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |
| 2-203 | | methyl (S)-2-((tert-butoxycarbonyl)amino)-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate |

TABLE 2-continued

Exemplary simple phosphate compounds.

| No. | Compound | Chemical Name |
|---|---|---|
| 2-204 | | methyl (S)-2-((tert-butoxycarbonyl)amino)-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate |
| 2-205 | | benzyl N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |
| 2-206 | | benzyl N-(((((2R,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate |

TABLE 3

Exemplary simple-amine phosphoramidate compounds.

| No. | Compound | Chemical Name |
|---|---|---|
| 109 | | methyl 3-((4R)-5,5-dimethyl-2-oxido-2-((2-(pyrrolidin-1-yl)ethyl)amino)-1,3,2-dioxaphosphinane-4-carboxamido)propanoate |
| 110 | | methyl 3-((4R)-2-((3-methoxy-3-oxopropyl)amino)-5,5-dimethyl-2-oxido-1,3,2-dioxaphosphinane-4-carboxamido)propanoate |
| 111 | | methyl 3-((4R)-5,5-dimethyl-2-oxido-2-((2-(pyridin-4-yl)ethyl)amino)-1,3,2-dioxaphosphinane-4-carboxamido)propanoate |

TABLE 3-continued

Exemplary simple-amine phosphoramidate compounds.

| No. | Compound | Chemical Name |
|---|---|---|
| 112 | | methyl 3-((4R)-5,5-dimethyl-2-oxido-2-(phenethylamino)-1,3,2-dioxaphosphinane-4-carboxamido)propanoate |
| 113 | | methyl 3-((4R)-2-((3-(1H-imidazol-1-yl)propyl)amino)-5,5-dimethyl-2-oxido-1,3,2-dioxaphosphinane-4-carboxamido)propanoate |
| 114 | | methyl 3-((4R)-2-amino-5,5-dimethyl-2-oxido-1,3,2-dioxaphosphinane-4-carboxamido)propanoate |
| 115 | | methyl 3-((2R,4R)-2-(benzylamino)-5,5-dimethyl-2-oxido-1,3,2-dioxaphosphinane-4-carboxamido)propanoate |
| 115A | | methyl 3-((4R)-2-(benzylamino)-5,5-dimethyl-2-oxido-1,3,2-dioxaphosphinane-4-carboxamido)propanoate |
| 116 | | methyl 3-((4R)-5,5-dimethyl-2-oxido-2-((((tetrahydrofuran-2-yl)methyl)amino)-1,3,2-dioxaphosphinane-4-carboxamido)propanoate |
| 117 | | benzyl 3-(((4R)-4-((3-methoxy-3-oxopropyl)carbamoyl)-5,5-dimethyl-2-oxido-1,3,2-dioxaphosphinan-2-yl)amino)propanoate |
| 118 | | methyl 3-((4R)-2-((2-(benzyloxy)-2-oxoethyl)amino)-5,5-dimethyl-2-oxido-1,3,2-dioxaphosphinane-4-carboxamido)propanoate |

TABLE 3-continued

Exemplary simple-amine phosphoramidate compounds.

| No. | Compound | Chemical Name |
|---|---|---|
| 119 | | methyl 3-((2S,4R)-5,5-dimethyl-2-oxido-2-(((tetrahydrofuran-2-yl)methyl)amino)-1,3,2-dioxaphosphinane-4-carboxamido)propanoate |
| 120 | | methyl 3-((2R,4R)-5,5-dimethyl-2-oxido-2-(((tetrahydrofuran-2-yl)methyl)amino)-1,3,2-dioxaphosphinane-4-carboxamido)propanoate |
| 121 | | methyl 3-((2R,4R)-2-((3-methoxy-3-oxopropyl)amino)-5,5-dimethyl-2-oxido-1,3,2-dioxaphosphinane-4-carboxamido)propanoate |
| 121A | | methyl 3-((4R)-2-((3-methoxy-3-oxopropyl)amino)-5,5-dimethyl-2-oxido-1,3,2-dioxaphosphinane-4-carboxamido)propanoate |
| 122 | | methyl 3-((4R)-2-((2-acetamidoethyl)amino)-5,5-dimethyl-2-oxido-1,3,2-dioxaphosphinane-4-carboxamido)propanoate |
| 123 | | methyl 3-((4R)-2-((furan-2-ylmethyl)amino)-5,5-dimethyl-2-oxido-1,3,2-dioxaphosphinane-4-carboxamido)propanoate |
| 124 | | methyl 3-((4R)-2-((3-(dimethylamino)-3-oxopropyl)amino)-5,5-dimethyl-2-oxido-1,3,2-dioxaphosphinane-4-carboxamido)propanoate |
| 125 | | methyl 3-((4R)-5,5-dimethyl-2-oxido-2-((pyridin-4-ylmethyl)amino)-1,3,2-dioxaphosphinane-4-carboxamido)propanoate |

TABLE 3-continued

Exemplary simple-amine phosphoramidate compounds.

| No. | Compound | Chemical Name |
|---|---|---|
| 126 | | methyl 3-((4R)-5,5-dimethyl-2-((2-morpholinoethyl)amino)-2-oxido-1,3,2-dioxaphosphinane-4-carboxamido)propanoate |
| 127 | | methyl 3-((4R)-5,5-dimethyl-2-oxido-2-((3-(2-oxopyrrolidin-1-yl)propyl)amino)-1,3,2-dioxaphosphinane-4-carboxamido)propanoate |
| 128 | | methyl 3-((4R)-5,5-dimethyl-2-((2-(4-methylpiperazin-1-yl)ethyl)amino)-2-oxido-1,3,2-dioxaphosphinane-4-carboxamido)propanoate |
| 129 | | methyl 3-((4R)-2-((4-fluorophenethyl)amino)-5,5-dimethyl-2-oxido-1,3,2-dioxaphosphinane-4-carboxamido)propanoate |
| 130 | | methyl 3-((4R)-5,5-dimethyl-2-oxido-2-((1-phenylethyl)amino)-1,3,2-dioxaphosphinane-4-carboxamido)propanoate |
| 131 | | 1-(tert-butyl) 2-methyl (2R,4R)-4-(((4R)-4-((3-methoxy-3-oxopropyl)carbamoyl)-5,5-dimethyl-2-oxido-1,3,2-dioxaphosphinan-2-yl)amino)pyrrolidine-1,2-dicarboxylate |
| 132 | | methyl (2R,4R)-4-(((4R)-4-((3-methoxy-3-oxopropyl)carbamoyl)-5,5-dimethyl-2-oxido-1,3,2-dioxaphosphinan-2-yl)amino)pyrrolidine-2-carboxylate |
| 133 | | methyl 3-((2R,4R)-5,5-dimethyl-2-oxido-2-(piperidin-1-yl)-1,3,2-dioxaphosphinane-4-carboxamido)propanoate |

TABLE 3-continued

Exemplary simple-amine phosphoramidate compounds.

| No. | Compound | Chemical Name |
|---|---|---|
| 133A | | methyl 3-((4R)-5,5-dimethyl-2-oxido-2-(piperidin-1-yl)-1,3,2-dioxaphosphinane-4-carboxamido)propanoate |
| 134 | | methyl 3-((4R)-2-(isobutylamino)-5,5-dimethyl-2-oxido-1,3,2-dioxaphosphinane-4-carboxamido)propanoate |
| 135 | | methyl 3-((2S,4R)-5,5-dimethyl-2-morpholino-2-oxido-1,3,2-dioxaphosphinane-4-carboxamido)propanoate |
| 136 | | methyl 3-((2R,4R)-5,5-dimethyl-2-morpholino-2-oxido-1,3,2-dioxaphosphinane-4-carboxamido)propanoate |
| 137 | | methyl 3-((2R,4R)-2-(1,1-dioxidothiomorpholino)-5,5-dimethyl-2-oxido-1,3,2-dioxaphosphinane-4-carboxamido)propanoate |
| 138 | | methyl 3-((2S,4R)-2-(1,1-dioxidothiomorpholino)-5,5-dimethyl-2-oxido-1,3,2-dioxaphosphinane-4-carboxamido)propanoate |
| 139 | | methyl 3-((4R)-2-(4-acetylpiperazin-1-yl)-5,5-dimethyl-2-oxido-1,3,2-dioxaphosphinane-4-carboxamido)propanoate |

Synthesis of Cyclic Phosphates and Cyclic Phosphoramidates

Yet another embodiment of the invention is a method of preparing a compound of Formula I.

Synthesis of Cyclic Phosphoramidates by Method A

Compounds from the invention can be accessed from pantothenic acid by those skilled in the art using modifications of procedures known in the literature for the synthesis of nucleoside prodrugs. In one approach, amino acid phosphoramidate compounds of the invention can be prepared by cyclisation of an acyclic phosphoramidate precursor as outlined in Method A below:

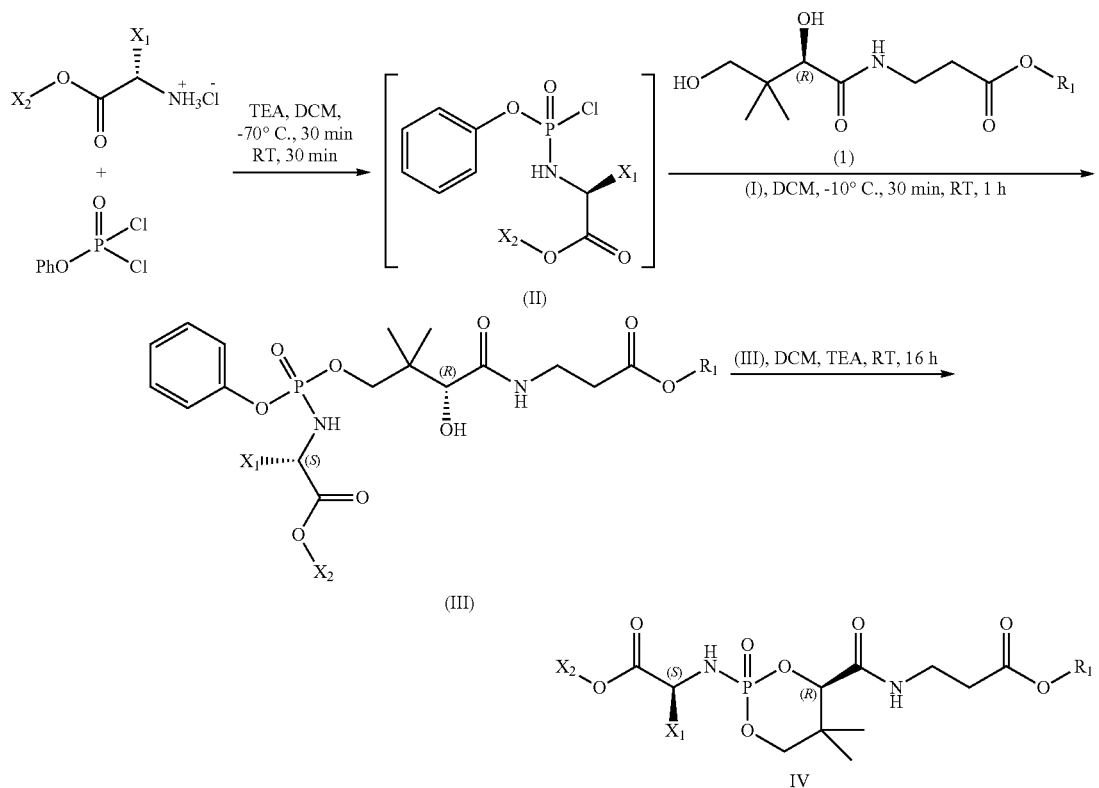

Synthesis of Cyclic Phosphates by Method B

An electrophilic cyclic phosphopantothenic acid analog (such as compound (V) below) may be used as a route toward the synthesis of cyclic phosphates as outlined in Method B below:

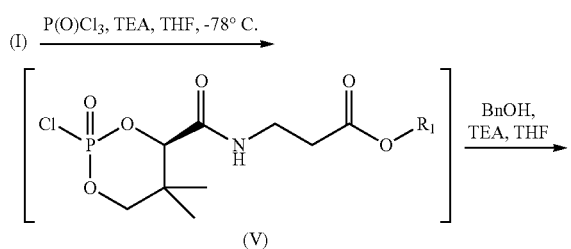

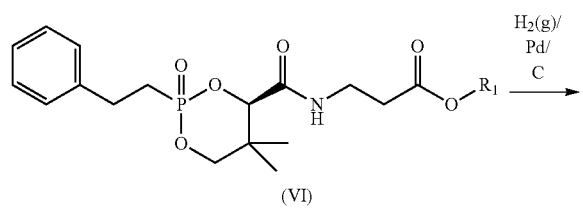

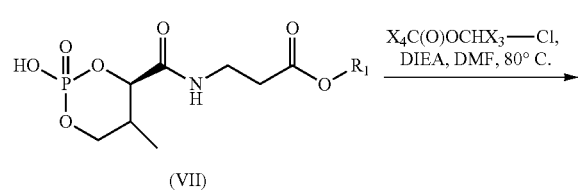

-continued

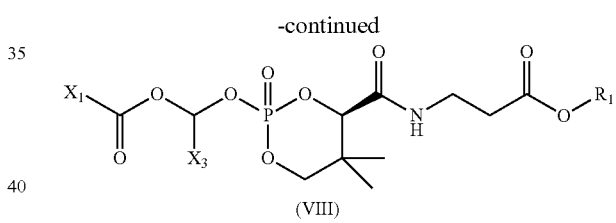

Method B further illustrates the use of a nucleophilic cyclic phosphopantothenic acid intermediate (compound (VII)) that may be functionalized in an alternative approach toward cyclic phosphates.

Synthesis of Cyclic Phosphoramidates by Method C

An electrophilic cyclic phosphopantothenic acid analog (such as compound (V) below) may also be used as a route toward the synthesis of cyclic phosphoramidates as outlined in Method C below:

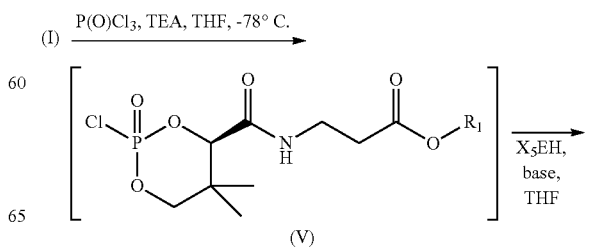

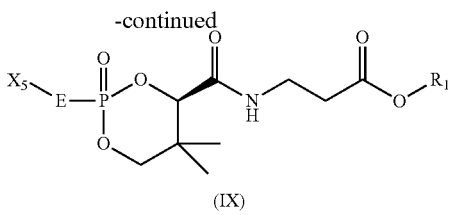

(IX)

Pharmaceutical Compositions and Methods of Treatment

In certain aspects, the present invention provides pharmaceutical compositions comprising a compound of the present invention, and a pharmaceutically acceptable excipient. In one embodiment, the pharmaceutical composition includes an effective amount of the compound to treat a neurologic disorder. In some embodiments, a pharmaceutical composition comprising a compound having a structure as set forth in Table 1, Table 2, or Table 3 and a pharmaceutically acceptable excipient is provided. The pharmaceutical compositions may be a dosage unit form, such as a tablet or capsule.

Yet another embodiment is a method of increasing 4'-phosphopantothenic acid production in a subject in need thereof by administering to the subject an effective amount of a compound or pharmaceutical composition of the present invention. In one embodiment, the subject in need of increased 4'-phosphopantothenic acid production exhibits overexpression of an enzyme for which Coenzyme A is a synthetic precursor. In one embodiment, the subject in need of increased 4'-phosphopantothenic acid production has a deficiency of Coenzyme A, a deficiency of pantothenate kinase enzyme, and/or a deficiency of 4'-phosphopantothenic acid. In one embodiment, the subject in need thereof has a defect or mutation in a pantothenate kinase gene (PANK). In one embodiment, a method of increasing 4'-phosphopantothenic acid production in a subject having a defect in the PANK1, PANK2, PANK3, or PANK4 gene, or any combination thereof, is provided. In one embodiment, a method of increasing 4'-phosphopantothenic acid production in a subject having a defect in the PANK2 gene is provided. In one embodiment, the compound administered to increase 4'-phosphopantothenic acid production has a structure as set forth in Table 1, Table 2, or Table 3.

Yet another embodiment is a method of treating a subject having a disorder associated with pantothenate kinase enzyme deficiency comprising administering to a subject in need thereof an effective amount of a compound or pharmaceutical composition of the present invention. In one embodiment, the compound administered to treat a subject having a disorder associated with pantothenate kinase enzyme deficiency has a structure as set forth in Table 1, Table 2, or Table 3. In one embodiment, the disorder is pantothenate kinase-associated neurodegeneration (PKAN). In another embodiment, the subject exhibits neurodegeneration with brain iron accumulation. In one embodiment, the subject having a disorder associated with pantothenate kinase enzyme deficiency has a pantothenate kinase gene (PANK) defect. In one embodiment, a method of treating a subject having a disorder associated with pantothenate kinase enzyme deficiency is provided, wherein the subject has a defect in the PANK1, PANK2, PANK3, or PANK4 gene, or any combination thereof. In one embodiment, a method of treating a subject having a disorder associated with pantothenate kinase enzyme deficiency is provided, wherein the subject has a PANK1 gene defect. In one embodiment, a method of treating a subject having a disorder associated with pantothenate kinase enzyme deficiency is provided, wherein the subject has a PANK2 gene defect. In one embodiment, a method of treating a subject having a disorder associated with pantothenate kinase enzyme deficiency is provided, wherein the subject has a PANK3 gene defect. In one embodiment, a method of treating a subject having a disorder associated with pantothenate kinase enzyme deficiency is provided, wherein the subject has a PANK4 gene defect.

Yet another embodiment is a method of treating a subject having a disorder associated with Coenzyme A deficiency, comprising administering to the subject an effective amount of a compound or pharmaceutical composition of the present invention. In one embodiment, the compound administered to treat a subject having a disorder associated with Coenzyme A deficiency has a structure as set forth in Table 1, Table 2, or Table 3.

Yet another embodiment is a method of treating a condition associated with abnormal neuronal function in a subject, comprising administering to the subject an effective amount of a compound or pharmaceutical composition of the present invention. In one embodiment, the condition may be Parkinson's disease, dystonia, extrapyramidal effects, dysphagia, rigidity and/or stiffness of limbs, choreoathetosis, tremor, dementia, spasticity, muscle weakness, or seizure. In one embodiment, the compound administered to treat the condition associated with abnormal neuronal function has a structure as set forth in Table 1, Table 2, or Table 3.

Yet another embodiment is a method of treating a condition associated with neuronal cell iron accumulation in a subject in need thereof, comprising administering to the subject an effective amount of a compound or pharmaceutical composition of the present invention. In one such embodiment, the compound administered to treat the condition associated with neuronal cell iron accumulation has a structure as set forth in Table 1, Table 2, or Table 3.

Another embodiment is a method of treating a subject having neurodegeneration with brain iron accumulation, comprising administering to the subject an effective amount of a compound or pharmaceutical composition of the present invention. In one embodiment, the compound administered to treat a subject having neurodegeneration with brain iron accumulation has a structure as set forth in Table 1, Table 2, or Table 3. In one embodiment, the subject having neurodegeneration with brain iron accumulation has pantothenate kinase-associated neurodegeneration (PKAN).

In some embodiments, the subject being treated or in need thereof is a child. In some embodiments, the child is 10 to 15 years old. In other embodiments, the subject being treated or in need thereof is an adult.

Pharmaceutical Formulations and Routes of Administration

The compounds and pharmaceutical compositions of the present invention may be administered by a variety of routes, including orally, nasally, and by injection (e.g., subcutaneously, intravenously, and intraperitoneally).

The compounds or pharmaceutical compositions may be administered orally in the form of a solid or liquid dosage form. In both, the compounds or pharmaceutical compositions may be coated in a material to protect it from the action of acids and other natural conditions which may inactivate the compound. The compounds or pharmaceutical compositions may be formulated as aqueous solutions, liquid dispersions, (ingestible) tablets, buccal tablets, troches, capsules, elixirs, suspensions, syrups, and wafers. The oral dosage forms may include excipients known in the art, such as binders, disintegrating agents, flavorants, antioxidants, and preservatives. Liquid dosage forms may include diluents such as saline or an aqueous buffer.

For nasal administration, the preparation can contain a compound or pharmaceutical composition of the invention, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens. Solutions or suspensions may be applied directly to the nasal cavity by conventional means, for example with a dropper, pipette, or spray. The formulations may be provided in single or multidose form. In the latter case of a dropper or pipette, this may be achieved by the patient administering an appropriate predetermined volume of the solution or suspension. In the case of a spray, this may be achieved for example by means of a metering atomizing spray pump. To improve nasal delivery and retention, the compounds according to the invention may be encapsulated with cyclodextrins, or formulated with their agents expected to enhance delivery and retention in the nasal mucosa.

The compounds and pharmaceutical compositions may also be administered by injection. Formulations suitable for injection may include sterile aqueous solutions (where water soluble) or dispersions, and sterile powders for the extemporaneous preparation of sterile injectable solutions or dispersions. The composition may be sterile and be fluid to the extent that easy syringability exists. It may be stable under the conditions of manufacture and storage and be preserved against the contaminating action of microorganisms such as bacteria and fungi. The carrier can be a solvent or dispersion medium containing, for example, water, ethanol, polyol (such as glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, and ascorbic acid. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound or pharmaceutical composition in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying, which yields a powder of the active ingredient (i.e., the therapeutic compound) plus any additional desired ingredient from a previously sterile-filtered solution thereof.

The actual dosage amount of the compound administered to a subject may be determined by physical and physiological factors such as age, sex, body weight, severity of condition, the type of disease being treated, previous or concurrent therapeutic interventions, idiopathy of the subject, and the route of administration. These factors may be determined by a skilled artisan. The practitioner responsible for administration will typically determine the concentration of active ingredient(s) in a composition and appropriate dose(s) for the individual subject.

In one embodiment, a human subject is administered the daily doses of from about 0.01 mg/kg to about 100 mg/kg.

Single or multiple doses of the compounds or pharmaceutical compositions are contemplated. Desired time intervals for delivery of multiple doses can be determined by one of ordinary skill in the art employing no more than routine experimentation. As an example, subjects may be administered two doses daily at approximately 12 hour intervals. In some embodiments, the compound or pharmaceutical composition is administered once a day. In other embodiments, the compound or pharmaceutical composition is delivered two times a day. In still other embodiments, the compound or pharmaceutical composition is delivered three times a day.

The compounds or pharmaceutical compositions may be administered on a routine schedule. As used herein a routine schedule refers to a predetermined designated period of time. The routine schedule may encompass periods of time which are identical or which differ in length, as long as the schedule is predetermined. For instance, the routine schedule may involve administration four times a day, three times a day, twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months. In other embodiments, the invention provides that the compound or pharmaceutical composition may be taken orally and that the timing of which is or is not dependent upon food intake. Thus, for example, the compound or pharmaceutical composition can be taken every morning and/or every evening, regardless of when the subject has eaten or will eat.

Combination Therapy

In addition to being used as a monotherapy, the compounds and pharmaceutical compositions may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

The additional agent or agents may be selected from any agent or agents useful for treating a neurological disorder, for example any agent or agents useful for treating a deficiency of pantothenate kinase, 4'-phosphopantothenate, or Coenzyme A. In one embodiment, the additional agent or agent is useful in improving cognitive function, e.g., an acetylcholinesterase inhibitor, such as physostigmine, neostigmine, pyridostigmine, ambenonium, demarcarium, rivastigmine, galantamine, donepezil, and combinations thereof. In another embodiment, the additional agent or agents is an iron chelator, such as deferiprone, deferoxamine, deferasirox, and combinations thereof.

EXAMPLES

Example 1

Benzyl ((4R)-4-((3-methoxy-3-oxopropyl)-5,5-dimethyl-2-oxido-1,3,2-dioxaphosphinan-2-yl)-L-alaninate (Compound No. 11)

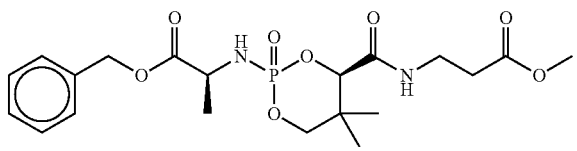

Benzyl ((4R)-4-((3-methoxy-3-oxopropyl)carbamoyl)-5,5-dimethyl-2-oxido-1,3,2-dioxaphosphinan-2-yl)-L-alaninate (Compound No. 11) was synthesized via Method A as described above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was $H_2O$ containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase $H_2O$ containing 0.1% of TFA and MeCN containing 0.1% of TFA.

Step 1. (R)-methyl 3-(2,4-dihydroxy-3,3-dimethylbutanamido)propanoate

A solution 0.25 M of D-calcium pantothenate (1.0 eq) in methanol was treated with $MeSO_3H$ (2.3 eq), added dropwise over a period of 30 min. During the addition the temperature gradually increased from 20° C. to 30° C. and a white suspension formed. Following the addition the reaction mixture was then stirred at 20° C. for 42 h. $NaHCO_3$ (0.5 eq) was added and the heterogeneous reaction mixture was stirred for 1 h, filtered through a sintered glass funnel to remove insoluble salts and the cake was washed with methanol. The combined filtrates were concentrated under reduced pressure (bath temperature ~30° C.). The residue was suspended in EtOAc and transferred to a reactor equipped with a mechanical stirrer and a thermometer. $MgSO_4$ (0.5 eq) was added and the slurry obtained was stirred for 2 h at 20° C. The slurry was filtered through a sintered glass funnel to remove insoluble salts, and the cake was washed with EtOAc. The combined filtrates were concentrated under reduced pressure (bath temperature ~30° C.) to give a colorless residue. This material was purified by flash chromatography column using Petroleum Ether/EtOAc as eluent to furnish the title compound (77%) as an oil. $^1$H-NMR (400 MHz, $CDCl_3$, 300 K) δ 4.01 (s, 1H), 3.70 (s, 3H), 3.65-3.45 (m, 4H), 2.57 (t, J=6.0 Hz, 2H), 1.02 (s, 3H), 0.91 (s, 3H).

Step 2. (2S)-Benzyl 2-((((R)-3-hydroxy-4-((3-methoxy-3-oxopropyl)amino)-2,2-dimethyl-4-oxobutoxy)(phenoxy)phosphoryl)amino)propanoate A suspension of benzyl L-alaninate hydrochloride (1.0 eq) in dry DCM (0.34 M) was treated at −70° C. with dichlorophosphoryloxybenzene (1.0 eq). A solution (4.4 M) of $Et_3N$ (2.0 eq) in dry DCM was added and the resulting white suspension was stirred for 30 min at −70° C. before being warmed to room temperature. After stirring for 30 min, the mixture was cooled to −10° C. and a solution (2.5 M) of (R)-methyl 3-(2,4-dihydroxy-3,3-dimethylbutanamido)propanoate (1.1 eq) in DCM was added dropwise. A solution (4.4 M) of freshly distilled NMI (2.0 eq) was then added and the resulting mixture was left to stir for 0.5 h at −10° C. then warmed to room temperature and stirred for a further 1 h. The reaction was quenched by addition of MeOH and then diluted with DCM. The organic phase was washed sequentially with $H_2O$, 5% citric acid solution, and brine, and then was dried over $Na_2SO_4$. The filtered organic phase was concentrated in vacuo to obtain an orange residue that was purified by flash chromatography on $SiO_2$ using Petroleum Ether/EtOAc to furnish a mixture (54:46*) of diastereoisomers of the title compound as a colorless oil (63%). $^1$H-NMR (400 MHz, $CDCl_3$, 300 K) δ 7.35-7.29 (m, 6H), 7.19-7.14 (m, 4H), 5.16* and 5.15 (s, 2H), 4.18-4.12 (m, 2H), 3.94* and 3.79 (s, 1H), 3.68* and 3.67 (s, 3H), 3.72-3.61 (m, 1H), 3.59-3.50 (m, 2H), 2.60-2.49 (m, 2H), 1.45-1.40 (m, 3H), 1.08 and 1.07* (s, 3H), 0.81* and 0.79 (s, 3H); $^{31}$P-NMR (162 MHz, $CDCl_3$, 300 K) δ 5.93 and 5.41*; UPLC tR 1.77 min and 1.80* min; MS ($ES^+$) m/z 551 $(M+H)^+$.

Step 3. Benzyl ((4R)-4-((3-methoxy-3-oxopropyl)carbamoyl)-5,5-dimethyl-2-oxido-1,3,2-dioxaphosphinan-2-yl)-L-alaninate A solution (0.08 M) of (2S)-Benzyl 2-((((R)-3-hydroxy-4-((3-methoxy-3-oxopropyl)amino)-2,2-dimethyl-4-oxobutoxy)(phenoxy)phosphoryl)amino)propanoate (1.0 eq) in DCM was treated with $Et_3N$ (2.0 eq) and the resulting mixture was stirred for 16 h at ambient temperature. The solvent was concentrated in vacuo and the residue was purified by flash chromatography using DCM/EtOAc/MeOH to afford a mixture of diastereoisomers (53:47*) of the title compound (74%) as a colorless oil. $^1$H-NMR (400 MHz, $CDCl_3$, 300 K) δ 7.39-7.34 (m, 5H), 7.28-7.25 and 7.10-7.05 (m, 1H), 5.19 and 5.18* (s, 2H), 4.74* and 4.46 (d, J=1.84 Hz, J*=4.9 Hz, 1H), 4.35-4.32 and 4.15-3.97 (m, 2H), 3.89-3.84 (m, 1H), 3.69* and 3.67 (s, 3H), 3.72-3.53 (m, 2H), 2.58-2.53 (m, 2H), 1.49 and 1.45* (d, J=7.0 Hz, J=7.1 Hz, 3H), 1.14 and 1.11* (s, 3H), 1.09* and 1.03 (s, 3H). $^{31}$P-NMR (162 MHz, $CDCl_3$, 300 K) δ 4.63 and 1.53; UPLC tR 1.51* min and 1.55 min; MS ($ES^+$) m/z 457 $(M+H)^+$.

Example 2

Methyl 3-((4R)-5,5-dimethyl-2-oxido-2-(((S)-1-oxo-1-phenethoxypropan-2-yl)amino)-1,3,2-dioxaphosphinane-4-carboxamido)propanoate (Compound No. 2)

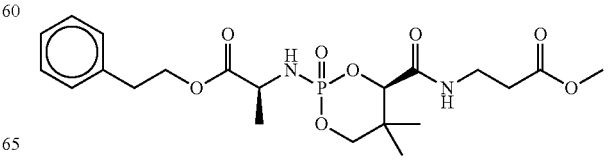

Methyl 3-((4R)-5,5-dimethyl-2-oxido-2-(((S)-1-oxo-1-phenethoxypropan-2-yl)amino)-1,3,2-dioxaphosphinane-4-carboxamido)propanoate (Compound No. 2) was synthesized via Method A as described above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was $H_2O$ containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase $H_2O$ containing 0.1% of TFA and MeCN containing 0.1% of TFA.

Step 1: phenethyl (tert-butoxycarbonyl)-L-alaninate (2S)-2-(tert-butoxycarbonylamino)propanoic acid (1.0 eq) was dissolved in DMF (2.8 M) and treated with $Cs_2CO_3$ (0.5 eq). After stirring for 0.5 h 2-phenylethylbromide (1.1 eq) was added dropwise and the mixture was then stirred overnight. The solvent was evaporated on a rotary evaporator and the residue was taken up in EtOAc then washed with saturated aqueous $NaHCO_3$ and aqueous HCl. The organic layer was separated and dried over $Na_2SO_4$. Evaporation of solvent gave a white solid, which was triturated with hexane/$Et_2O$ then filtered and dried to afford the title compound (69%) as a white solid. $^1$H-NMR (400 MHz, DMSO-$d_6$, 300 K) δ 7.32-7.20 (m, 5H), 4.29 (dt, $J_{AB}$=10.8, J=6.9 Hz, 1H), 4.20 (dt, $J_{AB}$=10.8, J=6.9 Hz, 1H), 3.97 (q, J=8.0 Hz, 1H), 2.76 (t, J=6.9 Hz, 2H), 1.39-1.30 (m, 9H), 1.17 (d, J=8.0 Hz, 3H).

Step 2: (S)-1-oxo-1-phenethoxypropan-2-aminium chloride

A solution (0.35 M) of phenethyl (tert-butoxycarbonyl)-L-alaninate (1.0 eq) in acetone was cooled to 0° C. and treated with aqueous HCl (37%, 3 eq). After the addition the ice bath was removed and the mixture was stirred for 3 h before the solvent was removed under reduced pressure. The residue was taken up in toluene and concentrated under reduced pressure, and this procedure was repeated three times. The solid obtained was triturated with $Et_2O$ then filtered to give the title compound (90%) as a white powder that was used directly in subsequent reactions. $^1$H-NMR (400 MHz, DMSO-$d_6$, 300 K) δ 8.19 (bs, 3H), 7.15-7.03 (m, 5H), 4.25 (dt, $J_{AB}$=10.8, J=6.8 Hz), 4.14 (dt, $J_{AB}$=10.8, J=6.8 Hz, 1H), 3.85 (q, J=7.2 Hz, 1H), 2.76 (t, J=6.8 Hz, 2H), 1.13 (d, J=7.2 Hz, 3H).

Step 3: Methyl 3-((4R)-5,5-dimethyl-2-oxido-2-(((S)-1-oxo-1-phenethoxypropan-2-yl)amino)-1,3,2-dioxaphosphinane-4-carboxamido)propanoate (Compound No. 2)

A suspension of (S)-1-oxo-1-phenethoxypropan-2-aminium chloride (1.0 eq) in dry DCM (0.8M) was cooled to −78° C., and treated slowly over 0.5 h with phenyl phosphorodichloridate (1.0 eq). A solution of $Et_3N$ (2.0 eq) in anhydrous DCM (10 M) was added over 3 h and after the addition the mixture was warmed to 20° C. then stirred for 1 h. After this time the mixture was cooled to −10° C. (ice/acetone) and treated over a period of 1 h with a solution of (R)-methyl 3-(2,4-dihydroxy-3,3-dimethylbutanamido)propanoate (1.0 eq) in anhydrous DCM (5M). A solution of NMI (2.0 eq) in anhydrous DCM (10 M) was added over 20 min and the mixture was allowed to warm to 20° C. over 1.5 h. $Et_3N$ (6.0 eq) was added and the resulting mixture was stirred for 24 h. The solution was diluted with DCM and stirred for 72 h then washed with water, 5% citric acid solution, and brine. After drying over $Na_2SO_4$ the organic solvents were concentrated to afford a residue that was purified by flash chromatography on $SiO_2$ cartridge eluting EtOAc/DCM to furnish the title compound (49%) as an oily solid. $^1$H-NMR (400 MHz, CDCl$_3$, 300 K) δ 7.34-7.23 (m, 5H), 7.01 (t, J=4.0 Hz, 1H), 4.67 and 4.44* (d, $J_{HP}$=1.8 Hz and J*$_{HP}$=5.0 Hz, 1H), 4.38-4.27 (m, 2H), 4.33-4.24 and 3.80* (m and dd, J*HP=20.0 Hz, 11.4 Hz, 1H), 4.04-3.87 (m, 1H), 4.03-3.89 and 3.67* (m and d*, J*=11.4 Hz, 1H), 3.63* and 3.61 (s, 3H), 3.56-3.42 (m, 2H), 3.56-3.42 and 3.35* (m and t*, J*=7.0 Hz, 1H), 2.90 (t, J=7.0 Hz, 2H), 2.49 (m, 2H), 1.34 and 1.30* (d, J=7.1 Hz and J*=7.1 Hz, 3H), 1.08 (s, 3H), 1.03*and 0.98 (s, 3H); UPLC tR 1.54 min and 1.56* min; MS (ES$_+$) m/z 471 (M+H)$^+$.

Example 3

(((4R)-4-((3-methoxy-3-oxopropyl)carbamoyl)-5,5-dimethyl-2-oxido-1,3,2-dioxaphosphinan-2-yl)oxy) methyl pivalate (Compound No. 65)

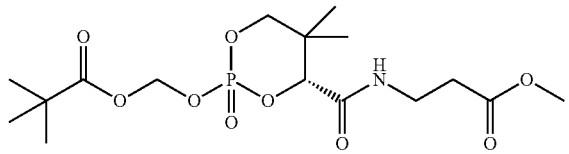 [SMILES: COC(=O)CCNC(=O)[C@@H]1OP(=O)(OCOC(=O)C(C)(C)C)OCC1(C)C]

(((4R)-4-((3-methoxy-3-oxopropyl)carbamoyl)-5,5-dimethyl-2-oxido-1,3,2-dioxaphosphinan-2-yl)oxy)methyl pivalate (Compound No. 65) was synthesized via Method B as described above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was $H_2O$ containing 0.1% Formic acid (A) and MeCN containing U. 1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase $H_2O$ containing 0.1% of TFA and MeCN containing 0.1% of TFA.

Step 1. Methyl 3-((4R)-2-(benzyloxy)-5,5-dimethyl-2-oxido-1,3,2-dioxaphosphinane-4-carboxamido) propanoate A solution (0.38 M) of (R)-methyl 3-(2,4-dihydroxy-3,3-dimethylbutanamido)propanoate (1.0 eq) in THF was treated with a solution (6 M) of TEA (2.1 eq) in THF. This mixture was cooled to −78° C. then a solution (4.7 M) of POCl$_3$ (1.1 eq) in THF was added dropwise. After stirring at −78° C. for 0.5 h the mixture was warmed to ambient temperature over 1 h. The mixture was cooled again to −78° C. then treated sequentially with a solution (6 M) of TEA (2.1 eq) in THF and a solution (4.7 M) of benzyl alcohol (1.1 eq) in THF. Stirring was continued at −78° C. for 0.5 h then the mixture was allowed to warm slowly to ambient temperature before being quenched by addition of H$_2$O and DCM. The organic layer was separated and washed with 5% aqueous citric acid solution, H$_2$O, and brine, and then dried over Na$_2$SO$_4$. Filtration and solvent removal afforded a residue that was purified by flash chromatography on SiO$_2$ using DCM/EtOAc as eluent to afford a single diastereoisomer of title compound (25%) as a white solid. $^1$H-NMR (400 MHz, CDCl$_3$, 300 K) δ 7.45-7.39 (m, 5H), 6.70 (bs, 1H), 5.26-5.22 (m, 2H), 4.74 (d, J=1.5 Hz, 1H), 4.36-4.32 (dd, J=3.0 Hz, J=3.2 Hz, 1H), 3.86-3.78 (m, 1H), 3.68 (s, 3H), 3.49-3.47 (m, 2H), 2.51 (t, J=6.4 Hz, 2H), 1.16 (s, 3H), 1.06 (s, 3H). $^{31}$P-NMR (162 MHz, CDCl$_3$, 300 K) δ −3.13; UPLC tR 1.42 min; MS (ES$^+$) m/z 386 (M+H)$^+$.

Step 2. Methyl 3-((4R)-2-hydroxy-5,5-dimethyl-2-oxido-1,3,2-dioxaphosphinane-4-carboxamido)propanoate (Compound No. 55)

A solution of methyl 3-((4R)-2-(benzyloxy)-5,5-dimethyl-2-oxido-1,3,2-dioxaphosphinane-4-carboxamido)propanoate (1.0 eq) was dissolved in EtOAc (0.15 M) and then treated with Pd/C (5% w/w). The mixture was stirred for 4 h at ambient temperature under an atmosphere of hydrogen gas. The reaction was judged complete by UPLC analysis and was quenched (N$_2$) and filtered. The filtrate was concentrated to afford the title compound (96%) as an oil that was used directly in the subsequent reaction. $^1$H-NMR (400 MHz, CDCl$_3$, 300 K) δ 7.99 (m, 1H), 4.4 (s, 1H), 4.0-3.98 (m, 1H), 3.77-3.69 (m, 1H), 3.57 (s, 3H), 3.41-3.29 (m, 2H), 2.48 (m, 2H), 0.95 (s, 3H), 0.91 (s, 3H). $^{31}$P-NMR (162 MHz, CDCl$_3$, 300 K) δ 6.48 and −6.63.

Step 3. (((4R)-4-((3-methoxy-3-oxopropyl)carbamoyl)-5,5-dimethyl-2-oxido-1,3,2-dioxaphosphinan-2-yl)oxy)methyl pivalate (Compound No. 65)

A solution of methyl 3-((4R)-2-hydroxy-5,5-dimethyl-2-oxido-1,3,2-dioxaphosphinane-4-carboxamido)propanoate (1.0 eq) in DMF (0.25 M) was cooled to −78° C. and treated with N,N-diisopropylethylamine (2.7 eq) and chloromethyl-2,2-dimethylpropanoate (1.7 eq). The cooling bath was removed and the mixture was warmed to room temperature over 1 h before heating at 80° C. for 16 h. The cooled mixture was concentrated in vacuo and the residue was purified by flash chromatography on C18 using H$_2$O/MeCN as eluent to produce after lyophilization a mixture of diastereoisomers (81:19*) of the title compound (30%) as a white solid. $^1$H-NMR (400 MHz, CDCl$_3$, 300 K) δ 7.13-7.10* and 7.00-6.92 (m, 1H), 5.78-5.76* and 5.71-5.68 (m, 2H), 4.77* and 4.55 (s, 1H), 4.35-4.27* and 4.09-4.17 (m, 2H), 3.87-3.81 (m, 1H), 3.7 (s, 3H), 3.64-3.47 (m, 2H), 2.62-2.49 (m, 2H), 1.25* and 1.22 (s, 9H), 1.18* and 1.12 (s, 3H), 1.11 and 1.09* (s, 3H). $^{31}$P-NMR (162 MHz, CDCl$_3$, 300 K) δ −5.34* and −9.26; UPLC tR 1.44 min and 1.48* min; MS (ES$^+$) m/z 410 (M+H)$^+$.

Example 4

(((2R,4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate (Compound No. 71)

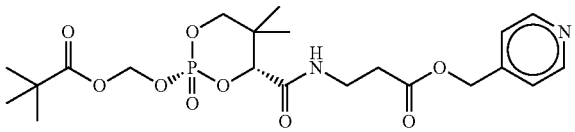

(((4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate (Compound No. 71) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 µm 2.1×50 mm column. The mobile phase was H$_2$O containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase H$_2$O containing 0.1% of TFA and MeCN containing 0.1% of TFA.

Step 1. tert-butyl(R)-3-(2,4-dihydroxy-3,3-dimethylbutanamido)propanoate 3-(tert-butoxy)-3-oxopropan-1-aminium chloride (1.0 eq) was treated with a saturated aqueous solution of NaHCO$_3$ and extracted with DCM. The combined organic extracts were dried over MgSO$_4$, and then the solvent was evaporated under reduced pressure to afford the free amino acid. This compound was treated with (3R)-4,4-dimethyl-3-oxidanyl-oxolan-2-one (1.0 eq) and heated with stirring at 85° C. This mixture melted giving a pale yellow oil that after 48 h was cooled and taken up in the minimum amount of DCM and purified by flash chromatography column on SiO$_2$ using Petroleum Ether/EtOAc as eluent to furnish the title compound (88%) as a colorless oil. $^1$H-NMR (400 MHz, CDCl3, 300 K) δ 7.18 (bs, 1H), 4.03 (s, 1H), 3.60-3.49 (m, 4H), 2.51-2.48 (t, J=5.8 Hz, 2H), 1.47 (s, 9H), 1.04 (s, 3H), 0.93 (s, 3H). UPLC tR 1.17 min; MS (ES) m/z 276 [M+H]$^+$.

Step 2. tert-butyl 3-((4R)-2-(benzyloxy)-5,5-dimethyl-2-oxido-1,3,2-dioxaphosphinane-4-carboxamido)propanoate (Compound No. 63)

A solution of tert-butyl(R)-3-(2,4-dihydroxy-3,3-dimethylbutanamido)propanoate (1.0 eq) was dissolved in THF (0.3M) and sequentially a solution of POCl$_3$ in THF (1.0 eq, 6 M) and TEA in THF (1.1 eq, 2.6 M) were added dropwise at −78° C. Stirring was continued to this temperature for 0.5 h then the cooling bath was removed and the reaction mixture was warmed to ambient temperature over 1 h. The mixture was cooled again to −78° C. then treated sequentially with a solution of benzyl alcohol in THF (1.2 eq, 7M)

and 1-methylimidazole in THF (2.1, 7M). Stirring was continued at −78° C. for 0.5 h then the mixture was allowed to warm slowly to ambient temperature and after 12 h was quenched with $H_2O$. The organic solvent was evaporated and DCM was added. The organic layer was separated and washed with 5% aqueous citric acid solution, water, and brine, and then dried over $Na_2SO_4$. Filtration and solvent removal afforded a residue that was purified by flash chromatography column on $SiO_2$ eluting with PE/EtOAc to afford the title compound (49%) as a white solid as mixture of two diastereomers 59:41*. This diateroisomer mixture was used directly in the subsequent step. $^1$H-NMR (400 MHz, $CDCl_3$, 300 K) δ 7.47-7.39 (m, 5H), 6.91* and 6.81 (bs, 1H), 5.26-5.24 and 5.16-5.13* (d, J=9.8 Hz and J=9.4 Hz*, 2H), 4.77 and 4.42* (m, 1H), 4.39-4.35 and 4.06-4.03* (m, 1H), 4.17-4.12 and 3.86-3.73* (m, 1H), 3.60-3.53 (m, 1H), 3.51-3.53 (m, 1H), 2.51-2.42 (m, 2H), 1.43* and 1.45 (s, 9H), 1.19 and 1.11* (s, 3H), 1.10 and 1.09* (s, 3H). $^{31}$P-NMR (162 MHz, $CDCl_3$, 300 K) δ −4.59, −8.67*. UPLC tR 1.72*, 1.80 min; MS (ES$^+$) m/z 428 [M+H]$^+$.

Step 3. tert-butyl 3-((4R)-2-hydroxy-5,5-dimethyl-2-oxido-1,3,2-dioxaphosphinane-4-carboxamido) propanoate (Compound No. 2-111)

Tert-butyl 3-((4R)-2-(benzyloxy)-5,5-dimethyl-2-oxido-1,3,2-dioxaphosphinane-4-carboxamido)propanoate (1.0 eq) was dissolved in EtOAc (0.26M) and then treated with Pd/C (10% w/w). The mixture was stirred for 4 h at ambient temperature under an atmosphere of hydrogen gas. The reaction was judged complete by UPLC analysis and was purged with $N_2$(g). The catalyst was removed by filtration and the filtrate was evaporated to afford the title compound (97%) as a colorless oil that was used directly in the subsequent reaction step. $^1$H-NMR (400 MHz, DMSO-$d_6$, 300 K) δ 7.91-7.88 (m, 1H), 4.39 (s, 1H), 4.02-3.96 (m, 1H), 3.73-3.67 (dd, $J_{AB}$=10.8, $J_{HP}$=23.7 Hz, 1H), 3.28-3.20 (m, 2H), 2.38-2.34 (t, J=7.0 Hz, 2H), 1.36 (s, 9H), 1.03 (s, 3H), 0.94 (s, 3H). $^{31}$P-NMR (162 MHz, DMSO-$d_6$, 300 K) δ −3.36. UPLC tR 0.89 min; MS (ES$^+$) m/z 338 [M+H]$^+$.

Step 4. (((4R)-4-((3-(tert-butoxy)-3-oxopropyl)carbamoyl)-5,5-dimethyl-2-oxido-1,3,2-dioxaphosphinan-2-yl)oxy)methyl pivalate (Compound No. 75)

A solution of tert-butyl 3-((4R)-2-hydroxy-5,5-dimethyl-2-oxido-1,3,2-dioxaphosphinane-4-carboxamido)propanoate (1.0 eq) in DMF (0.25M) was cooled to −78° C. and treated with chloromethyl-2,2-dimethylpropanoate (1.7 eq) and N,N-diisopropylethylamine (2.8 eq). The cooling bath was removed and the mixture was warmed to room temperature over 1 h before heating at 80° C. for 16 h. The mixture was cooled and concentrated in vacuo to give a residue that was taken up in a minimum amount of DCM and filtered through a $SiO_2$ cartridge preconditioned with DCM using DCM/EtOAc as eluent. The residue obtained after evaporation was further purified by flash chromatography column on C18 eluting with $H_2O$/MeCN. Fractions containing product were concentrated under reduced pressure to remove the acetonitrile then neutralized by addition of a saturated aqueous $NaHCO_3$. The aqueous mixture was extracted with DCM and the combined organics were dried over $Na_2SO_4$. Filtration and removal of organic solvents afforded a mixture of diastereomers (5*:95) of the title compound (58%) as a white solid. $^1$H-NMR (400 MHz, $CDCl_3$, 300 K) δ 7.02 (bs, 1H), 5.73-5.7 (d, $J_{HP}$=13.2 Hz, 2H), 4.82* and 4.59 (s, 1H), 4.4-4.36* and 4.21-4.18 (d, J=15.6 Hz* and J=11.1 Hz, 1H), 3.91-3.82 (dd, $J_{AB}$=11.2 Hz, $J_{HP}$=24.8 Hz, 1H), 3.64-3.56 (m, 1H), 3.52-3.44 (m, 1H), 2.51-2.47 (m, 2H), 1.48 (s, 9H), 1.28* and 1.25 (s, 9H), 1.21* and 1.15 (s, 3H), 1.14 and 1.12*(s, 3H). $^{31}$P-NMR (162 MHz, $CDCl_3$, 300 K) δ −5.50* and −9.36. UPLC tR 2.14 and 2.20* min; MS (ES+) m/z 452 [M+H]$^+$.

Step 5. 3-((2S,4R)-5,5-dimethyl-2-oxido-2-((pivaloyloxy)methoxy)-1,3,2-dioxaphosphinane-4-carboxamido)propanoic acid (Compound No. 91)

(((4R)-4-((3-(tert-butoxy)-3-oxopropyl)carbamoyl)-5,5-dimethyl-2-oxido-1,3,2-dioxaphosphinan-2-yl)oxy)methyl pivalate (1.0 eq) was dissolved in DCM (0.15 M) and TFA (0.32M) was added dropwise. The reaction was stirred for 45 min then the solvent was evaporated and the residue was purified by flash chromatography column C18 eluting with $H_2O$/$CH_3CN$. Fractions containing product were concentrated under reduced pressure to give the title compound (87%) as a white solid. $^1$H-NMR (400 MHz, DMSO-$d_6$, 300 K) δ 12.24 (bs, 1H), 8.13 (bs, 1H), 5.68-5.60 (m, 2H), 4.54 (s, 1H), 4.11-4.08 (d, J=10.1 Hz, 1H), 4.02-3.92 (dd, $J_{AB}$=11.2 Hz, $J_{HP}$=24.4 Hz, 1H), 3.31 (m, 2H), 2.41 (m, 2H), 1.17 (s, 9H), 1.02 (s, 3H), 0.95 (s, 3H). $^{31}$P-NMR (162 MHz, DMSO-$d_6$, 300 K) δ −10.32. UPLC tR 1.25 min. MS (ES+) m/z 418 [M+Na]$^+$.

Step 6. (((2S,4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate (Compound No. 71)

3-((2S,4R)-5,5-dimethyl-2-oxido-2-((pivaloyloxy)methoxy)-1,3,2-dioxaphosphinane-4-carboxamido)propanoic acid (1.0 eq) was dissolved in MeCN (0.2 M) and TBTU (1.5 eq) was added. The mixture was stirred for 20 min, and then 4-pyridylmethanol (1.2 eq) and N,N-diisopropylethylamine (2.0 eq) were added. After stirring for 12 h the solvent was evaporated and the residue was diluted in DCM then washed with saturated aqueous $NaHCO_3$. The organic phase was dried over $Na_2SO_4$, filtered, and concentrated to give a residue that was purified by flash chromatography column C18 eluting with $H_2O$/MeCN. Fractions containing product were concentrated to evaporate the acetonitrile then neutralized with saturated aqueous $NaHCO_3$. The aqueous mixture was extracted with DCM and the combined organics were dried over $Na_2SO_4$ then filtered. Evaporation of solvents gave the title compound (20%) as a pale yellow powder. $^1$H-NMR (400 MHz, $CDCl_3$, 300 K) δ 8.83-8.81 (d, J=6.2 Hz, 2H), 7.86-7.84 (d, J=5.4 Hz, 2H), 6.98 (bs, 1H), 5.78-5.77 (m, 2H), 5.39 (s, 2H), 4.58 (s, 1H), 4.20-4.17 (d, J=11.6 Hz, 1H), 3.91-3.82 (dd, $J_{AB}$=11.5 Hz, $J_{HP}$=24.6 Hz, 1H), 3.73-3.59 (m, 2H), 2.77-2.73 (t, J=6.4 Hz, 2H), 1.25 (s, 9H), 1.15 (s, 3H), 1.11 (s, 3H). $^{31}$P-NMR (162 MHz, $CDCl_3$, 300 K) δ −9.45. UPLC tR 1.39 min. MS (ES+) m/z 487 [M+H]$^+$.

Example 5

Methyl 3-((2R,4R)-2-(benzylamino)-5,5-dimethyl-2-oxido-1,3,2-dioxaphosphinane-4-carboxamido)propanoate (Compound No. 115)

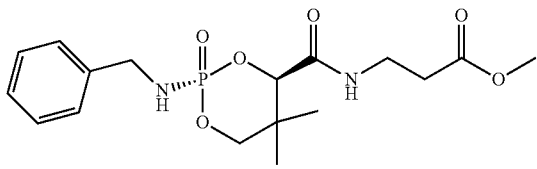 [SMILES: COC(=O)CCNC(=O)[C@@H]1O[P@@](=O)(NCc2ccccc2)OCC1(C)C]

Methyl 3-((2R,4R)-2-(benzylamino)-5,5-dimethyl-2-oxido-1,3,2-dioxaphosphinane-4-carboxamido)propanoate was prepared using Method C as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was $H_2O$ containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase $H_2O$ containing 0.1% of TFA and MeCN containing 0.1% of TFA.

A solution (0.38 M) of (R)-methyl 3-(2,4-dihydroxy-3,3-dimethylbutanamido)propanoate (1.0 eq) in THF was treated with a solution (6 M) of TEA (2.1 eq) in THF. This mixture was cooled to −78° C., then a solution (4.7 M) of $POCl_3$ (1.1 eq) in THF was added dropwise. After stirring at −78° C. for 0.5 h the mixture was warmed to ambient temperature over 1 h. The mixture was cooled again to −78° C. then treated sequentially with a solution (6 M) of TEA (2.1 eq) in THF and a solution (4.7 M) of benzyl amine (1.1 eq) in THF. Stirring was continued at −78° C. for 0.5 h then the mixture was allowed to warm slowly to ambient temperature then quenched with $H_2O$ and DCM. The organic layer was separated and washed with 5% aqueous citric acid solution, $H_2O$, and brine, and then dried over $Na_2SO_4$. Filtration and solvent removal afforded a residue that was purified by flash chromatography on $SiO_2$ using DCM/EtOAc as eluent to afford a single diastereoisomer of the title compound (25%). $^1$H-NMR (400 MHz, $CDCl_3$, 300 K) δ 7.32-7.38 (m, 5H), 4.46 (d, J=7.1 Hz, 1H), 4.16-4.2 (m, 2H), 3.9-4.03 (m, 2H), 3.73 (s, 3H), 3.6-3.68 (m, 1H), 3.48-3.56 (m, 1H), 2.88 (bs, 1H), 2.59 (t, J=6.6 Hz, 2H), 1.18 (s, 3H), 1.13 (s, 3H). $^{31}$P-NMR (162 MHz, $CDCl_3$, 300 K) δ 3.35. UPLC tR 1.19 min; MS (ES+) m/z 385 (M+H)+.

Example 6

(((4R)-4-((3-methoxy-3-oxopropyl)carbamoyl)-5,5-dimethyl-2-oxido-1,3,2-dioxaphosphinan-2-yl)oxy)methyl thiazole-5-carboxylate (Compound No. 70)

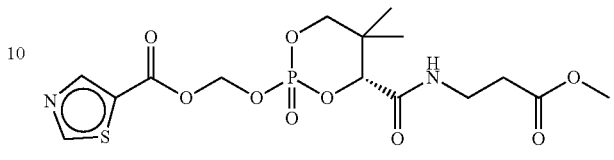

(((4R)-4-((3-methoxy-3-oxopropyl)carbamoyl)-5,5-dimethyl-2-oxido-1,3,2-dioxaphosphinan-2-yl)oxy)methyl thiazole-5-carboxylate (Compound No. 70) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was $H_2O$ containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase $H_2O$ containing 0.1% of TFA and MeCN containing 0.1% of TFA.

Step 1. Methyl 3-((4R)-2-(chloromethoxy)-5,5-dimethyl-2-oxido-1,3,2-dioxaphosphinane-4-carboxamido)propanoate Methyl 3-((4R)-2-hydroxy-5,5-dimethyl-2-oxido-1,3,2-dioxaphosphinane-4-carboxamido)propanoate (Compound No. 55) (synthesized as in Example 3, Step 2) (1.0 eq) was dissolved in water (0.1 M) and tetrabutylammonium hydrogen sulfate (0.1 eq) and $NaHCO_3$ (4.0 eq) were sequentially added at 0° C. The mixture was stirred to this temperature for 10 minutes; then DCM (0.1 M) and chloromethyl sulfurochloridate (2.0 eq) were added. The reaction was left to react for 16 h then the organic phase was separated, washed with brine, and dried over $Na_2SO_4$. Filtration and solvent removal afforded a residue that was purified by flash chromatography on $SiO_2$ using PE/EtOAc as eluent, giving the title compound (10%) as a colorless oil and mixture of diastereomers (58:42*). $^1$H-NMR (400 MHz, CDCl3, 300 K) δ 7.01 and 6.96* (bs, 1H), 5.86-5.72 (m, 2H), 4.80 and 4.68* (d and s*, J=2.4 Hz, 1H), 4.38 and 4.27 (dd and d*, J=3.6, 12.2 Hz, J*=10.9 Hz, 1H), 4.0-3.87 (m, 1H), 3.73 (s, 3H), 3.67-3.55 (m, 2H), 2.62-2.58 (m, 2H), 1.23 and 1.19* (s, 3H), 1.16 and 1.14* (s, 3H). $^{31}$P-NMR (162 MHz, $CDCl_3$, 300 K) δ −5.0, −8.93. UPLC tR 1.13* and 1.15 min. MS (ES+) m/z 366 [M+Na]+.

Step 2. (((4R)-4-((3-methoxy-3-oxopropyl)carbamoyl)-5,5-dimethyl-2-oxido-1,3,2-dioxaphosphinan-2-yl)oxy)methyl thiazole-5-carboxylate (Compound No. 70)

Thiazole-5-carboxylic acid (1.2 eq) and $Cs_2CO_3$ (1.2 eq) were dissolved in DMF (0.25 M) and methyl 3-((4R)-2-

(chloromethoxy)-5,5-dimethyl-2-oxido-1,3,2-dioxaphosphinane-4-carboxamido)propanoate (1.0 eq) was finally added. The reaction mixture was stirred at ambient temperature for 5 h then filtered on a pad of SiO₂, concentrated and purified by flash chromatography on C18 using H₂O/CH₃CN as eluent to produce after lyophilization a mixture of diastereomers (88:12*) of the title compound (20%) as a white powder. ¹H-NMR (400 MHz, CDCl3, 300 K) δ 9.08 and 9.07* (s, 1H), 9.69 and 8.64* (s, 1H), 7.08 and 6.96* (bs, 1H), 6.03-5.92 (m, 2H), 4.81 and 4.61* (d and s*, J=2.4 Hz, 1H), 4.38 and 4.21* (dd and d*, $J_{HP}$=3.6, $J_{AB}$=10.9 Hz, J*=10.9 Hz, 1H), 3.91 (dd, $J_{AB}$=10.9 Hz, $J_{HP}$=23.1 Hz, 1H), 3.73* and 3.71 (s, 3H), 3.60-3.55 (m, 2H), 2.59 (t, J=6.1 Hz, 2H), 1.22 and 1.15* (s, 3H), 1.14* and 1.12 (s, 3H). ³¹P-NMR (162 MHz, CDCl₃, 300 K) δ −5.33, −9.61. UPLC tR 1.05* and 1.08 min. MS (ES+) m/z 459 [M+Na]⁺.

Example 7

(((4R)-4-((3-methoxy-3-oxopropyl)carbamoyl)-5,5-dimethyl-2-oxido-1,3,2-dioxaphosphinan-2-yl)oxy)methyl benzoate (Compound No. 64)

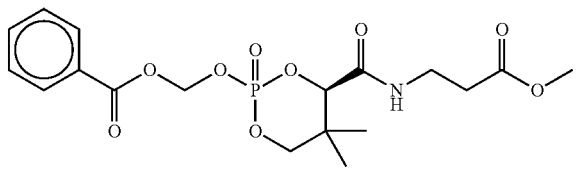

(((4R)-4-((3-methoxy-3-oxopropyl)carbamoyl)-5,5-dimethyl-2-oxido-1,3,2-dioxaphosphinan-2-yl)oxy)methyl benzoate (Compound No. 64) was synthesized according to the procedure described in Example 3 above with respect to Compound No. 65, except that the reagent chloromethyl benzoate was used instead of chloromethyl-2,2-dimethylpropanoate, giving a mixture of diastereomers (17*:83) of the title compound (30%) as a colorless oil.

¹H-NMR (400 MHz, CDCl₃, 300 K) δ 8.14*-8.10 (d, J=8.3 Hz, 2H), 7.67-7.65* and 7.64-7.62 (m, 1H), 7.53-7.47 (m, 2H), 7.09-7.05* and 6.89-6.85 (m, 1H), 6.04* and 5.99-5.92 (dd* and m, J*=4.9, 12.2 Hz, 2H), 4.80* and 4.59 (d* and s, J*=2.4 Hz, 1H), 4.35* and 4.17 (dd* and d, $J_{HP}$*=3.5, $J_{AB}$*=10.9 Hz, J=10.9 Hz, 1H), 3.89* and 3.82 (dd, $J_{AB}$=10.9 Hz, $J_{HP}$=24.3 Hz, 1H), 3.71 (s, 3H), 3.58-3.50 (m, 1H), 3.43-3.35 (m, 1H), 2.55-2.45 (m, 2H), 1.20* and 1.10 (s, 6H). ³¹P-NMR (162 MHz, CDCl₃, 300 K) δ −5.29* and −9.34. UPLC tR 1.43 and 1.47* min. MS (ES+) m/z 452 [M+Na]⁺.

Example 8

(((4R)-4-((3-methoxy-3-oxopropyl)carbamoyl)-5,5-dimethyl-2-oxido-1,3,2-dioxaphosphinan-2-yl)oxy)methyl butyrate (Compound No. 66)

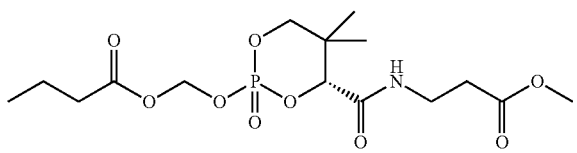 [SMILES: CCCC(=O)OCOP1(=O)OCC(C)(C)[C@H](C(=O)NCCC(=O)OC)O1]

(((4R)-4-((3-methoxy-3-oxopropyl)carbamoyl)-5,5-dimethyl-2-oxido-1,3,2-dioxaphosphinan-2-yl)oxy)methyl butyrate (Compound No. 66) was synthesized according to the procedure described in Example 3 with respect to Compound No. 65, except that the reagent chloromethyl butyrate was used instead of chloromethyl-2,2-dimethylpropanoate, giving a mixture of diastereomers (36*:64) of the title compound (32%) as a colorless oil.

¹H-NMR (400 MHz, CDCl₃, 300 K) δ 7.12* and 6.94 (bs, 1H), 5.80-5.75* and 5.73-5.68 (dd* and m, J*=4.9, 8.2 Hz, 2H), 4.77* and 4.57 (d* and s, J*=2.4 Hz, 1H), 4.34* and 4.17 (dd* and d, $J_{HP}$*=3.6, $J_{AB}$*=12.2 Hz, J=10.9 Hz, 1H), 3.90-3.80 (m, 1H), 3.71 and 3.70* (s, 3H), 3.65-3.49 (m, 2H), 2.60-2.55 (m, 2H), 2.43 (t, J=7.3 Hz, 1H), 2.37 (t, J=7.3 Hz, 1H), 1.73-1.67 (m, 2H), 1.19* and 1.13 (s, 3H), 1.12 and 1.10* (s, 3H), 1.0-0.95 (m, 3H). ³¹P-NMR (162 MHz, CDCl₃, 300 K) δ −5.34* and −9.49. UPLC tR 1.31 and 1.36* min. MS (ES+) m/z 418 [M+Na]+.

Example 9

(((4R)-4-((3-methoxy-3-oxopropyl)carbamoyl)-5,5-dimethyl-2-oxido-1,3,2-dioxaphosphinan-2-yl)oxy)methyl 2-ethylbutanoate (Compound No. 67)

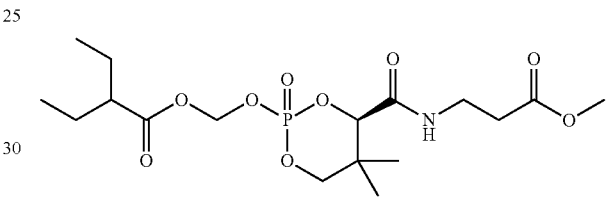

(((4R)-4-((3-methoxy-3-oxopropyl)carbamoyl)-5,5-dimethyl-2-oxido-1,3,2-dioxaphosphinan-2-yl)oxy)methyl 2-ethylbutanoate (Compound No. 67) was synthesized according to the procedure described in Example 3 with respect to Compound No. 65, except that the reagent chloromethyl 2-ethylbutanoate was used instead of chloromethyl-2,2-dimethylpropanoate, giving a mixture of diastereomers (11*:89) of the title compound (39%) as a colorless oil.

¹H-NMR (400 MHz, CDCl₃, 300 K) δ 6.93 (bs, 1H), 5.81-5.75* and 5.73-5.70 (m, 2H), 4.77* and 4.57 (s, 1H), 4.34* and 4.17 (dd* and d, $J_{HP}$*=3.6 Hz, $J_{AB}$*=10.9 Hz, J=10.9 Hz, 1H), 3.83 (dd, $J_{AB}$=12.2 Hz, $J_{HP}$=25.5 Hz, 1H), 3.71 and 3.70* (s, 3H), 3.65-3.58 (m, 1H), 3.55-3.47 (m, 1H), 2.59-2.55 (m, 2H), 2.34-2.26 (m, 1H), 1.72-1.53 (m, 4H), 1.19* and 1.13 (s, 3H), 1.12 and 1.09* (s, 3H), 0.91 (t, J=7.3 Hz, 6H). ³¹P-NMR (162 MHz, CDCl₃, 300 K) δ −5.32* and −9.43. UPLC tR 1.58 and 1.61* min. MS (ES+) m/z 446 [M+Na]⁺.

Example 10

Methyl 3-((4R)-2-(acetoxymethoxy)-5,5-dimethyl-2-oxido-1,3,2-dioxaphosphinane-4-carboxamido)propanoate (Compound No. 68)

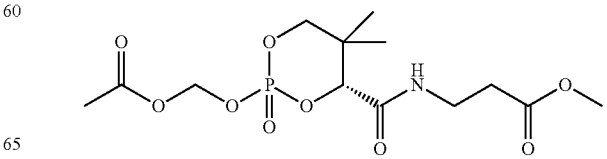

Methyl 3-((4R)-2-(acetoxymethoxy)-5,5-dimethyl-2-oxido-1,3,2-dioxaphosphinane-4-carboxamido)propanoate (Compound No. 68) was synthesized according to the procedure described in Example 3 with respect to Compound No. 65, except that the reagent chloromethyl acetate was used instead of chloromethyl-2,2-dimethylpropanoate, giving a mixture of diastereomers (31*:69) of the title compound (29%) as a colorless oil.

$^1$H-NMR (400 MHz, CDCl$_3$, 300 K) δ 7.10* and 6.93 (bs, 1H), 5.78-5.65 (m, 2H), 4.77* and 4.58 (d* and s, J*=2.4 Hz, 1H), 4.35* and 4.17 (dd* and d, J$_{HP}$*=2.4 Hz, J$_{AB}$*=10.9 Hz, J=10.9 Hz, 1H), 3.87* and 3.85 (dd, J$_{AB}$*=10.9 Hz, J$_{HP}$*=23.5 Hz, J$_{AB}$=12.2 Hz, J$_{HP}$=25.5 Hz, 1H), 3.71 (s, 3H), 3.66-3.49 (m, 2H), 2.60-2.56 (m, 2H), 2.2* and 2.15 (s, 3H), 1.19* and 1.14 (s, 3H), 1.12 and 1.10* (s, 3H). $^{31}$P-NMR (162 MHz, CDCl$_3$, 300 K) δ −5.22* and −9.56. UPLC tR 1.00 and 1.04* min. MS (ES+) m/z 390 [M+Na]$^+$.

Example 11

Methyl 3-((4R)-2-(((isopropoxycarbonyl)oxy)methoxy)-5,5-dimethyl-2-oxido-1,3,2-dioxaphosphinane-4-carboxamido)propanoate (Compound No. 69)

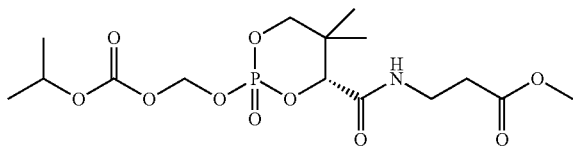 [SMILES: COC(=O)CCNC(=O)[C@@H]1OP(=O)(OCOC(=O)OC(C)C)OCC1(C)C]

Methyl 3-((4R)-2-(((isopropoxycarbonyl)oxy)methoxy)-5,5-dimethyl-2-oxido-1,3,2-dioxaphosphinane-4-carboxamido)propanoate (Compound No. 69) was synthesized according to the procedure described in Example 3 with respect to Compound No. 65, except that chloromethyl isobutyrate was used instead of chloromethyl-2,2-dimethylpropanoate, giving a mixture of diastereomers (43*:57) of the title compound (6%) as a colorless oil.

$^1$H-NMR (400 MHz, CDCl$_3$, 300 K) δ 7.13* and 6.96 (bs, 1H), 5.79-5.69 (m, 2H), 5.03-4.93 (m, 1H), 4.81* and 4.61 (d* and s, J*=2.4 Hz, 1H), 4.39* and 4.22 (dd* and d, J$_{HP}$*=3.6 Hz, J$_{AB}$*=10.9 Hz, J=10.9 Hz, 1H), 3.90 (dd, J$_{AB}$=12.2 Hz, J$_{HP}$=23.1 Hz, 1H), 3.73 (s, 3H), 3.69-3.49 (m, 2H), 2.63-2.58 (m, 2H), 1.37 (d, J=6.09 Hz, 3H), 1.35 (d, J=6.09 Hz, 3H), 1.22* and 1.16 (s, 3H), 1.15 and 1.12* (s, 3H). $^{31}$P-NMR (162 MHz, CDCl$_3$, 300 K) δ −5.91 and −9.78*. UPLC tR 1.31 and 1.35* min. MS (ES+) m/z 434 [M+Na]$^+$.

Example 12

(((4R)-4-((3-methoxy-3-oxopropyl)carbamoyl)-5,5-dimethyl-2-oxido-1,3,2-dioxaphosphinan-2-yl)oxy)methyl isonicotinate (Compound No. 72)

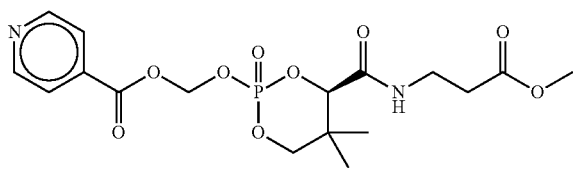

(((4R)-4-((3-methoxy-3-oxopropyl)carbamoyl)-5,5-dimethyl-2-oxido-1,3,2-dioxaphosphinan-2-yl)oxy)methyl isonicotinate (Compound No. 72) was synthesized according to the procedure described in Example 6 above with respect to Compound No. 70, except that isonicotinic acid was used instead of thiazole-5-carboxylic acid, affording a mixture of diastereomers (81:19*) of the title compound (25%) as a colorless oil.

$^1$H-NMR (400 MHz, DMSO-d$_6$, 300 K) δ 8.87-8.85 (m, 2H), 8.20 and 8.13* (m, 1H), 7.88 and 7.86* (d, J=6.09 Hz, J*=6.09 Hz, 2H), 5.97-5.90 (m, 2H), 4.71 and 4.61 (d and s*, J=7.3 Hz, 1H), 4.27-4.13 and 4.05-3.93* (m, 2H), 3.59 (s, 3H), 3.29-3.21 (m, 2H), 2.47 (t, J=6.1 Hz, 2H), 1.08 and 1.01* (s, 3H), 0.94 and 0.93* (s, 3H). $^{31}$P-NMR (162 MHz, DMSO-d$_6$, 300 K) δ. −7.77 and −9.22*. UPLC tR 1.36 min. MS (ES+) m/z 453 [M+Na]$^+$.

Example 13

(((4R)-4-((3-methoxy-3-oxopropyl)carbamoyl)-5,5-dimethyl-2-oxido-1,3,2-dioxaphosphinan-2-yl)oxy)methyl acetyl-L-leucinate (Compound No. 73)

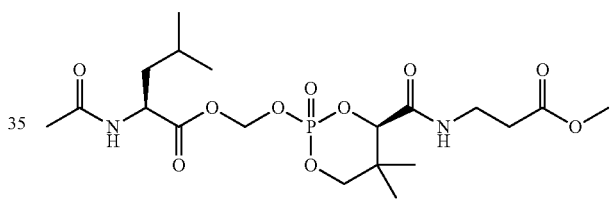

(((4R)-4-((3-methoxy-3-oxopropyl)carbamoyl)-5,5-dimethyl-2-oxido-1,3,2-dioxaphosphinan-2-yl)oxy)methyl acetyl-L-leucinate (Compound No. 72) was synthesized according to the procedure described in Example 6 with respect to Compound No. 70, except that acetyl-L-leucine cesium salt was used instead of thiazole-5-carboxylic acid, affording a mixture of diastereomers (84:16*) of the title compound (19%) as a colorless oil.

$^1$H-NMR (400 MHz, CDCl$_3$, 300 K) δ 7.44 and 7.02* (bs, 1H), 6.55 and 6.03* (d, J=8.5 Hz, 1 H), 5.94 and 5.78* (dd, J=4.9, 12.2 Hz, 1H), 5.72* and 5.58 (dd, J=4.9, 13.4 Hz, 1H), 4.81 and 4.63* (s, 1H), 4.75-4.69 and 4.68-4.65* (m, 1H), 4.40 and 4.19* (dd and d*, J$_{HP}$=2.4, J$_{AB}$=10.9 Hz, J*=10.9 Hz, 1H), 3.90 and 3.87* (dd, J$_{AB}$=10.9 Hz, J$_{HP}$=23.1 Hz, J$_{AB}$*=10.9 Hz, J$_{HP}$*=24.3 Hz, 1H), 3.74 (s, 3H), 3.7-3.64 (m, 1H), 3.61-3.51 (m, 1H), 2.71-2.68* and 2.66-2.58 (m, 2H), 2.09 and 2.07* (s, 3H), 1.78-1.55 (m, 2H), 1.21 and 1.16* (s, 3H), 1.15 and 1.14* (s, 3H), 0.99-0.97 (m, 7H). $^{31}$P-NMR (162 MHz, CDCl$_3$, 300 K) δ. −6.21 and −9.49*. UPLC tR 1.27* and 1.29 min. MS (ES+) m/z 503 [M+Na]$^+$.

Example 14

(((2S,4R)-5,5-dimethyl-4-((3-((5-methylisoxazol-3-yl)methoxy)-3-oxopropyl)carbamoyl)-2-oxido-1,3,2-dioxaphosphinan-2-yl)oxy)methyl pivalate (Compound No. 74)

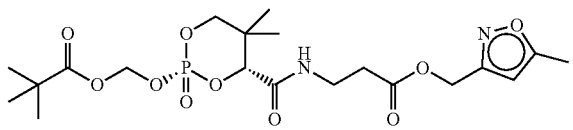

(((2S,4R)-5,5-dimethyl-4-((3-((5-methylisoxazol-3-yl)methoxy)-3-oxopropyl)carbamoyl)-2-oxido-1,3,2-dioxaphosphinan-2-yl)oxy)methyl pivalate (Compound No. 74) was synthesized according to the procedure described in Example 4 with respect to Compound No. 71, except that (5-methylisoxazol-3-yl)methanol was used instead of 4-pyridylmethanol, affording, after purification, a single diastereomer (0:100) of the title compound (40%) as a yellow solid.

$^1$H-NMR (400 MHz, CDCl$_3$, 300 K) δ 7.08 (bs, 1H), 6.07 (s, 1H), 5.76-5.69 (m, 2H), 5.18 (s, 2H), 4.58 (s, 1H), 4.18 (d, J=10.9 Hz, 1H), 3.87 (dd, J$_{AB}$=10.9 Hz, J$_{HP}$=24.3 Hz, 1H), 3.69-3.53 (m, 2H), 2.66-2.62 (m, 2H), 2.45 (s, 3H), 1.24 (s, 9H), 1.13 (s, 3H), 1.10 (s, 3H). $^{31}$P-NMR (162 MHz, CDCl$_3$, 300 K) δ. −9.35. UPLC tR 1.95 min. MS (ES+) m/z 513 [M+Na]$^+$.

Example 15

(((4R)-4-((3-methoxy-3-oxopropyl)carbamoyl)-5,5-dimethyl-2-oxido-1,3,2-dioxaphosphinan-2-yl)oxy)methyl 4-(pyrrolidin-1-ylmethyl)benzoate (Compound No. 76)

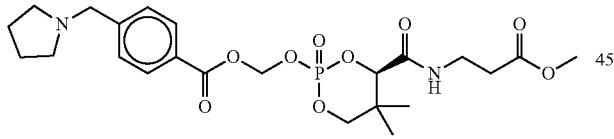

(((4R)-4-((3-methoxy-3-oxopropyl)carbamoyl)-5,5-dimethyl-2-oxido-1,3,2-dioxaphosphinan-2-yl)oxy)methyl 4-(pyrrolidin-1-ylmethyl)benzoate (Compound No. 76) was synthesized according to the procedure described in Example 6 above, with respect to Compound No. 70, except that 4-(pyrrolidin-1-ylmethyl)benzoic acid was used instead of thiazole-5-carboxylic acid, affording a mixture of diastereomers (74:26*) of the title compound (51%) as a colorless oil.

$^1$H-NMR (400 MHz, DMSO-d$_6$, 300 K) δ 9.89 (bs, 1H), 8.22-8.20* and 8.15-8.07 (m, 2H), 7.73-7.70 (m, 2H), 5.94-5.87 (m, 2H), 4.72 and 4.59* (d and s*, J=7.3 Hz, 1H), 4.48 (d, J=6.09 Hz, 2H), 4.24-4.13 and 4.01-3.93* (m, 2H), 3.59 and 3.60* (s, 3H), 3.34-3.29 and 3.26-3.20* (m, 2H), 3.15-3.07 (m, 2H), 2.49-2.44 (m, 4H), 2.07-2.01 (m, 2H), 1.92-1.86 (m, 2H), 1.08 and 1.01* (s, 3H), 1.96 and 0.93 (s, 3H).). $^{31}$P-NMR (162 MHz, DMSO-d$_6$, 300 K) δ. −7.52, −9.16*. UPLC tR 0.88 min. MS (ES+) m/z 513 [M+H]$^+$.

Example 16

(((2S,4R)-4-((3-(2-cyanoethoxy)-3-oxopropyl)carbamoyl)-5,5-dimethyl-2-oxido-1,3,2-dioxaphosphinan-2-yl)oxy)methyl pivalate (Compound No. 77)

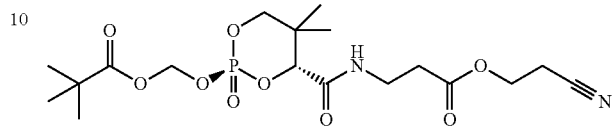

(((2S,4R)-4-((3-(2-cyanoethoxy)-3-oxopropyl)carbamoyl)-5,5-dimethyl-2-oxido-1,3,2-dioxaphosphinan-2-yl)oxy)methyl pivalate (Compound No. 77) was synthesized according to the procedure described in Example 4 with respect to Compound No. 71, except that 3-hydroxypropanenitrile was used instead of 4-pyridylmethanol, affording, after purification, a single diastereomer (0:100) of the title compound (6%) as a yellow solid.

$^1$H-NMR (400 MHz, CDCl$_3$, 300 K) δ 6.98 (bs, 1H), 5.76-5.68 (m, 2H), 4.59 (s, 1H), 4.36-4.33 (m, 2H), 4.19 (d, J=11.3 Hz, 1H), 3.87 (dd, J$_{AB}$=11.6 Hz, J$_{HP}$=25.2 Hz, 1H), 3.67-3.55 (m, 2H), 2.77 (t, J=6.1 Hz, 2H), 2.67-2.63 (m, 2H), 1.26 (s, 9H), 1.16 (s, 3H), 1.15 (s, 3H). $^{31}$P-NMR (162 MHz, CDCl$_3$, 300 K) δ −10.68. UPLC tR 1.44 min. MS (ES+) m/z 471 [M+Na]$^+$.

Example 17

(((2S,4R)-5,5-dimethyl-4-((3-(2-(methylsulfonyl)ethoxy)-3-oxopropyl)carbamoyl)-2-oxido-1,3,2-dioxaphosphinan-2-yl)oxy)methyl pivalate (Compound No. 78)

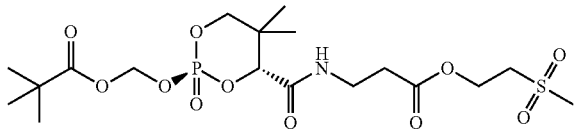 [SMILES: CC(C)(C)C(=O)OCO[P@@]1(=O)OCC(C)(C)[C@H](C(=O)NCCC(=O)OCCS(C)(=O)=O)O1]

(((2S,4R)-5,5-dimethyl-4-((3-(2-(methylsulfonyl)ethoxy)-3-oxopropyl)carbamoyl)-2-oxido-1,3,2-dioxaphosphinan-2-yl)oxy)methyl pivalate (Compound No. 78) was synthesized according to the procedure described in Example 4 with respect to Compound No. 71, except that 2-(methylsulfonyl)ethan-1-ol was used instead of 4-pyridylmethanol, affording, after purification, a single diastereomer (0:100) of the title compound (23%) as a colorless oil.

$^1$H-NMR (400 MHz, CDCl$_3$, 300 K) δ 7.19 (bs, 1H), 5.58-5.47 (m, 2H), 4.48-4.45 (m, 2H), 4.40 (s, 1H), 4.0 (d, J=11.2 Hz, 1H), 3.68 (dd, J$_{AB}$=11.3 Hz, J$_{HP}$=24.7 Hz, 1H), 3.47-3.36 (m, 2H), 3.31-3.24 (m, 1H), 3.21-3.13 (m, 1H), 2.91 (s, 3H), 2.42 (t, J=6.1 Hz, 2H), 1.06 (s, 9H), 0.97 (s, 3H), 0.95 (s, 3H). $^{31}$P-NMR (162 MHz, CDCl$_3$, 300 K) δ −9.15. UPLC tR 1.34 min. MS (ES+) m/z 524 [M+Na]$^+$.

Example 18

(((2S,4R)-5,5-dimethyl-2-oxido-4-((3-oxo-3-(thiazol-5-ylmethoxy)propyl)carbamoyl)-1,3,2-dioxaphosphinan-2-yl)oxy)methyl pivalate (Compound No. 79)

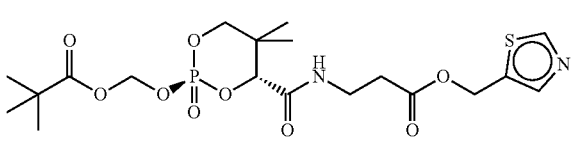

(((2S,4R)-5,5-dimethyl-2-oxido-4-((3-oxo-3-(thiazol-5-ylmethoxy)propyl)carbamoyl)-1,3,2-dioxaphosphinan-2-yl)oxy)methyl pivalate (Compound No. 79) was synthesized according to the procedure described in Example 4 with respect to Compound No. 71, except that thiazol-5-ylmethanol was used instead of 4-pyridylmethanol, affording, after purification, a single diastereomer (0:100) of the title compound (21%) as a white solid.

$^1$H-NMR (400 MHz, CDCl$_3$, 300 K) δ 9.0 (s, 1H), 7.97 (s, 1H), 6.94 (bs, 1H), 5.75-5.69 (m, 2H), 5.39 (s, 2H), 4.56 (s, 1H), 4.17 (d, J=10.9 Hz, 1H), 3.85 (dd, $J_{AB}$=10.9 Hz, $J_{HP}$=25.5 Hz, 1H), 3.67-3.52 (m, 2H), 2.65-2.61 (m, 2H), 1.25 (s, 9H), 1.14 (s, 3H), 1.06 (s, 3H). $^{31}$P-NMR (162 MHz, CDCl$_3$, 300 K) δ. −9.33. UPLC tR 1.34 min. MS (ES+) m/z 493 [M+H]$^+$.

Example 19

(((2S,4R)-5,5-dimethyl-2-oxido-4-((3-oxo-3-((5-oxopyrrolidin-2-yl)methoxy)propyl)carbamoyl)-1,3,2-dioxaphosphinan-2-yl)oxy)methyl pivalate (Compound No. 2-113)

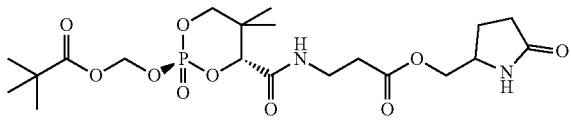 [SMILES: CC(C)(C)C(=O)OCO[P@@]1(=O)OCC(C)(C)[C@H](C(=O)NCCC(=O)OCC2CCC(=O)N2)O1]

(((2S,4R)-5,5-dimethyl-2-oxido-4-((3-oxo-3-((5-oxopyrrolidin-2-yl)methoxy)propyl)carbamoyl)-1,3,2-dioxaphosphinan-2-yl)oxy)methyl pivalate (Compound No. 2-113) was synthesized according to the procedure described in Example 4 with respect to Compound No. 71, except that 5-(hydroxymethyl)pyrrolidin-2-one was used instead of 4-pyridylmethanol, affording, after purification, a single epimer at phosphorous (0:100) of the title compound (21%) as a white solid.

$^1$H-NMR (400 MHz, CDCl$_3$, 300 K) δ 7.04 (bs, 1H), 5.77-5.69 (m, 2H), 4.60 (s, 1H), 4.27 (d, J=8.53 Hz, 1H), 4.19 (d, J=8.53 Hz, 1H), 4.02 (m, 2H), 3.86 (dd, $J_{AB}$=12.2 Hz, $J_{HP}$=25.5 Hz, 1H), 3.72-3.64 (m, 1H), 3.59-3.52 (m, 1H), 2.63 (bs, 1H), 2.48 (t, J=7.3 Hz, 2H), 2.38-2.31 (m, 2H), 1.91-1.82 (m, 2H), 1.26 (s, 9H), 1.16 (s, 3H), 1.14 (s, 3H). $^{31}$P-NMR (162 MHz, CDCl$_3$, 300 K) δ. −9.34. UPLC tR 1.27 min. MS (ES+) m/z 493 [M+H]$^+$.

Example 20

(((2S,4R)-5,5-dimethyl-2-oxido-4-((3-oxo-3-(2-(pyridin-2-yl)ethoxy)propyl)carbamoyl)-1,3,2-dioxaphosphinan-2-yl)oxy)methyl pivalate (Compound No. 82)

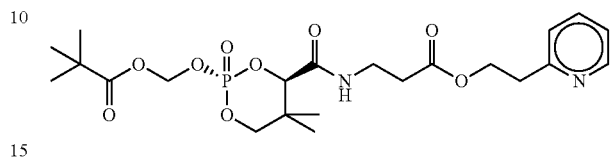

(((2S,4R)-5,5-dimethyl-2-oxido-4-((3-oxo-3-(2-(pyridin-2-yl)ethoxy)propyl)carbamoyl)-1,3,2-dioxaphosphinan-2-yl)oxy)methyl pivalate (Compound No. 82) was synthesized according to the procedure described in Example 4 with respect to Compound No. 71, except that 2-(pyridin-2-yl)ethan-1-ol was used instead of 4-pyridylmethanol, affording, after purification, a single diastereomer (0:100) of the title compound (61%) as a yellow oil.

$^1$H-NMR (400 MHz, CDCl$_3$, 300 K) δ 8.88 (d, J=6.1 Hz, 1H), 8.34 (t, J=8.5 Hz, 1H), 7.81-7.76 (m, 2H), 6.99 (bs, 1H), 5.77-5.68 (m, 2H), 4.60-4.58 (m, 3H), 4.18 (d, J=10.9 Hz, 1H), 3.87 (dd, $J_{AB}$=12.2 Hz, $J_{HP}$=25.5 Hz, 1H), 2.58-2.56 (t, J=6.1 Hz, 2H), 3.53-3.48 (m, 2H), 3.58-3.55 (m, 2H), 1.25 (s, 9H), 1.14 (s, 3H), 1.12 (s, 3H). $^{31}$P-NMR (162 MHz, CDCl$_3$, 300 K) δ. −10.67. UPLC tR 1.09 min. MS (ES+) m/z 501 [M+H]$^+$.

Example 21

(((4R)-4-((3-methoxy-3-oxopropyl)carbamoyl)-5,5-dimethyl-2-oxido-1,3,2-dioxaphosphinan-2-yl)oxy)methyl 1-carbamoylcyclopropane-1-carboxylate (Compound No. 83)

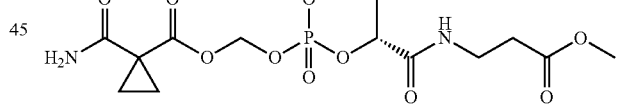

(((4R)-4-((3-methoxy-3-oxopropyl)carbamoyl)-5,5-dimethyl-2-oxido-1,3,2-dioxaphosphinan-2-yl)oxy)methyl 1-carbamoylcyclopropane-1-carboxylate (Compound No. 83) was synthesized according to the procedure described in Example 6 with respect to Compound No. 70, except that 1-carbamoylcyclopropane-1-carboxylic acid was used instead of thiazole-5-carboxylic acid, affording a mixture of diastereomers (86:14*) of the title compound (26%) as a colorless oil.

$^1$H-NMR (400 MHz, CDCl$_3$, 300 K) δ 8.41 and 8.33* (bs, 1H), 7.07 and 6.97* (bs, 1H), 5.82-5.70 (m, 2H), 4.79 and 4.60* (d and s*, J=2.4 Hz, 1H), 4.36 and 4.17* (dd and d*, $J_{HP}$=4.87 Hz, $J_{AB}$=12.2 Hz, J*=12.2 Hz, 1H), 3.91 and 3.90* (dd, $J_{AB}$=12.2 Hz, $J_{HP}$=23.1 Hz, $J_{AB}$*=10.9 Hz, $J_{HP}$*=25.5 Hz, 1H), 3.73 (s, 2H), 3.61-3.57 (m, 2H), 2.62-2.59 (m, 2H), 1.88-1.75 (m, 4H), 1.22 and 1.17* (s, 3H), 1.15* and 1.11 (s, 3H). $^{31}$P-NMR (162 MHz, CDCl$_3$, 300 K) δ. −4.68, −9.69*. UPLC tR 0.96 min. MS (ES+) m/z 459 [M+Na]$^+$.

Example 22

(((4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 84)

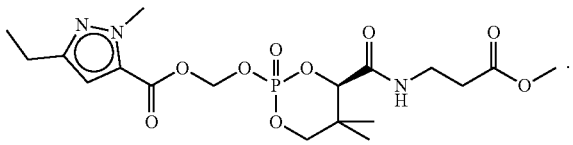

(((4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 84) was synthesized according to the procedure described in Example 6 with respect to Compound No. 70, except that 3-ethyl-1-methyl-1H-pyrazole-5-carboxylic acid was used instead of thiazole-5-carboxylic acid, affording a mixture of diastereomers (75:25*) of the title compound (40%) as a colorless oil.

$^1$H-NMR (400 MHz, DMSO-$d_6$, 300 K) δ 8.18 and 8.13* (t, J=6.1 Hz, 1H), 6.77 and 6.74* (s, 1H), 5.89-5.82 (m, 2H), 4.70 and 4.59* (d and s*, J=6.1 Hz, 1H), 4.25-4.13 (m, 2H), 4.04 and 4.03* (s, 3H), 3.59 (s, 3H), 3.33-3.27 (m, 2H), 2.58 (q, J=7.3 Hz, 2H), 2.50-2.47 (m, 2H), 1.18 (t, J=8.5 Hz, 3H), 1.07 and 1.01* (s, 3H), 0.95 and 0.94* (s, 3H). $^{31}$P-NMR (162 MHz, DMSO-$d_6$, 300 K) δ. −7.56, −9.22*. UPLC tR 1.37 and 1.40* min. MS (ES+) m/z 484 [M+Na]$^+$.

Example 23

1-(tert-butyl) 3-((((4R)-4-((3-methoxy-3-oxopropyl)carbamoyl)-5,5-dimethyl-2-oxido-1,3,2-dioxaphosphinan-2-yl)oxy)methyl) 3-methylazetidine-1,3-dicarboxylate (Compound No. 85)

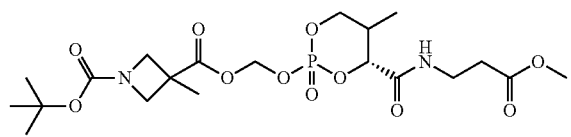 [SMILES: COC(=O)CCNC(=O)[C@@H]1OP(=O)(OCOC(=O)C2(C)CN(C(=O)OC(C)(C)C)C2)OCC1C]

1-(tert-butyl) 3-((((4R)-4-((3-methoxy-3-oxopropyl)carbamoyl)-5,5-dimethyl-2-oxido-1,3,2-dioxaphosphinan-2-yl)oxy)methyl) 3-methylazetidine-1,3-dicarboxylate (Compound No. 85) was synthesized according to the procedure described in Example 6 with respect to Compound No. 70, except that 1-(tert-butoxycarbonyl)-3-methylazetidine-3-carboxylic acid was used instead of thiazole-5-carboxylic acid, affording a mixture of diastereomers (57:43*) of the title compound (15%) as a colorless oil.

$^1$H-NMR (400 MHz, DMSO-$d_6$, 300 K) δ 7.11 and 6.99*, 5.87-5.76 (m, 2H), 4.80 and 4.60* (d and s*, J=2.4 Hz, 1H), 4.36 and 4.17* (dd and d*, $J_{HP}$=3.6 Hz, $J_{AB}$=12.2 Hz, J*=12.2 Hz, 1H), 4.29 and 4.27-4.25* (d and m*, J=8.5 Hz, 2H), 3.95-3.94 (m, 2H), 3.76-3.73 (m, 5H), 3.69-3.51 (m, 2H), 2.62-2.59 (m, 2H), 1.59 (s, 3H), 1.47 (s, 9H), 1.22 and 1.16* (s, 3H), 1.14* and 1.11 8 s, 3H). $^{31}$P-NMR (162 MHz, DMSO-$d_6$, 300 K) δ. −5.26, −9.65*. UPLC tR 1.58 min. MS (ES+) m/z 545 [M+Na]$^+$.

Example 24

(((4R)-4-((3-methoxy-3-oxopropyl)carbamoyl)-5,5-dimethyl-2-oxido-1,3,2-dioxaphosphinan-2-yl)oxy)methyl oxazole-5-carboxylate (Compound No. 87)

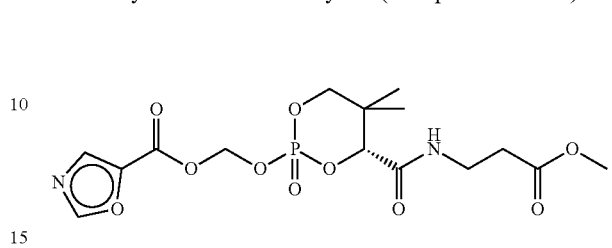

(((4R)-4-((3-methoxy-3-oxopropyl)carbamoyl)-5,5-dimethyl-2-oxido-1,3,2-dioxaphosphinan-2-yl)oxy)methyl oxazole-5-carboxylate (Compound No. 87) was synthesized according to the procedure described in Example 6 with respect to Compound No. 70, except that oxazole-5-carboxylic acid was used instead of thiazole-5-carboxylic acid, affording a mixture of diastereomers (53:47*) of the title compound (1%) as a colorless oil.

$^1$H-NMR (400 MHz, CDCl$_3$, 300 K) δ 8.03 and 8.01* (s, 1H), 7.9 and 7.84* (s, 1H), 6.97 and 6.83 (bs, 1H), 5.91-5.82 (m, 2H), 4.71 and 4.52* (d and s*, J=2.2 Hz, 1H), 4.27 and 4.12* (dd and d*, $J_{HP}$=3.95 Hz, $J_{AB}$=11.8 Hz, J*=11.4 Hz, 1H), 3.86-3.74 (m, 1H), 3.64 and 3.62* (s, 3H), 3.55-3.39 (m, 2H), 2.51-2.46 (m, 2H), 1.13 and 1.06* (s, 3H), 1.05* and 1.02 (s, 3H). $^{31}$P-NMR (162 MHz, CDCl$_3$, 300 K) δ. −6.53, −11.0*. UPLC tR 1.03* and 1.06 min. MS (ES+) m/z 443 [M+Na]$^+$.

Example 25

(((2R,4R)-4-((3-methoxy-3-oxopropyl)carbamoyl)-5,5-dimethyl-2-oxido-1,3,2-dioxaphosphinan-2-yl)oxy)methyl pivalate (Compound No. 89)

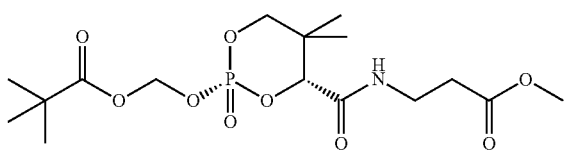 [SMILES: COC(=O)CCNC(=O)[C@@H]1O[P@](=O)(OCOC(=O)C(C)(C)C)OCC1(C)C]

(((2R,4R)-4-((3-methoxy-3-oxopropyl)carbamoyl)-5,5-dimethyl-2-oxido-1,3,2-dioxaphosphinan-2-yl)oxy)methyl pivalate (Compound No. 89) was synthesized according to the procedure described in Example 3 with respect to Compound No. 65 giving, after purification, a single diastereomer (100:0) of the title compound as a yellow oil.

$^1$H-NMR (400 MHz, CDCl$_3$, 300 K) δ 7.05 (bs, 1H), 5.71 (dd, J=4.82, 11.4 Hz, 1H), 5.62 (dd, J=4.82, 14.0 Hz, 1H), 4.70 (d, J=1.75 Hz, 1H), 4.26 (dd, $J_{HP}$=3.9 Hz, $J_{AB}$=11.8 Hz, 1H), 3.78 (dd, $J_{AB}$=11.4 Hz, $J_{HP}$=22.8 Hz, 1H), 3.63 (s, 3H), 3.55-3.46 (m, 2H), 2.54-2.50 (m, 2H), 1.19 (s, 9H), 1.12 (s, 3H), 1.02 (s, 3H). $^{31}$P-NMR (162 MHz, CDCl$_3$, 300 K) δ. −6.69. UPLC tR 1.44 min. MS (ES+) m/z 410 [M+H]$^+$.

Example 26

(((2S,4R)-4-((3-methoxy-3-oxopropyl)carbamoyl)-5,5-dimethyl-2-oxido-1,3,2-dioxaphosphinan-2-yl)oxy)methyl pivalate (Compound No. 90)

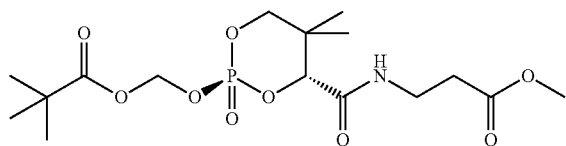 [SMILES: COC(=O)CCNC(=O)[C@@H]1O[P@@](=O)(OCOC(=O)C(C)(C)C)OCC1(C)C]

(((2S,4R)-4-((3-methoxy-3-oxopropyl)carbamoyl)-5,5-dimethyl-2-oxido-1,3,2-dioxaphosphinan-2-yl)oxy)methyl pivalate (Compound No. 90) was synthesized according to the procedure described in Example 3 with respect to Compound No. 65 giving, after purification, a single diastereomer (0:100) of the title compound as a pale yellow solid.

$^1$H-NMR (400 MHz, CDCl$_3$, 300 K) δ 6.85 (bs, 1H), 5.66-5.63 (m, 1H), 5.63-5.60 (m, 1H), 4.48 (s, 1H), 4.09 (d, J=10.9 Hz, 1H), 3.77 (dd, J$_{AB}$=11.4 Hz, J$_{HP}$=24.9 Hz, 1H), 3.64 (s, 3H), 3.58-3.49 (m, 1H), 3.49-3.41 (m, 1H), 2.51-2.47 (m, 2H), 1.16 (s, 9H), 1.06 (s, 3H), 1.05 (s, 3H). $^{31}$P-NMR (162 MHz, CDCl$_3$, 300 K) δ. −10.6. UPLC tR 1.48 min. MS (ES+) m/z 410 [M+H]$^+$.

Example 27

(((2S,4R)-4-((3-((1-benzylpyrrolidin-3-yl)oxy)-3-oxopropyl)carbamoyl)-5,5-dimethyl-2-oxido-1,3,2-dioxaphosphinan-2-yl)oxy)methyl pivalate (Compound No. 93)

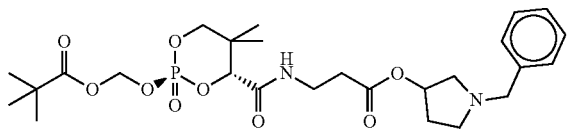

(((2S,4R)-4-((3-((1-benzylpyrrolidin-3-yl)oxy)-3-oxopropyl)carbamoyl)-5,5-dimethyl-2-oxido-1,3,2-dioxaphosphinan-2-yl)oxy)methyl pivalate (Compound No. 93) was synthesized according to the procedure described in Example 4 with respect to Compound No. 71, except that 1-benzylpyrrolidin-3-ol was used instead of 4-pyridylmethanol, giving, after purification, a single epimer at phosphorous (0:100) of the title compound (29%) as a yellow oil.

$^1$H-NMR (400 MHz, CDCl$_3$+TFA, 300 K) δ 8.99 and 8.86 (bs, 1H), 7.94 (m, 1H), 7.51-7.47 (m, 3H), 7.42-7.40 (m, 2H), 5.84-5.77 (m, 2H), 5.56-5.49 (m, 1H), 4.90-4.88 (m, 1H), 4.50-4.44 (m, 2H), 4.36-4.32 (m, 1H), 4.15-3.95 (m, 2H), 3.89-3.86 (m, 1H), 3.77-3.63 (m, 2H), 3.48-3.31 (m, 2H), 2.80-2.77 (m, 1H), 2.73-2.69 (m, 1H), 2.65-2.43 (m, 1H), 2.35-2.28 (m, 1H), 1.29-1.28 (m, 9H), 1.19-1.14 (m, 6H). $^{31}$P-NMR (162 MHz, CDCl$_3$+TFA, 300 K) δ. −9.48. UPLC tR 1.14 min. MS (ES+) m/z 555 [M+H]$^+$.

Example 28

(((2S,4R)-5,5-dimethyl-2-oxido-4-((3-oxo-3-(pyrrolidin-3-yloxy)propyl)carbamoyl)-1,3,2-dioxaphosphinan-2-yl)oxy)methyl pivalate (Compound No. 92)

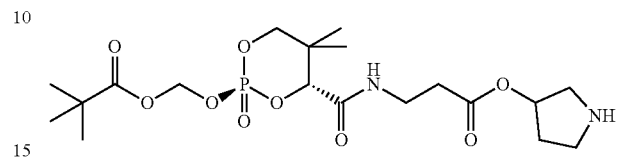

(((2S,4R)-5,5-dimethyl-2-oxido-4-((3-oxo-3-(pyrrolidin-3-yloxy)propyl)carbamoyl)-1,3,2-dioxaphosphinan-2-yl)oxy)methyl pivalate (Compound No. 92) was synthesized from Compound No. 93. The latter was treated with Pd/C under hydrogen atmosphere to afford after filtration a single epimer at phosphorous (0:100) of the title compound (59%) as a white solid.

$^1$H-NMR (400 MHz, DMSO-d$_6$+TFA, 300 K) δ 9.02 and 8.92 (bs, 2H), 8.21 (bs, 1H), 5.64 (d, J=15.8 Hz, 2H), 5.30-5.27 (m, 1H), 4.54 (s, 1H), 4.10 (d, J=10.9 Hz, 1H), 3.96 (dd, J$_{AB}$=10.9 Hz, J$_{HP}$=24.4 Hz, 1H), 3.46-3.24 (m, 6H), 2.5-2.48 (m, 2H), 2.19-2.10 (m, 1H), 2.1-2.0 (m, 1H), 1.15 (s, 9H), 1.02 (s, 3H), 0.95 (s, 3H). $^{31}$P-NMR (162 MHz, DMSO-d$_6$+TFA, 300 K) δ. −10.38. UPLC tR 1.05 min. MS (ES+) m/z 465 [M+H]$^+$.

Example 29

(((4R)-5,5-dimethyl-2-oxido-4-((3-oxo-3-((tetrahydrofuran-3-yl)oxy)propyl)carbamoyl)-1,3,2-dioxaphosphinan-2-yl)oxy)methyl pivalate (Compound No. 94)

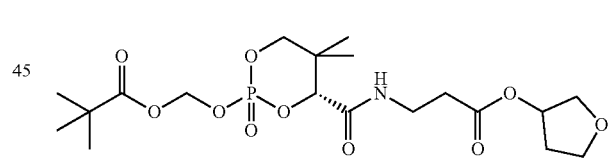

(((2S,4R)-4-((3-((1-benzylpyrrolidin-3-yl)oxy)-3-oxopropyl)carbamoyl)-5,5-dimethyl-2-oxido-1,3,2-dioxaphosphinan-2-yl)oxy)methyl pivalate (Compound No. 94) was synthesized according to the procedure described in Example 4 with respect to Compound No. 71, except that tetrahydrofuran-3-ol was used instead of 4-pyridylmethanol, affording a mixture of epimers at phosphorous (5*:95) of the title compound (31%) as a white solid.

$^1$H-NMR (400 MHz, CDCl$_3$, 300 K) δ 6.98 (bs, 1H), 5.82-5.78* and 5.76-5.69 (m, 2H), 5.37-5.34 (m, 1H), 4.81* and 4.59 (d* and s, J*=1.7 Hz, 1H), 4.37 and 4.19 (dd* and d, J$_{HP}$*=2.6 Hz, J$_{AB}$*=10.9 Hz, J=11.4 Hz, 1H), 3.98-3.82 (m, 4H), 3.67-3.50 (m, 2H), 2.60-2.57 (m, 2H), 2.27-2.17 (m, 1H), 2.07-1.99 (m, 1H), 1.28* and 1.25 (s, 9H), 1.21* and 1.16 (s, 3H), 1.14 and 1.12* (s, 3H). $^{31}$P-NMR (162 MHz, CDCl$_3$, 300 K) δ. −6.84*, −10.68. UPLC tR 1.43 and 1.44* min. MS (ES+) m/z 488 [M+Na]$^+$.

Example 30

(((4R)-5,5-dimethyl-2-oxido-4-((3-oxo-3-(pyrimidin-2-ylmethoxy)propyl)carbamoyl)-1,3,2-dioxaphosphinan-2-yl)oxy)methyl pivalate (Compound No. 95)

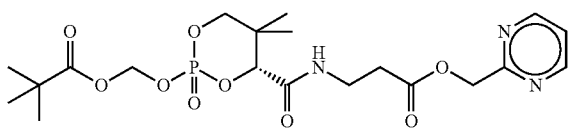

(((4R)-5,5-dimethyl-2-oxido-4-((3-oxo-3-(pyrimidin-2-ylmethoxy)propyl)carbamoyl)-1,3,2-dioxaphosphinan-2-yl)oxy)methyl pivalate (Compound No. 95) was synthesized according to the procedure described in Example 4 with respect to Compound No. 71, except that pyrimidin-2-ylmethanol was used instead of 4-pyridylmethanol, affording a mixture of diastereomers (6*:94) of the title compound (40%) as a yellow oil.

$^1$H-NMR (400 MHz, CDCl$_3$, 300 K) δ 8.77 and 8.72* (d, J=5.3 Hz, J*=4.8 Hz, 2H), 7.52 (t, J=5.7 Hz, 1H), 7.24 (t, J=4.8 Hz, 1H), 5.65-5.58 (m, 2H), 5.36 (d, J=15.3 Hz, 1H), 5.3 (d, J=14.9 Hz, 1H), 4.82* and 4.53 (s, 1H), 4.27* and 4.10 (dd* and d, J$_{HP}$*=3.9 Hz, J$_{AB}$*=11.4 Hz, J=10.9 Hz, 1H), 3.80-3.71 (m, 1H), 3.58-3.48 (m, 2H), 2.69-2.67* and 2.65-2.62 (m, 2H), 1.18* and 1.16 (m, 9H), 1.06* and 1.05 (s, 3H), 1.03 and 0.99* (s, 3H). $^{31}$P-NMR (162 MHz, CDCl$_3$, 300 K) δ. −6.38*, −10.53. UPLC tR 1.36 and 1.37* min. MS (ES+) m/z 510 [M+Na]$^+$.

Example 31

(((2S,4R)-4-((3-(3-ethoxypropoxy)-3-oxopropyl)carbamoyl)-5,5-dimethyl-2-oxido-1,3,2-dioxaphosphinan-2-yl)oxy)methyl pivalate (Compound No. 96)

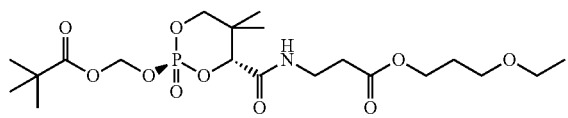 [SMILES: CCOCCCOC(=O)CCNC(=O)[C@@H]1O[P@@](=O)(OCOC(=O)C(C)(C)C)OCC1(C)C]

(((2S,4R)-4-((3-(3-ethoxypropoxy)-3-oxopropyl)carbamoyl)-5,5-dimethyl-2-oxido-1,3,2-dioxaphosphinan-2-yl)oxy)methyl pivalate (Compound No. 96) was synthesized according to the procedure described in Example 4 with respect to Compound No. 71, except that 3-ethoxypropan-1-ol was used instead of 4-pyridylmethanol, affording, after purification, a single diastereomer (0:100) of the title compound (13%) as a white solid.

$^1$H-NMR (400 MHz, CDCl$_3$, 300 K) δ 6.99 (t, J=5.7 Hz, 1H), 5.75-5.69 (m, 2H), 4.58 (s, 1H), 4.23 (t, J=6.1 Hz; 2H), 4.18 (d, J=10.9 Hz, 1H), 3.86 (dd, J$_{AB}$=11.4 Hz, J$_{HP}$=25.0 Hz, 1H), 3.67-3.57 (m, 1H), 3.56-3.47 (m, 5H), 2.59-2.56 (m, 2H), 1.96-1.90 (m, 2H), 1.25 (s, 9H), 1.22 (t, J=7.0 Hz, 3H), 1.15 (s, 3H), 1.14 (s, 3H). $^{31}$P-NMR (162 MHz, CDCl$_3$, 300 K) δ. −10.63. UPLC tR 1.69 min. MS (ES+) m/z 482 [M+H]$^+$.

Example 32

Methyl 3-((4R)-5,5-dimethyl-2-oxido-2-((((pyridin-3-ylmethoxy)carbonyl)oxy)methoxy)-1,3,2-dioxaphosphinane-4-carboxamido)propanoate (Compound No. 97)

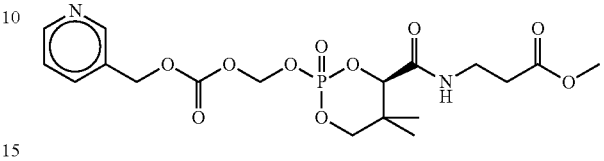

Methyl 3-((4R)-5,5-dimethyl-2-oxido-2-((((pyridin-3-ylmethoxy)carbonyl)oxy)methoxy)-1,3,2-dioxaphosphinane-4-carboxamido)propanoate (Compound No. 97) was synthesized according to the procedure described in Example 3 with respect to Compound No. 65, except that chloromethyl (pyridin-3-ylmethyl) carbonate was used instead of chloromethyl pivalate, affording a mixture of diastereomers (38*:62) of the title compound (0.6%) as a brown oil.

$^1$H-NMR (400 MHz, CDCl$_3$, 300 K) δ 8.91-8.88 (m, 1H), 8.79-8.78 (m, 1H), 8.24 (t, J=9.3 Hz, 1H), 7.78 (t, J=7.4 Hz, 1H), 7.09* and 6.98 (bs, 1H), 5.83-5.72 (m, 2H), 5.45-5.38 (m, 2H), 4.80* and 4.58 (d* and s, J=2.2 Hz, 1H), 4.37* and 4.19 (dd* and d, J$_{HP}$*=3.5 Hz, J$_{AB}$*=11.4 Hz, J=10.9 Hz, 1H), 3.94* and 3.89 (dd, J$_{AB}$*=11.4 Hz, J$_{HP}$*=22.8 Hz, J$_{AB}$=8.7 Hz, J$_{AB}$=25.4 Hz, 1H), 3.73 and 3.71* (s, 3H), 3.66-3.53 (m, 2H), 2.62-2.58 (m, 2H), 1.22* and 1.15 and 1.11* (s, 6H). $^{31}$P-NMR (162 MHz, CDCl$_3$, 300 K) δ. −7.15*, −11.31. UPLC tR 1.66 and 1.69* min. MS (ES+) m/z 483 [M+Na]$^+$.

Example 33

(((4R)-5,5-dimethyl-4-((3-((1-methylpiperidin-3-yl)oxy)-3-oxopropyl)carbamoyl)-2-oxido-1,3,2-dioxaphosphinan-2-yl)oxy)methyl pivalate (Compound No. 99)

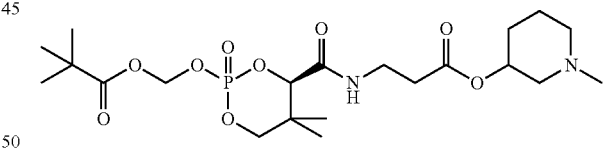

(((4R)-5,5-dimethyl-4-((3-((1-methylpiperidin-3-yl)oxy)-3-oxopropyl)carbamoyl)-2-oxido-1,3,2-dioxaphosphinan-2-yl)oxy)methyl pivalate (Compound No. 99) was synthesized according to the procedure described in Example 4 with respect to Compound No. 71, except that 1-methylpiperidin-3-ol was used instead of 4-pyridylmethanol, affording a mixture of epimers at phosphorous (47*:53) of the title compound (24%) as a colorless oil.

$^1$H-NMR (400 MHz, CDCl3, 300 K) δ 7.67* and 7.62 (bs, 1H), 5.77* and 5.69 and 5.63* (dd* and d, J*=4.9, 13.6 Hz, J=13.0 Hz, 2H), 5.27-5.24 (m, 1H), 4.60* and 4.56 (s, 1H), 4.19-4.16 (m, 1H), 3.89-3.76 (m, 3H), 3.70-3.52 (m, 2H), 2.93 and 2.90* (s, 3H), 2.86-2.82 (m, 1H), 2.79-2.74 (m, 1H), 2.70-2.58 (m, 2H), 2.32-2.55 (m, 1H), 2.11-2.09 (m, 1H), 1.88-1.86 (m, 1H), 1.70-1.64 (m, 1H), 1.25 and 1.24* (s, 9H), 1.17* and 1.18 (s, 3H), 1.13 and 1.12*

(s, 3H). ³¹P-NMR (162 MHz, CDCl₃, 300 K) δ. −10.51*, −10.76. UPLC tR 0.98 min. MS (ES+) m/z 493 [M+H]⁺.

Example 34

(((4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate (Compound No. 101)

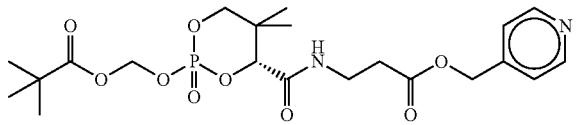

(((4R)-5,5-dimethyl-2-oxido-4-((3-oxo-3-(pyridin-4-ylmethoxy)propyl)carbamoyl)-1,3,2-dioxaphosphinan-2-yl)oxy)methyl pivalate (Compound No. 101) was synthesized according to the procedure described in Example 4 with respect to Compound No. 71, except that pyridin-4-ylmethanol was used instead of 4-pyridylmethanol, affording a mixture of diastereomers (43*:57) of the title compound (16%) as a white solid.

¹H-NMR (400 MHz, DMSO-d₆, 300 K) δ 8.68 and 8.25-8.20* (d and m*, J=4.4 Hz, 2H), 8.25-8.20* and 7.60-7.56 (m, 2H), 5.69-5.61 (m, 2H), 5.24 (s, 2H), 4.71* and 4.54 (d* and s, J*=5.2 Hz, 1H), 4.16-4.08 (m, 1H), 4.02-3.93 (m, 1H), 3.50-3.32 (m, 2H), 2.67 (dd, J=6.1, 12.8 Hz, 2H), 1.17* and 1.16 (s, 9H); 1.04* and 1.00 (s, 3H), 0.95* and 0.94 (s, 3H). ³¹P-NMR (162 MHz, DMSO-d₆, 300 K) δ. −8.37* and −10.36. UPLC tR 1.08* and 1.11 min. MS (ES+) m/z 487 [M+H]⁺.

Example 35

(((4R)-4-((3-methoxy-3-oxopropyl)carbamoyl)-5,5-dimethyl-2-oxido-1,3,2-dioxaphosphinan-2-yl)oxy)methyl isobutyrate (Compound No. 103)

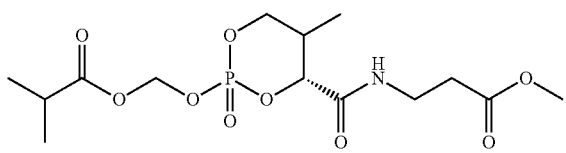 [SMILES: COC(=O)CCNC(=O)[C@@H]1OP(=O)(OCOC(=O)C(C)C)OCC1C]

(((4R)-4-((3-methoxy-3-oxopropyl)carbamoyl)-5,5-dimethyl-2-oxido-1,3,2-dioxaphosphinan-2-yl)oxy)methyl isobutyrate (Compound No. 103) was synthesized according to the procedure described in Example 6 with respect to Compound No. 70, except that isobutyric acid was used instead of thiazole-5-carboxylic acid, affording a mixture of diastereomers (78:22*) of the title compound (12%) as a colorless oil.

¹H-NMR (400 MHz, CDCl₃, 300 K) 7.05 and 6.86* (t, J=5.2 Hz, 1H), 5.71 and 5.63 and 5.66-5.59* (dd and m*, J=4.8, 11.4 Hz, 2H), 4.70 and 4.49* (d and s*, J=2.2 Hz, 1H), 4.27 and 4.09* (dd and d*, $J_{HP}$=3.5 Hz, $J_{AB}$=11.4 Hz, J*=11.4 Hz, 1H), 3.78 and 3.77* (dd, $J_{AB}$=11.8 Hz, $J_{HP}$=23.2 Hz, $J_{AB}$*=11.4 Hz, $J_{HP}$*=24.9 Hz, 1H), 3.64* and 3.63 (s, 3H), 3.57-3.42 (m, 2H), 2.64-2.57 (m, 1H), 2.55-2.48 (m, 2H), 1.17 and 1.14*(s, 3H), 1.15 and 1.13* (s, 3H), 1.12 and 1.06* (s, 3H), 1.05* and 1.02 (s, 3H). ³¹P-NMR (162 MHz, CDCl₃, 300 K) δ. −6.64, −10.70*. UPLC tR 1.30 and 1.35* min. MS (ES+) m/z 418 [M+Na]⁺.

Example 36

3-((4R)-2-(((isopropoxycarbonyl)oxy)methoxy)-5,5-dimethyl-2-oxido-1,3,2-dioxaphosphinane-4-carboxamido)propanoic acid (Compound No. 104)

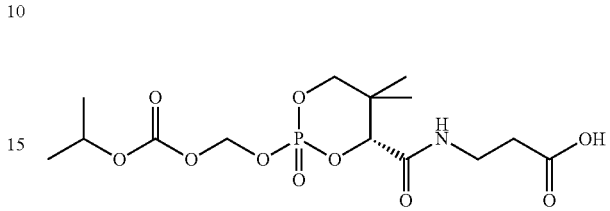

3-((4R)-2-(((isopropoxycarbonyl)oxy)methoxy)-5,5-dimethyl-2-oxido-1,3,2-dioxaphosphinane-4-carboxamido)propanoic acid (Compound No. 104) was synthesized according to the procedure described in Example 4 with respect to Compound No. 91, except that chloromethyl isopropyl carbonate was used instead of chloromethyl pivalate, affording a mixture of diastereomers (34*:66) of the title compound (12%) as a colorless oil.

¹H-NMR (400 MHz, DMSO-d₆, 300 K) δ 12.23 (bs, 1H), 8.15-8.10 (m, 1H), 5.65* and 5.62 (d, J*=13.5 Hz, J=13.5 Hz, 2H), 4.88-4.81 (m, 1H), 4.72* and 4.58 (d* and s, J*=6.1 Hz, 1H), 4.19-4.10 (m, 1H), 3.99 (dd, $J_{AB}$=10.9 Hz, $J_{HP}$=24.1 Hz, 1H), 3.40-3.22 (m, 2H), 2.45-2.42 (m, 2H), 1.28-1.25 (m, 6H), 1.07* and 1.03 (s, 3H), 0.96 (s, 3H). ³¹P-NMR (162 MHz, DMSO-d₆, 300 K) δ. −8.96*, −10.81. UPLC tR 1.15 min. MS (ES+) m/z 398[M+H]⁺.

Example 37

(((2S,4R)-4-((3-ethoxy-3-oxopropyl)carbamoyl)-5,5-dimethyl-2-oxido-1,3,2-dioxaphosphinan-2-yl)oxy)methyl pivalate (Compound No. 107)

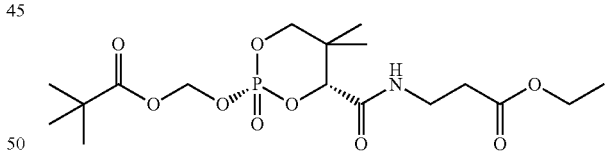

(((2S,4R)-4-((3-ethoxy-3-oxopropyl)carbamoyl)-5,5-dimethyl-2-oxido-1,3,2-dioxaphosphinan-2-yl)oxy)methyl pivalate (Compound No. 107) was synthesized according to the procedure described in Example 4 with respect to Compound No. 71, except that ethanol was used instead of 4-pyridylmethanol, affording, after purification, a single diastereomer (0:100) of the title compound (40%) as a white solid.

¹H-NMR (400 MHz, CDCl₃, 300 K) δ 6.97 (t, J=5.7 Hz, 1H), 5.75-5.69 (m, 2H), 4.58 (s, 1H), 4.22-4.16 (m, 3H), 3.83 (dd, $J_{AB}$=11.0 Hz, $J_{HP}$=25.0 Hz, 1H), 3.67-3.59 (m, 1H), 3.58-3.49 (m, 1H), 2.59-2.55 (m, 2H), 1.30 (t, J=7.0 Hz, 3H), 1.25 (s, 9H), 1.15 (s, 3H), 1.14 (s, 3H). ³¹P-NMR (162 MHz, CDCl₃, 300 K) δ −10.61. UPLC tR 1.56 min. MS (ES+) m/z 446[M+Na]⁺.

Example 38

Methyl 3-((2R,4R)-5,5-dimethyl-2-(4-nitrophenoxy)-2-oxido-1,3,2-dioxaphosphinane-4-carboxamido)propanoate (Compound No. 2-120)

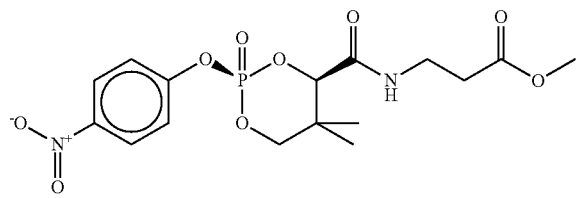

Methyl 3-((2R,4R)-5,5-dimethyl-2-(4-nitrophenoxy)-2-oxido-1,3,2-dioxaphosphinane-4-carboxamido)propanoate (Compound No. 2-120) was synthesized according to the procedure described in Example 3, Step 1, with respect to the compound Methyl 3-((4R)-2-(benzyloxy)-5,5-dimethyl-2-oxido-1,3,2-dioxaphosphinane-4-carboxamido)propanoate, except that 4-nitrophenyl phosphorodichloridate was used instead of phosphoryl trichloride. After purification, a single diastereomer (100:0) of the title compound (50%) was obtained as a white solid.

$^1$H-NMR (400 MHz, CDCl$_3$, 300 K) δ 8.33 (d, J=8.7 Hz, 2H), 7.49 (d, J=8.7 Hz, 2H), 7.07 (bs, 1H), 4.86 (d, J=2.6 Hz, 1H), 4.43 (dd, J$_{HP}$=3.5 Hz, J$_{AB}$=11.4 Hz, 1H), 4.01 (dd, J$_{AB}$=11.8 Hz, J$_{HP}$=22.8 Hz, 1H), 3.75 (s, 3H), 3.67-3.51 (m, 2H), 5.58 (t, J=5.7 Hz, 2H), 1.22 (s, 3H), 0.95 (s, 3H). $^{31}$P-NMR (162 MHz, CDCl$_3$, 300 K) δ. −11.93. UPLC tR 1.44 min. MS (ES+) m/z 417 [M+H]$^+$.

Example 39

Methyl 3-((2R,4R)-5,5-dimethyl-2-oxido-2-(4-(pentafluoro-l6-sulfanyl)phenoxy)-1,3,2-dioxaphosphinane-4-carboxamido)propanoate (Compound No. 2-125)

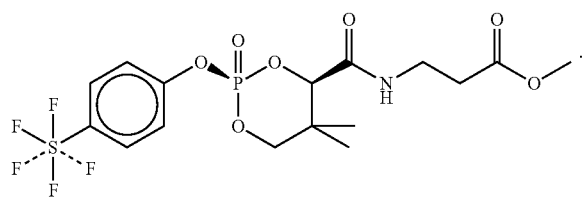

Methyl 3-((2R,4R)-5,5-dimethyl-2-oxido-2-(4-(pentafluoro-16-sulfanyl)phenoxy)-1,3,2-dioxaphosphinane-4-carboxamido)propanoate (Compound No. 2-125) was synthesized according to the procedure described in Example 5 with respect to Compound No. 115, except that 4-(Pentafluorothio)phenol was used instead of benzyl amine, affording, after purification, a single diastereomer (100:0) of the title compound (9%) as a colorless oil.

$^1$H-NMR (400 MHz, CDCl$_3$, 300 K) δ 7.84 (d, J=8.7 Hz, 2H), 7.42 (d, J=8.7 Hz, 2H), 7.06 (bs, 1H), 4.84 (d, J=2.2 Hz, 1H), 4.42 (dd, J$_{HP}$=3.9 Hz, J$_{AB}$=11.4 Hz, 1H), 3.97 (dd, J$_{AB}$=11.4 Hz, J$_{HP}$=22.8 Hz, 1H), 3.73 (s, 3H), 3.68-3.51 (m, 2H), 5.58 (t, J=5.7 Hz, 2H), 1.22 (s, 3H), 0.97 (s, 3H). $^{31}$P-NMR (162 MHz, CDCl$_3$, 300 K) δ −11.35. UPLC tR 1.79 min. MS (ES+) m/z 498 [M+H]$^+$.

Example 40

Methyl 3-((2S,4R)-2-((1,1-dioxido-3-oxobenzo[d]isothiazol-2(3H)-yl)methoxy)-5,5-dimethyl-2-oxido-1,3,2-dioxaphosphinane-4-carboxamido)propanoate (Compound No. 2-126)

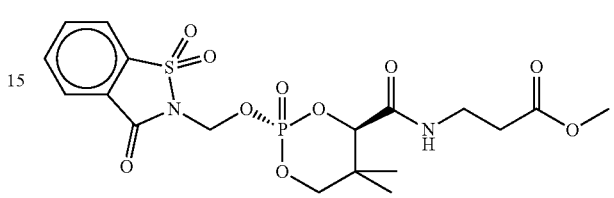

Methyl 3-((2S,4R)-2-((1,1-dioxido-3-oxobenzo[d]isothiazol-2(3H)-yl)methoxy)-5,5-dimethyl-2-oxido-1,3,2-dioxaphosphinane-4-carboxamido)propanoate (Compound No. 2-126) was synthesized according to the procedure described in Example 3 with respect to Compound No. 65, except that 2-(chloromethyl)benzo[d]isothiazol-3(2H)-one 1,1-dioxide was used instead of chloromethyl pivalate, affording, after purification, a single diastereomer (0:100) of the title compound (1%) as a pale yellow solid.

$^1$H-NMR (400 MHz, CDCl3, 300 K) δ 8.17 (d, J=7.4 Hz, 1H), 8.01-7.91 (m, 3H), 6.95 (bs, 1H), 5.87-5.76 (m, 2H), 4.64 (s, 1H), 4.27 (d, J=11.8 Hz, 1H), 3.86 (dd, J$_{AB}$=11.4 Hz, J$_{HP}$=25.0 Hz, 1H), 3.74 (s, 3H), 3.62-3.51 (m, 2H), 2.59-2.56 (m, 2H), 1.13 (s, 6H). $^{31}$P-NMR (162 MHz, CDCl$_3$, 300 K) δ. −11.14. UPLC tR 1.28 min. MS (ES+) m/z 513 [M+Na]$^+$.

Example 41

(((2S,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 2-127)

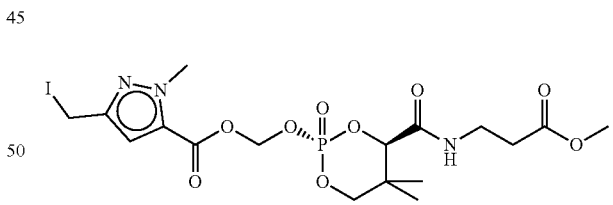

(((2S,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 2-127) was synthesized according to the procedure described in Example 6 with respect to Compound No. 70, except that 5-ethyl-2-methyl-pyrazole-3-carboxylic acid was used instead thiazole-5-carboxylic acid, affording a single diastereomer (0:100) of the title compound (19%) as a colorless oil after purification.

$^1$H-NMR (400 MHz, DMSO-d$_6$, 300 K) δ 8.16 (t, J=5.3 Hz, 1H), 6.74 (s, 1H), 5.87-5.80 (m, 2H), 4.59 (s, 1H), 4.14 (d, J=11.4 Hz, 1H), 4.03 (s, 3H), 3.99-3.93 (m, 1H), 3.59 (s, 3H), 3.39-3.39 (m, 1H), 3.28-3.22 (m, 1H), 2.6-2.54 (m, 2H), 2.48-2.45 (m, 2H), 1.18 (t, J=4.45 Hz, 3H), 1.01 (s,

3H), 0.94 (s, 3H). $^{31}$P-NMR (162 MHz, DMSO-d$_6$, 300 K) δ. −10.56. UPLC tR 1.37 min. MS (ES+) m/z 484 [M+Na]$^+$.

Example 42

(((2S,4R)-4-((3-isopropoxy-3-oxopropyl)carbamoyl)-5,5-dimethyl-2-oxido-1,3,2-dioxaphosphinan-2-yl)oxy)methyl pivalate (Compound No. 2-128)

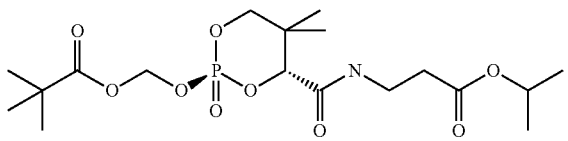 [SMILES: CC(C)OC(=O)CCNC(=O)[C@@H]1O[P@@](=O)(OCOC(=O)C(C)(C)C)OCC1(C)C]

(((2S,4R)-4-((3-isopropoxy-3-oxopropyl)carbamoyl)-5,5-dimethyl-2-oxido-1,3,2-dioxaphosphinan-2-yl)oxy)methyl pivalate (Compound No. 2-128) was synthesized according to the procedure described in Example 4 with respect to Compound No. 71, except that propan-2-ol was used instead of 4-pyridylmethanol, affording, after purification, a single diastereomer (0:100) of the title compound (37%) as an off-white solid.

$^1$H-NMR (400 MHz, CDCl$_3$, 300 K) δ 6.85 (t, J=5.3 Hz, 1H), 5.64-5.57 (m, 2H), 5.0-4.90 (m, 1H), 4.46 (s, 1H), 4.07 (d, J=10.9 Hz, 1H), 3.74 (dd, J$_{AB}$=11.4 Hz, J$_{HP}$=25.0 Hz, 1H), 3.55-3.47 (m, 1H), 3.45-3.37 (m, 1H), 2.48-2.36 (m, 2H), 1.17 (d, J=2.6 Hz, 3H), 1.15 (d, J=2.6 Hz, 3H), 1.14 (s, 9H), 1.04 (s, 3H), 1.02 (s, 3H). $^{31}$P-NMR (162 MHz, DMSO-d$_6$, 300 K) δ. −10.64. UPLC tR 1.69 min. MS (ES+) m/z 460 [M+Na]$^+$.

Example 43

(((2R,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 2-129)

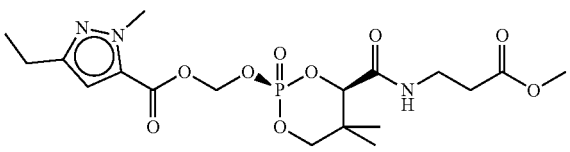

(((2R,4R)-4-((3-methoxy-3-oxopropyl)carbamoyl)-5,5-dimethyl-2-oxido-1,3,2-dioxaphosphinan-2-yl)oxy)methyl 3-ethyl-1-methyl-1H-pyrazole-5-carboxylate (Compound No. 2-129) was synthesized according to the procedure described in Example 6 with respect to Compound No. 70, except that 5-ethyl-2-methyl-pyrazole-3-carboxylic acid was used instead of thiazole-5-carboxylic acid, affording, after purification, a single diastereomer (100:0) of the title compound (25%) as a colorless oil.

$^1$H-NMR (400 MHz, CDCl$_3$, 300 K) δ 6.89 (bs, 1H), 6.76 (s, 1H), 5.90 (d, J=13.1 Hz, 2H), 4.61 (s, 1H), 4.19 (d, J=11.4 Hz, 1H), 4.16 (s, 3H), 3.86 (dd, J$_{AB}$=11.4 Hz, J$_{HP}$=25.4 Hz, 1H), 3.73 (s, 3H), 3.65-3.57 (m, 1H), 3.49-3.42 (m, 1H), 2.67 (q, J=7.4 Hz, 2H), 2.58-2.53 (m, 2H), 1.27 (t, J=7.4 Hz, 3H), 1.14 (s, 3H), 1.13 (s, 3H). $^{31}$P-NMR (162 MHz, CDCl$_3$, 300 K) δ. −10.87. UPLC tR 1.40 min. MS (ES+) m/z 462 [M+H]$^+$.

Example 44

Methyl 3-((4R)-5,5-dimethyl-2-oxido-2-(2-(pivaloylthio)ethoxy)-1,3,2-dioxaphosphinane-4-carboxamido)propanoate (Compound No. 2-133)

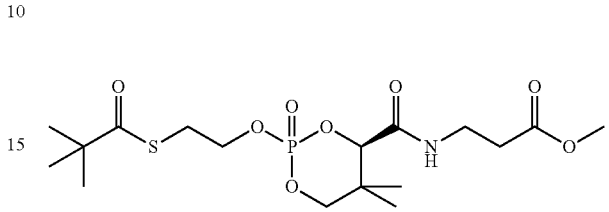

Methyl 3-((4R)-5,5-dimethyl-2-oxido-2-(2-(pivaloylthio)ethoxy)-1,3,2-dioxaphosphinane-4-carboxamido)propanoate (Compound No. 2-133) was synthesized according to the procedure described in Example 5 with respect to Compound No. 115, except that S-(2-hydroxyethyl) 2,2-dimethylpropanethioate was used instead of benzyl amine and DBU was used instead of TEA. The title compound (14%) was obtained after purification as a mixture of diastereomers (27*:73) and as a colorless oil.

$^1$H-NMR (400 MHz, CDCl$_3$, 300 K) δ 7.13* and 6.88 (bs, 1H), 4.70* and 4.52 (d* and s, J*=1.3 Hz, 1H), 4.28* and 4.11-4.09 (dd* and m, J$_{HP}$=2.6 Hz, J$_{AB}$=11.4 Hz, 1H), 4.21-4.15* and 4.12-4.09 (m, 2H), 3.76 and 3.75* (dd, J$_{AB}$=11.4 Hz, J$_{HP}$=24.5 Hz, J$_{AB}$*=11.4 Hz, J$_{HP}$*=22.2 Hz, 1H), 3.64 and 3.63* (s, 3H), 3.60-3.40 (m, 2H), 3.21-3.14* and 3.12-3.06 (m, 2H), 2.53-2.49 (m, 2H), 1.18* and 1.16 (s, 9H), 1.10* and 1.08 (s, 3H), 1.04 and 1.02* (s, 3H). $^{31}$P-NMR (162 MHz, CDCl$_3$, 300 K) δ. −4.99*, −9.22. UPLC tR 1.65 and 1.68* min. MS (ES+) m/z 462 [M+Na]$^+$.

Example 45

Methyl 3-((4R)-5,5-dimethyl-2-(4-nitrophenoxy)-2-oxido-1,3,2-dioxaphosphinane-4-carboxamido)propanoate (Compound No. 2-134)

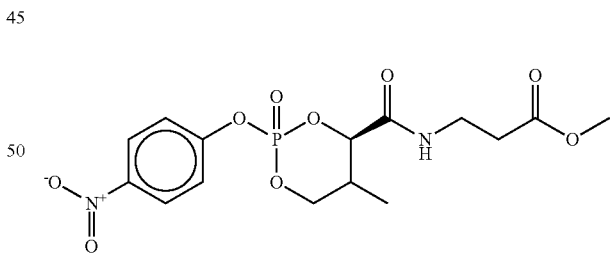

Methyl 3-((4R)-5,5-dimethyl-2-(4-nitrophenoxy)-2-oxido-1,3,2-dioxaphosphinane-4-carboxamido)propanoate (Compound No. 2-134) was synthesized according to the procedure described in Example 3, Step 1, with respect to compound Methyl 3-((4R)-2-(benzyloxy)-5,5-dimethyl-2-oxido-1,3,2-dioxaphosphinane-4-carboxamido)propanoate, except that 4-nitrophenyl phosphorodichloridate was used instead of phosphoryl trichloride, affording the title compound (66%) as a white solid and as a mixture of diastereomers (24*:76).

$^1$H-NMR (400 MHz, CDCl$_3$, 300 K) δ 8.25-8.23* and 8.21-8.19 (m, 2H), 7.41-7.39* and 7.35-7.33 (m, 2H), 6.97* and 6.92 (t, J=5.3 Hz, 1H), 4.75* and 4.66 (d* and s, J*=2.6 Hz, 1H), 4.33* and 4.22 (dd* and d, $J_{HP}$*=3.9 Hz, $J_{AB}$*=11.4 Hz, J=11.4 Hz, 1H), 3.92 and 3.91* (dd, $J_{AB}$=11.8 Hz, $J_{HP}$=25.8 Hz, $J_{AB}$*=11.8 Hz, $J_{HP}$*=22.8 Hz, 1H), 3.65* and 3.64 (s, 3H), 3.59-3.43 (m, 2H), 2.53-2.47 (m, 2H), 1.14 (s, 3H), 1.13 (s, 3H). $^{31}$P-NMR (162 MHz, CDCl$_3$, 300 K) δ. −11.86*, −15.96. UPLC tR 1.40. MS (ES+) m/z 439 [M+Na]$^+$.

Example 46

(((4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-139)

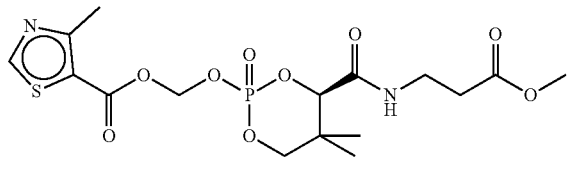

(((4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-139) was synthesized according to the procedure described in Example 6 with respect to Compound No. 70, except that 4-methylthiazole-5-carboxylic acid was used instead of thiazole-5-carboxylic acid, affording a mixture of diastereomers (69:31*) of the title compound (37%) as a white solid.

$^1$H-NMR (400 MHz, CDCl$_3$, 300 K) δ 8.89 and 8.88* (s, 1H), 7.08 and 6.90* (bs, 1H), 6.01-5.89 (m, 2H), 4.80 and 4.60* (d and s*, J=1.7 Hz, 1H), 4.36 and 4.20* (dd and d*, $J_{HP}$=3.9 Hz, $J_{AB}$=11.4 Hz, J*=10.9 Hz, 1H), 3.90 and 3.87* (dd, $J_{AB}$=11.4 Hz, $J_{HP}$=22.8 Hz, $J_{AB}$*=11.4 Hz, $J_{HP}$*=25.8 Hz, 1H), 3.73* and 3.70 (s, 3H), 3.60-3.54 and 3.64-3.42* (m, 2H), 2.85 and 2.83 (s, 3H), 2.60-2.54 (m, 2H), 1.22 and 1.14* (s, 3H), 1.13* and 1.12 (s, 3H). $^{31}$P-NMR (162 MHz, CDCl$_3$, 300 K) δ. −6.50, −10.87*. UPLC tR 1.17*, 1.21. MS (ES+) m/z 473 [M+Na]$^+$.

Example 47

(((4R)-4-((3-methoxy-3-oxopropyl)carbamoyl)-5,5-dimethyl-2-oxido-1,3,2-dioxaphosphinan-2-yl)oxy)methyl isothiazole-5-carboxylate (Compound No. 2-140)

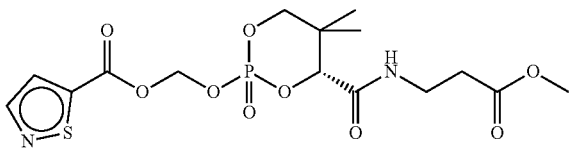

(((4R)-4-((3-methoxy-3-oxopropyl)carbamoyl)-5,5-dimethyl-2-oxido-1,3,2-dioxaphosphinan-2-yl)oxy)methyl isothiazole-5-carboxylate (Compound No. 2-140) was synthesized according to the procedure described in Example 6 with respect to Compound No. 70, except that isothiazole-5-carboxylic acid was used instead of thiazole-5-carboxylic acid, affording a mixture of diastereomers (92:8*) of the title compound (5%) as a colorless oil.

$^1$H-NMR (400 MHz, CDCl$_3$, 300 K) δ 8.62 (d, J=1.7 Hz, 1H), 7.94 and 7.90*(d, J=1.7 Hz, 1H), 7.04 (bs, 1H), 6.03-5.93 and 5.86-5.76*(m, 2H), 4.80 and 4.60* (d and s*, J=2.2 Hz, 1H), 4.36 and 4.20* (dd and d*, $J_{HP}$=3.9 Hz, $J_{AB}$=11.8 Hz, J*=10.9 Hz, 1H), 3.91 (dd, $J_{AB}$=11.4 Hz, $J_{HP}$=22.8 Hz, 1H), 3.73* and 3.70 (s, 3H), 3.61-3.52 (m, 2H), 2.61-2.53 (m, 2H), 1.22 and 1.14* (s, 3H), 1.15* and 1.12 (s, 3H). $^{31}$P-NMR (162 MHz, CDCl$_3$, 300 K) δ. −6.58, −11.00*. UPLC tR 1.22*, 1.26. MS (ES+) m/z 459 [M+Na]$^+$.

Example 48

(((4R)-4-((3-methoxy-3-oxopropyl)carbamoyl)-5,5-dimethyl-2-oxido-1,3,2-dioxaphosphinan-2-yl)oxy)methyl isoxazole-5-carboxylate (Compound No. 2-141)

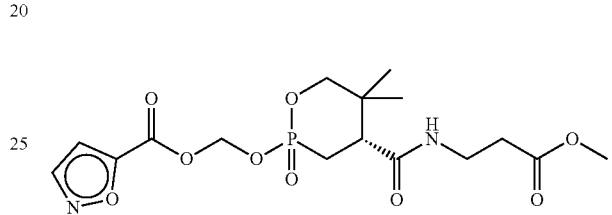

(((4R)-4-((3-methoxy-3-oxopropyl)carbamoyl)-5,5-dimethyl-2-oxido-1,3,2-dioxaphosphinan-2-yl)oxy)methyl isoxazole-5-carboxylate (Compound No. 2-141) was synthesized according to the procedure described in Example 6 with respect to Compound No. 70, except that isoxazole-5-carboxylic acid was used instead of thiazole-5-carboxylic acid and except that Ag$_2$O (1.5 eq) and CH$_3$CN were used instead of DIEA and DMF. A mixture of diastereomers (73:27*) of the title compound (6%) as a white solid was obtained.

$^1$H-NMR (400 MHz, CDCl$_3$, 300 K) δ 8.45-8.44 (m, 1H), 7.16 and 7.11* (d, J=2.2 Hz, J*=1.7 Hz, 1H), 7.07 and 6.94* (bs, 1H), 6.06-5.99 and 5.99-5.94* (m, 2H), 4.81 and 4.62* (d and s*, J=2.2 Hz, 1H), 4.37 and 4.21* (dd and d*, $J_{HP}$=3.5 Hz, $J_{AB}$=11.4 Hz, J*=11.4 Hz, 1H), 3.93 and 3.89* (dd, $J_{AB}$=11.4 Hz, $J_{HP}$=22.8 Hz, $J_{AB}$*=11.4 Hz, $J_{HP}$*=25.8 Hz, 1H), 3.73* and 3.70 (s, 3H), 3.62-3.57 and 3.64-3.49* (m, 2H), 2.61-2.56 (m, 2H), 1.22 and 1.16* (s, 3H), 1.14* and 1.12 (s, 3H). $^{31}$P-NMR (162 MHz, CDCl$_3$, 300 K) δ. −6.67, −11.06*. UPLC tR 1.16. MS (ES+) m/z 443 [M+Na]$^+$.

Example 49

(((4R)-4-((3-methoxy-3-oxopropyl)carbamoyl)-5,5-dimethyl-2-oxido-1,3,2-dioxaphosphinan-2-yl)oxy)methyl 1-methyl-1H-pyrazole-5-carboxylate (Compound No. 7.142)

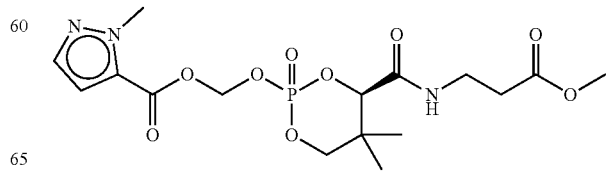

(((4R)-4-((3-methoxy-3-oxopropyl)carbamoyl)-5,5-dimethyl-2-oxido-1,3,2-dioxaphosphinan-2-yl)oxy)methyl 1-methyl-1H-pyrazole-5-carboxylate (Compound No. 2-142) was synthesized according to the procedure described in Example 5 above, with respect to Compound No. 70, except that 1-methyl-1H-pyrazole-5-carboxylic acid was used instead of thiazole-5-carboxylic acid giving a mixture of diastereomers (85:15*) of the title compound (8%) as a colorless oil.

$^1$H-NMR (400 MHz, CDCl$_3$, 300 K) δ 7.54 and 7.53* (d, J=2.2 Hz, 1H), 7.01 and 6.97* (d, J=2.2 Hz, 1H), 7.03 and 6.91* (bs, 1H), 6.02-5.90 (m, 2H), 4.81 and 4.61* (d and s*, J=1.7 Hz, 1H), 4.37 and 4.20* (dd and d*, J$_{HP}$=3.5 Hz, J$_{AB}$=11.4 Hz, J*=11.4 Hz, 1H), 4.25 and 4.23* (s, 3H), 3.90 and 3.86* (dd, J$_{AB}$=11.8 Hz, J$_{HP}$=23.2 Hz, J$_{AB}$*=11.4 Hz, J$_{HP}$*=25.4 Hz, 1H), 3.73* and 3.69 (s, 3H), 3.57-3.51 and 3.63-3.42* (m, 2H), 2.58-2.55 (m, 2H), 1.22 and 1.14* (s, 3H), 1.13* and 1.11 (s, 3H). $^{31}$P-NMR (162 MHz, CDCl$_3$, 300 K) δ. −6.33, −10.87*. UPLC tR 1.17* and 1.20. MS (ES+) m/z 456 [M+Na]$^+$.

Example 50

(((4R)-4-((3-methoxy-3-oxopropyl)carbamoyl)-5,5-dimethyl-2-oxido-1,3,2-dioxaphosphinan-2-yl)oxy)methyl 3-(tert-butyl)-1-methyl-1H-pyrazole-5-carboxylate (Compound No. 2-144)

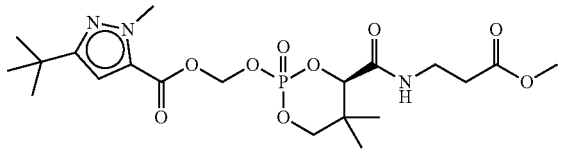

(((4R)-4-((3-methoxy-3-oxopropyl)carbamoyl)-5,5-dimethyl-2-oxido-1,3,2-dioxaphosphinan-2-yl)oxy)methyl 3-(tert-butyl)-1-methyl-1H-pyrazole-5-carboxylate (Compound No. 2-144) was synthesized according to the procedure described in Example 6 with respect to Compound No. 70, except that 3-(tert-butyl)-1-methyl-1H-pyrazole-5-carboxylic acid was used instead of thiazole-5-carboxylic acid, affording a mixture of diastereomers (39*:61) of the title compound (6%) as a colorless oil.

$^1$H-NMR (400 MHz, CDCl3, 300 K) δ 7.05* and 6.90 (bs, 1H), 3.84* and 6.80 (s, 1H), 6.0-5.89* and 5.91-5.88 (m, 2H), 4.80* and 4.82 (d* and s, J=1.75 Hz, 1H), 4.37 and 4.20 (dd* and d, J$_{HP}$=3.5 Hz, J$_{AB}$=11.4 Hz, J*=11.4 Hz, 1H), 4.18* and 4.16 (s, 3H), 3.89 and 3.87* (dd, J$_{AB}$=12.2 Hz, J$_{HP}$=23.2 Hz, J$_{AB}$*=11.4 Hz, J$_{HP}$*=25.4 Hz, 1H), 3.72 and 3.69* (s, 3H), 3.66-3.41 (m, 2H), 2.58-2.53 (m, 2H), 1.33 (s, 9H), 1.21* and 1.15 (s, 3H), 1.13 and 1.11* (s, 3H). $^{31}$P-NMR (162 MHz, CDCl$_3$, 300 K) δ. −6.52*, −10.93. UPLC tR 1.68 and 1.70*. MS (ES+) m/z 512 [M+Na]$^+$.

Example 51

(((4R)-4-((3-methoxy-3-oxopropyl)carbamoyl)-5,5-dimethyl-2-oxido-1,3,2-dioxaphosphinan-2-yl)oxy)methyl 1,3-dimethyl-1H-pyrazole-5-carboxylate (Compound No. 2-145)

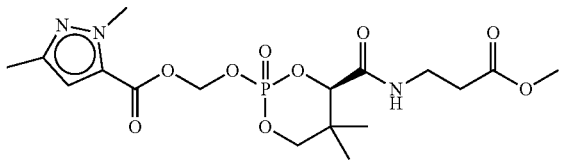

(((4R)-4-((3-methoxy-3-oxopropyl)carbamoyl)-5,5-dimethyl-2-oxido-1,3,2-dioxaphosphinan-2-yl)oxy)methyl 1,3-dimethyl-1H-pyrazole-5-carboxylate (Compound No. 2-145) was synthesized according to the procedure described in Example 6 with respect to Compound No. 70, except that 1,3-dimethyl-1H-pyrazole-5-carboxylic acid was used instead of thiazole-5-carboxylic acid, affording a mixture of diastereomers (61:39*) of the title compound (8%) as a colorless oil.

$^1$H-NMR (400 MHz, CDCl$_3$, 300 K) δ 6.94 and 6.81* (bs, 1H), 6.68 and 6.64* (s, 1H), 5.90-5.79 (m, 2H), 4.71 and 4.51* (d and s*, J=1.7 Hz, 1H), 4.27 and 4.10* (dd and d*, J$_{HP}$=3.5 Hz, J$_{AB}$=11.4 Hz, J*=11.4 Hz, 1H), 4.08 and 4.06* (s, 3H), 3.81 and 3.78* (dd, J$_{AB}$=11.8 Hz, J$_{HP}$=22.8 Hz, 1H), 3.63* and 3.60 (s, 3H), 3.54-3.32* and 3.48-3.42 (m, 2H), 2.49-2.44 (m, 2H), 2.21 and 2.22* (s, 3H), 1.12 and 1.05* (s, 3H), 1.04* and 1.02 (s, 3H). 31P-NMR (162 MHz, CDCl$_3$, 300 K) δ. −6.33, −10.87*. UPLC tR 1.21* and 1.25. MS (ES+) m/z 470 [M+Na]$^+$.

Example 52

(((4R)-4-((3-methoxy-3-oxopropyl)carbamoyl)-5,5-dimethyl-2-oxido-1,3,2-dioxaphosphinan-2-yl)oxy)methyl 3-(tert-butyl)-1H-pyrazole-5-carboxylate (Compound No. 2-146)

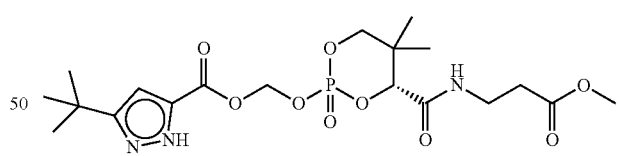

(((4R)-4-((3-methoxy-3-oxopropyl)carbamoyl)-5,5-dimethyl-2-oxido-1,3,2-dioxaphosphinan-2-yl)oxy)methyl 3-(tert-butyl)-1H-pyrazole-5-carboxylate (Compound No. 2-146) was synthesized according to the procedure described in Example 6 with respect to Compound No. 70, except that 3-(tert-butyl)-1H-pyrazole-5-carboxylic acid was used instead of thiazole-5-carboxylic acid, affording a mixture of diastereomers (79:21*) of the title compound (8%) as a white solid.

$^1$H-NMR (400 MHz, CDCl$_3$, 300 K) δ 7.46 and 7.12* (bs, 1H), 6.69 and 6.67* (s, 1H), 6.60 (bs, 1H), 6.04 and 5.86* and 5.62 (dd and d*, J=5.3 Hz, 17.9 Hz, J*=13.6 Hz, 2H), 4.77 and 4.58* (s, 1H), 4.35 and 4.13* (dd and d*, J$_{HP}$=2.2 Hz, J$_{AB}$=11.8 Hz, J*=11.8 Hz, 1H), 3.84 and 3.78* (dd, $J_{AB}$=11.4 Hz, $J_{HP}$=23.6 Hz, $J*_{AB}$=10.9 Hz, $J*_{H}$p=24.9 Hz, 1H), 3.68 and 3.64* (s, 3H), 3.58-3.53 and 3.58-3.42* (m, 2H), 2.67-2.58 and 2.48* (m and t*, J*=6.5 Hz, 2H), 1.31 and 1.30* (s, 9H), 1.13 and 1.07* (s, 3H), 1.07 and 1.03 (s, 3H). $^{31}$P-NMR (162 MHz, CDCl$_3$, 300 K) δ. −6.77, −10.73*. UPLC tR 1.44. MS (ES+) m/z 470 [M+Na]$^+$.

Example 53

(((4R)-4-((3-methoxy-3-oxopropyl)carbamoyl)-5,5-dimethyl-2-oxido-1,3,2-dioxaphosphinan-2-yl)oxy)methyl 4-methyloxazole-5-carboxylate (Compound No. 2-147)

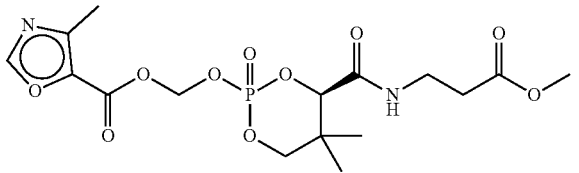

(((4R)-4-((3-methoxy-3-oxopropyl)carbamoyl)-5,5-dimethyl-2-oxido-1,3,2-dioxaphosphinan-2-yl)oxy)methyl 4-methyloxazole-5-carboxylate (Compound No. 2-147) was synthesized according to the procedure described in Example 3 with respect to Compound No. 65, except that chloromethyl 4-methyl-1,3-oxazole-5-carboxylate was used instead of chloromethyl pivalate, and Ag$_2$O (1.5 eq) and CH$_3$CN were used instead of DIEA and DMF. A mixture of diastereomers (10*:90) of the title compound (5%) as a colorless oil was obtained.

$^1$H-NMR (400 MHz, CDCl$_3$, 300 K) δ 7.99* and 7.97 (s, 1H), 7.07* and 6.94 (bs, 1H), 5.98-5.91 (m, 2H), 4.81* and 4.63 (d* and s, J*=1.7 Hz, 1H), 4.37* and 4.21 (dd* and d, $J_{HP}$*=3.9 Hz, $J_{AB}$*=11.4 Hz, J=11.4 Hz, 1H), 3.80 (dd, $J_{AB}$=11.4 Hz, $J_{HP}$=24.9 Hz, 1H), 3.73 and 3.71* (s, 3H), 3.67-3.56 (m, 1H), 3.54-3.45 (m, 1H), 2.59-2.56 (m, 5H), 1.22* and 1.15 (s, 3H), 1.14 and 1.12* (s, 3H). $^{31}$P-NMR (162 MHz, CDCl$_3$, 300 K) δ −6.57*, −10.97. UPLC tR 1.10 and 1.17*. MS (ES+) m/z 457 [M+Na]$^+$.

Example 54

(((2S,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-149)

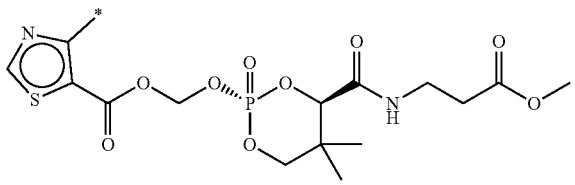

(((2S,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-147) was synthesized according to the procedure described in Example 6 with respect to Compound No. 70, except that 4-methylthiazole-5-carboxylic acid was used instead of thiazole-5-carboxylic acid, affording, after purification, a single diastereomer (0:100) of the title compound (2.2%) as a colorless oil.

$^1$H-NMR (400 MHz, CDCl$_3$, 300 K) δ 8.79 (s, 1H), 6.82 (bs, 1H), 5.82 (d, J=13.1 Hz, 2H), 4.51 (s, 1H), 4.12 (d, J=11.4 Hz, 1H), 3.77 (dd, $J_{AB}$=11.4 Hz, $J_{HP}$=24.9 Hz, 1H), 3.64 (s, 3H), 3.55-3.45 (m, 1H), 3.41-3.33 (m, 1H), 2.74 (s, 3H), 2.51-2.42 (m, 2H), 1.05 (s, 3H), 1.04 (s, 3H). $^{31}$P-NMR (162 MHz, CDCl$_3$, 300 K) δ. −10.89. UPLC tR 1.17. MS (ES+) m/z 473 [M+Na]$^+$.

Example 55

(((2R,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-150)

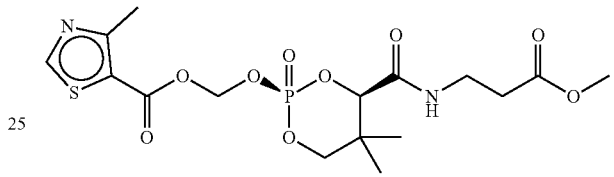

(((2R,4R)-4-((3-methoxy-3-oxopropyl)carbamoyl)-5,5-dimethyl-2-oxido-1,3,2-dioxaphosphinan-2-yl)oxy)methyl 4-methylthiazole-5-carboxylate (Compound No. 2-150) was synthesized according to the procedure described in Example 6 with respect to Compound No. 70, except that 4-methylthiazole-5-carboxylic acid was used instead of thiazole-5-carboxylic acid, affording, affording after purification, a single diastereomer (100:0) of the title compound (39%) as a white solid.

$^1$H-NMR (400 MHz, CDCl$_3$, 300 K) δ 8.79 (s, 1H), 7.0 (s, 1H), 5.92-5.80 (m, 2H), 4.71 (d, J=2.2 Hz, 1H), 4.27 (dd, $J_{HP}$=3.9 Hz, $J_{AB}$=11.4 Hz, 1H), 3.80 (dd, $J_{AB}$=11.4 Hz, $J_{HP}$=22.8 Hz, 1H), 3.60 (s, 3H), 3.53-3.43 (m, 2H), 2.76 (s, 3H), 2.49 (t, J=5.7 Hz, 2H), 1.12 (s, 3H), 1.03 (s, 3H). $^{31}$P-NMR (162 MHz, CDCl$_3$, 300 K) δ. −6.53. UPLC tR 1.21. MS (ES+) m/z 473 [M+Na]$^+$.

Example 56

(((2S,4R)-4-((3-methoxy-3-oxopropyl)carbamoyl)-5,5-dimethyl-2-oxido-1,3,2-dioxaphosphinan-2-yl)oxy)methyl oxazole-5-carboxylate (Compound No. 2-151)

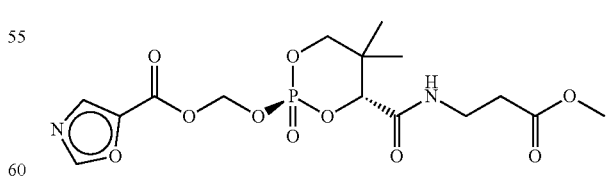

(((2S,4R)-4-((3-methoxy-3-oxopropyl)carbamoyl)-5,5-dimethyl-2-oxido-1,3,2-dioxaphosphinan-2-yl)oxy)methyl oxazole-5-carboxylate (Compound No. 2-151) was synthesized according to the procedure described in Example 6 with respect to Compound No. 70, except that oxazole-5-carboxylic acid was used instead of thiazole-5-carboxylic acid, affording, after purification, a single diastereomer (0:100) of the title compound (2%) as a colorless, sticky solid.

¹H-NMR (400 MHz, CDCl₃, 300 K) δ 7.99 (s, 1H), 7.82 (s, 1H), 6.84 (bs, 1H), 5.86-5.79 (m, 2H), 4.49 (s, 1H), 4.09 (d, J=11.4 Hz, 1H), 3.76 (dd, J$_{AB}$=11.4 Hz, J$_{HP}$=25.4 Hz, 1H), 3.62 (s, 3H), 3.54-3.46 (m, 1H), 3.43-3.35 (m, 1H), 2.48-2.44 (m, 2H), 1.03 (s, 3H), 1.02 (s, 3H). ³¹P-NMR (162 MHz, CDCl₃, 300 K) δ. −11.01. UPLC tR 1.03. MS (ES+) m/z 443 [M+Na]⁺.

Example 57

2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl ((benzyloxy)carbonyl)-L-valinate (Compound No. 2-160)

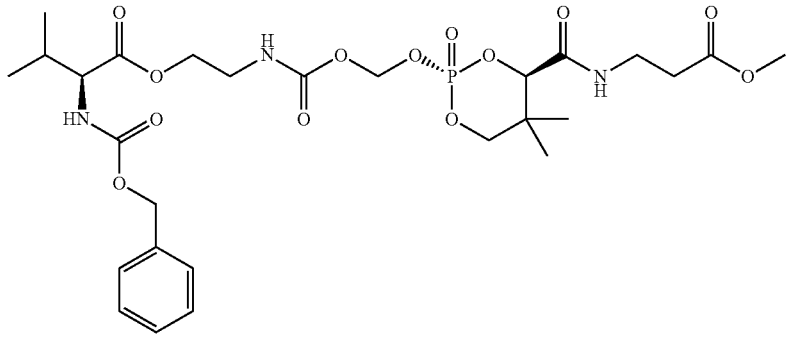 [SMILES: COC(=O)CCNC(=O)[C@@H]1O[P@@](=O)(OCOC(=O)NCCOC(=O)[C@@H](NC(=O)OCc2ccccc2)C(C)C)OCC1(C)C]

2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl ((benzyloxy)carbonyl)-L-valinate (Compound 2-160) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was H₂O containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min.

Step 1. 2-((tert-butoxycarbonyl)amino)ethyl ((benzyloxy)carbonyl)-L-valinate

Tert-butyl (2-hydroxyethyl)carbamate (1.0 eq), DMAP (0.2 eq) and ((benzyloxy)carbonyl)-L-valine (1.0 eq) were dissolved in DCM (0.4 M) and the solution was cooled to 0° C. EDC HCl (1.2 eq) was added, and the temperature was raised to 20° C. and stirring was continued for 16 h. The resulting mixture was filtered on a pad of silica eluting with DCM/EtOAc and the seolvent evaporated. The crude was dissolved in DCM and washed with 5% aqueous citric acid solution, saturated aqueous solution of NaHCO₃, water, and brine, dried over Na₂SO₄, and the solvent evaporated to afford the title compound (85%) as a pale yellow oil, which was used directly in the subsequent reaction step. ¹H-NMR (400 MHz, DMSO-d₆, 300 K) δ 7.64 (d, J=8.3 Hz, 1H), 7.40 (m, 5H), 6.89 (t, J=4.8 Hz, 1H), 5.05 (s, 2H), 4.10-3.95 (m, 3H), 3.17-3.15 (m, 2H), 2.11-2.03 (m, 1H), 1.38 (s, 9H), 0.88 (d, J=3.1 Hz, 3H), 0.86 (d, J=3.07 Hz, 3H).

Step 2. 2-((((benzyloxy)carbonyl)-L-valyl)oxy)ethan-1-aminium chloride 2-((tert-butoxycarbonyl)amino)ethyl ((benzyloxy)carbonyl)-L-valinate (1.0 eq) was dissolved in DCM (0.3 M) and a solution (2M) of HCl in Et₂O (7.0 eq) was added at 0° C. The mixture was stirred at ambient temperature for 1 h. The solvent was then evaporated under reduced pressure to afford the title compound (99%) as a white solid.

¹H-NMR (400 MHz, DMSO-d₆, 300 K) δ 8.29 (bs, 3H), 7.71 (d, J=8.3 Hz, 1H), 7.40-7.30 (m, 5H), 5.06 (s, 2H), 4.32-4.27 (m, 1H), 4.23-4.17 (m, 1H), 4.12-4.08 (m, 1H), 3.09-3.06 (m, 2H), 2.19-2.09 (m, 1H), 0.89 (d, J=6.58 Hz, 3H), 0.87 (d, J=6.6 Hz, 3H). UPLC tR 1.15 min; MS (ES⁺) m/z 295 (M+H)⁺.

Step 3. 2-(((chloromethoxy)carbonyl)amino)ethyl ((benzyloxy)carbonyl)-L-valinate 2-((((benzyloxy)carbonyl)-L-valyl)oxy)ethan-1-aminium chloride was dissolved in saturated aqueous solution of NaHCO₃ and extracted with DCM. The organic solvent was evaporated under reduced pressure to obtain 2-aminoethyl ((benzyloxy)carbonyl)-L-valinate (1.1 eq) and chloromethyl carbonochloridate (1.0 eq). These compounds were dissolved in DCM (0.1 M) and cooled to 0° C. TEA (1.1 eq) was added and the solution was allowed to warm to ambient temperature and stirred for 0.2 h. This solution was washed with water, washed with brine, dried over Na₂SO₄, and concentrated and purified by flash chromatography on SiO₂ using PE/EtOAc as eluent, to afford the title compound (20%) as a white solid. ¹H-NMR (400 MHz, CDCl₃, 300 K) δ 7.41-7.34 (m, 5H), 6.17 (t, J=5.2 Hz, 1H), 5.75 (s, 2H), 5.14 (s, 2H), 4.3-4.31 (m, 2H), 4.0-3.96 (m, 1H), 3.63-3.59 (m, 2H), 2.20-2.15 (m, 1H), 0.99 (d, J=6.58 Hz, 3H), 0.94 (d, J=6.58 Hz, 3H). UPLC tR 1.68 min; MS (ES⁺) m/z 409 (M+Na)⁺.

Step 4. 2-((((((2S,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl ((benzyloxy)carbonyl)-L-valinate (Compound No. 2-160)

2-(((chloromethoxy)carbonyl)amino)ethyl ((benzyloxy)carbonyl)-L-valinate (1.0 eq) was dissolved in MeCN (0.1 M) and treated with methyl 3-((4R)-2-hydroxy-5,5-dimethyl-2-oxido-1,3,2-dioxaphosphinane-4-carboxamido)propanoate (Compound No. 55) (synthesized as reported in the Example 3, Step 2) (1.0 eq) and Ag₂O (1.5 eq). The reaction mixture was stirred in the dark at 80° C. for 2h and then filtered on a plug of Solka-Floc, eluting with EtOAc. The solvent was concentrated and the resulting mixture of diastereomers was purified by flash chromatography on SiO$_2$ using PE/EtOAc as eluent, to afford the single diastereomer (0:100) of the title compound (22%) as a white solid. $^1$H-NMR (400 MHz, CDCl3, 300 K) δ 8.19-8.14 (m, 2H), 7.37-7.31 (m, 5H), 7.25 (d, J=8.7 Hz, 1H), 5.83 (d, J=13.1 Hz, 2H), 5.07-4.99 (m, 2H), 4.61 (s, 1H), 4.18-4.12 (m, 3H), 3.98 (dd, J$_{AB}$=11.4 Hz, J$_{HP}$=24.5 Hz, 1H), 3.81 (dd, J=7.0 Hz, 7.9 Hz, 1H), 3.59 (s, 3H), 3.47-3.37 (m, 2H), 3.31-3.27 (m, 2H), 2.53-2.50 (m, 2H), 1.97-1.89 (m, 1H), 1.02 (s, 3H), 0.95 (s, 3H), 0.85 (d, J=1.7 Hz, 3H), 0.83 (d, J=1.7 Hz, 3H). $^{31}$P-NMR (162 MHz, DMSO-d$_6$, 300 K) δ −10.94. UPLC tR 1.60 min. MS (ES$^+$) m/z 668 [M+Na]$^+$.

Example 58

2-((((((2R,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl ((benzyloxy)carbonyl)-L-valinate (Compound No. 2-161)

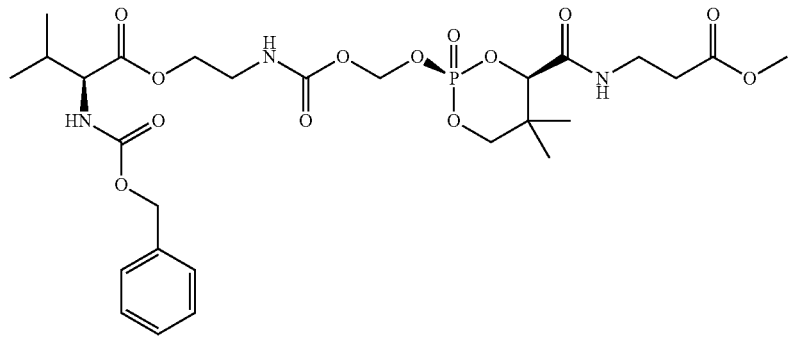 [SMILES: COC(=O)CCNC(=O)[C@@H]1O[P@](=O)(OCOC(=O)NCCOC(=O)[C@@H](NC(=O)OCc2ccccc2)C(C)C)OCC1(C)C]

2-((((((2R,4R)-4-((3-methoxy-3-oxopropyl)carbamoyl)-5,5-dimethyl-2-oxido-1,3,2-dioxaphosphinan-2-yl)oxy)methoxy)carbonyl)amino)ethyl ((benzyloxy)carbonyl)-L-valinate was prepared according to the procedure reported in Example 57, affording, after purification, the single diastereomer (100:0) of the title compound (2.5%) as a white solid.

$^1$H-NMR (400 MHz, DMSO-d$_6$, 300 K) 8.19-8.15 (m, 2H), 7.37-7.36 (m, 4H), 7.32-7.30 (m, 1H), 7.25 (d, J=8.7 Hz, 1H), 5.70-5.63 (m, 2H), 5.07-4.99 (m, 2H), 4.71 (d, J=5.7 Hz, 1H), 4.22-4.13 (m, 4H), 3.81 (t, J=8.3 Hz, 1H), 3.59 (s, 3H), 3.47-3.28 (m, 4H), 2.53-2.50 (m, 2H), 1.97-1.89 (m, 1H), 1.06 (s, 3H), 0.95 (s, 3H), 0.84 (d, J=2.6 Hz, 3H), 0.83 (d, J=2.2 Hz, 3H). $^{31}$P-NMR (162 MHz, DMSO-d$_6$, 300 K) δ −8.92. UPLC tR 1.57 min. MS (ES$^+$) m/z 668 [M+Na]$^+$.

Example 59

Methyl (S)-2-amino-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-162)

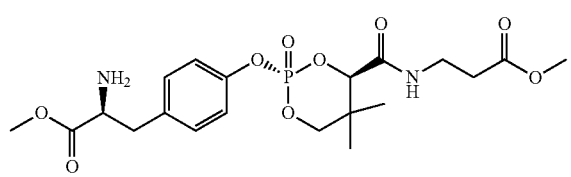

Methyl (S)-2-amino-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-162) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was H$_2$O containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min.

Step 1. Methyl (S)-2-((tert-butoxycarbonyl)amino)-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-204)

A solution (0.85 M) of POCl$_3$ (1.0 eq) in THF was cooled to −78° C. and a solution (1.1 M) of methyl (tert-butoxycarbonyl)-L-tyrosinate (1.0 eq) and TEA (1.0 eq) in DCM was slowly added. After stirring at −78° C. for 0.5 h, the mixture was warmed to ambient temperature over 1 h then filtered through a pad of Solka-Floc. Filtrate was concentrated under vacuum, dissolved (0.42 M) in DCM and cooled again to −78° C. then treated sequentially with a solution (1.7 M) of methyl (R)-3-(2,4-dihydroxy-3,3-dimethylbutanamido)propanoate (1.0 eq) in DCM and TEA (2.0 eq). Stirring was continued at −78° C. for 0.5 h, and then the mixture was allowed to warm slowly to ambient temperature over 0.5 h. The mixture was washed with 5% aqueous citric acid solution, 1N aqueous NaOH solution, and brine, and then dried over Na$_2$SO$_4$. After filtration the solvent was concentrated and the obtained mixture of diastereomers was purified by flash chromatography on SiO$_2$ using PE/EtOAc as eluent to afford the single diastereomer (0:100) of the title compound (10%) as a white solid. $^1$H-NMR (400 MHz, CDCl$_3$, 300 K) δ 7.17 (d, J=7.2 Hz, 2H), 7.12 (d, J=7.2 Hz, 2H), 6.97 (t, J=5.7 Hz, 1H), 4.99-4.97 (m, 1H), 4.72 (s, 1H), 4.60-4.55 (m, 1H), 4.27 (d, J=10.9 Hz, 1H), 3.94 (dd, J$_{AB}$=11.4 Hz, J$_{HP}$=25.4 Hz, 1H), 3.73 (s, 3H), 3.72 (s, 3H), 3.70-3.61 (m, 1H), 3.57-3.49 (m, 1H), 3.15-3.01 (m, 2H), 2.61-2.58 (m, 2H), 1.56 and 1.43 (s, 9H), 1.19 (s, 3H), 1.18

(s, 3H). $^{31}$P-NMR (162 MHz, CDCl$_3$, 300 K) δ −14.99. UPLC tR 1.60 min. MS (ES$^+$) m/z 495 [M+Na]$^+$.

Step 2. Methyl (S)-2-amino-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-162)

A solution (0.3 M) of methyl (S)-2-((tert-butoxycarbonyl)amino)-3-(4-(((2S,4R)-4-((3-methoxy-3-oxopropyl)carbamoyl)-5,5-dimethyl-2-oxido-1,3,2-dioxaphosphinan-2-yl)oxy)phenyl)propanoate (1.0 eq) in DCM (2M) was cooled to 0° C. then a solution of HCl in Et$_2$O (9 eq) was slowly added. The mixture was stirred at ambient temperature for 1 h then the solvent was evaporated under reduced pressure to afford the title compound (a single diastereomer) (80%) as a white solid. $^1$H-NMR (400 MHz, DMSO-d$_6$, 300 K) δ 8.37 (bs, 3H), 8.29 (t, J=5.7 Hz, 1H), 7.34 (s, 4H), 4.90 (s, 1H), 4.40-4.34 (m, 2H), 4.10 (dd, J$_{AB}$=11.4 Hz, J$_{HP}$=25.0 Hz, 1H), 3.76 (s, 3H), 3.65 (s, 3H), 3.49-3.43 (m, 1H), 3.40-3.34 (m, 1H), 3.15 (d, J=6.6 Hz, 2H), 2.60-2.57 (m, 2H), 1.13 (s, 3H), 1.08 (s, 3H). $^{31}$P-NMR (162 MHz, DMSO-d$_6$, 300 K) δ −14.50. UPLC tR 0.9 min. MS (ES$^+$) m/z 473 [M+H]$^+$.

Example 60

Methyl (S)-2-amino-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-163)

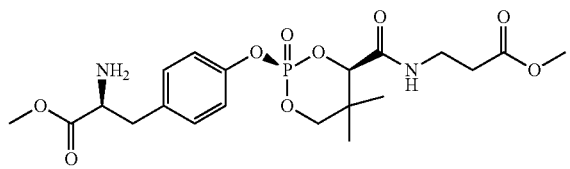

Methyl (S)-2-amino-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-163) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was H$_2$O containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min.

Step 1. Methyl (S)-2-((tert-butoxycarbonyl)amino)-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2 203)

Methyl (S)-2-((tert-butoxycarbonyl)amino)-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate was prepared according to the procedure reported in Example 59, Step 1, to afford, after purification, the title compound (10%) as a white solid. $^1$H-NMR (400 MHz, CDCl$_3$, 300 K) δ 7.23 (d, J=7.9 Hz, 2H), 7.18 (d, J=8.3 Hz, 2H), 6.94 (t, J=5.7 Hz, 1H), 5.04-5.01 (m, 1H), 4.81 (d, J=1.3 Hz, 1H), 4.62-4.58 5 (m, 1H), 4.40 (dd, J$_{HP}$=3.5 Hz, J$_{AB}$=11.8 Hz, 1H), 3.89 (dd, J$_{AB}$=11.4 Hz, J$_{HP}$=23.2 Hz, 1H), 3.76 (s, 3H), 3.73 (s, 3H), 3.69-3.61 (m, 1H), 3.54-3.48 (m, 1H), 3.17-3.05 (m, 2H), 2.58 (t, J=5.7 Hz, 2H), 1.57 and 1.44 (s, 9H), 1.17 (s, 3H), 0.86 (s, 3H). $^{31}$P-NMR (162 MHz, CDCl$_3$, 300 K) δ −10.87. UPLC tR 1.67 min. MS (ES+) m/z 595 [M+Na]$^+$.

Step 2. Methyl (S)-2-amino-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate (Compound No. 2-163)

Methyl (S)-2-amino-3-(4-(((2R,4R)-4-((3-methoxy-3-oxopropyl)carbamoyl)-5,5-dimethyl-2-oxido-1,3,2-dioxaphosphinan-2-yl)oxy)phenyl)propanoate was synthesized according to the procedure reported in the Example 59, Step 2 to afford the title compound (63%) as a white solid. $^1$H-NMR (400 MHz, DMSO-d$_6$, 300 K) δ 8.52 (bs, 3H), 8.34 (t, J=5.7 Hz, 2H), 7.32 (d, J=8.7 Hz, 2H), 7.28 (d, J=8.7 Hz, 2H), 4.78 (d, J=8.7 Hz, 1H), 4.43 (dd, J=10.9 Hz, J=14.5 Hz, 1H), 4.34 (t, J=7.0 Hz, 1H), 4.21 (t, J=10.9 Hz), 3.75 (s, 3H), 3.66 (s, 3H), 3.46-3.37 (m, 2H), 3.19-3.02 (m, 2H), 2.59-2.55 (m, 2H), 1.01 (s, 3H), 0.88 (s, 3H). $^{31}$P-NMR (162 MHz, DMSO-d$_6$, 300 K) δ −13.33. UPLC tR 0.89 min. MS (ES$^+$) m/z 473 [M+H]$^+$.

Example 61

Benzyl N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate (Compound No. 2-164)

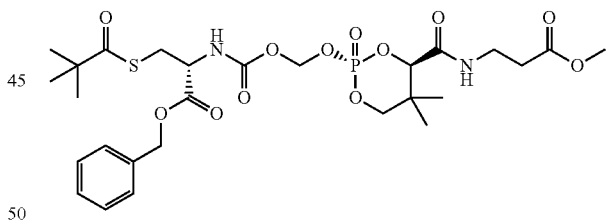

Benzyl N-(((((2S,4R)-4-((3-methoxy-3-oxopropyl)carbamoyl)-5,5-dimethyl-2-oxido-1,3,2-dioxaphosphinan-2-yl)oxy)methoxy)carbonyl)-S-pivaloyl-L-cysteinate (Compound No. 2-164) was prepared using Method B as outlined above. Unless otherwise stated, all reagents were obtained from commercial sources and were used as received without further purification. NMR spectra were collected on Bruker instruments at the indicated frequencies. UPLC-MS analysis was conducted on a Waters UPLC system with both Diode Array detection and Electrospray (+'ve and −'ve ion) MS detection. The stationary phase was a Waters Acquity UPLC BEH C18 1.7 um 2.1×50 mm column. The mobile phase was H$_2$O containing 0.1% Formic acid (A) and MeCN containing 0.1% Formic acid (B) in the following linear gradient: 90% A (0.1 min), 90%-0% A (2.5 min), 0% A (0.3 min), 90% A (0.1 min) with a flow rate of 0.5 mL/min. Reverse phase (C18) column chromatography was carried out using as mobile phase H$_2$O containing 0.1% of TFA and MeCN containing 0.1% of TFA.

Step 1. S-pivaloyl-L-cysteine

A solution (2.0 M) of L-cysteine (1.0 eq) in TFA was cooled to 0° C., and then pivaloyl chloride (1.5 eq) was slowly added. The mixture was stirred at ambient temperature for 2h then Et$_2$O was added. The resulting precipitate was filtered and washed with additional Et$_2$O to afford the title compound (99%) as a white solid. $^1$H-NMR (400 MHz, DMSO-d$_6$, 300 K) δ 13.99 (bs, 1H), 8.52 (bs, 3H), 4.12 (bs, 1H), 3.36-3.34 (m, 2H), 1.20 (s, 9H).

Step 2.
N-(tert-butoxycarbonyl)-S-pivaloyl-L-cysteine

A solution (0.46 M) of (R)-1-carboxy-2-(pivaloylthio) ethan-1-aminium chloride (1.0 eq) was dissolved in THF and cooled to 0° C. Di-tert-butyl dicarbonate (1.3 eq) and TEA (2.5 eq) were sequentially added. After stirring at 0° C. for 0.5 h the mixture was warmed to ambient temperature over 2 h, and then DCM and 1N aqueous NaHCO$_3$ solution were added. The water phase was separated, and then DCM and 6N aqueous HCl solution until were added until pH=2. The organic phase was isolated, dried over MgSO$_4$ and concentrated to afford the title compound (40%), which was used in the next step without further purification. $^1$H-NMR (400 MHz, CDCl$_3$, 300 K) δ 5.21 (bs, 1H), 4.41 (bs, 1H), 3.31 (dd, J=4.8 Hz, J=14.0 Hz, 1H), 3.23 (dd, J=5.3 Hz, J-14.0 Hz, 1H), 1.38 (s, 9H), 1.18 (s, 9H).

Step 3. benzyl
N-(tert-butoxycarbonyl)-S-pivaloyl-L-cysteinate

N-(tert-butoxycarbonyl)-S-pivaloyl-L-cysteine (1.0 eq) was dissolved in DMF (0.4 M) and (bromomethyl)benzene (1.0 eq) and Cs$_2$CO$_3$ (0.5 eq) were sequentially added. After stirring for 0.5 h at ambient temperature, the mixture was filtered on a pad of Solka-Floc, eluting with DCM. Organic solvent was concentrated and obtained crude purified by flash chromatography on SiO$_2$ using DCM/EtOAc as eluent, to afford the title compound (43%) as a yellow oil. $^1$H-NMR (400 MHz, CDCl$_3$, 300 K) δ 7.44-7.41 (m, 5H), 5.20 (bs, 1H), 5.16 (d, J=3.1 Hz, 2H), 4.60-4.55 (m, 1H), 3.38-3.28 (m, 2H), 1.44 (s, 9H), 1.23 (s, 9H). UPLC tR 2.44 min. MS (ES$^+$) m/z 396 [M+H]$^+$.

Step 4. benzyl S-pivaloyl-L-cysteinate

A solution (0.2 M) of benzyl N-(tert-butoxycarbonyl)-S-pivaloyl-L-cysteinate (1.0 eq) in DCM was cooled to 0° C. then a solution of HCl in Et$_2$O (23 eq, 2.0M) was slowly added. The mixture was stirred at ambient temperature for 5 h, and then the solvent was evaporated under reduced pressure. Et$_2$O was added and the precipitate filtered to afford the title compound (99%) as a white solid. $^1$H-NMR (400 MHz, CDCl$_3$, 300 K) δ 8.52 (bs, 3H), 7.46-7.38 (m, 5H), 5.28-5.15 (m, 2H), 4.37 (t, J=5.70 Hz, 1H), 3.41-3.34 (m, 2H), 1.17 (s, 9H). UPLC tR 1.30 min. MS (ES$^+$) m/z 296 [M+H]$^+$.

Step 5. benzyl N-((chloromethoxy)carbonyl)-S-pivaloyl-L-cysteinate (R)-1-(benzyloxy)-1-oxo-3-(pivaloylthio)propan-2-aminium chloride was dissolved in saturated aqueous solution of NaHCO$_3$ and extracted with DCM. The organic solvent was evaporated under reduced pressure to afford 2-aminoethyl ((benzyloxy)carbonyl)-L-valinate. The latter (1.0 eq) was dissolved in DCM (0.1 M), and the solution was cooled to 0° C. Chloromethyl carbonochloridate (1.1 eq) and TEA (1.1 eq) were sequentially added. After stirring for 0.2 h the mixture was filtered on a pad of Solka-Floc, eluting with DCM. The organic phase was then washed with water, washed with brine, dried over Na$_2$SO$_4$, and concentrated to afford the title compound (99%) as a yellow oil that was used in the next step without further purification. $^1$H-NMR (400 MHz, CDCl$_3$, 300 K) δ 7.31-7.27 (m, 5H), 6.41 (d, J=6.6 Hz, 1H), 5.89-5.85 (m, 2H), 5.12 (s, 2H), 4.81-4.77 (m, 1H), 3.45 (dd, J=4.38 Hz, J=14.5 Hz, 1H), 3.33 (dd, J=6.1 Hz, J=14.5 Hz, 1H), 1.13 (s, 9H).

Step 6. benzyl N-(((((2S,4R)-4-((3-methoxy-3-oxo-propyl)carbamoyl)-5,5-dimethyl-2-oxido-1,3,2-di-oxaphosphinan-2-yl)oxy)methoxy)carbonyl)-S-pivaloyl-L-cysteinate (Compound 2-164)

Methyl 3-((4R)-2-hydroxy-5,5-dimethyl-2-oxido-1,3,2-dioxaphosphinane-4-carboxamido)propanoate (Compound No. 55) (synthesized as reported in Example 3, Step 2) (1.0 eq), benzyl N-((chloromethoxy)carbonyl)-S-pivaloyl-L-cysteinate (1.1 eq), and Ag$_2$O (1.5 eq) were dissolved in MeCN (0.14 M) and the obtained mixture was stirred in the dark at 80° C. for 7 h. The mixture was then filtered on a plug of Solka-Floc, eluting with EtOAc. The solvent was concentrated and the obtained crude was purified by flash chromatography on SiO$_2$ using PE/EtOAc as eluent, to afford the title compound (8%) as a white solid. $^1$H-NMR (400 MHz, DMSO-d$_6$, 300 K) δ 8.16 (t, J=5.7 Hz, 1H), 8.02 (d, J=7.9 Hz, 1H), 7.39-7.32 (m, 5H), 5.74-5.65 (m, 2H), 5.12 (dd, J=12.7 Hz, J=17.5 Hz, 2H), 4.57 (s, 1H), 4.49-4.44 (m, 1H), 4.09 (d, J=10.9 Hz, 1H), 3.97 (dd, J$_{AB}$=11.4 Hz, J$_{HP}$=24.5 Hz, 1H), 3.58 (s, 3H), 3.48-3.43 (m, 1H), 3.41-3.35 (m, 1H), 3.22-3.27 (m, 2H), 2.52-2.48 (m, 2H), 1.07 (s, 9H), 1.0 (s, 3H), 0.94 (s, 3H). $^{31}$P-NMR (162 MHz, DMSO-d$_6$, 300 K) δ -10.84. UPLC tR 1.74 min. MS (ES$^+$) m/z 669 [M+Na]$^+$.

Example 62

Exemplary Compounds

Table 4 provides descriptive data for the compounds shown in Tables 1-3. The compounds in Table 4 were each prepared and analyzed by mass spectrometry and/or $^1$H or $^{31}$P NMR. Experimental mass spectrometry data are included in Table 4. General methods by which the compounds may be prepared are provided above and indicated in Table 4. Exemplary synthetic procedures are described in more detail in Examples 1-61 above.

TABLE 4

| Exemplary compounds. | | | |
|---|---|---|---|
| Compound No. | MWt[a] | MS (m/z)[b] | Synthesis[c] |
| 1 | 408 | 409 | A |
| 2 | 470 | 471 | A |
| 3 | 484 | 485 | A |
| 4 | 498 | 499 | C |
| 5 | 380 | 381 | A |
| 6 | 484 | 485 | C |
| 7 | 450 | 451 | C |
| 8 | 436 | 437 | A |
| 9 | 456 | 457 | A |

TABLE 4-continued

Exemplary compounds.

| Compound No. | MWt[a] | MS (m/z)[b] | Synthesis[c] |
|---|---|---|---|
| 10 | 532 | 533 | A |
| 11 | 456 | 457 | A |
| 12 | 448 | 449 | A |
| 13 | 484 | 485 | A |
| 14 | 490 | 491 | A |
| 15 | 570 | 571 | A |
| 16 | 380 | 381 | A |
| 17 | 450.46 | 451 | A |
| 18 | 457.41 | 458 | A |
| 19 | 463.46 | 464 | A |
| 20 | 457.41 | 458 | A |
| 21 | 461.4 | 462 | A |
| 22 | 460.42 | 461 | A |
| 23 | 463.42 | 464 | A |
| 24 | 457.41 | 458 | A |
| 25 | 457.41 | 458 | A |
| 26 | 470.45 | 471 | A |
| 27 | 479.46 | 480 | A |
| 28 | 457.41 | 458 | A |
| 29 | 539.54 | 540 | A |
| 30 | 533.51 | 534 | A |
| 31 | 491.5 | 492 | A |
| 32 | 491.5 | 492 | A |
| 33 | 512.53 | 513 | A |
| 34 | 436.39 | 437 | A |
| 35 | 471.44 | 472 | A |
| 36 | 547.54 | 548 | A |
| 37 | 510.52 | 511 | A |
| 38 | 547.54 | 548 | A |
| 39 | 548.53 | 549 | A |
| 40 | 551.53 | 552 | A |
| 41 | 456.43 | 457 | A |
| 42 | 458.4 | 457 [M − H]− | A |
| 43 | 482.46 | 483 | A |
| 44 | 553.58 | 554 | A |
| 45 | 498.51 | 499 | A |
| 46 | 484.48 | 485 | A |
| 47 | 553.54 | 554 | A |
| 48 | 470.45 | 471 | A |
| 49 | 540.59 | 541 | A |
| 50 | 365.4 | 366 | C |
| 51 | 371.3 | 370 [M − H]− | C |
| 52 | 422.4 | 423 | C |
| 53 | 443.4 | 444 | C |
| 54 | 385.4 | 386 | C |
| 55 | 295.2 | 294 [M − H]− | C |
| 56 | 385.4 | 386 | C |
| 57 | 409.4 | 410 | C |
| 58 | 399.4 | 400 | C |
| 59 | 510.5 | 511 | C |
| 60 | 405.4 | 406 | C |
| 61 | 400.6 | 401 | C |
| 62 | 386.3 | 387 | C |
| 63 | 427.43 | 428 | B |
| 64 | 429.4 | 430 | B |
| 65 | 409.4 | 410 | B |
| 66 | 395.4 | 396 | B |
| 67 | 423.4 | 424 | B |
| 68 | 367.3 | 368 | B |
| 69 | 411.34 | 412 | B |
| 70 | 436.37 | 437 | B |
| 71 | 486.45 | 487 | B |
| 72 | 430.35 | 431 | B |
| 73 | 480.45 | 481 | B |
| 74 | 490.44 | 491 | B |
| 75 | 451.45 | 452 | B |
| 76 | 512.49 | 513 | B |
| 77 | 448.4 | 449 | B |
| 78 | 501.49 | 502 | B |
| 79 | 492.48 | 493 | B |
| 80 | 493.45 | 494 | B |
| 2-113 | 492.46 | 493 | B |
| 82 | 500.48 | 501 | B |
| 83 | 436.35 | 437 | B |
| 84 | 461.4 | 462 | B |
| 85 | 522.48 | 523 | B |
| 86 | 431.33 | 432 | B |
| 87 | 420.31 | 421 | B |
| 88 | 425.37 | 426 | B |
| 89 | 409.37 | 410 | B |
| 90 | 409.37 | 410 | B |
| 91 | 395.34 | 418 [M + Na]+ | B |
| 92 | 464.45 | 465 | B |
| 93 | 554.57 | 555 | B |
| 94 | 465.43 | 466 | B |
| 95 | 487.44 | 488 | B |
| 96 | 481.47 | 482 | B |
| 97 | 460.37 | 461 | B |
| 98 | 443.38 | 444 | B |
| 99 | 492.5 | 493 | B |
| 100 | 395.34 | 394 | B |
| 101 | 486.45 | 487 | B |
| 102 | 423.4 | 446 [M + Na]+ | B |
| 103 | 395.34 | 396 | B |
| 104 | 397.31 | 398 | B |
| 105 | 453.42 | 454 | B |
| 106 | 409.37 | 432 [M + Na]+ | B |
| 107 | 423.4 | 424 | B |
| 108 | 281.2 | 280 [M − H]− | B |
| 109 | 391.4 | 392 | C |
| 110 | 380.3 | 381 | A |
| 111 | 399.4 | 400 | C |
| 112 | 398.4 | 399 | C |
| 113 | 402.4 | 403 | C |
| 114 | 294.2 | 295 | C |
| 115 | 384.4 | 385 | C |
| 116 | 378.4 | 379 | C |
| 117 | 456.4 | 457 | A |
| 118 | 442.4 | 443 | A |
| 119 | 378.4 | 379 | C |
| 120 | 378.4 | 379 | C |
| 121 | 380.3 | 381 | C |
| 122 | 379.4 | 380 | C |
| 123 | 374.3 | 375 | C |
| 124 | 393.4 | 394 | C |
| 125 | 385.4 | 386 | C |
| 126 | 407.4 | 408 | C |
| 127 | 419.4 | 420 | C |
| 128 | 420.4 | 421 | C |
| 129 | 416.4 | 417 | C |
| 130 | 398.4 | 399 | C |
| 131 | 521 | 522 | A |
| 132 | 421.38 | 422 | A |
| 133 | 362.36 | 363 | A |
| 134 | 350.4 | 351 | C |
| 1-54 | 572.59 | 573 | A |
| 1-55 | 526.52 | 527 | A |
| 2-114 | 422.37 | 423 | C |
| 2-115 | 380.33 | 381 | C |
| 2-116 | 396.33 | 397 | C |
| 2-117 | 429.36 | 430 | C |
| 2-118 | 389.31 | 390 | C |
| 2-119 | 439.32 | 440 | C |
| 2-120 | 416.32 | 417 | A |
| 2-121 | 416.32 | 417 | A |
| 2-122 | 440.31 | 441 | C |
| 2-123 | 377.25 | 378 | C |
| 2-124 | 497.37 | 498 | C |
| 2-125 | 497.37 | 498 | A |
| 2-126 | 490.42 | 491 | B |
| 2-127 | 461.4 | 462 | B |
| 2-128 | 437.42 | 438 | B |
| 2-129 | 461.4 | 462 | B |
| 2-130 | 397.31 | 398 | B |
| 2-131 | 436.35 | 437 | B |
| 2-132 | 375.31 | 376 | C |
| 2-133 | 439.46 | 440 | C |
| 2-134 | 416.32 | 417 | A |
| 2-135 | 571.56 | 572 | B |

TABLE 4-continued

Exemplary compounds.

| Compound No. | MWt[a] | MS (m/z)[b] | Synthesis[c] |
|---|---|---|---|
| 2-136 | 470.43 | 471 | B |
| 2-137 | 544.49 | 545 | B |
| 2-138 | 377.25 | 378 | C |
| 2-139 | 450.4 | 451 | B |
| 2-140 | 436.37 | 437 | B |
| 7-141 | 420.31 | 421 | B |
| 2-142 | 433.35 | 434 | B |
| 2-143 | 512.51 | 513 | B |
| 2-144 | 489.46 | 490 | B |
| 2-145 | 447.38 | 448 | B |
| 2-146 | 475.43 | 476 | B |
| 2-147 | 434.33 | 435 | B |
| 2-148 | 570.55 | 571 | B |
| 2-149 | 450.4 | 451 | B |
| 2-150 | 450.4 | 451 | B |
| 2-151 | 420.31 | 421 | B |
| 2-152 | 482.42 | 483 | B |
| 135 | 364.33 | 365 | C |
| 136 | 364.33 | 365 | C |
| 137 | 412.4 | 413 | C |
| 138 | 412.4 | 413 | C |
| 139 | 405.38 | 406 | C |
| 1-50 | 450.46 | 451 | A |
| 1-51 | 366.31 | | A |
| 1-52 | 380.33 | 381 | A |
| 1-53 | 380.33 | 381 | A |
| 2-109 | 375.29 | 376 | A |
| 2-110 | 323.28 | 324 | B |
| 2-111 | 337.31 | 336 [M − H]− | B |
| 2-112 | 465.42 | 466 | B |
| 2-160 | 645.59 | 668 [M + Na]+ | B |
| 2-161 | 645.59 | 668 [M + Na]+ | B |
| 2-162 | 472.43 | 473 | B |
| 2-163 | 472.43 | 473 | B |
| 2-164 | 646.64 | 647 | B |
| 2-165 | 396.33 | 397 | C |
| 2-166 | 429.36 | 430 | C |
| 2-167 | 524.5 | 525 | B |
| 2-168 | 454.37 | 477 [M + Na]+ | B |
| 2-169 | 489.46 | 512 [M + Na]+ | B |
| 2-170 | 489.46 | 490 | B |
| 2-171 | 539.51 | 540 | B |
| 2-172 | 673.65 | 696 [M + Na]+ | B |
| 2-173 | 492.48 | 493 | B |
| 2-174 | 646.64 | 669 [M + Na]+ | B |
| 2-175 | 661.66 | 662 | B |
| 2-176 | 450.4 | 473 [M + Na]+ | B |
| 2-177 | 450.4 | 473 [M + Na]+ | B |
| 2-178 | 389.31 | 412 [M + Na]+ | C |
| 2-179 | 389.31 | 390 | C |
| 2-180 | 556.52 | 579 [M + Na]+ | B |
| 2-181 | 645.59 | 668 [M + Na]+ | B |
| 2-182 | 447.38 | 470 [M + Na]+ | B |
| 2-183 | 496.45 | 519 [M + Na]+ | B |
| 2-184 | 433.35 | 456 [M + Na]+ | B |
| 2-185 | 433.35 | 456 [M + Na]+ | B |
| 2-186 | 475.43 | 498 [M + Na]+ | B |
| 2-187 | 478.45 | 501 [M + Na]+ | B |
| 2-188 | 478.45 | 501 [M + Na]+ | B |
| 2-189 | 538.44 | 561 [M + Na]+ | B |
| 2-190 | 447.38 | 470 [M + Na]+ | B |
| 2-191 | 438.32 | 461 [M + Na]+ | B |
| 2-192 | 492.48 | 515 [M + Na]+ | B |
| 2-193 | 527.53 | 528 | B |
| 2-194 | 527.53 | 528 | B |
| 2-195 | 511.46 | 512 | B |
| 2-196 | 538.44 | 561 [M + Na]+ | B |
| 2-197 | 439.32 | 462 [M + Na]+ | C |
| 2-198 | 440.31 | 463 [M + Na]+ | C |
| 2-199 | 674.65 | 697 [M + Na]+ | B |
| 2-200 | 556.52 | 579 [M + N]+ | B |
| 2-201 | 556.52 | 579 [M + Na]+ | B |
| 2-202 | 674.65 | 697 [M + Na]+ | B |
| 2-203 | 572.54 | 595 [M + Na]+ | C |
| 2-204 | 572.54 | 595 [M + Na]+ | C |
| 2-205 | 371.32 | | C |
| 2-206 | 646.64 | 647 | B |

[a]Molecular weight.
[b]Mass spectrum mass-to-charge ratio, [M + H]+ unless otherwise indicated.
[c]Method of synthesis, as described herein.

Example 63

Coenzyme A Assay in PANK2 Silenced Cells

Compounds of the invention show attractive pharmaceutical and biological properties for the treatment of PKAN disorders. Compounds from the invention demonstrate the ability to increase Coenzyme A (CoA or CoA-SH) levels in cell lines (e.g., neuroblastoma) in which the PANK2 gene has been silenced (Table 5).

A human neuroblastoma IMR32 cell line (ATCC) with stably PANK2 silencing was obtained by lentiviral-delivered small hairpin RNA and cultured in MEM (Invitrogen) supplemented with 10% fetal bovine serum, 2 mM glutamine, 1% penicillin-streptomycin, 1 mM sodium pyruvate, 1 mM non essential amino acids and 1.5 g/l sodium bicarbonate.

Development of a PANK2−/− Cell Model

For lentiviral shRNA expression, Human Emryonic Kidney HEK-293T cells (ATCC) were transfected with the appropriate pGFP-Lenti-shRNA constructs and packaging plasmids according to manufacturer's protocol (Origene Technologies, Inc.). Four different gene-specific shRNA expression vectors designed against multiple splice variants of PANK2 (Gene ID 80025) were used for transfection. A non-silencing shRNA construct (scrambled shRNA) and an empty vector expressing GFP alone were used as negative controls. The GFP tag subcloned into the lentiviral vectors was used to monitor the transfection efficiency.

IMR32 cells were plated on 150 cm dishes 48 h before transduction with lentiviral particles.

Three days after transduction medium was removed and replaced with fresh medium containing 1 μg/μl puromycin. Medium was replaced every 48 h. Levels of PANK2 expression on selected clones was assessed by Western Blot analysis.

Cell-based Assay on PANK2$^{-/-}$ Cells

To quantify CoA, PANK2$^{-/-}$ IMR32 cells were plated on 12-well culture plates (Corning) at a density of 0.2×10$^6$ cells per well. After 72 h, compounds were freshly dissolved in DMSO and added to the culture medium to yield a final solvent concentration of 0.1% (v/v). Controls with medium containing 0.1% DMSO without test compounds were also included in each plate. Compound treated cells were incubated for 24 h at 37° C. Treatment was repeated after 24 h with newly dissolved compound and cells were further incubated at 37° C. for additional 24 h. Before LC-MS analysis of CoA levels, cells were harvested, counted, and collected in a 15 ml falcon tube and centrifuged at 200×g for 5 min at 4° C. Supernatant was removed and cell pellet was washed in 10 ml of ice-cold PBS. To further confirm that the numbers of cells in each sample were equivalent, an equal fraction of pellet was collected from each sample and subjected to protein determination analysis. After centrifugation and supernatant removal, the cell pellet was rapidly frozen in Liquid Nitrogen and stored at −80° C. until analysis.

Intracellular CoA levels were calculated considering an intracellular volume of 1 million cells=2 μl.

The 1×10$^6$ cellular pellet was extracted with 120 μl of aqueous 20% TFA. This solution was stirred for 2 min, sonicated in ultrasonic bath for 2 min, then stirred again for 1 min, and centrifuged for 15 min at 14000 g and at 4° C.

100 μL samples of supernatant were dried under N$_2$ at 20° C. in the dark.

Samples were re-dissolved in 100 μl of 10 mM NH$_4^+$ AcO$^-$ buffer pH 5.1+IS (Dextrorphan 50 ng/ml), stirred for 2 min, sonicated in ultrasonic bath for 1 min, then stirred again for 1 min, and injected into LC-MS.

LC-MS/MS was performed using an Agilent HPLC (1100 Series, USA). The LC system was interfaced with an API-4000 Q-Trap triple quadrupole mass spectrometer (AB Sciex, Toronto, Canada) equipped with a TurboIonSpray ionization source operating in positive ion mode. Analyst™ software version 1.6 (AB Sciex, Toronto, Canada) was used for data acquisition and processing. CoA was separated using a Luna C18 column (2.0×50 mm; 5 μm particle size), column at 25° C. and flow rate of 0.2 ml/min. Injection volume was 15 μl. The mobile phases consisted of water containing 10 mM ammonium acetate pH 7 (mobile phase A) and MeCN-2-propanol 9:1 (mobile phase B). Elution was performed using a gradient starting at 2% B, holding at 2% B until 0.1 min, increasing to 98% B at 3.2 min, holding at 98% B until 4.5 min, returning to 2% B at 4.6 min and holding at 2% B until 7.5 min. Precursor ions and MRM transitions used were: CoA m/z 768.1→261.6 and 768.1→136.1.

Results for selected compounds tested in PANK2 silenced cells are reported in Table 5. Results are expressed as fold increase in CoA levels relative to controls (using LC-MS quantification of free CoA).

TABLE 5

Fold increase in Coenzyme A (CoA) levels relative to controls (PANK2$^{-/-}$ CoA) in PANK2 silenced cells treated with compounds.

| Compound No. | PANK2$^{-/-}$ CoA (Fold Increase) |
|---|---|
| 1 | 1.51 |
| 2 | 6.80 |
| 3 | 1.65 |
| 4 | 1.2 |
| 5 | 1.15 |
| 6 | 1.11 |
| 7 | 1.56 |
| 8 | 0.69 |
| 9 | 1.83 |
| 10 | 1.05 |
| 11 | 0.99 |
| 12 | 1.28 |
| 13 | 1 |
| 14 | 1.59 |
| 15 | 0.5 |
| 16 | 1.21 |
| 18 | 2.06 |
| 19 | 1.73 |
| 20 | 0.9 |
| 23 | 2.08 |
| 24 | 0.92 |
| 25 | 0.95 |
| 26 | 2.29 |
| 27 | 1.49 |
| 28 | 0.87 |
| 29 | 1.17 |
| 30 | 0.93 |
| 31 | 1.1 |
| 32 | 1.49 |
| 33 | 0.8 |
| 34 | 1.3 |
| 35 | 2.23 |
| 36 | 2.44 |
| 37 | 1.9 |
| 38 | 2.76 |
| 39 | 2.18 |
| 40 | 2.77 |
| 41 | 2.02 |
| 42 | 2.42 |
| 43 | 1.97 |
| 44 | 1.62 |
| 45 | 1.3 |
| 46 | 2.74 |
| 47 | 1.38 |
| 48 | 2.16 |
| 49 | 1.09 |
| 52 | 1.58 |
| 55 | 1.92 |
| 59 | 1.52 |
| 61 | 1.93 |
| 63 | 2.24 |
| 64 | 278.1 |
| 65 | 222.6 |
| 66 | 83.72 |
| 67 | 122.4 |
| 68 | 125.97 |
| 69 | 181.1 |
| 70 | 87.75 |
| 71 | 39.37 |
| 72 | 34.64 |
| 73 | 6.92 |
| 74 | 176 |
| 75 | 1.52 |
| 76 | 79.95 |
| 77 | 93.86 |
| 78 | 120.6 |
| 79 | 133.6 |
| 80 | 1.48 |
| 82 | 99.82 |
| 83 | 12.02 |
| 84 | 325.47 |
| 85 | 216.8 |
| 86 | 2.45 |

TABLE 5-continued

Fold increase in Coenzyme A (CoA) levels relative to controls (PANK2$^{-/-}$ CoA) in PANK2 silenced cells treated with compounds.

| Compound No. | PANK2$^{-/-}$ CoA (Fold Increase) |
|---|---|
| 87 | 58.7 |
| 88 | 2.66 |
| 89 | 154.1 |
| 90 | 286.0 |
| 91 | 4.03 |
| 92 | 5.13 |
| 93 | 206.8 |
| 94 | 13.14 |
| 95 | 54.03 |
| 96 | 29.43 |
| 97 | 77.04 |
| 98 | 4.01 |
| 99 | 10.44 |
| 101 | 81.66 |
| 102 | 2.5 |
| 103 | 105.8 |
| 104 | 75.24 |
| 105 | 4.72 |
| 106 | 2.66 |
| 107 | 85.06 |
| 108 | 1.07 |
| 109 | 1.87 |
| 112 | 1.42 |
| 117 | 1.06 |
| 118 | 2.96 |
| 119 | 1.44 |
| 125 | 1.99 |
| 126 | 1.33 |
| 129 | 0.9 |
| 132 | 1.88 |
| 133 | 1.45 |
| 1-54 | 1.13 |
| 1-55 | 2.09 |
| 2-114 | 1.87 |
| 2-115 | 1.6 |
| 2-116 | 0.95 |
| 2-117 | 1.11 |
| 2-118 | 1.38 |
| 2-119 | 1.67 |
| 2-120 | 21.05 |
| 2-121 | 1.59 |
| 2-122 | 1.21 |
| 2-123 | 1.46 |
| 2-124 | 1.12 |
| 2-125 | 34.02 |
| 2-126 | 138.56 |
| 2-127 | 14.41 |
| 2-129 | 88.66 |
| 2-130 | 43.5 |
| 2-131 | 1.44 |
| 2-132 | 0.93 |
| 2-133 | 89.53 |
| 2-134 | 5.37 |
| 2-135 | 1.7 |
| 2-136 | 1.41 |
| 2-137 | 1.1 |
| 2-138 | 1.13 |
| 2-139 | 44.21 |
| 2-140 | 37.02 |
| 2-141 | 7.62 |
| 2-142 | 58.1 |
| 2-143 | 1.39 |
| 2-144 | 77.8 |
| 2-145 | 42.44 |
| 2-146 | 84.86 |
| 2-147 | 39.19 |
| 2-148 | 4.19 |
| 2-149 | 24.48 |
| 2-150 | 43.4 |
| 2-151 | 17.56 |
| 2-152 | 1.24 |
| 135 | 1.3 |
| 136 | 1.93 |
| 137 | 1.76 |
| 138 | 1.7 |
| 139 | 2.72 |
| 1-52 | 2.09 |
| 1-53 | 2.37 |
| 2-109 | 2.04 |
| 2-113 | 7.93 |
| 2-110 | 2.17 |
| 2-111 | 1.16 |
| 2-160 | 7.99 |
| 2-161 | 71.14 |
| 2-162 | 9.73 |
| 2-163 | 81.21 |
| 2-164 | 101.86 |
| 2-165 | 6.87 |
| 2-166 | 3.61 |
| 2-167 | 3.26 |
| 2-168 | 2.69 |
| 2-169 | 20.26 |
| 2-170 | 82.88 |
| 2-158 | 2.72 |
| 2-172 | 1.95 |
| 2 173 | 2.57 |
| 2-174 | 93.99 |
| 2-175 | 9.31 |
| 2-176 | 53.24 |
| 2-177 | 77.18 |
| 2-178 | 2.3 |
| 2-179 | 87.22 |
| 2-180 | 26.8 |
| 2-181 | 49.59 |
| 2-182 | 24.98 |
| 2-183 | 3.5 |
| 2-184 | 21.67 |
| 2-185 | 114.15 |
| 2-186 | 101.14 |
| 2-187 | 112.41 |
| 2-188 | 131.48 |
| 2-189 | 3.86 |
| 2-190 | 52.24 |
| 2-191 | 1.59 |
| 2-192 | 2.52 |
| 2-193 | 5.03 |
| 2-194 | 11.44 |
| 2-195 | 1.91 |
| 2-196 | 1.97 |
| 2-197 | 101.95 |
| 2-198 | 13.6 |
| 2-199 | 1.98 |
| 2-200 | 1.84 |
| 2-201 | 0.92 |
| 2-202 | 2.62 |
| 2-204 | 5.75 |
| 2 206 | 64.41 |

Example 64

Stability of Compounds in Aqueous Solution

Compounds disclosed herein have desirable stability properties when measured in aqueous solution. For example, in phosphate buffered saline solution both diastereoisomers of Compound No. 11 have half-lives >3600 min.

To measure chemical stability in aqueous solution, the half-life ($t_{1/2}$), or time needed for the concentration to decrease by half, was determined for select compounds in phosphate buffered saline solution. Compounds were dissolved in a solution containing 10 mM phosphate buffer (pH 7.5) and 5% of $D_2O$ to a final concentration of ~1 mM. All spectra were obtained at 37° C. on a Bruker Avance 600 NMR spectrometer equipped with an inverse broad-band probe with z-gradients. Data were obtained every 15 min for a total time period of 4 h or longer, according to the observed stability. $^{31}$P NMR was performed at 242.55 MHz, with gated decoupling of the protons. An observation frequency range of 14619.9 Hz and 32 K complex data points were used for acquisition. A pulse angle of 90° and a 4-sec pulse cycle were utilized. Thirty-two accumulations were obtained before Fourier transformation of the free induction decay. $^1$H NMR spectra were acquired using the 1DNOESY experiment with water presaturation for better solvent suppression. An observation frequency range of 12019.23 Hz, a 10-sec pulse cycle, and 32 K complex data points were used for acquisition. Sixty-four scans were added prior to Fourier transformation. Integral data were obtained using the TopSpin software.

Stability was determined based on analysis of disappearance of the compounds as a function of incubation time. Quantification of test compounds was measured as a peak area relative to an internal standard. The elimination constant, k, was calculated by plotting mean disappearance values on a semi-logarithmic scale and fitting with a best fit linear regression. The half-life ($t_{1/2}$) expressed in hours was derived using Equation 1:

$$t_{1/2} = \ln 2/(-k).$$  Equation 1:

Table 6 summarizes chemical stability data for some exemplary compounds.

TABLE 6

Chemical stabilities as measured by half-lives in phosphate buffered saline solutions for compounds of Formula I.

| | $t_{1/2}$ (h) | |
|---|---|---|
| Compound | Diastereoisomer A[a] | Diastereoisomer B[a] |
| 109 | 48 | 15.4 |
| 64 | 87 | 13 |
| 50[b] | >80 | |
| 3 | >80 | >80 |
| 5 | 40 | 40 |
| 108[c] | >100 | |
| 52 | 23.5 | 5.1 |
| 53 | >80 | >80 |
| 7[b] | >>40 | |
| 114 | >>40 | >>40 |
| 115[b] | >60 | |
| 55[c] | | >60 |
| 56[b] | 4.6 | |
| 116 | >>40 | >>40 |
| 58[b] | >80 | |
| 11 | >100 | >60 |
| 65 | 40.5 | 7.2 |
| 59 | 80 | 6 |

TABLE 6-continued

Chemical stabilities as measured by half-lives in phosphate buffered saline solutions for compounds of Formula I.

| | $t_{1/2}$ (h) | |
|---|---|---|
| Compound | Diastereoisomer A[a] | Diastereoisomer B[a] |
| 16 | >80 | >80 |
| 132 | 4.8 | 3.6 |
| 19 | 4.7 | 3.7 |
| 20 | >80 | >80 |

[a]In all cases, "Diastereoisomer A" refers to the upfield shift in the $^{31}$P NMR.
[b]Only one diastereoisomer present in the sample analyzed.
[c]Not chiral at phosphorous.

Example 65

Stability of Compounds in Plasma

Compounds disclosed herein have desirable stability properties in plasma.

Compounds and positive control samples were dissolved in 100% DMSO at 3 mM. To investigate the stability of the test compounds in plasma, samples were made by diluting test compounds into plasma from the stock solutions to obtain a test compound concentration of 3 μM (0.1% DMSO). Before addition of a test compound, 990 μl of plasma were preincubated at 37° C. for 5 min in eppendorf. After addition of a test compound, 70 μl for each time point were transferred to a 96-deepwell plate, previously warmed at 37° C. in a DUBNOFF water bath. Each compound was tested at five time points, in duplicate (10, 20, 30, 40 and 60 min). At each time point, an aliquot of 50 μl was taken and transferred to a new 96-deepwell plate, and the reaction was stopped with 200 μl of 100% acetonitrile containing 0.1% formic acid and the appropriate internal standard. Then samples were centrifuged at 1100×g for 30 min at +4° C. and supernatants were transferred to a new 96-deepwell plate. Samples were evaporated under N$_2$ and reconstituted in H$_2$O/ACN 0.1% Formic Acid (98:2). Analysis was performed without a calibration curve (Acquity UPLC-Waters; SciexAPI4000). Time 0 was obtained by adding acetonitrile before addition of the test compound. Stability was determined based on analysis of disappearance of the compounds as a function of incubation time. Quantification of test compounds was measured as a peak area relative to an internal standard. The elimination constant k was calculated by plotting mean disappearance values on a semi-logarithmic scale and fitting with a best fit linear regression. The half-life ($t_{1/2}$) expressed in hours was derived using Equation 1 as shown in Example 64. For those compounds for which half-life could not be calculated, data are reported as: <0.16 or >1. Stability data for compounds in mouse and human plasma are shown in Table 7.

TABLE 7

Stability as measured by half-life ($t_{1/2}$) in mouse and human plasma for compounds of Formula I.

| | $t_{1/2}$, Mouse Plasma (h) | | $t_{1/2}$, Human Plasma (h) | |
|---|---|---|---|---|
| Compound | Diastereoisomer A[b] | Diastereoisomer B[a] | Diastereoisomer A[b] | Diastereoisomer B[a] |
| 109 | <0.16 | NA | >1 | NA |
| 1 | <0.16 | <0.16 | >1 | >1 |
| 64 | <0.16 | <0.16 | <0.16 | <0.16 |
| 2 | <0.16 | <0.16 | 0.95 | 0.9 |
| 3 | <0.16 | <0.16 | >1 | >1 |
| 4 | <0.16 | NA | >1 | NA |
| 5 | <0.16 | <0.16 | >1 | >1 |

TABLE 7-continued

Stability as measured by half-life ($t_{1/2}$) in mouse and human plasma for compounds of Formula I.

| | $t_{1/2}$, Mouse Plasma (h) | | $t_{1/2}$, Human Plasma (h) | |
|---|---|---|---|---|
| Compound | Diastereoisomer A[b] | Diastereoisomer B[a] | Diastereoisomer A[b] | Diastereoisomer B[a] |
| 52 | <0.16 | <0.16 | >1 | >1 |
| 117 | <0.16 | <0.16 | >1 | >1 |
| 65 | <0.16 | <0.16 | >1 | <0.16 |
| 118 | <0.16 | <0.16 | >1 | >1 |
| 13 | <0.16 | <0.16 | >1 | >1 |
| 14 | <0.16 | <0.16 | >1 | >1 |
| 125 | <0.16 | NA | >1 | NA |
| 126 | <0.16 | <0.16 | >1 | >1 |
| 129 | <0.16 | <0.16 | >1 | >1 |
| 15 | <0.16 | <0.16 | >1 | >1 |
| 61 | <0.16 | <0.16 | >1 | >1 |
| 67 | <0.16 | <0.16 | >1 | <0.16 |
| 16 | <0.16 | <0.16 | >1 | >1 |
| 19 | <0.16 | <0.16 | 0.45 | >1 |
| 20 | <0.16 | <0.16 | 0.74 | >1 |
| 23 | <0.16 | <0.16 | <0.16 | 0.96 |
| 24 | <0.16 | <0.16 | 0.26 | 0.82 |
| 25 | <0.16 | NA | >1 | NA |
| 69 | <0.16 | <0.16 | >1 | <0.16 |
| 26 | <0.16 | <0.16 | >1 | >1 |
| 27 | <0.16 | NA | >1 | NA |
| 70 | <0.16 | <0.16 | <0.16 | <0.16 |
| 28 | <0.16 | <0.16 | >1 | 0.65 |
| 71 | <0.16 | <0.16 | >1 | <0.16 |
| 29 | <0.16 | <0.16 | >1 | >1 |
| 72 | <0.16 | <0.16 | <0.16 | <0.16 |
| 73 | <0.16 | <0.16 | <0.23 | <0.16 |
| 74 | <0.16 | <0.16 | 0.78 | <0.16 |
| 75 | <0.16 | <0.16 | >1 | <0.16 |
| 76 | <0.16 | <0.16 | <0.16 | <0.16 |
| 78 | <0.16 | <0.16 | >1 | <0.16 |
| 79 | <0.16 | <0.16 | >1 | <0.16 |
| 80 | <0.16 | NA | 0.67 | NA |
| 82 | <0.16 | NA | 0.48 | NA |
| 30 | <0.16 | <0.16 | 0.83 | >1 |
| 31 | <0.16 | <0.16 | >1 | >1 |
| 83 | <0.16 | <0.16 | >1 | <0.16 |
| 84 | <0.16 | <0.16 | >1 | 0.96 |
| 85 | <0.16 | <0.16 | <0.16 | <0.16 |
| 86 | <0.16 | <0.16 | <0.16 | <0.16 |
| 32 | <0.16 | <0.16 | >1 | >1 |
| 88 | <0.16 | <0.16 | 0.71 | 0.36 |
| 89 | <0.16 | NA | <0.16 | NA |
| 90 | <0.16 | NA | 0.76 | NA |
| 91 | 0.51 | NA | >1 | NA |
| 92 | <0.16 | NA | 0.45 | NA |
| 93 | <.0.16 | NA | >1 | NA |
| 94 | <0.16 | <0.16 | 0.68 | <0.16 |
| 95 | <0.16 | <0.16 | >1 | <0.16 |
| 96 | <0.16 | NA | 0.28 | NA |
| 97 | <0.16 | NA | <0.16 | NA |
| 98 | <0.16 | <0.16 | >1 | 0.3 |
| 33 | <0.16 | <0.16 | >1 | >1 |
| 99 | | | 0.66 | NA |
| 34 | | | >1 | >1 |
| 35 | | | >1 | 0.89 |
| 36 | | | >1 | >1 |
| 37 | | | >1 | >1 |
| 38 | | | >1 | >1 |
| 39 | <0.16 | <0.16 | >1 | >1 |
| 40 | <0.16 | <0.16 | >1 | >1 |
| 41 | 0.2 | NA | >1 | NA |
| 42 | <0.16 | NA | >1 | NA |
| 43 | <0.16 | NA | >1 | NA |
| 44 | | | >1 | NA |
| 45 | | | >1 | NA |
| 46 | | | 0.95 | NA |
| 47 | | | >1 | NA |
| 48 | | | >1 | NA |
| 49 | | | >1 | NA |
| 103 | | | <0.16 | <0.16 |
| 108 | | | 0.83 | NA |

TABLE 7-continued

Stability as measured by half-life ($t_{1/2}$) in mouse and human plasma for compounds of Formula I.

| | $t_{1/2}$, Mouse Plasma (h) | | $t_{1/2}$, Human Plasma (h) | |
|---|---|---|---|---|
| Compound | Diastereoisomer A[b] | Diastereoisomer B[a] | Diastereoisomer A[b] | Diastereoisomer B[a] |
| 1-54 | | | <0.16 | <0.16 |
| 1-55 | | | >1 | >1 |
| 2-113 | <0.16 | NA | 0.56 | NA |

[a]"NA" means not applicable (i.e., only one diastereoisomer tested).
[b]In all cases, "Diastereoisomer A" refers to the upfield shift in the $^{31}$P NMR.

Example 66

Stability of Compounds in Hepatocytes

Stability in hepatocytes for select compounds disclosed in the application was evaluated in two species (mouse and human) according to the following procedure. Compounds and positive control samples were dissolved in 100% DMSO at 5 mM. Cryopreserved hepatocytes were thawed and resuspended in Hepatocyte Basal Medium (HBM-Lonza CC-3199) supplemented with CC-4182 (complete hepatocyte culture medium). Test compounds were diluted into cell suspension (1 million cells/ml) from the stock solutions to have a test compound concentration of 5 µM (0.1% DMSO). Incubation was performed in 24-well plates, at 37° C. in a DUBNOFF water bath, under low shaking. Each compound was tested at 6 time points, in duplicates (0, 15, 30, 60, 120 and 240 min). At each time point, an aliquot of 120 µl was taken and transferred to a 96-well deep plate. The reaction was stopped with the addition of one volume of 100% acetonitrile plus 0.1% formic acid and the appropriate internal standard. Then samples were centrifuged at 1100×g for 30 min at +4° C. and supernatants were transferred to a new 96-deepwell plate. Samples were evaporated under $N_2$ and reconstituted in $H_2O$/ACN 0.1% Formic Acid (98:2). Analysis was performed without a calibration curve (Acquity UPLC-Waters; Sciex API4000). Time 0 was obtained adding acetonitrile before addition of the test compound. Stability was determined based on analysis of disappearance of the compounds as a function of incubation time. Quantification of test compounds was measured as a peak area relative to an internal standard. The elimination constant, k, is calculated by plotting mean disappearance values on a semi-logarithmic scale and fitting with a best fit linear regression. The half-life ($t_{1/2}$) expressed in hours is derived using Equation 1 as shown in Example 64. For those compounds for which half-life could not be calculated, data are reported as: <0.25 or >4. Stability data for compounds in hepatocytes are shown in Table 8.

TABLE 8

Stability as measured by half-life ($t_{1/2}$) in mouse and human hesatoc tes for compounds of Formula I.

| | $t_{1/2}$, Mouse Hepatocytes (h) | | $t_{1/2}$, Human Hepatocytes (h) | |
|---|---|---|---|---|
| Compound | Diastereoisomer A[b] | Diastereoisomer B[a] | Diastereoisomer A[b] | Diastereoisomer B[a] |
| 109 | 3.39 | NA | >4 | NA |
| 1 | 0.43 | <0.25 | 1.29 | 1.31 |
| 64 | <0.25 | <0.25 | <0.25 | <0.25 |
| 2 | 0.39 | 0.44 | <0.25 | <0.25 |
| 3 | <0.25 | <0.25 | <0.25 | <0.25 |
| 4 | 0.58 | NA | 0.44 | NA |
| 5 | 0.38 | 0.3 | 2.65 | 1 |
| 111 | 0.48 | NA | 2.85 | NA |
| 53 | 0.28 | <0.25 | 0.57 | <0.25 |
| 54 | <0.25 | NA | <0.25 | NA |
| 10 | <0.25 | <0.25 | <0.25 | <0.25 |
| 115 | <0.25 | NA | 0.64 | NA |
| 56 | <0.25 | NA | <0.25 | NA |
| 117 | <0.25 | <0.25 | 0.31 | <0.25 |
| 11 | <0.25 | <0.25 | 0.46 | <0.25 |
| 65 | <0.25 | <0.25 | <0.25 | <0.25 |
| 59 | 0.34 | <0.25 | 2.89 | 1.54 |
| 118 | <0.25 | <0.25 | 0.43 | <0.25 |
| 13 | 0.47 | 0.4 | 0.53 | <0.25 |
| 14 | <0.25 | <0.25 | 0.29 | <0.25 |
| 15 | <0.25 | <0.25 | 0.31 | <0.25 |
| 67 | <0.25 | <0.25 | <0.25 | <0.25 |
| 68 | <0.25 | <0.25 | <0.25 | <0.25 |
| 16 | 0.72 | 0.26 | >4 | 1.34 |
| 132 | 0.91 | NA | 2.39 | NA |
| 19 | 0.37 | 0.31 | 1.26 | 1.16 |
| 20 | <0.25 | <0.25 | 2.36 | 1.09 |
| 21 | <0.25 | <0.25 | 1.18 | 0.67 |
| 22 | 0.62 | NA | >4 | NA |
| 23 | 1.18 | 0.55 | >4 | >4 |
| 24 | <0.25 | <0.25 | >4 | 3.18 |
| 25 | 0.6 | NA | >4 | NA |

TABLE 8-continued

Stability as measured by half-life ($t_{1/2}$) in mouse and human hepatocytes for compounds of Formula I.

| | $t_{1/2}$, Mouse Hepatocytes (h) | | $t_{1/2}$, Human Hepatocytes (h) | |
|---|---|---|---|---|
| Compound | Diastereoisomer A[b] | Diastereoisomer B[a] | Diastereoisomer A[b] | Diastereoisomer B[a] |
| 69 | <0.25 | <0.25 | <0.25 | <0.25 |
| 26 | <0.25 | <0.25 | 0.31 | <0.25 |
| 71 | <0.25 | <0.25 | <0.25 | <0.25 |
| 29 | <0.25 | <0.25 | 0.6 | 0.26 |
| 76 | <0.25 | <0.25 | 0.52 | <0.25 |
| 78 | <0.25 | <0.25 | 0.44 | 0.33 |
| 84 | <0.25 | <0.25 | <0.25 | <0.25 |
| 89 | <0.25 | NA | <0.25 | NA |
| 90 | <0.25 | NA | <0.25 | NA |
| 91 | 0.3 | NA | 1.12 | NA |
| 98 | <0.25 | <0.25 | <0.25 | <0.25 |
| 108 | 0.25 | NA | 0.25 | NA |
| 2-127 | <0.25 | NA | 0.29 | NA |
| 2-129 | | <0.25 | | <0.25 |
| 2-133 | <0.25 | <0.25 | <0.25 | <0.25 |
| 2-138 | | | >4 | NA |
| 2-139 | | | 0.51 | 0.26 |
| 2-140 | | | <0.25 | <0.25 |
| 2-118 | | | 0.55 | 0.6 |
| 2-119 | | | 0.51 | NA |
| 2-143 | | | 0.42 | 0.32 |
| 2-160 | <0.25 | NA | 0.61 | NA |
| 2-161 | <0.25 | NA | 0.43 | NA |

[a]"NA" means not applicable (i.e., only one diastereoisomer tested).
[b]In all cases, "Diastereoisomer A" refers to the upfield shift in the $^{31}$P NMR.

Example 67

Permeability in a Porcine Brain Endothelial Cell Model

Compounds disclosed herein show the potential to reach mammalian brain by crossing the blood-brain barrier (BBB) from systemic circulation. Both diastereoisomers of selected exemplary compounds of the invention exhibit permeability in a porcine brain endothelial cell (PBEC) model of the mammalian BBB, as summarized in Table 9. The porcine brain endothelial cell permeability assay is an in vitro BBB model to be used for the prediction of central nervous system (CNS) drug permeability in vivo and for ranking or prioritization of compounds according to their permeability. This system can also be used for mechanistic studies and drug delivery strategies via receptor-mediated transport (transcytosis). The system is a two-dimensional co-culture, non-contact model of two types of primary cells: primary brain endothelial cells obtained from fresh porcine brains, and primary rat astrocytes, obtained from neonatal rats. This ensures barrier formation and functional expression of key transporters.

The endothelial cells were cultured on rat-tail collagen type I and human fibronectin coated Transwell polycarbonate inserts (surface area 0.7 cm$^2$; pore size 0.4 µm) and the inserts were placed in 24-well plates containing confluent rat astrocytes. This system allows for the formation of a differentiated BBB model suitable for compound permeability in 10 days.

On the day of the experiment, culture medium was removed and cells were pre-incubated for 30 min with HBSS containing 20 mM Hepes pH 7.4 and 0.1% BSA. Donor volume (apical) was 400 µl and receiver volume (basal) 900 µl. Compounds were diluted in assay medium (at the desired concentration) and added to the luminal side (to mimic blood to brain passage). Transport was measured usually after 60 min by detecting the amount of compound from the basal (brain side). The integrity of the cell layers was assessed by measuring the transendothelial electrical resistance (TEER) and by monitoring FITC-dextran (40 KDa) permeation. Inserts with TEER values >500 Ω/cm$^2$ were selected for permeability studies. As FITC-dextran cannot freely permeate lipophilic barriers, a high degree of FITC-dextran transport indicates poor integrity of the cell layer and wells with high FITC-dextran permeability were excluded. FITC-dextran was included as internal control in each insert used for permeability studies. Fluorescence was measured using a fluorimetric detector. Radioactivity was measured by scintillation counting. For LC-MS/MS analysis, aliquots (200 µl) from the basal compartment were diluted with an equal volume of 100% acetonitrile containing 0.1% formic acid, centrifuged to remove cell debris, and evaporated under N$_2$. After reconstitution, samples were analyzed by LC-MS/MS. Mass balance was determined considering the amount of compound recovered in the donor and receiver chamber at the end of the assay relative to the amount added to the donor chamber at time 0.

Permeability was defined as the apparent permeability coefficient ($P_{app}$), which is a measure of the appearance rate of the compound in the receiver chamber, expressed in cm/s. $P_{app}$ is calculated according the following equation:

$$P_{app}[\text{cm/sec}] = V_d * \Delta M_r / A * M_d * \Delta t, \quad \text{Equation 2:}$$

where
$V_d$=volume in the donor compartment in cm$^3$ or mL;
$\Delta M_r$=total amount of compound in the receiver compartment after t seconds;
$M_d$=donor amount (added at time 0)
$\Delta t$=time measured in seconds
A=filter area in cm$^2$ (for 24 well plate, A=0.7 cm$^2$).

To correct for the contribution of filter and substrate, $P_{app}$ was also determined for the cell-free system. Permeability of the endothelial cell layer was determined using the following equation:

$$1/P_e = 1/(P_{total} - (1/P_f)), \quad \text{Equation 3:}$$

where $P_{total}$=the P of the total system, $P_f$=P for the cell-free filter, and $P_e$=P for the endothelial cell layer alone. In this equation, the total resistance of the system towards passage of a substance is additively composed of two parallel resistances: that of the cell monolayer and that of the filter.

TABLE 9

In vitro apparent permeability ($P_{app}$) in the blood-brain barrier model of procine brain endothelial cells, co-cultured with rat astrocytes (PBECs/As).

| | $P_{app}$ (×10$^{-6}$ cm/s) | |
|---|---|---|
| Compound | Diastereoisomer A | Diastereoisomer B |
| 109 | 5.26 | |
| 64 | 16.04 | 20.66 |
| 2 | 3.35 | 2.61 |
| 3 | 9.99 | 8.47 |
| 5 | 6.27 | 5.06 |
| 111 | 0.7 | |
| 54 | 18.07 | |
| 10 | 10.12 | 14.04 |
| 115 | 4.03 | |
| 56 | 18.66 | |
| 117 | 1.95 | 2.9 |
| 11 | 3.52 | 3.12 |
| 65 | 20.27 | 18.33 |
| 16 | 3.33 | 4.35 |
| 20 | 4.79 | 3.38 |
| 24 | 0.54 | 0.6 |
| 69 | 22.78 | 29.91 |
| 70 | 1.58 | 2.56 |
| 91 | 0.45 | |
| 108 | 0.58 | |
| 2-126 | 2.74 | |
| 2-127 | 11.79 | |
| 2-129 | | 11.46 |
| 2-130 | 1.84 | |
| 2-133 | 21.12 | 20.97 |
| 2-138 | 15.55 | |
| 84 | 10.11 | 14.51 |

All of the U.S. patents, U.S. patent application publications, U.S. patent applications, foreign patents, foreign patent applications, and non-patent publications referred to in this specification or listed in the Application Data Sheet, including but not limited to U.S. Provisional Patent Application No. 62/264,735, filed Dec. 8, 2015, are incorporated herein by reference, in their entirety. Aspects of the embodiments can be modified, if necessary to employ concepts of the various patents, applications, and publications to provide yet further embodiments.

While specific embodiments of the invention have been illustrated and described, it will be readily appreciated that the various embodiments described above can be combined to provide further embodiments, and that various changes can be made therein without departing from the spirit and scope of the invention. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound having the following structure (I):

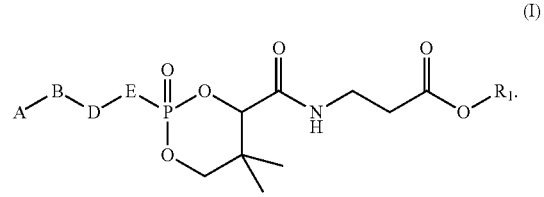

or a pharmaceutically acceptable salt thereof, wherein:

E is O;

D is absent, aryl, $C_1$-$C_3$ alkylene, $C_1$-$C_3$ alkylene substituted with $R_3$, C(O)O(alkylene) or C(O)O(alkylene) substituted with $R_3$;

B is absent, $C_1$-$C_3$ alkylene, $C_3$-$C_6$ cycloalkylene, ($C_1$-$C_3$ alkylene)$NR_2$, C(O)$NR_2$(alkylene), aryl, heteroaryl or heterocyclyl, wherein each of said $C_1$-$C_3$ alkylene, $C_3$-$C_6$ cycloalkylene, ($C_1$-$C_3$ alkylene)$NR_2$, C(O)$NR_2$ (alkylene), aryl, heteroaryl and heterocyclyl is unsubstituted or substituted with $R_6$ or $R_8$;

A is absent, H, $OR_5$, $R_5C(O)$, $R_5OC(O)$, $R_5OC(O)O$, $R_5C(O)O$, $R_5C(O)S$, $NR_2R_5C(O)$, $R_5C(O)NR_2$, $R_5S(O)NR_2$, $R_5SO_2NR_2$, $NR_2R_5$, CN, $C_1$-$C_6$ alkyl, $C_3$-$C_6$ cycloalkyl, heterocyclyl or aryl, wherein each of said $C_1$-$C_6$ alkyl, $C_3$-$C_6$ cycloalkyl, heterocyclyl and aryl is unsubstituted or substituted with $R_6$;

$R_1$ is H, $C_1$-$C_6$ alkyl, aryl, arylalkyl, heteroaryl, heteroarylalkyl, heterocyclyl, heterocyclylalkyl, $C_3$-$C_6$ cycloalkyl, or cycloalkylalkyl, wherein each of said $C_1$-$C_6$ alkyl, aryl, arylalkyl, heteroaryl, heteroarylalkyl, heterocyclyl, heterocyclylalkyl, $C_3$-$C_6$ cycloalkyl, and cycloalkylalkyl is unsubstituted or substituted with $R_6$;

$R_2$ is H or $C_1$-$C_6$ alkyl;

$R_3$ is H, $C_1$-$C_6$ alkyl, hydroxy, amino, arylalkyl, heteroarylalkyl or $C_3$-$C_6$ cycloalkyl, wherein each of said $C_1$-$C_6$ alkyl, arylalkyl, heteroarylalkyl and $C_3$-$C_6$ cycloalkyl is unsubstituted or substituted with $R_4$;

$R_4$ is $C_1$-$C_6$ alkyl, $C_1$-$C_6$ alkoxy, hydroxy or amino;

$R_5$ is H, $C_1$-$C_6$ alkyl, $C_1$-$C_6$ alkoxy, aryl, arylalkyl, heteroaryl, heteroarylalkyl, heterocyclyl, heterocyclylalkyl, $C_3$-$C_6$ cycloalkyl, cycloalkylalkyl, amino, alkylamino, dialkylamino, aminoalkyl, alkylaminoalkyl or dialkylaminoalkyl, wherein each of said $C_1$-$C_6$ alkyl, $C_1$-$C_6$ alkoxy, aryl, arylalkyl, heteroaryl, heteroarylalkyl, heterocyclyl, heterocyclylalkyl, amino, alkylamino, dialkylamino, aminoalkyl, alkylaminoalkyl and dialkylaminoalkyl is unsubstituted or substituted with $R_6$ or $R_8$;

$R_6$ is $C_1$-$C_6$ alkyl, $C_1$-$C_6$ alkoxy, hydroxyl, amino, halo, oxo, CN, $NO_2$, $SF_5$, heterocyclyl, heterocyclylalkyl, aryl, arylalkyl, $C_3$-$C_6$ cycloalkyl, $C_3$-$C_4$ spiro-substituted cycloalkyl, cycloalkylalkyl, $SO_2R_7$, $R_7C(O)S$, $R_7C(O)$, $R_7C(O)NR_2$, $R_7OC(O)$ or $R_7OC(O)NR_2$, wherein each of said $C_1$-$C_6$ alkyl, $C_1$-$C_6$ alkoxy, heterocyclyl, heterocyclylalkyl, aryl, arylalkyl, $C_3$-$C_6$ cycloalkyl, $C_3$-$C_4$ spiro-substituted cycloalkyl and cycloalkylalkyl is unsubstituted or substituted with $R_7$;

$R_7$ is H, $C_1$-$C_6$ alkyl, $C_1$-$C_6$ alkoxy, hydroxyl, halo, oxo, CN, $NO_2$, $SF_5$, arylakyl, heteroarylalkyl, amino, alkylamino or dialkylamino; and $R_8$ is $R_6OC(O)$ or $R_6OC(O)NR_2$;

or

D is absent, and A, B, and E together form a 6-membered heterocyclic or heteroaryl ring, wherein said heterocyclic or heteroaryl ring is unsubstituted or substituted with $R_6$.

2. The compound according to claim 1, wherein D is absent, aryl, $C_1$-$C_3$ alkylene, C(O)O(alkylene) or $C_1$-$C_3$ alkylene substituted with $R_3$.

3. The compound according to claim 2, wherein D is aryl or C(O)O(alkylene).

4. The compound according to claim 1, wherein B is absent, $C_1$-$C_3$ alkylene, $C_1$-$C_3$ alkylene substituted with $R_6$, $C_3$-$C_6$ cycloalkylene, C(O)NR$_2$(alkylene), heterocyclyl, ($C_1$-$C_3$ alkylene)NR$_2$, ($C_1$-$C_3$ alkylene)NR$_2$ substituted with $R_8$, heteroaryl or heteroaryl substituted with $R_6$.

5. The compound according to claim 1, wherein B is $C_1$-$C_3$ alkylene, $C_1$-$C_3$ alkylene substituted with $R_6$, ($C_1$-$C_3$ alkylene)NR$_2$, ($C_1$-$C_3$ alkylene)NR$_2$ substituted with $R_8$, heteroaryl or heteroaryl substituted with $R_6$.

6. The compound according to claim 5, wherein $R_8$ is $R_6$OC(O).

7. The compound according to claim 1, wherein A is absent, H, $R_5$C(O), $R_5$C(O) substituted with $R_6$, OR$_5$, $R_5$OC(O), $R_5$OC(O)O, $R_5$C(O)O, $R_5$C(O)S, NR$_2$R$_5$C(O), $R_5$C(O)NR$_2$, $R_5$S(O)NR$_2$, $R_5$SO$_2$NR$_2$, NR$_2$R$_5$, $C_1$-$C_6$ alkyl, $C_3$-$C_6$ cycloalkyl, heterocyclyl or aryl.

8. The compound according to claim 7, wherein A is absent H, $R_5$C(O), $R_5$C(O) substituted with $R_6$, $R_5$OC(O), $R_5$OC(O)O, $R_5$C(O)O, $R_5$C(O)S or aryl.

9. The compound according to claim 8, wherein A is absent, $R_5$C(O), $R_5$C(O) substituted with $R_6$, $R_5$OC(O) or $R_5$C(O)S.

10. The compound according to claim 9, wherein $R_6$ is $C_1$-$C_6$ alkyl or $R_7$OC(O).

11. The compound according to claim 9, wherein $R_5$ is H, $C_1$-$C_6$ alkyl, aryl, arylalkyl, heteroaryl, heteroarylalkyl, heterocyclyl, heterocyclylalkyl or alkylaminoalkyl, wherein each of said $C_1$-$C_6$ alkyl, aryl, arylalkyl, heteroaryl, heteroarylalkyl, heterocyclyl, heterocyclylalkyl or alkylaminoalkyl is unsubstituted or substituted with $R_6$ or $R_8$.

12. The compound according to claim 11, wherein $R_5$ is $C_1$-$C_6$ alkyl, $C_1$-$C_6$ alkyl substituted with $R_8$, aryl, heteroaryl or alkylaminoalkyl.

13. The compound according to claim 11, wherein $R_5$ is $C_1$-$C_6$ alkyl, $C_1$-$C_6$ alkyl substituted with $R_8$ or alkylaminoalkyl.

14. The compound according to claim 1, wherein $R_6$ is $C_1$-$C_6$ alkyl, oxo, CN, amino, heterocyclylalkyl, aryl, arylalkyl, $C_3$-$C_4$ spiro-substituted cycloalkyl, SO$_2$R$_7$, R$_7$C(O) or R$_7$OC(O).

15. The compound according to claim 1, wherein:
$R_1$ is $C_1$-$C_6$ alkyl;
D is aryl;
B is $C_1$-$C_3$ alkylene substituted with $R_6$, wherein $R_6$ is amino; and
A is $R_5$OC(O), wherein $R_5$ is $C_1$-$C_6$ alkyl.

16. The compound according to claim 1, wherein:
$R_1$ is $C_1$-$C_6$ alkyl;
D is C(O)O(alkylene);
B is (a) (alkylene)NR$_2$, (b) (alkylene)NR$_2$ substituted with $R_8$, wherein $R_8$ is $R_6$OC(O) and $R_6$ is arylalkyl, or (c) heteroaryl substituted with $R_6$, wherein $R_6$ is $C_1$-$C_6$ alkyl; and
A is (a) absent, (b) $R_5$C(O), wherein $R_5$ is alkylaminoalkyl substituted with $R_6$, or (c) $R_5$C(O)S, wherein $R_5$ is $C_1$-$C_6$ alkyl.

17. The compound according to claim 1, wherein the compound is

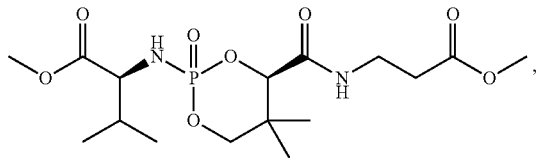,

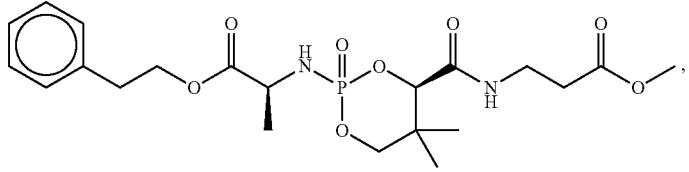,

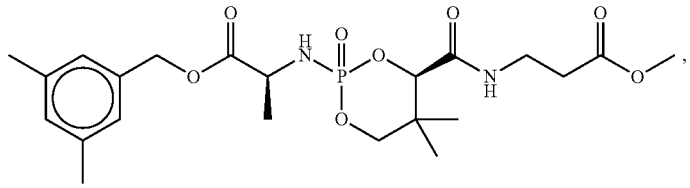,

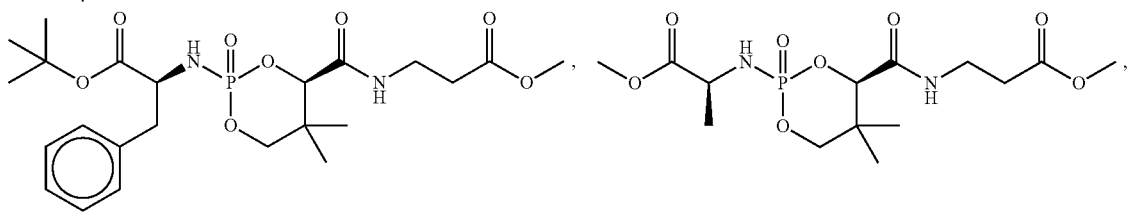

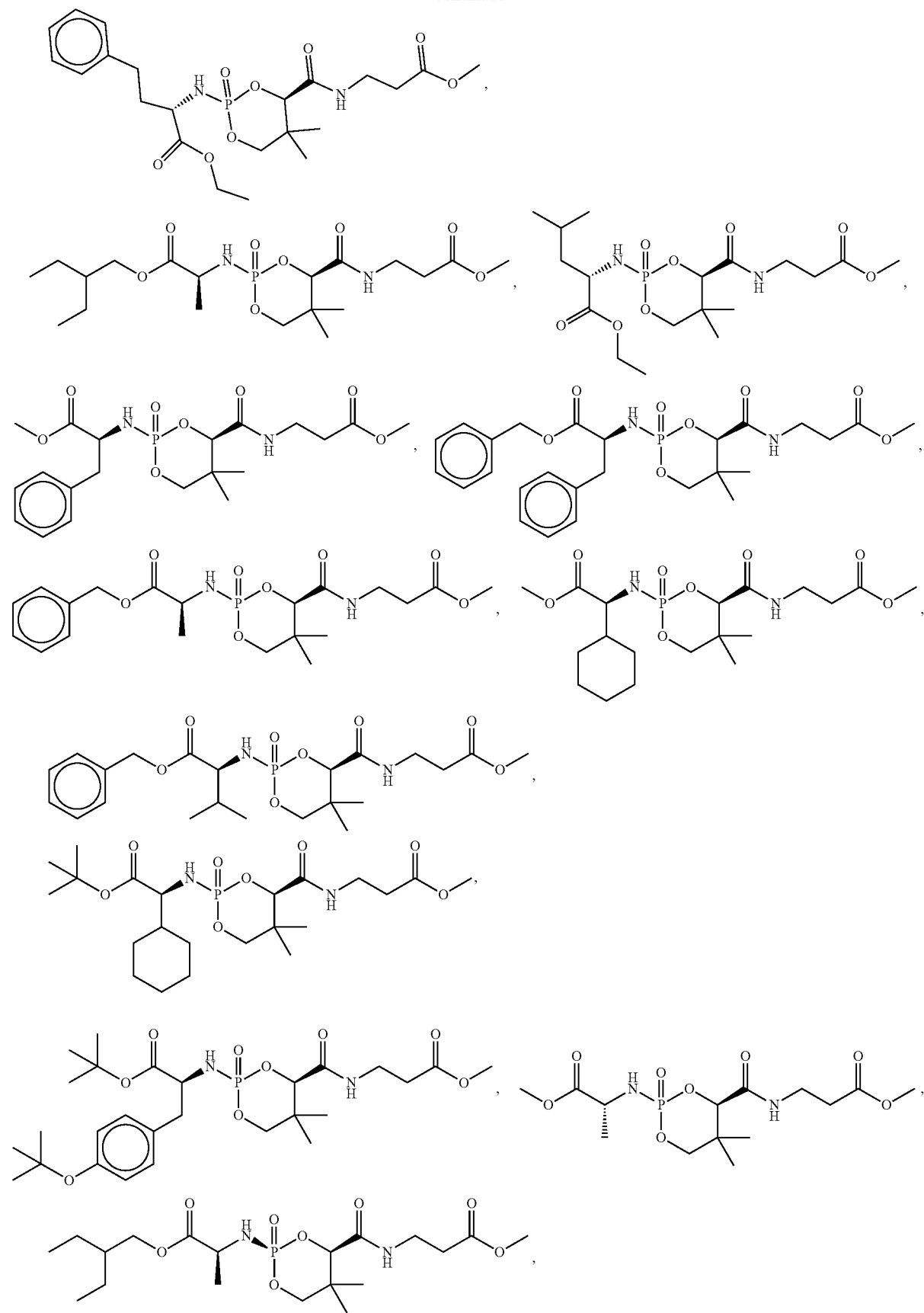

-continued
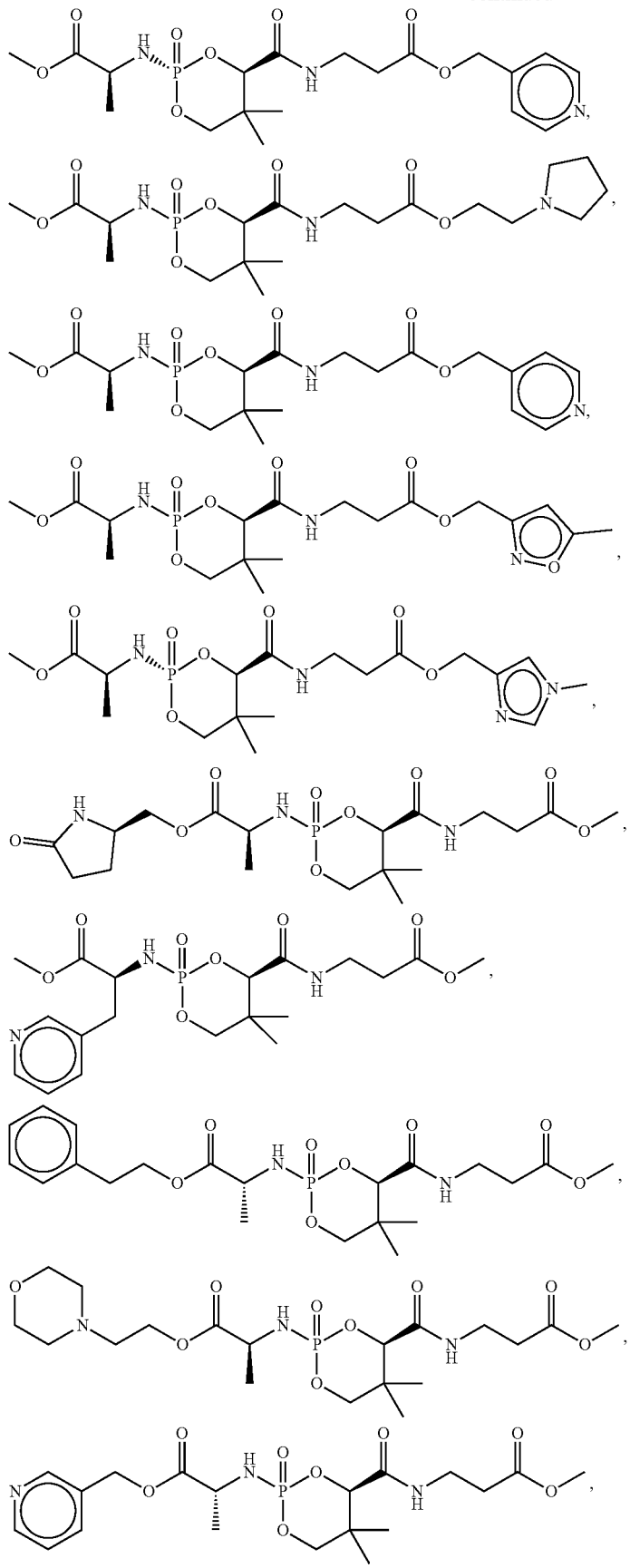

-continued
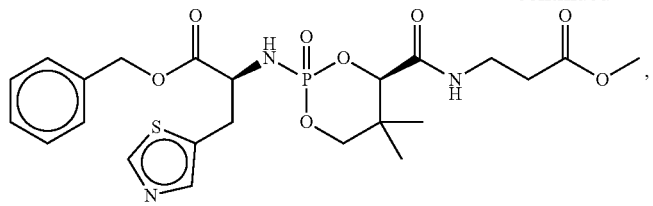
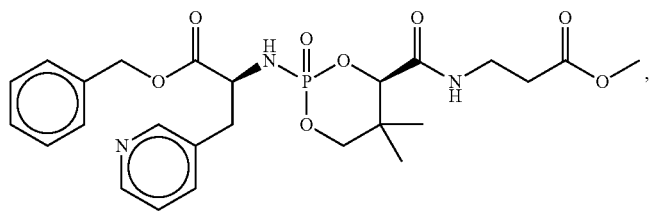
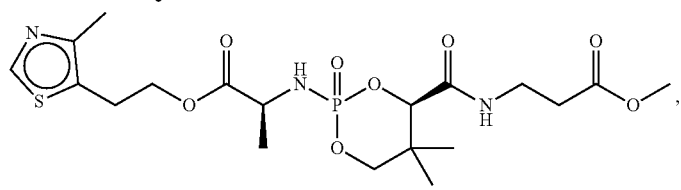
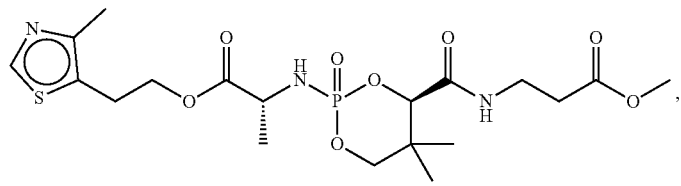
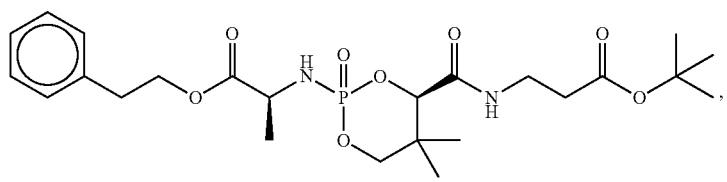
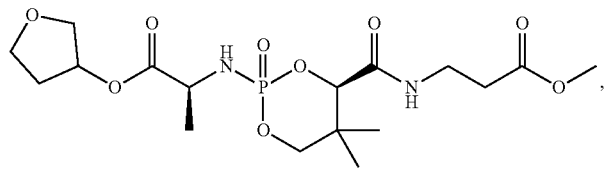
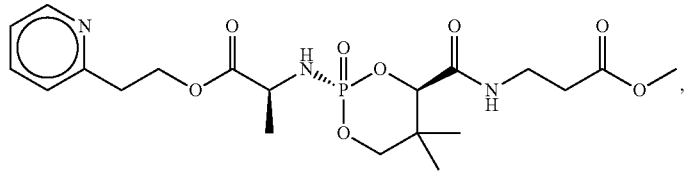
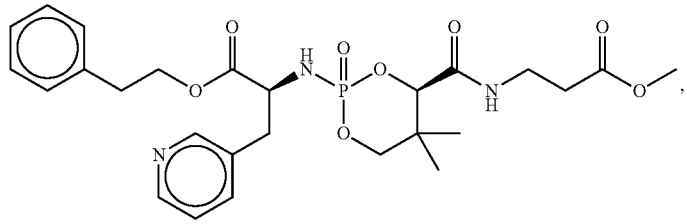
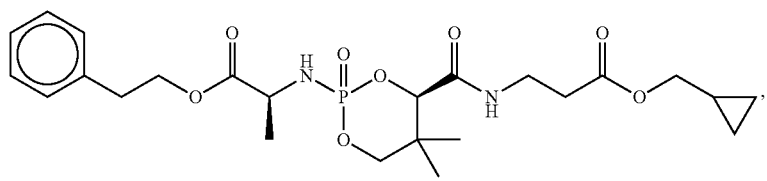

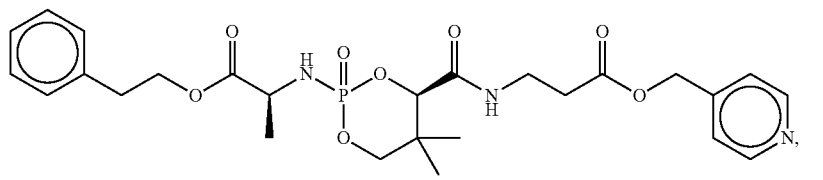
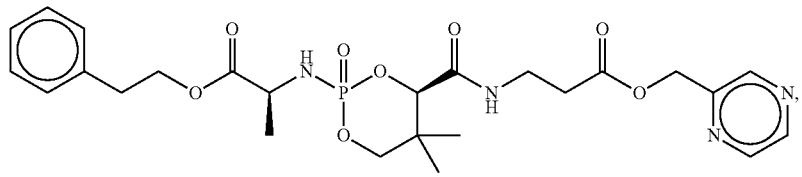
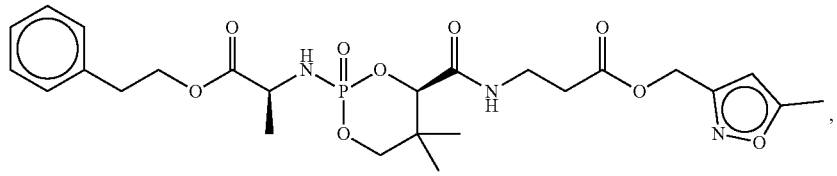
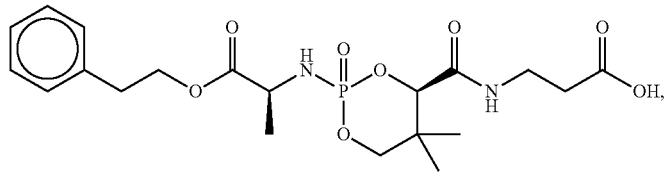
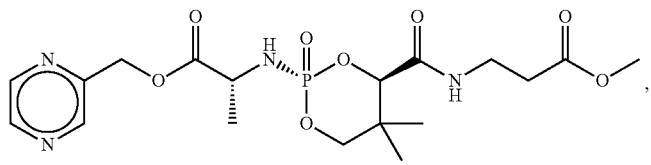
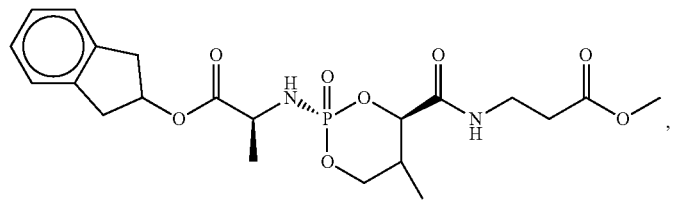
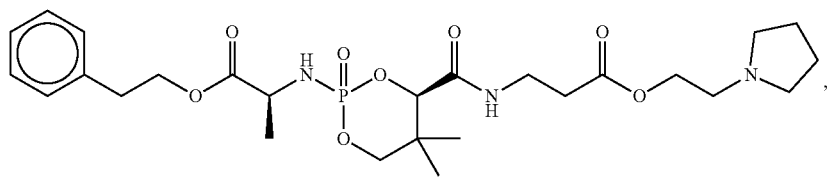
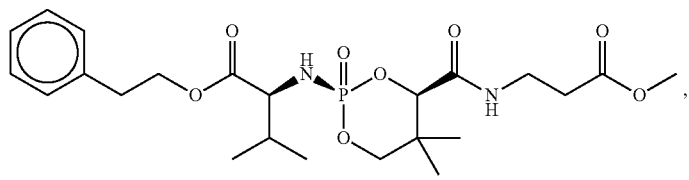
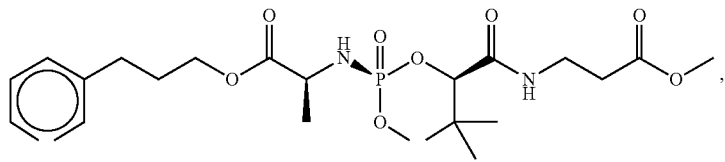

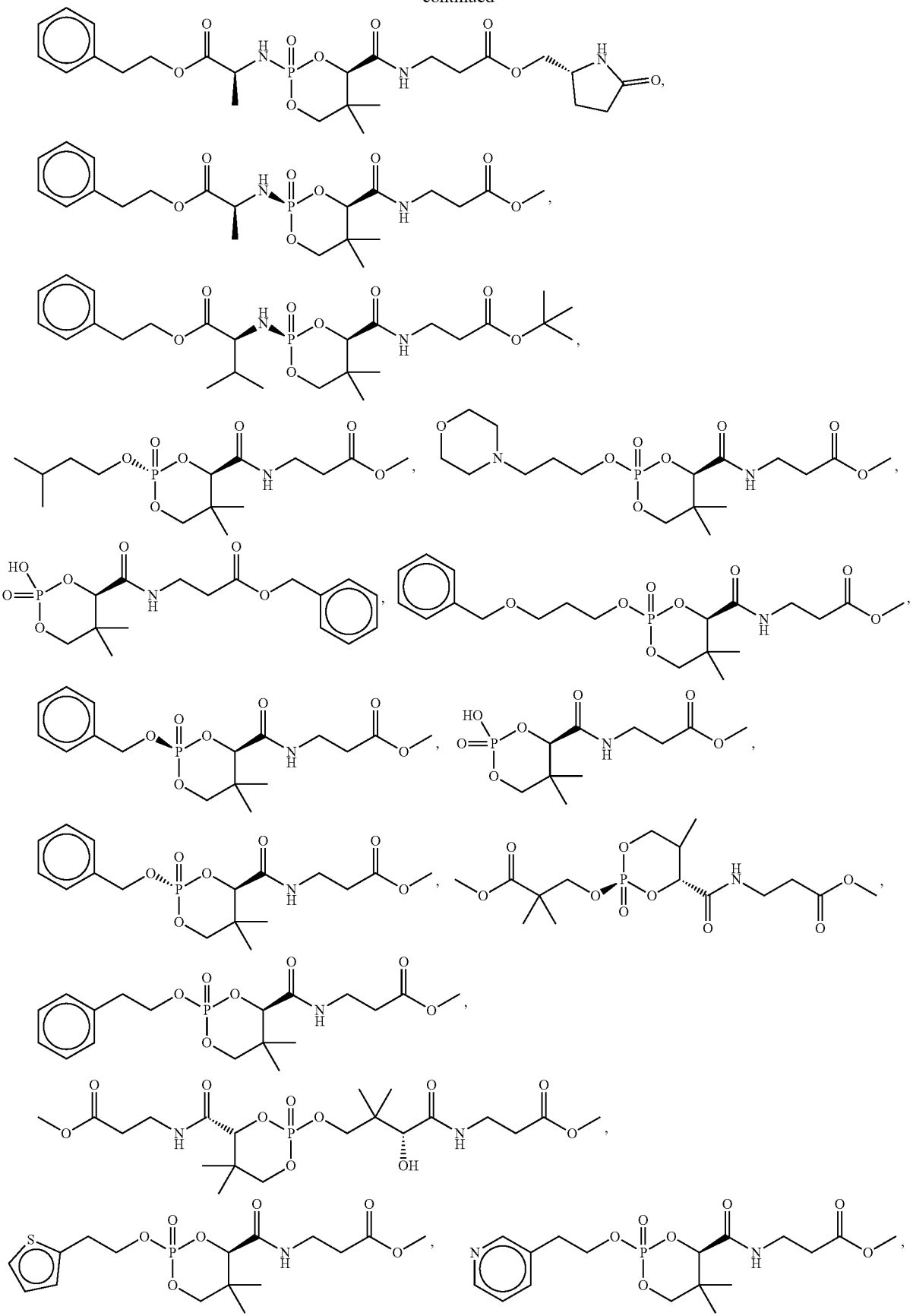

-continued
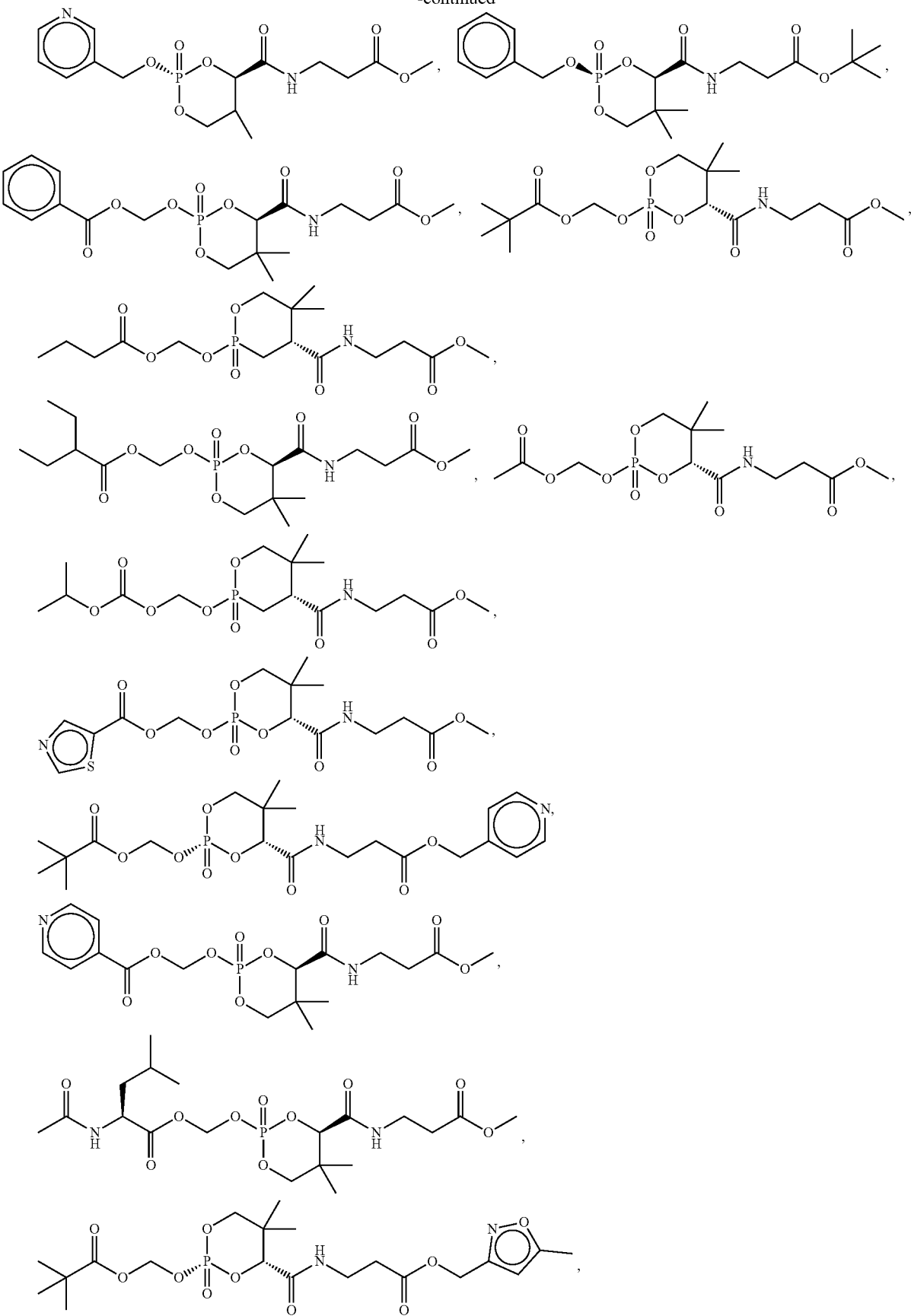

-continued
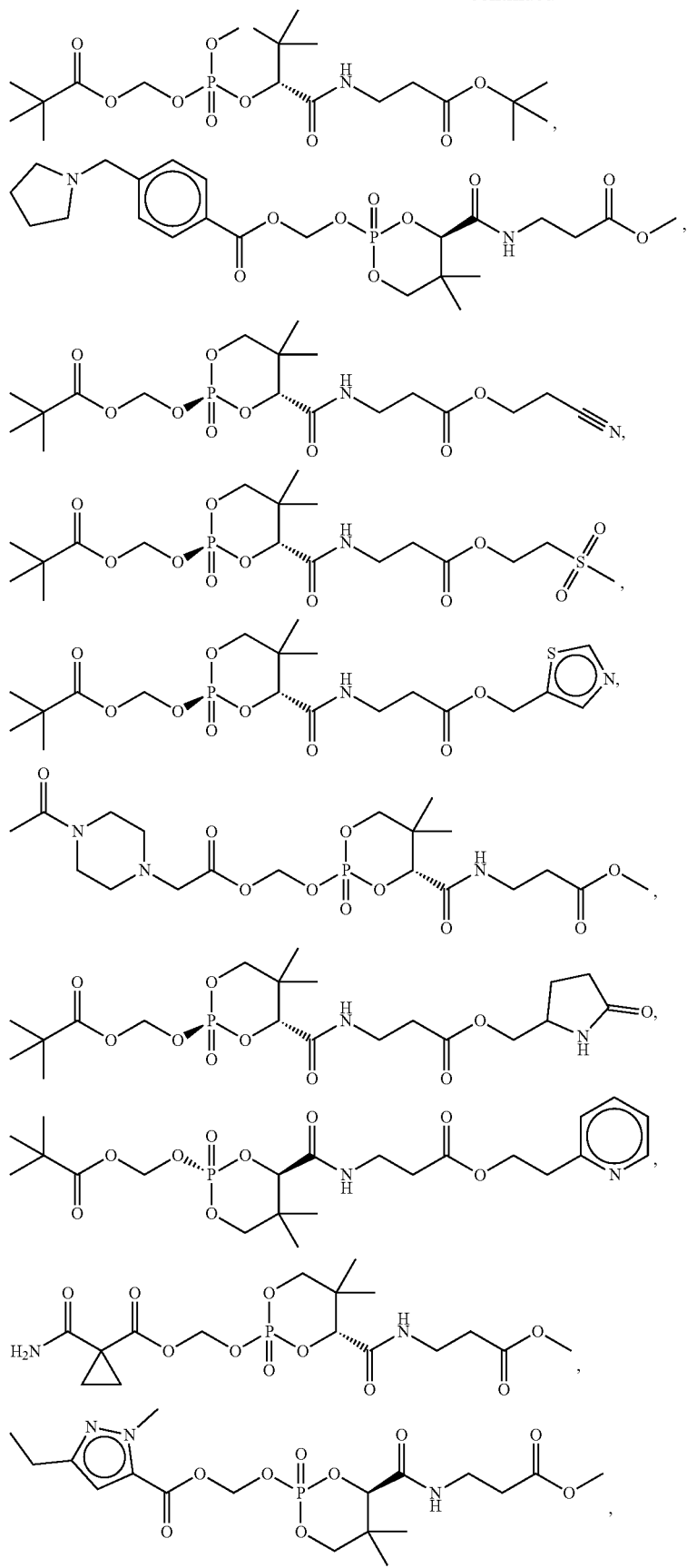

-continued
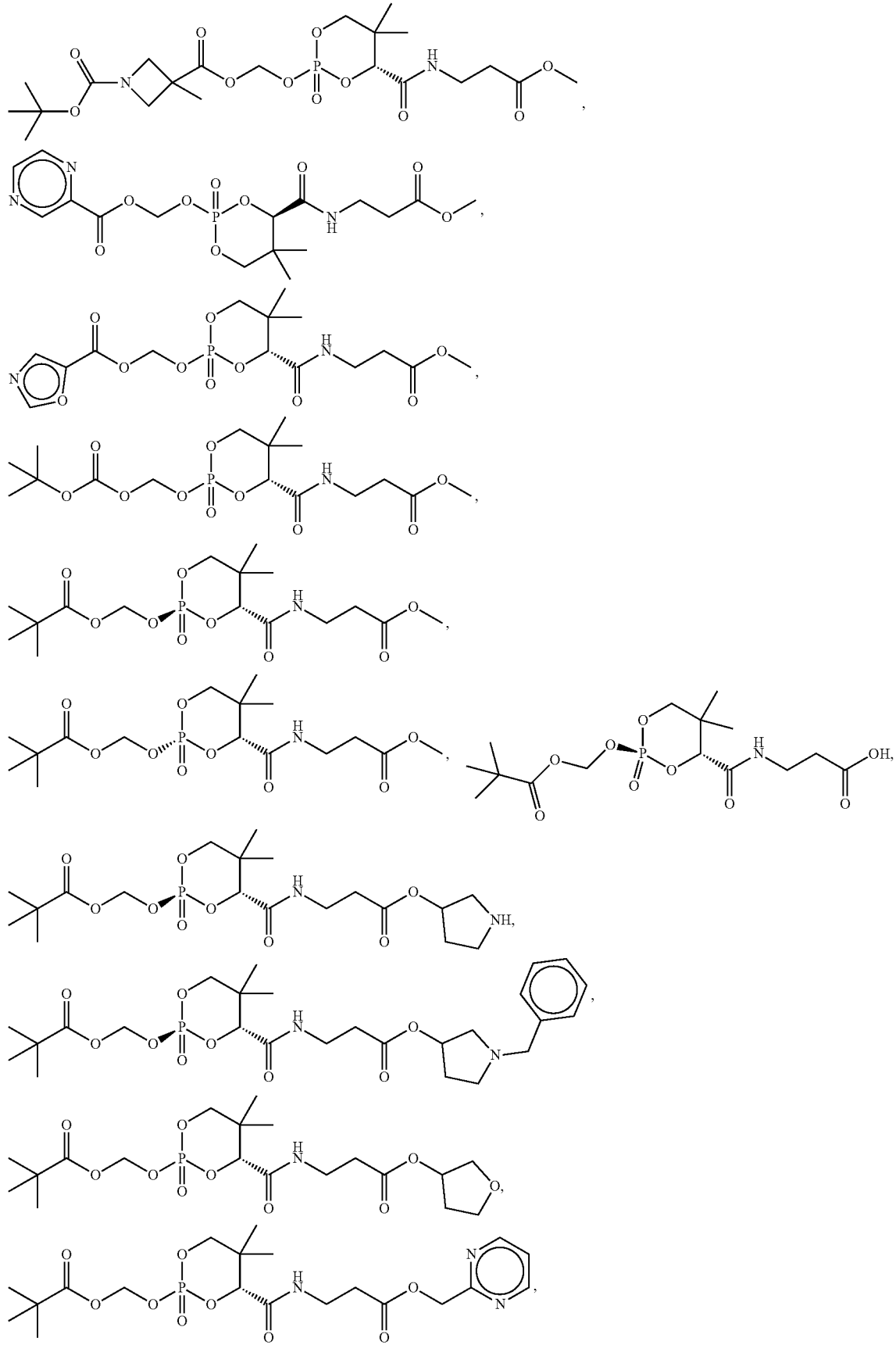

-continued
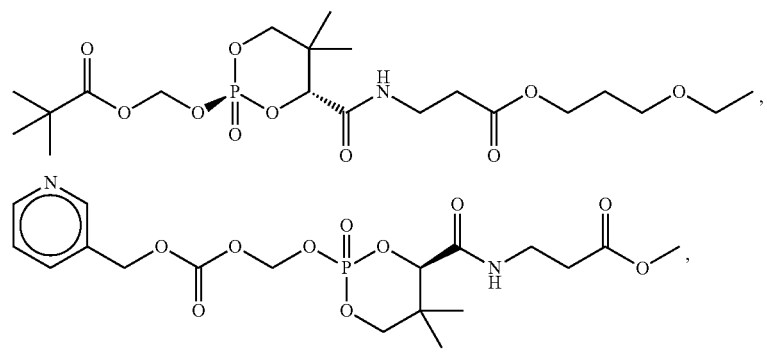
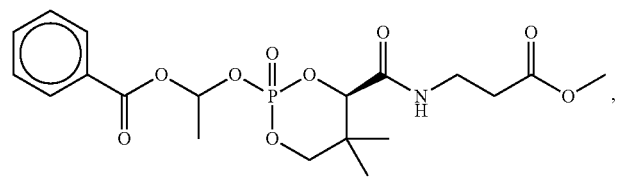
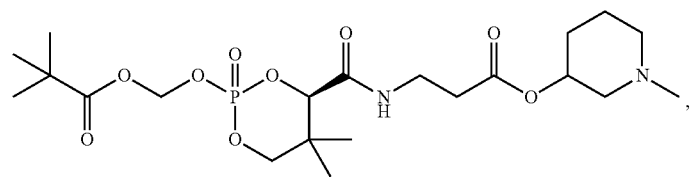
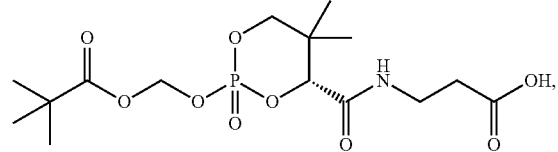
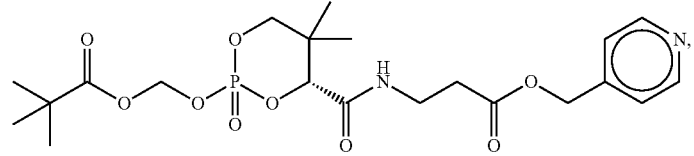
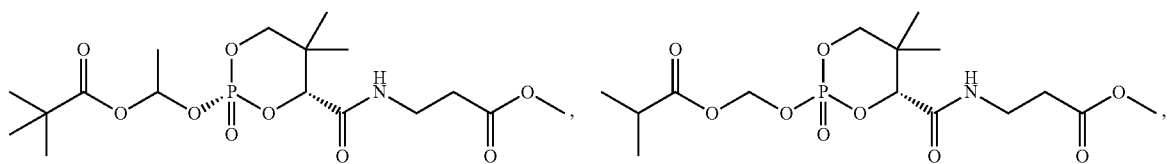
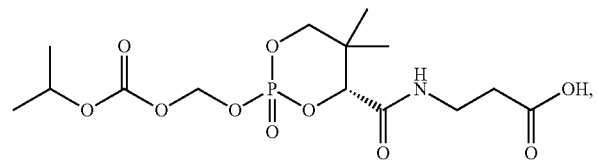
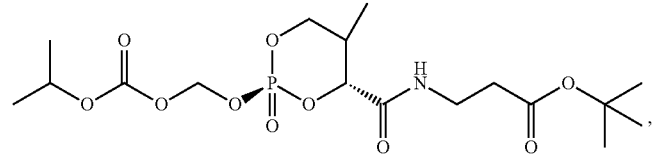
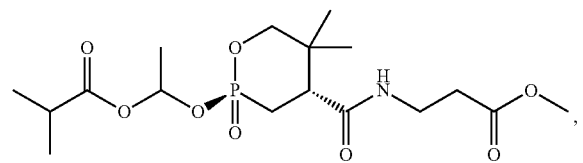

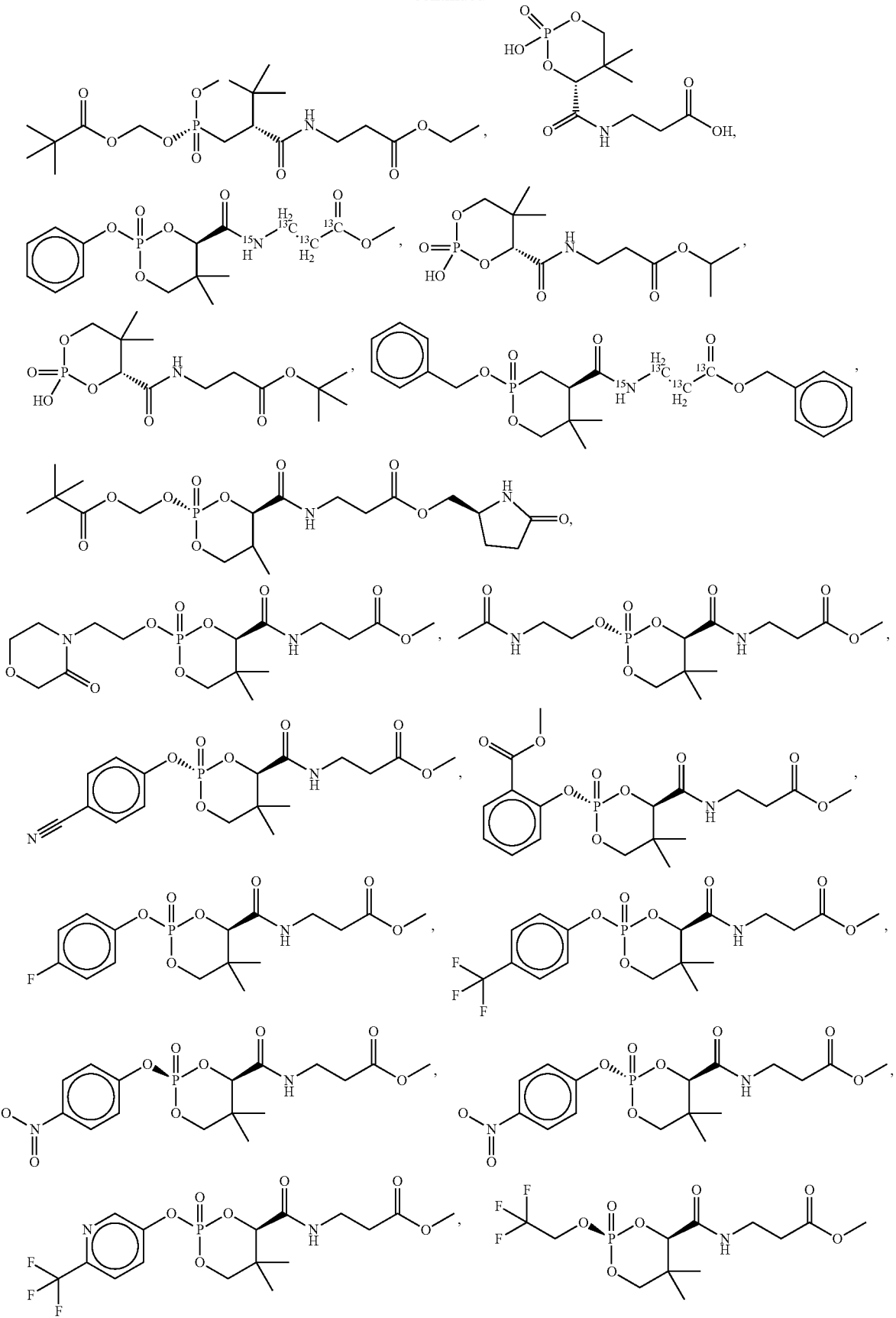

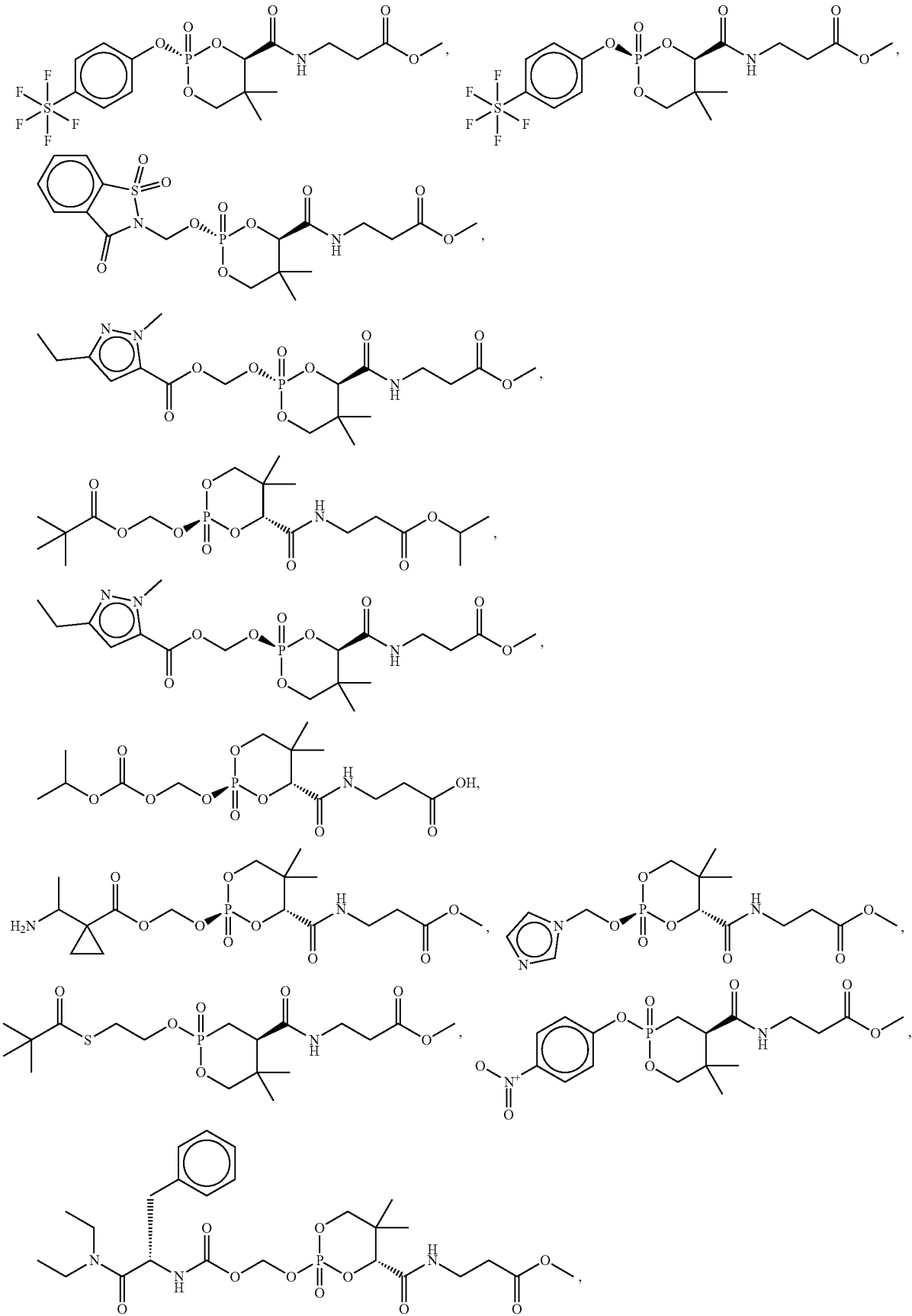

-continued
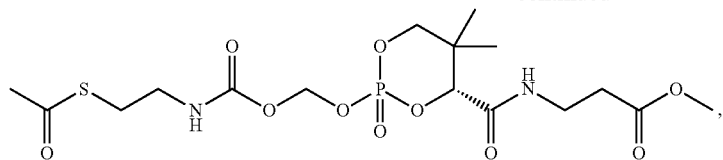
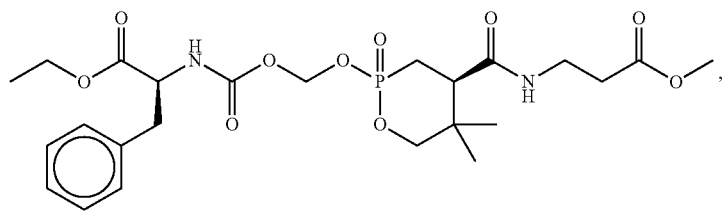
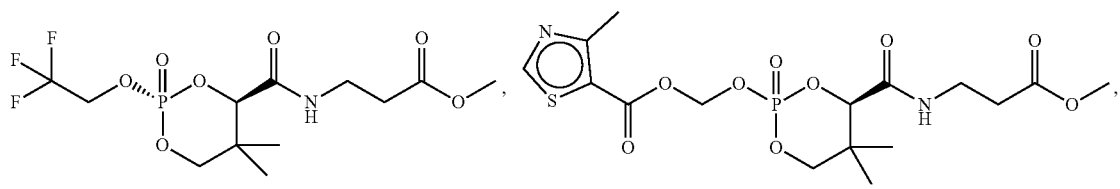
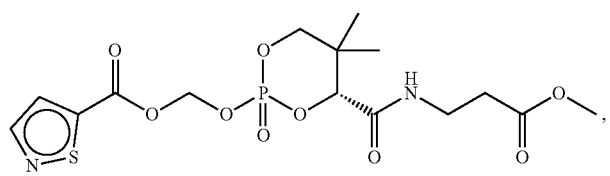
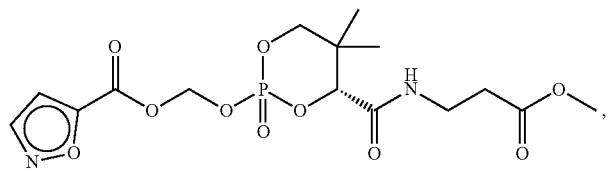
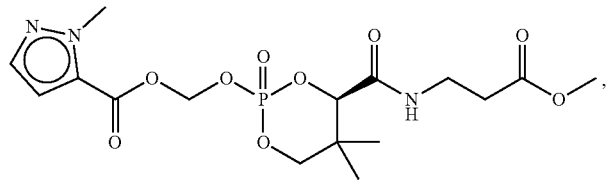
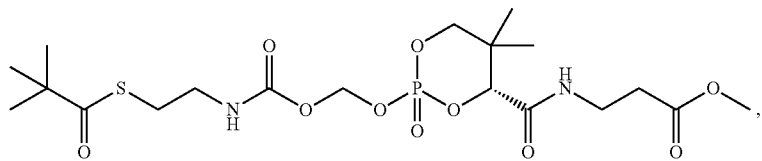
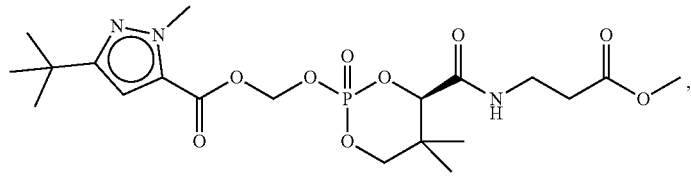
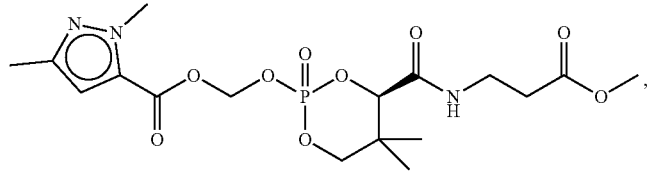

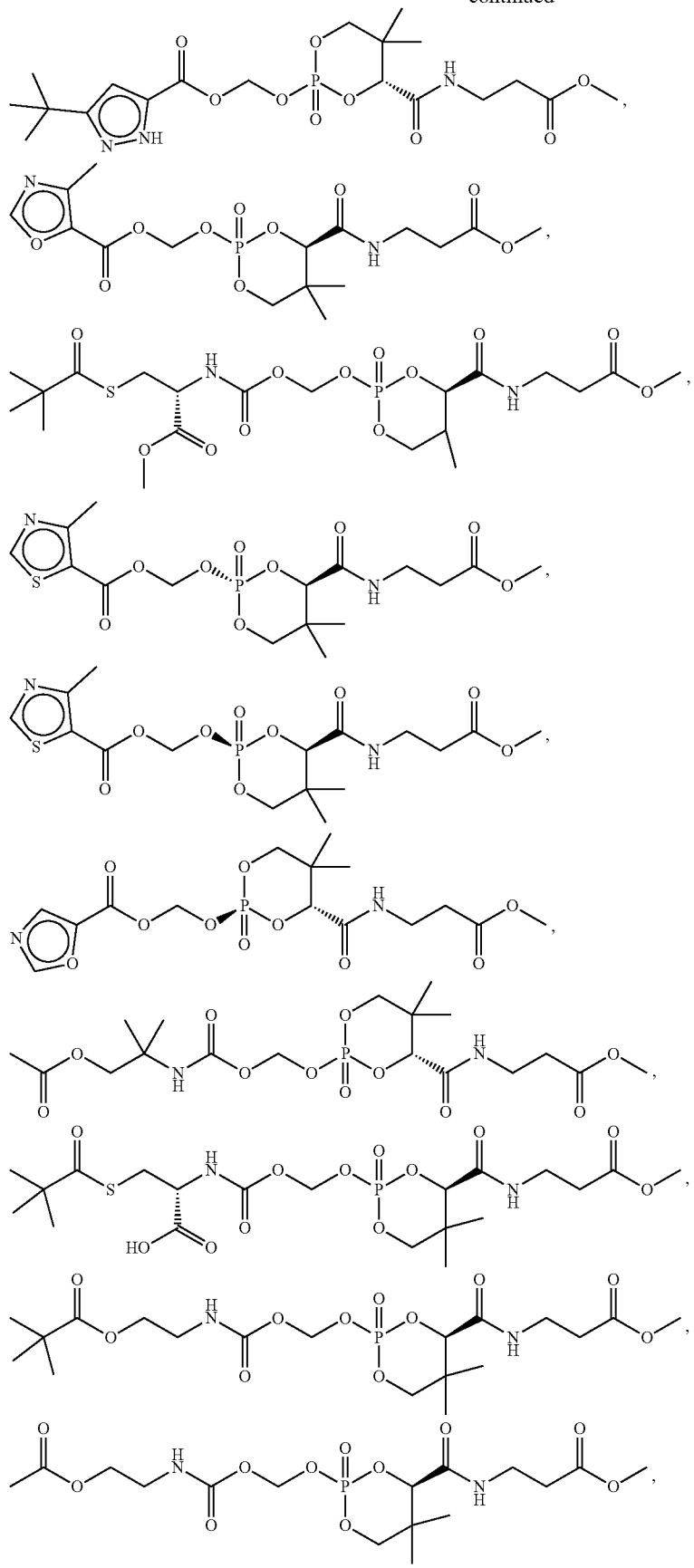

-continued
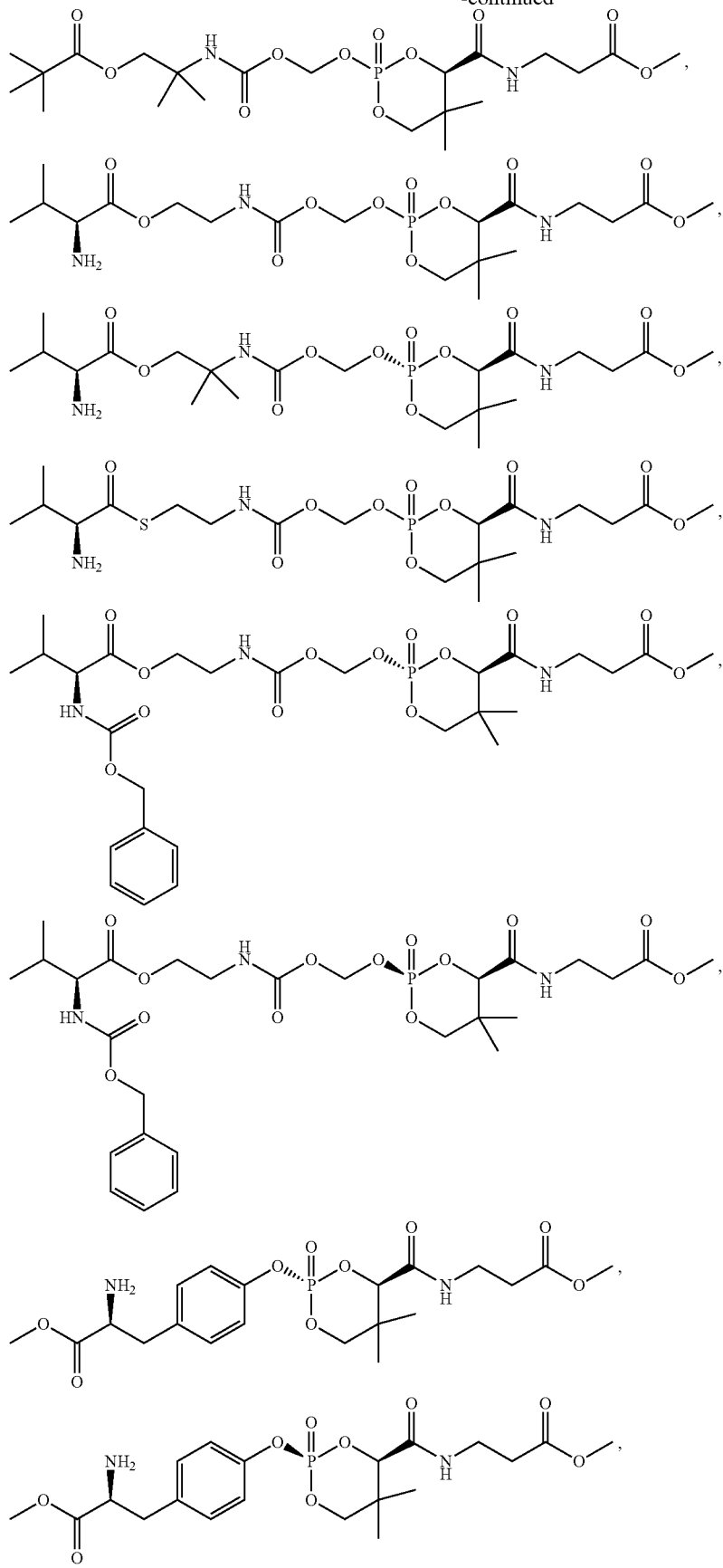

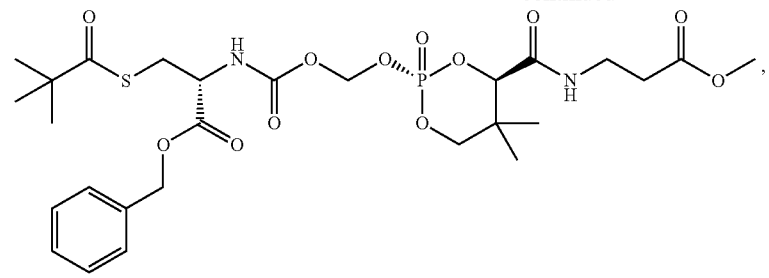
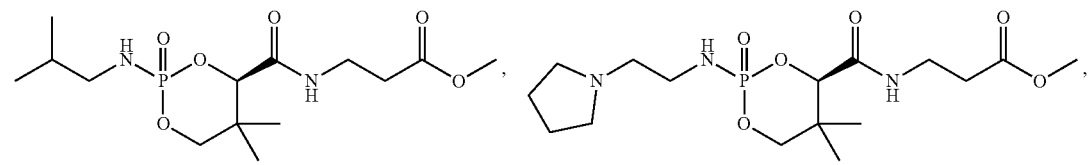
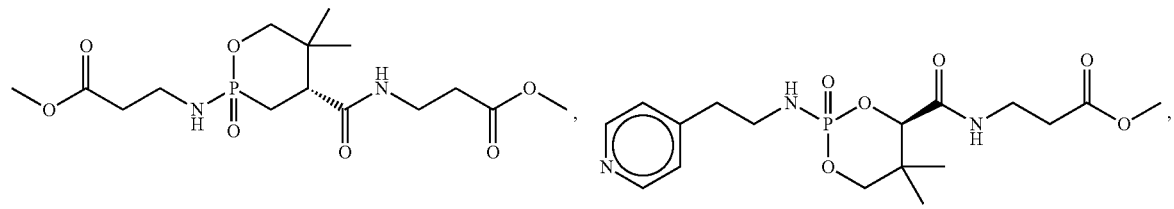
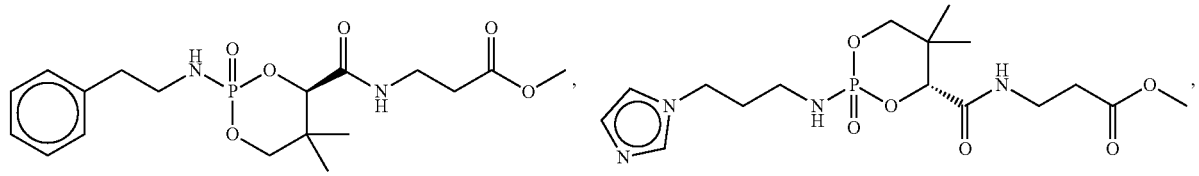
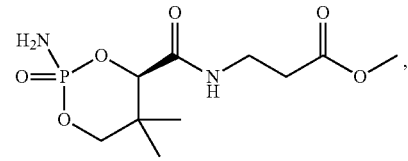
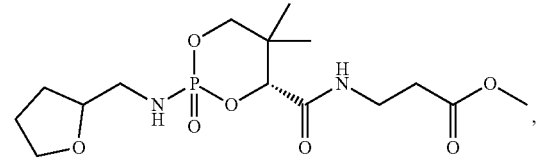
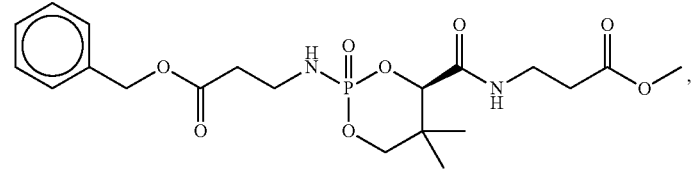
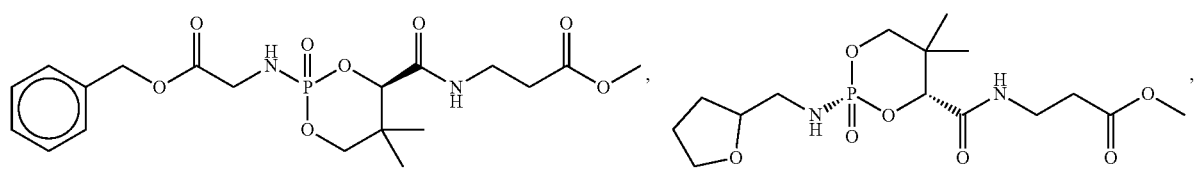
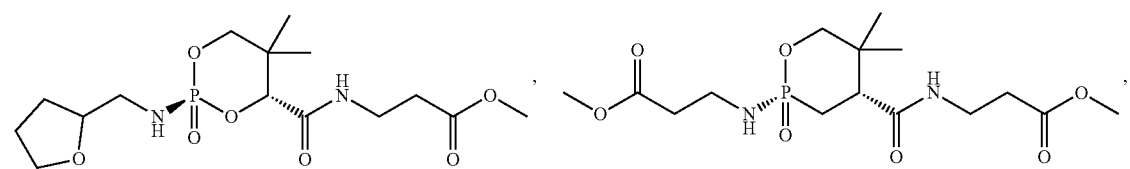

189 190
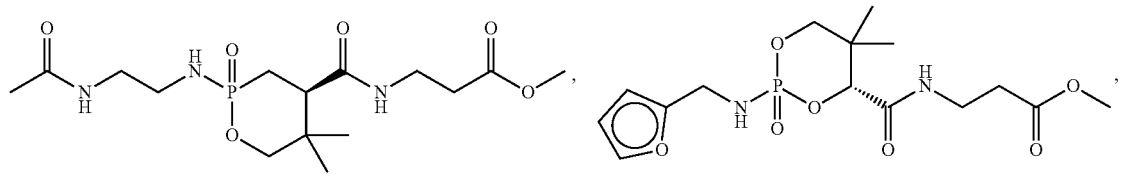
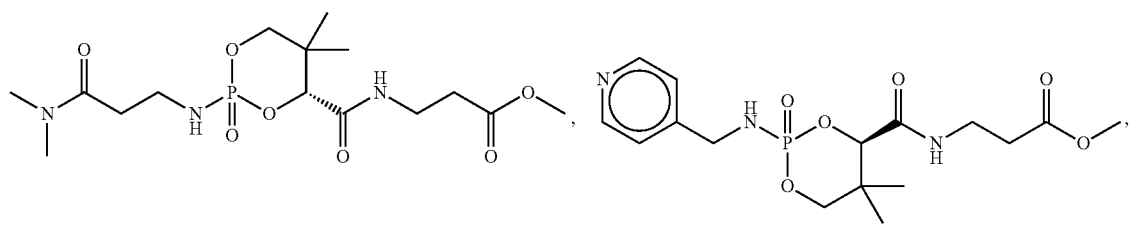
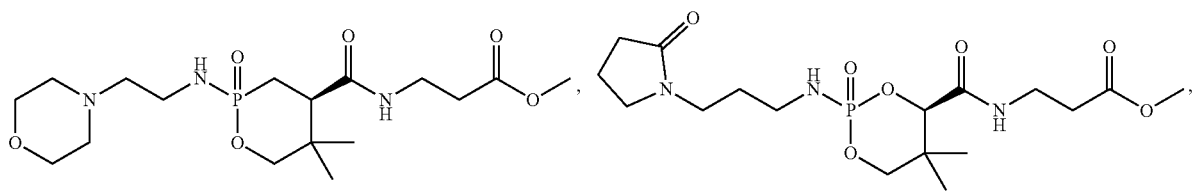
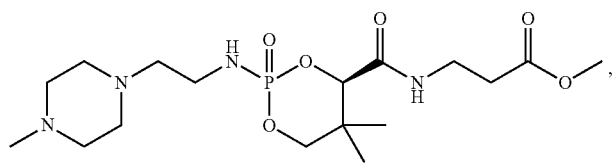
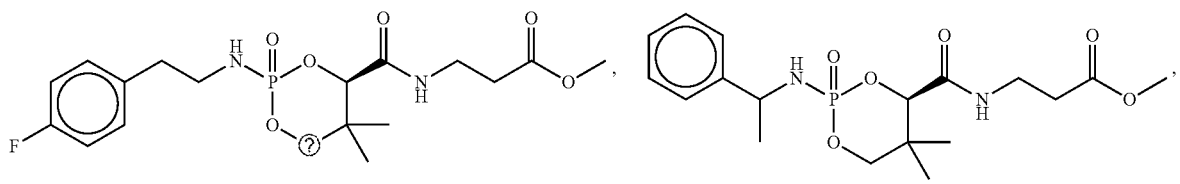
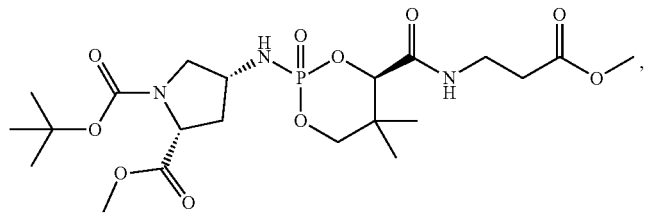
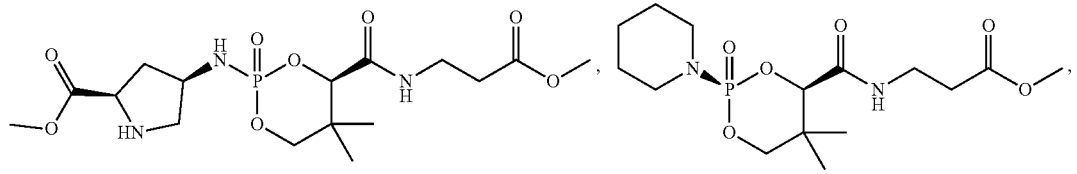
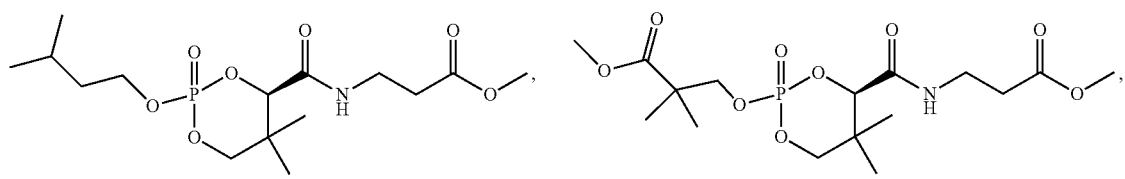
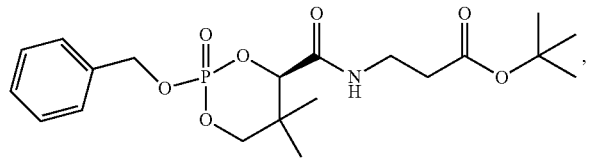

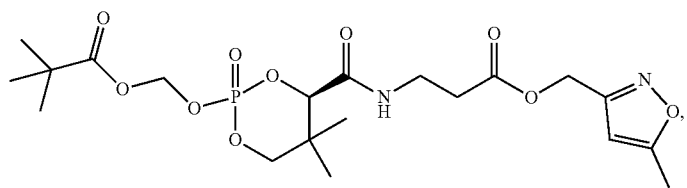
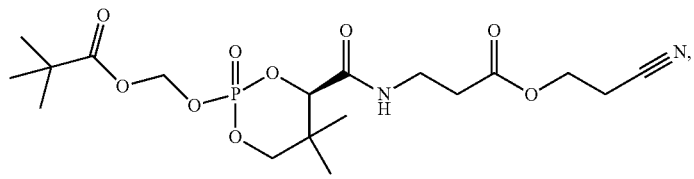
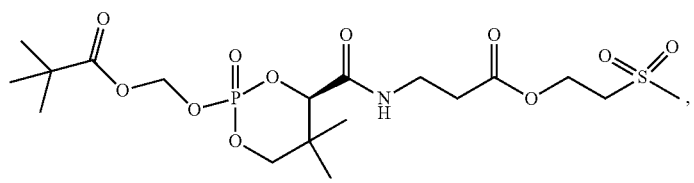
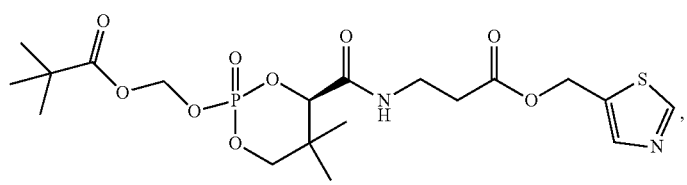
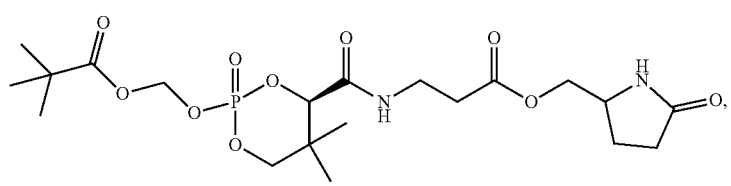
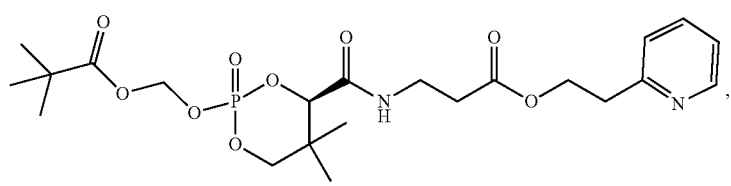
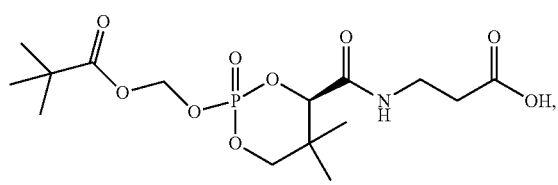
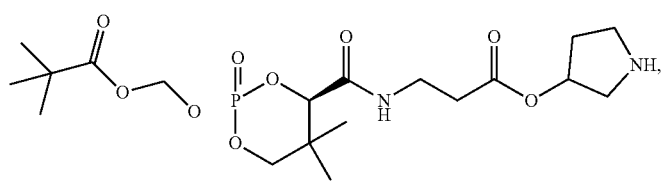
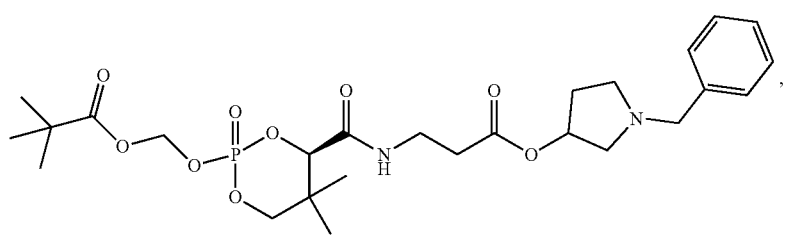

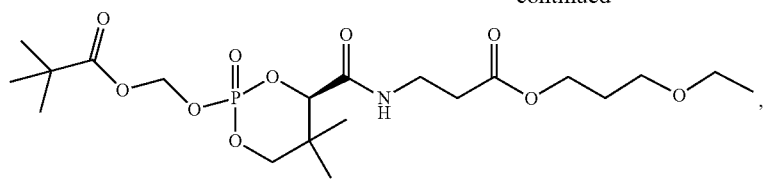
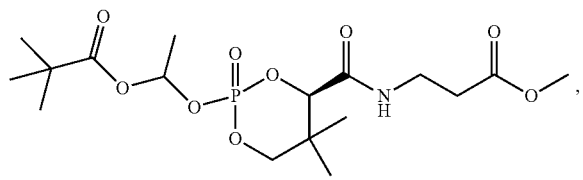
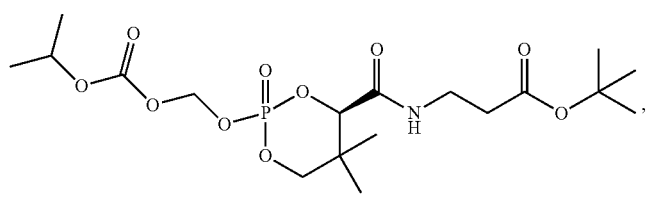
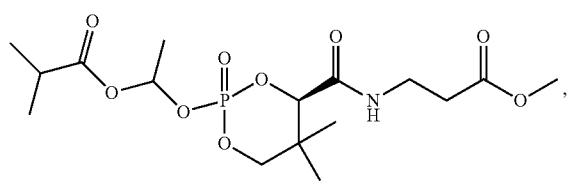
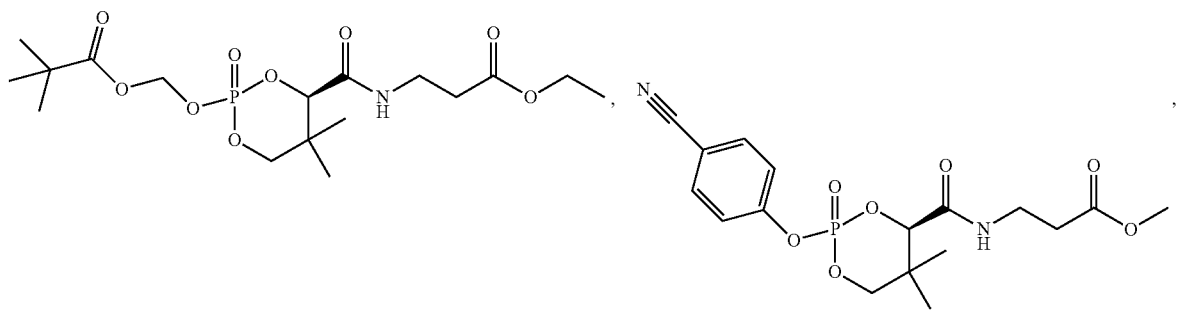
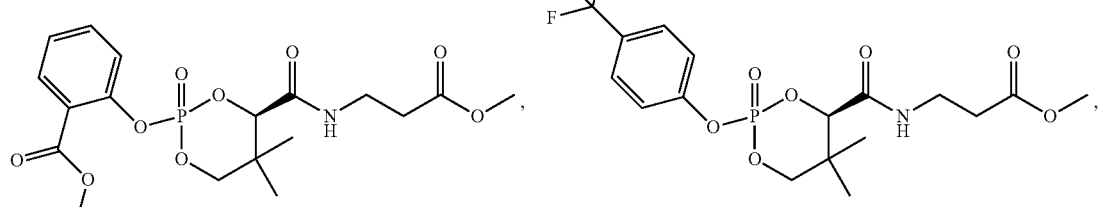
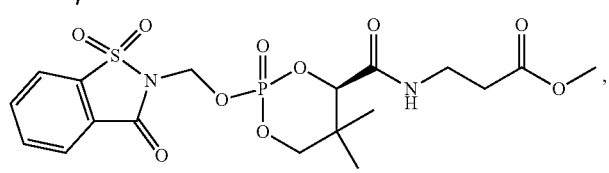
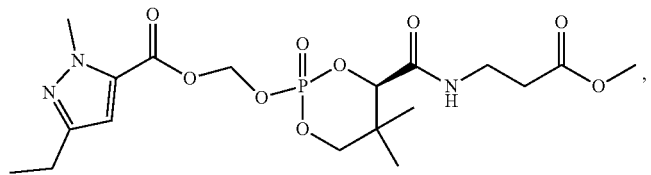

-continued
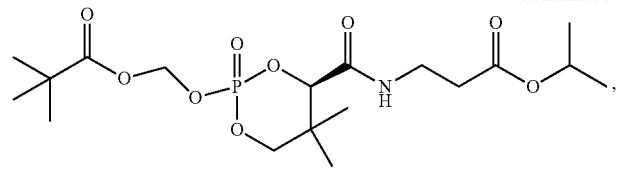
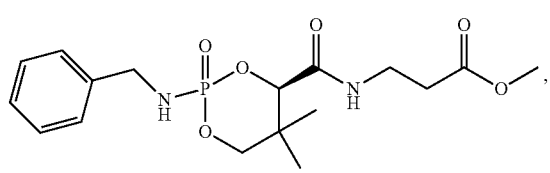
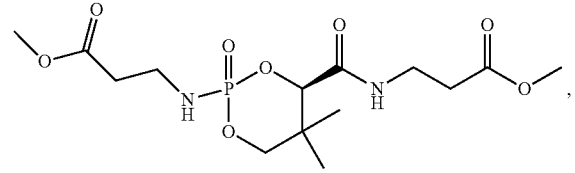
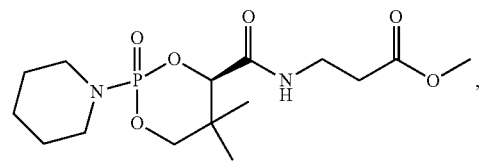
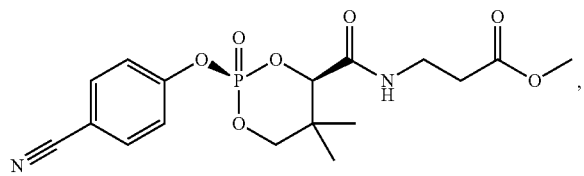
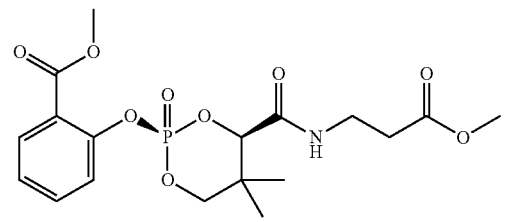
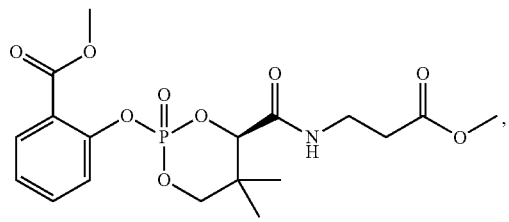
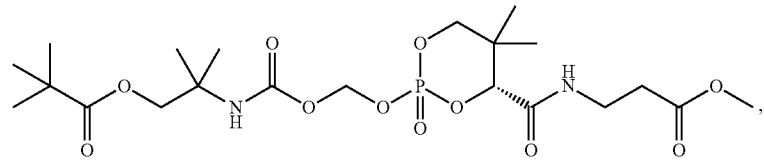
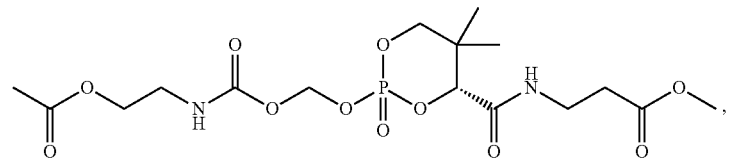
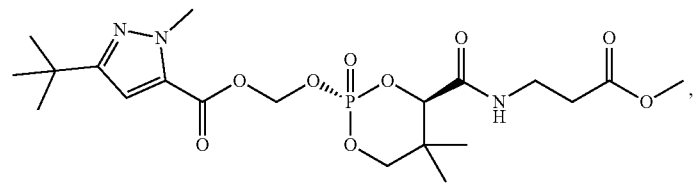
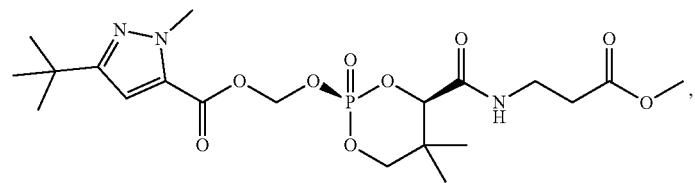
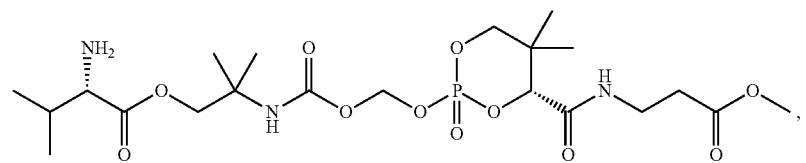

-continued
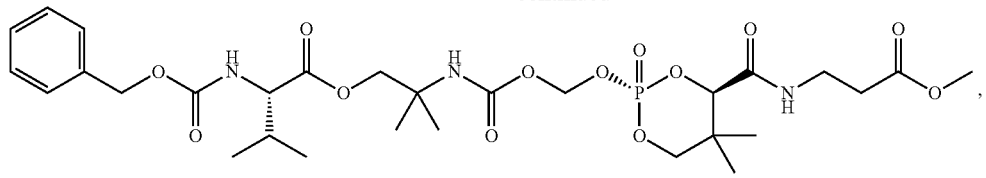
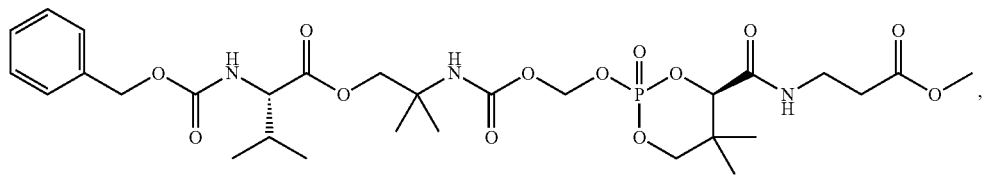
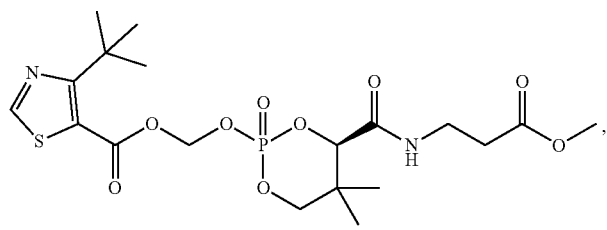
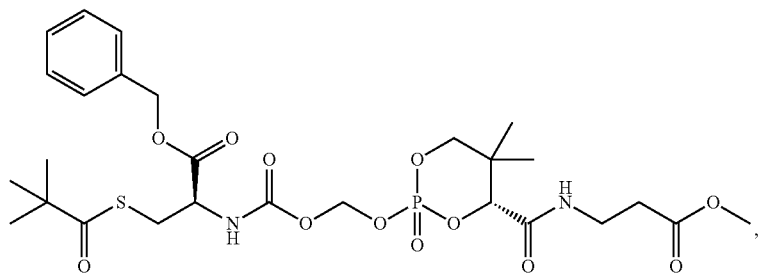
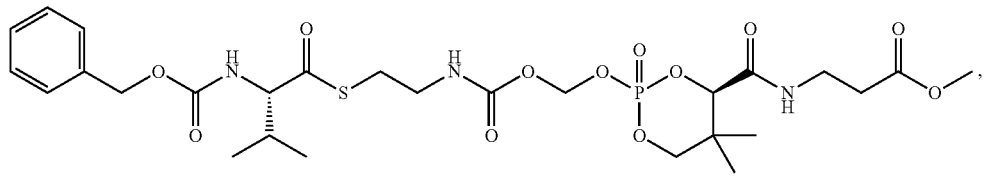
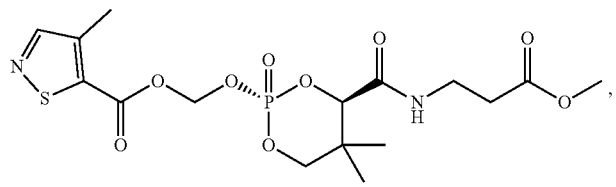
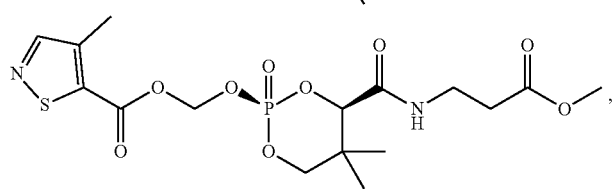
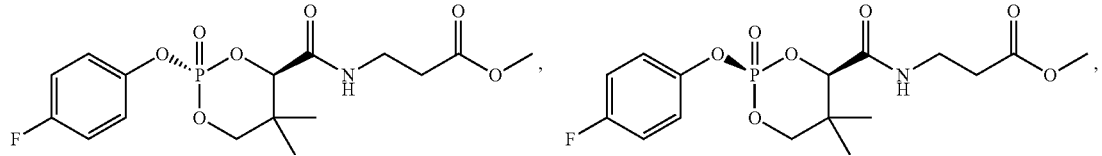
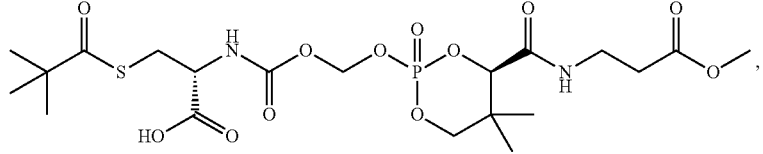

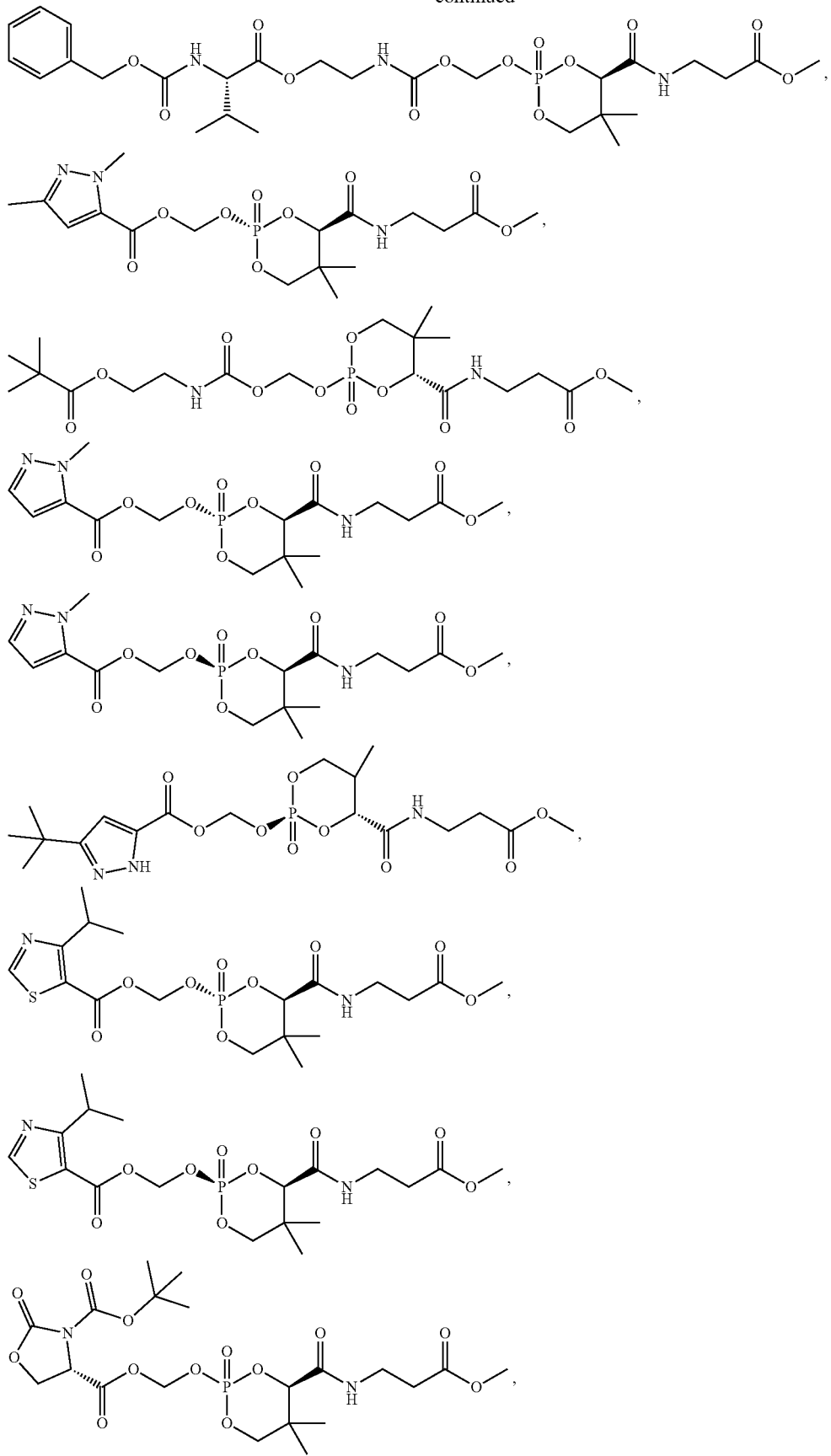

-continued
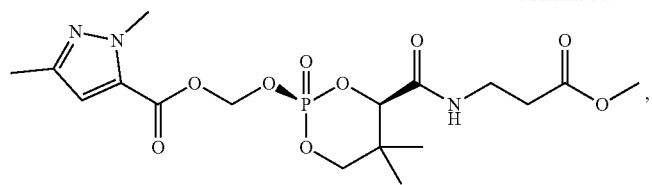
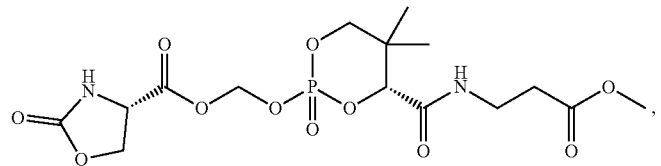
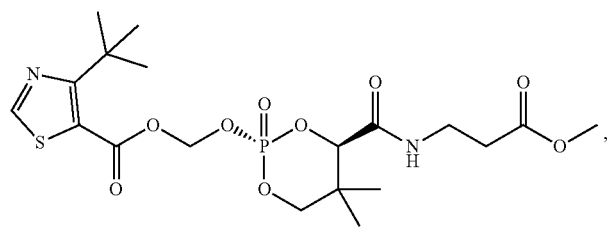
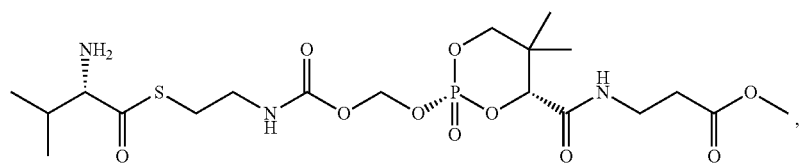
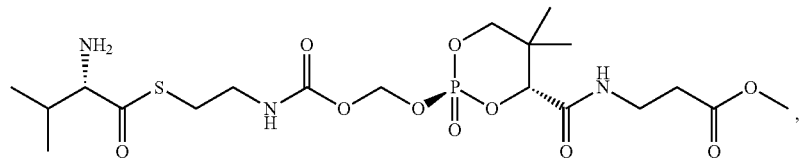
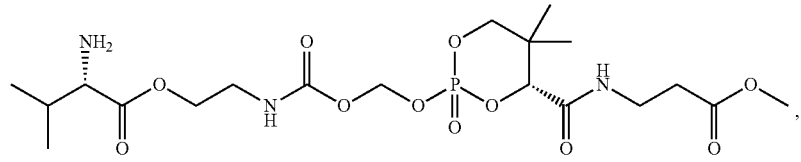
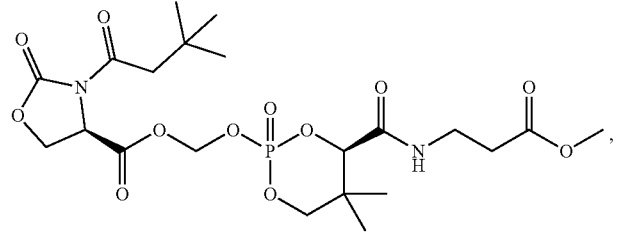
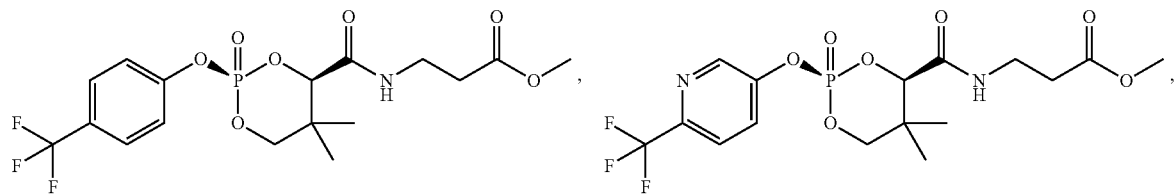

-continued
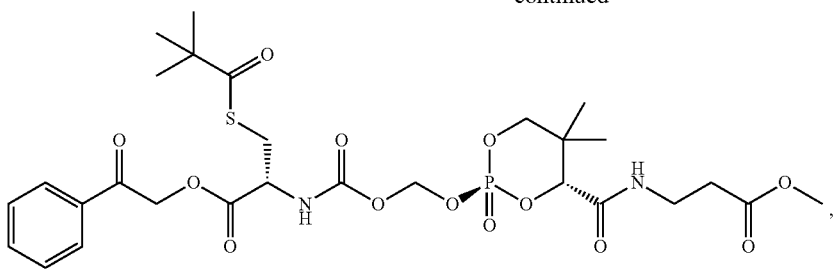
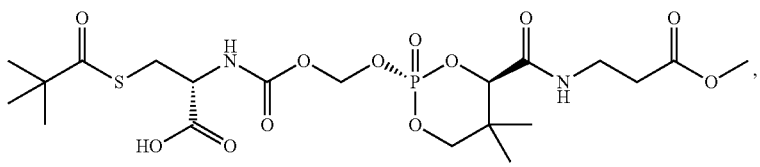
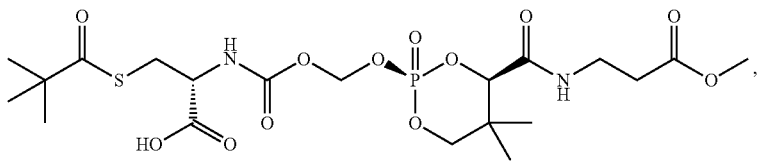
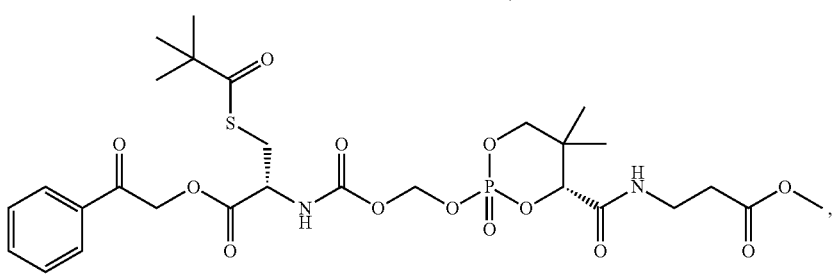
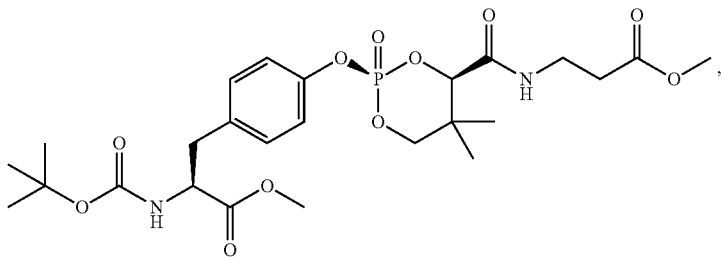
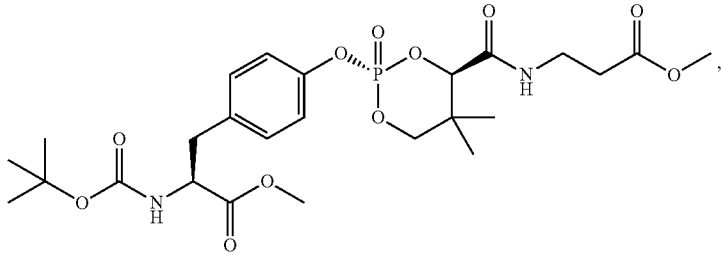
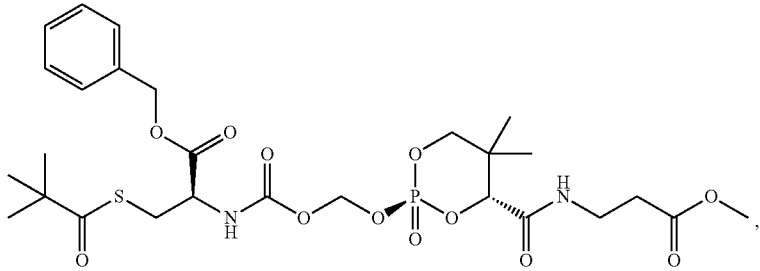

-continued

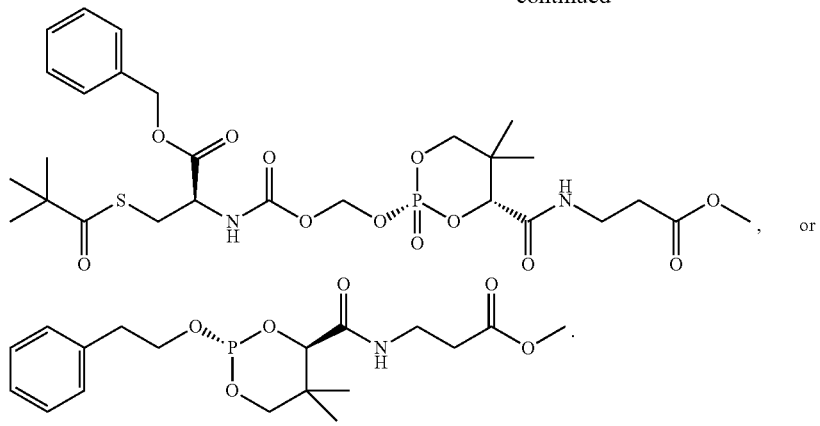

18. A pharmaceutical composition comprising a compound of claim 1, or a pharmaceutically acceptable salt thereof, and a pharmaceutically acceptable carrier, diluent or excipient.

19. A method of increasing 4'-phosphopantothenic acid production in a subject in need thereof, the method comprising administering to the subject an effective amount of the pharmaceutical composition of claim 18.

20. The method of claim 19, wherein said subject exhibits overexpression of an enzyme for which Coenzyme A is a synthetic precursor.

21. A method of treating a subject having a disorder associated with pantothenate kinase enzyme deficiency, a disorder associated with Coenzyme A deficiency or neurodegeneration with brain iron accumulation, wherein (a) said disorder associated with pantothenate kinase enzyme deficiency is pantothenate kinase-associated neurodegeneration, (b) said disorder associated with pantothenate kinase enzyme deficiency is 4'-phosphopantothenic acid deficiency, (c) said subject exhibits neurodegeneration with brain iron accumulation or (d) said subject has a pantothenate kinase gene (PANK) defect, comprising administering to a subject in need thereof an effective amount of a pharmaceutical composition of claim 18.

22. A method of treating Parkinson's disease, dystonia, extrapyramidal effects, dysphagia, rigidity and/or stiffness of limbs, choreoathetosis, tremor, dementia, spasticity, muscle weakness, or seizure, comprising administering to the subject an effective amount of a pharmaceutical composition of claim 18.

* * * * *